(12) United States Patent
Hirata et al.

(10) Patent No.: US 6,540,670 B1
(45) Date of Patent: Apr. 1, 2003

(54) ENDOSCOPE SYSTEM

(75) Inventors: Yasuo Hirata, Hachioji (JP); Hideyuki Adachi, Sagamihara (JP); Hironobu Takizawa, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/526,664

(22) Filed: Mar. 15, 2000

(30) Foreign Application Priority Data

Mar. 19, 1999 (JP) .......................................... 11-076725

(51) Int. Cl.[7] .............................................. A61B 1/005
(52) U.S. Cl. ....................................... 600/152; 600/146
(58) Field of Search ................................. 600/139–142, 600/144, 146, 152; 604/95.01, 95.04

(56) References Cited

U.S. PATENT DOCUMENTS 5,048,956 A * 9/1991 Sakamoto et al. ........ 356/241.4
5,860,914 A * 1/1999 Chiba et al. ................. 600/139
5,897,488 A * 4/1999 Ueda .......................... 600/143

* cited by examiner

Primary Examiner—John Mulcahy
(74) Attorney, Agent, or Firm—Frishauf, Holtz, Goodman & Chick, P.C.

(57) ABSTRACT

In this invention, a drum around which an insertion portion is wound is integrally housed in a carrying case, and a cylinder for supplying a fluid to a hydropneumatic actuator and a solenoid valve unit for controlling the application of a hydropneumatic pressure are housed in the carrying case or drum. In addition, a joystick for operating the controlled variables of the solenoid valve unit can be housed in the carrying case.

24 Claims, 63 Drawing Sheets

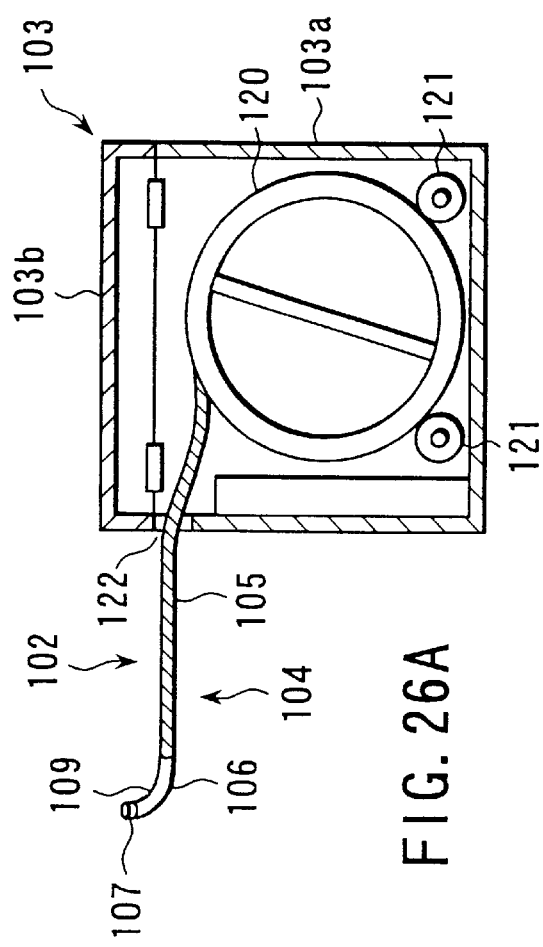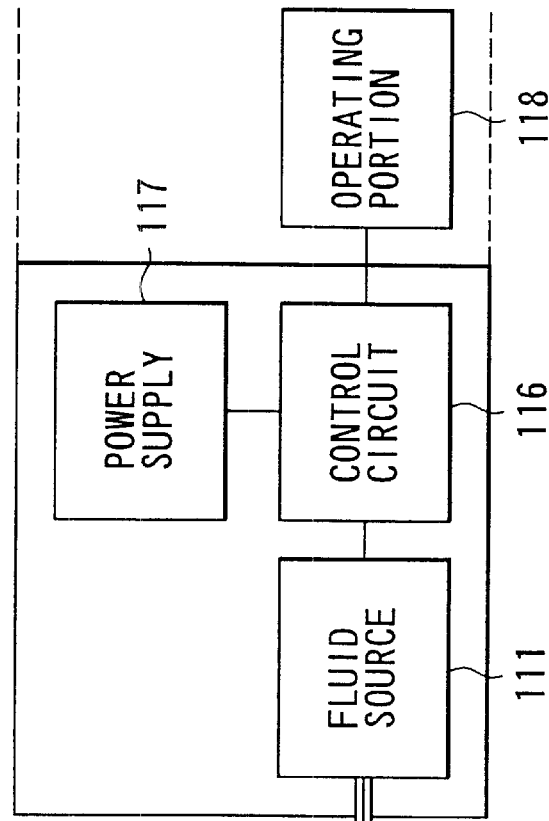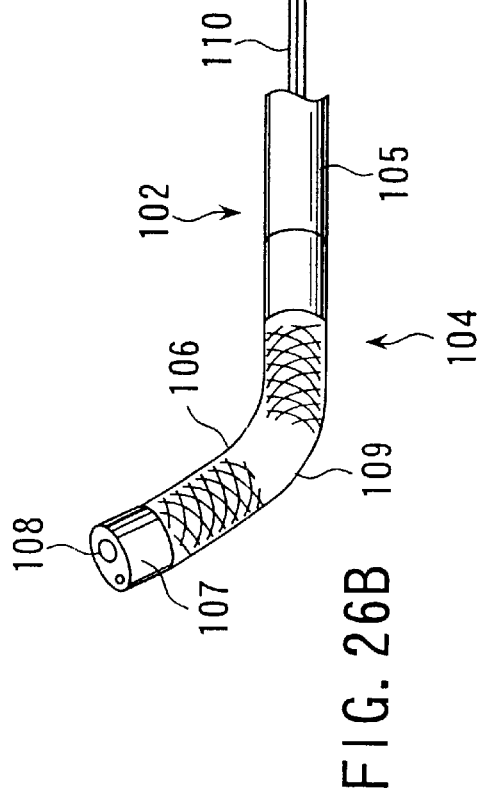
FIG. 26A
FIG. 26B

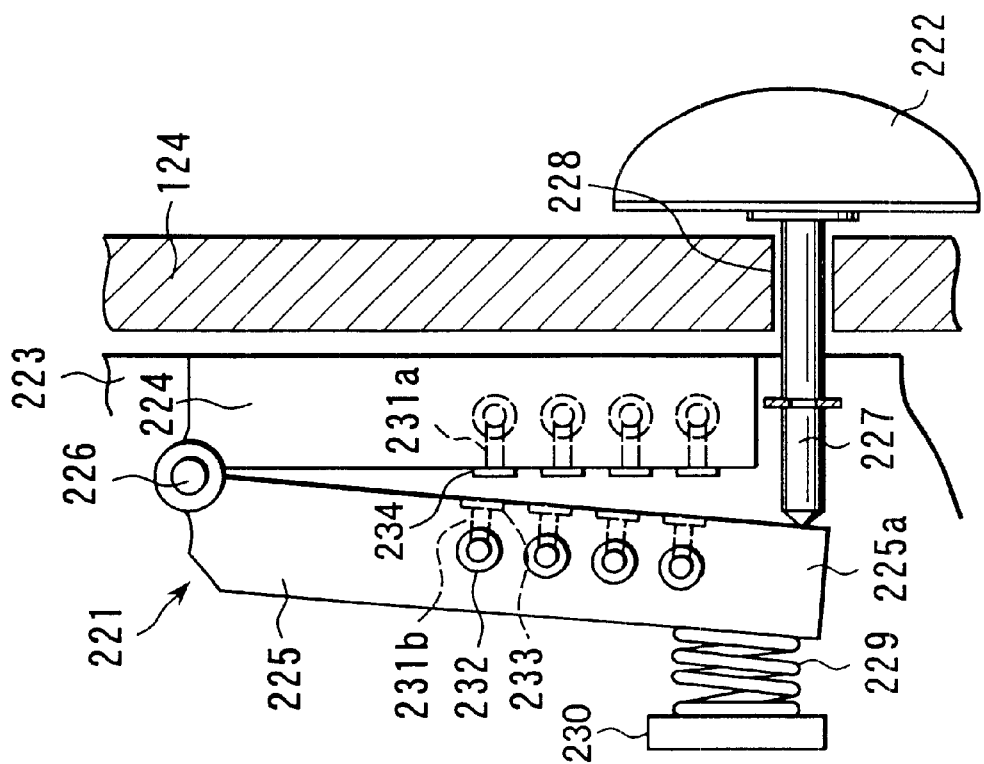
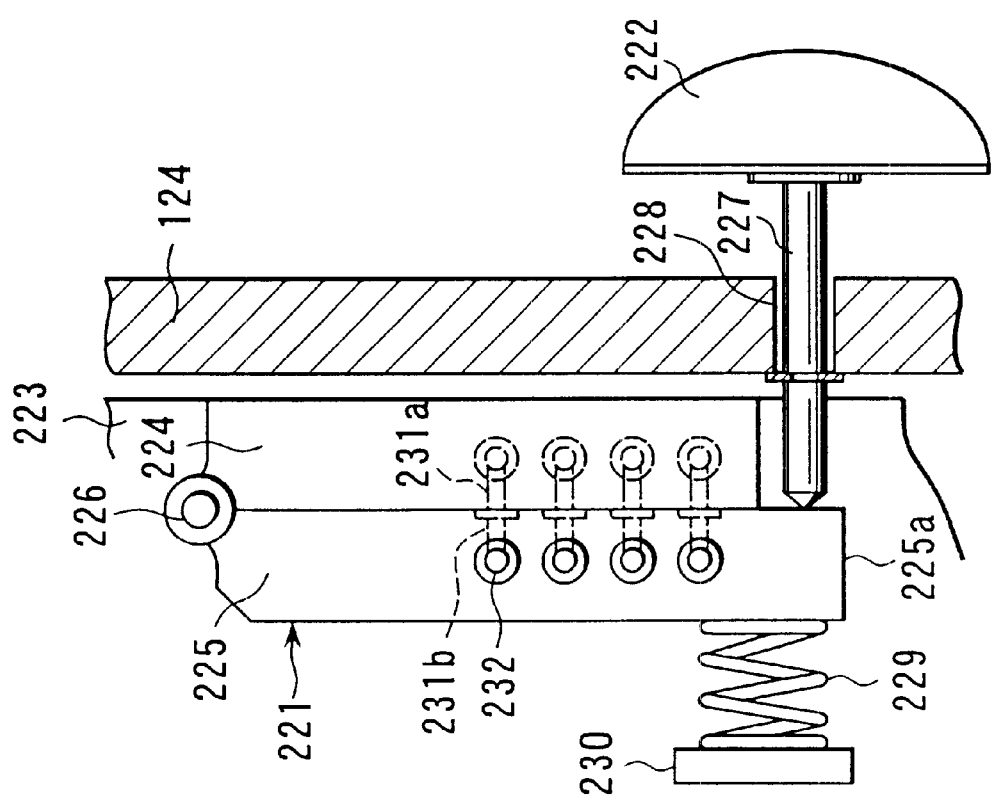
FIG. 39A
FIG. 39B

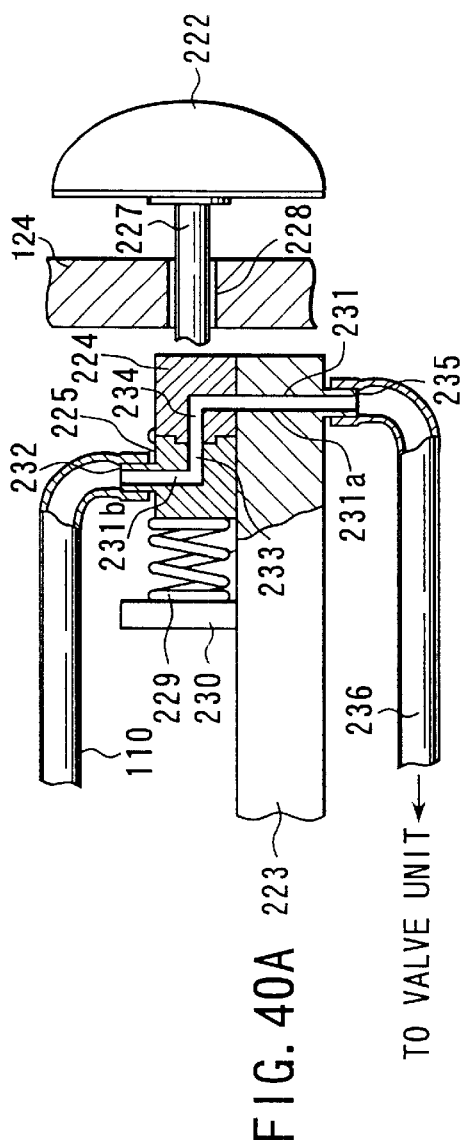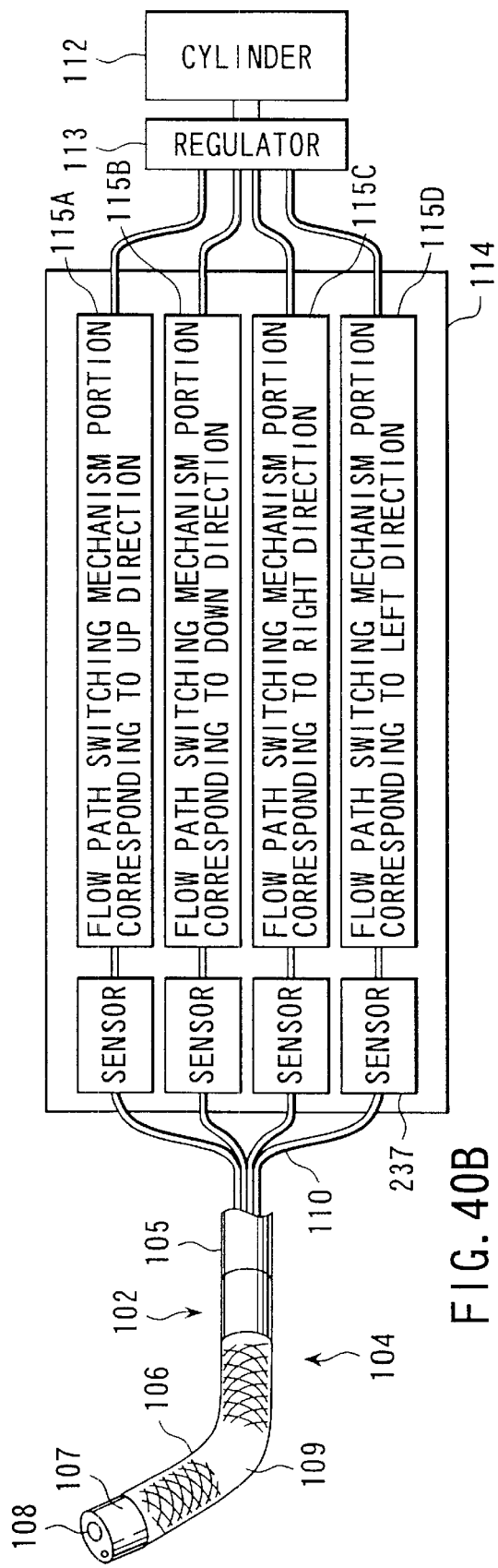
FIG. 40A
FIG. 40B

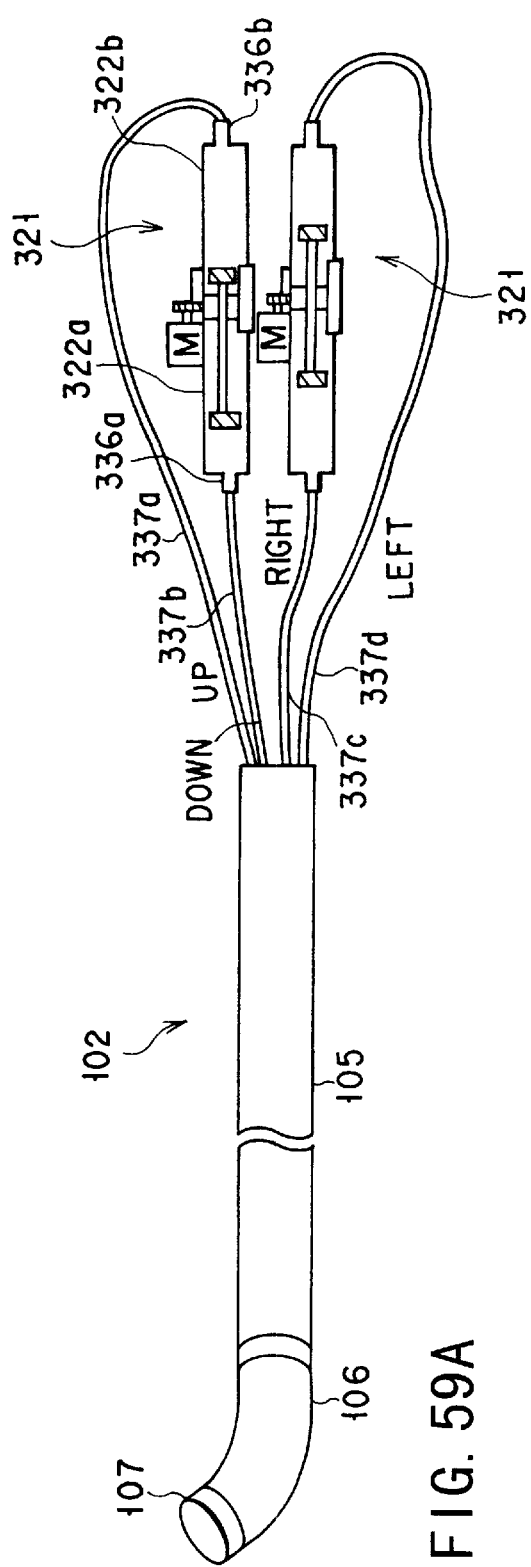
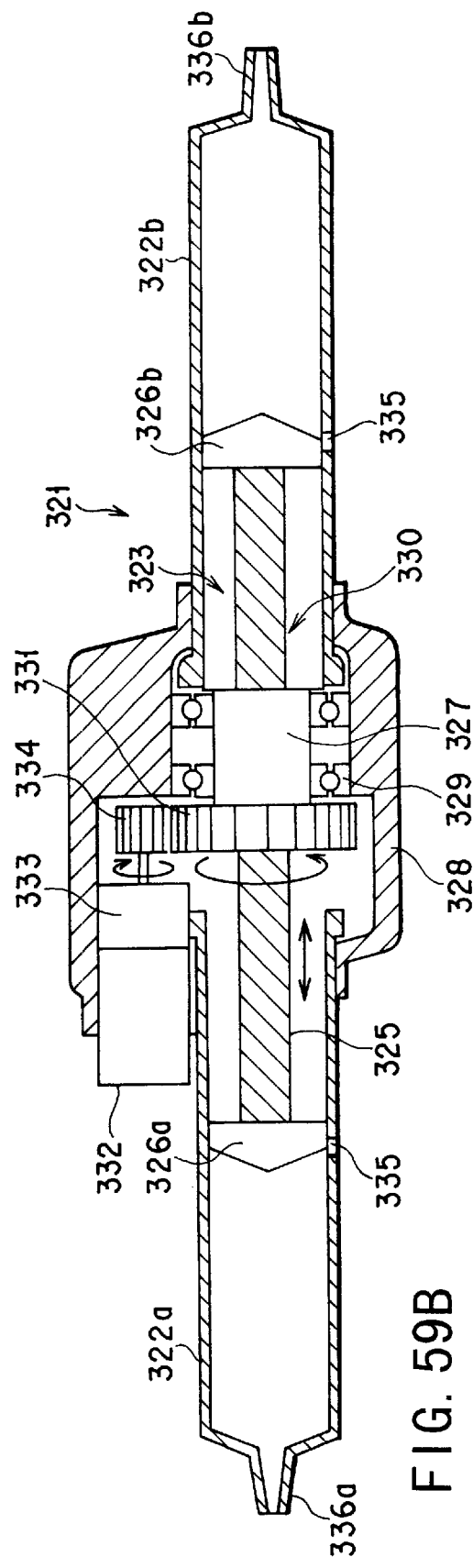
FIG. 59A
FIG. 59B

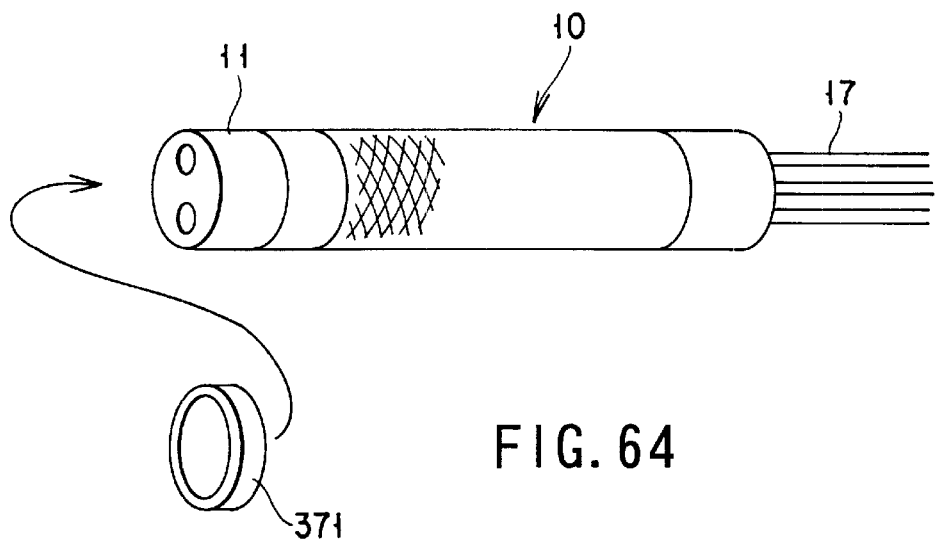
FIG. 64
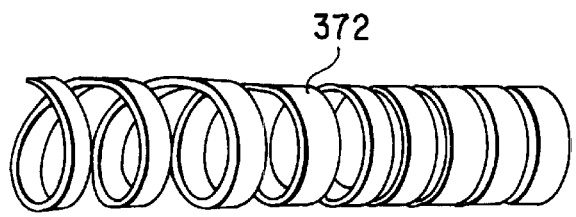
FIG. 65
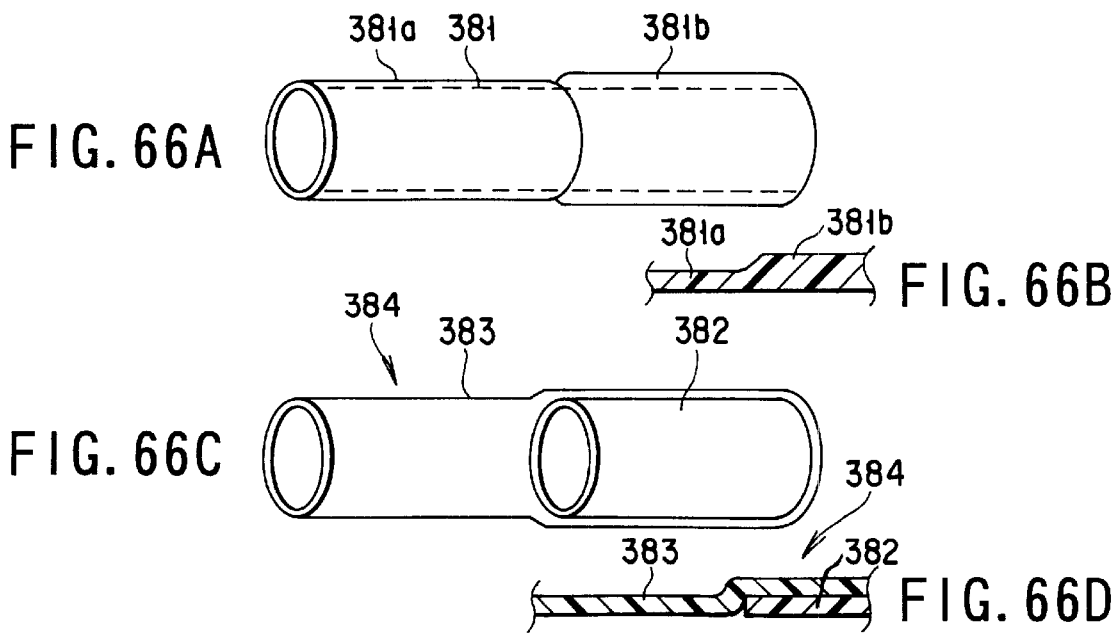
FIG. 66A
FIG. 66B
FIG. 66C
FIG. 66D

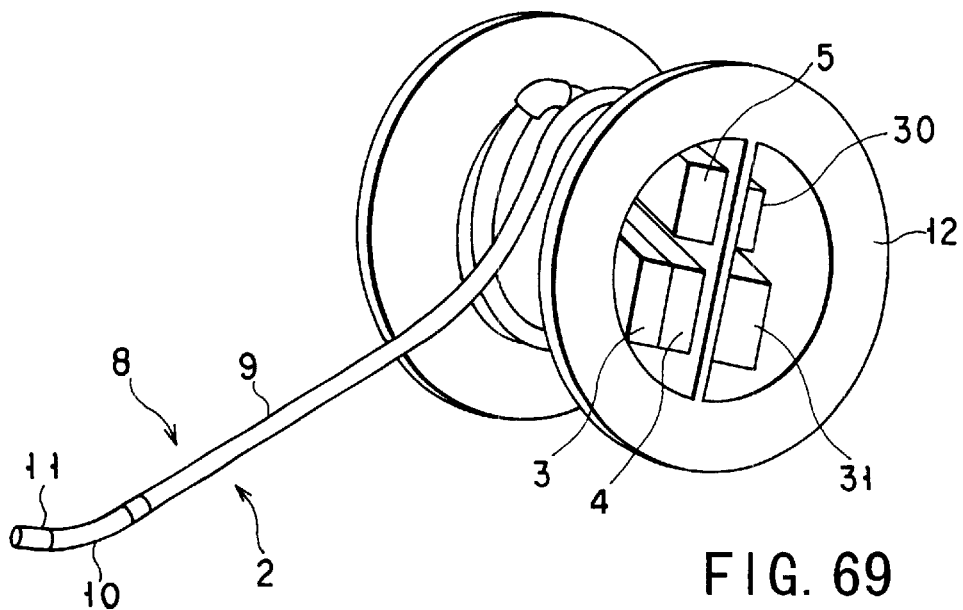
FIG. 69
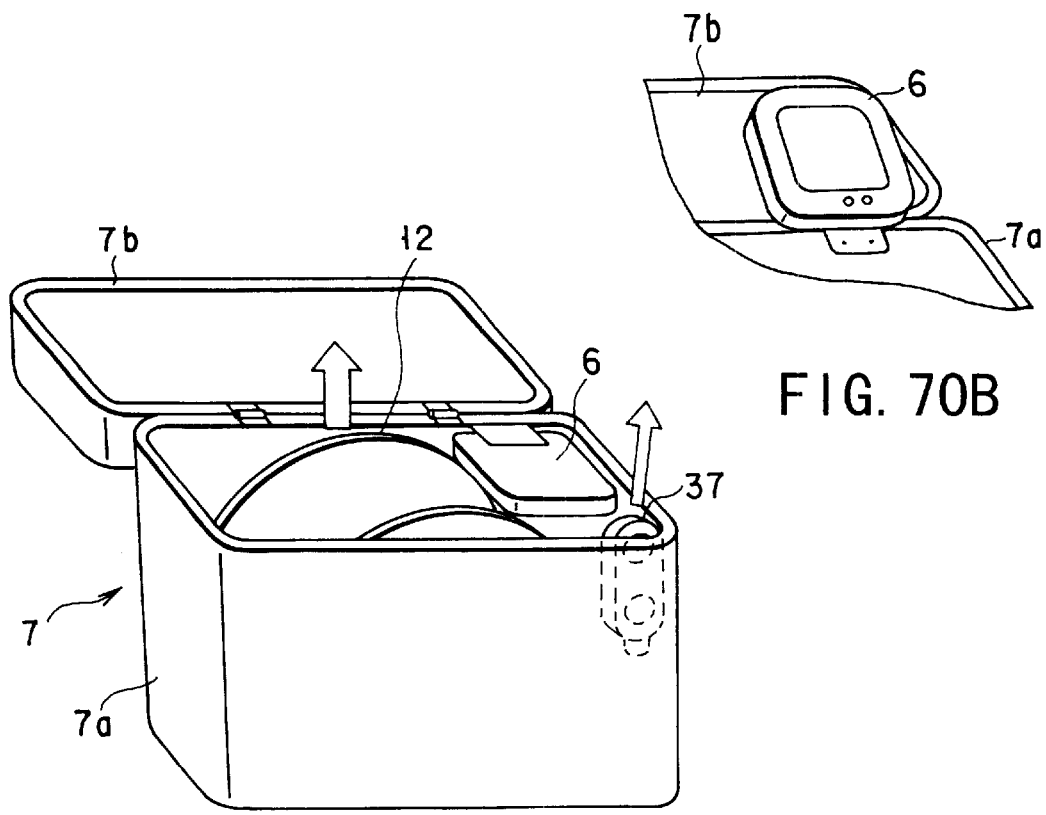
FIG. 70B
FIG. 70A

ENDOSCOPE SYSTEM

CROSS-REFERENCE TO RELATED APPLICATION(S)

This application is based upon and claims the benefit of priority from the prior Japanese Patent Application(s) No. 11-76725, filed Mar. 19, 1999, the entire contents of which are incorporated herein by reference.

BACKGROUND OF THE INVENTION

The present invention relates to an endoscope system which has a bending portion formed from a hydropneumatic actuator on the distal end of an elongated insertion portion to be inserted into a tubular cavity and can be applied to, for example, an industrial endoscope and medical endoscope.

In general, an endoscope that can be applied to, for example, both an industrial endoscope and a medical endoscope has an elongated insertion portion to be inserted into a tubular cavity. An endoscope of this type has a bending portion on the distal end portion of the insertion portion. An operator can set the observation direction of the endoscope in an arbitrary direction by bending this bending portion.

As a bending portion attached to the distal end portion of an insertion portion, for example, a bending portion having a pneumatic actuator is described in Jpn. Pat. Appln. KOKAI Publication Nos. 4-135570 and 5-305053.

In addition, the bending portion described in Jpn. Pat. Appln. KOKAI Publication No. 5-76600 has a protective member around the outer surface of an actuator which changes in length in the axial direction and in diameter. This protective member restricts the expansion of the actuator in the radial direction.

A bending portion of this type includes an elastic tubular member on the distal end portion of an insertion portion. A plurality of pressurization chambers are arranged on the tube wall of this elastic tubular member along the circumferential direction. Pneumatic pressures are selectively supplied to the pressurization chambers to pressurize them. As a consequence, the elastic tubular member is bent in a direction opposite to the pressurized pressurization chambers.

An endoscope system is generally comprised of an endoscope body, a light source unit connected to the endoscope body, a CCU (Camera Control Unit), and the like. An endoscope system has been proposed, which has improved portability by housing the constituents of the system in one cart or a small case.

Consideration similar to that given to the endoscope system designed to improve portability in the above manner is given to an endoscope having a pneumatic actuator in a bending portion. The above conventional endoscope having the pneumatic actuator requires a relatively large compressor as a pneumatic source for bending the pneumatic actuator. For this reason, the endoscope system increases in size as a whole, and the portability deteriorates.

In the endoscope having the bending mechanism using the pneumatic actuator, the bending portion is bent by sending air supplied from the compressor, which is an external unit connected to the endoscope body, to the pneumatic actuator on the distal end side of the insertion portion through the air duct inserted into the insertion portion of the endoscope body.

If, however, the insertion portion of the endoscope is long, it takes much time to send air from the compressor to the pneumatic actuator. This causes a time lag in bending operation, and may interfere with accurate bending operation.

In addition, in the endoscope having the bending mechanism using the pneumatic actuator, the elastic tubular member of the bending portion is made of an extensible material such as silicone resin. A compressed fluid is selectively supplied to a plurality of pressurization chambers disposed on the tube wall of this elastic tubular member to pressurize the pressurization chambers, thereby bending the bending portion. A bend tube formed from an elastic tubular member, however, exhibits a unique phenomenon of hysteresis with respect to an increase/decrease in pressure. This makes it difficult to match bending operation using the operating portion at hand with the bending operation of the bending portion.

With a protective member like the one described in Jpn. Pat. Appln. KOKAI Publication No. 5-76600, which is placed around the outer surface of an elastic tubular member, an attempt has been made to restrict the expansion of the elastic tubular member in the radial direction by using the protective member as a restricting member when pneumatic pressures are supplied to pressurization chambers in the elastic tubular member so as to extend the pressurization chambers only in the axis direction, thereby efficiently bending the bending portion and preventing the bending portion from extremely expanding when it is bent.

A protective member like the one described in Jpn. Pat. Appln. KOKAI Publication No. 5-76600 is smaller in change amount than an elastic tubular member when extending in the axial direction. If, therefore, a protective member like the one described in Jpn. Pat. Appln. KOKAI Publication No. 5-76600 is placed around the outer surface of the elastic tubular member, the bending operation of the bending portion tends to be restricted by the protective member during the bending operation of the bending portion. This makes it difficult to set a large bending angle for the bending portion, posing a problem in improving bending performance.

BRIEF SUMMARY OF THE INVENTION

The present invention has been made in consideration of the above situation, and has as its object to provide an endoscope system in which excellent controllability is realized in an endoscope having a bending mechanism using a pneumatic actuator at the distal end portion of a long insertion portion.

It is another object of the present invention to provide an endoscope system with excellent portability of the overall system.

In order to achieve the above objects, according to the present invention, there is provided an endoscope system having image sensing means at a distal end of an insertion portion to be inserted into a tubular cavity under examination, a bending portion behind the image sensing means, and a hydropneumatic actuator for bending the bending portion with a hydropneumatic pressure, comprising:

a cylinder filled with a fluid to be supplied to the hydropneumatic actuator;

a fluid flow rate adjusting portion for adjusting a flow rate of fluid supplied from the cylinder;

a control unit for controlling the fluid flow rate adjusting portion; and an operating portion for operating a controlled variable of the control unit.

An endoscope system can therefore be provided, in which excellent controllability is realized in an endoscope having a bending mechanism using a pneumatic actuator at the distal end portion of a long insertion portion.

According to the present invention, there is provided an endoscope system having image sensing means at a distal end of an insertion portion to be inserted into a tubular cavity under examination, a bending portion behind the image sensing means, and a hydropneumatic actuator for bending the bending portion with a hydropneumatic pressure, the hydropneumatic actuator having a multi lumen tube, and the multi lumen tube being constituted by a central hole housing a built-in member, and a plurality of pressurization chambers arranged around the central hole, comprising:

a syringe for supplying a fluid to the hydropneumatic actuator;

an actuator for driving the syringe back and forth;

a control unit for controlling the actuator; and an operating portion for operating a controlled variable of the control unit.

According to the present invention, the fluid supplied from the syringe as a fluid source is supplied to one of the pressurization chambers around the hole of the multi lumen tube to bend the hydropneumatic actuator in a direction opposite to the pressurized pressurization chamber. An endoscope system can therefore be provided, in which excellent controllability is realized in an endoscope having a bending mechanism using a hydropneumatic actuator at the distal end portion of a long insertion portion.

In addition, according to the present invention, there is provided an endoscope system having image sensing means at a distal end of an insertion portion to be inserted into a tubular cavity under examination, a bending portion behind the image sensing means, and a hydropneumatic actuator for bending the bending portion with a hydropneumatic pressure, the hydropneumatic actuator having a multi lumen tube, the multi lumen tube being constituted by a central hole housing a built-in member, and a plurality of pressurization chambers arranged around the central hole, and the bending portion having a cylindrical member that is extensible in an axial direction, and bending portion protecting means mounted on an outer surface between front and rear ends of the bending portion while the cylindrical member is made shorter than a natural length in an axial direction of the bending portion.

An endoscope system can therefore be provided, in which excellent controllability is realized in an endoscope having a bending mechanism using a hydropneumatic actuator at the distal end portion of a long insertion portion.

Furthermore, according to the present invention, there is provided an endoscope system having image sensing means at a distal end of an insertion portion to be inserted into a tubular cavity under examination, a bending portion behind the image sensing means, and a hydropneumatic actuator for bending the bending portion with a hydropneumatic pressure, the hydropneumatic actuator having a multi lumen tube, the multi lumen tube being constituted by a central hole housing a built-in member, and a plurality of pressurization chambers arranged around the central hole, comprising:

a take-up drum which can take up the insertion portion and in which the hydropneumatic actuator is housed;

a cylinder for supplying a fluid to the hydropneumatic actuator in the drum;

a housing case for integrally housing the insertion portion and the drum;

a control unit for controlling a fluid amount in the cylinder housed in the housing case or the drum; and an operating portion which can be housed in the housing case and operates a controlled variable of the control unit, wherein the operating portion includes a monitor for displaying a picture from the image sensing means, controlled variable display means, placed on a display screen of the monitor or near the monitor, for displaying a controlled variable of the control unit, and a touch panel which is placed on the display screen of the monitor to display a press on a surface of the monitor and a position of the press, and a controlled variable of the control unit is adjusted in accordance with a press position signal from the touch panel.

According to the present invention, the drum around which the insertion portion is wound is integrally housed in the housing case, and the hydropneumatic pressure control portion having the hydropneumatic pressure source for supplying a fluid to the hydropneumatic actuator and the fluid supply amount control unit for controlling the hydropneumatic pressure source is also housed in the housing case or drum. In addition, the operating portion for operating the controlled variable of the fluid supply amount control unit can be housed in the housing case. An endoscope system having excellent portability of the overall system can therefore be provided.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 26A is a cross-sectional view showing how the endoscope body and drum are housed in a carrying case in the endoscope apparatus according to the eighth embodiment;

FIG. 26B is a schematic view showing the main part of the endoscope system;

FIG. 39A is a longitudinal sectional view of main part of the endoscope apparatus according to the 11th embodiment and shows the closed state of a batch release valve in the drum of the endoscope apparatus;

FIG. 39B is longitudinal sectional view of the main part and shows the open state of the batch release valve;

FIG. 40A is a longitudinal sectional-view of main part of the endoscope apparatus according to the 11th embodiment and shows a gas supply flow path to a hydropneumatic actuator when the batch release valve is closed;

FIG. 40B is a schematic view showing the flow path arrangement of a hydropneumatic actuator in the 11th embodiment;

FIG. 59A is a schematic view showing the arrangement of the driving mechanism of a pneumatic actuator in the endoscope apparatus according to the 17th embodiment;

FIG. 59B is a schematic view showing the arrangement of main part of the driving mechanism of a pneumatic actuator;

FIG. 64 is a perspective view showing the second modification of the bending portion of the endoscope apparatus according to the 19th embodiment;

FIG. 65 is a perspective view showing a coil member in the third modification of the 19th embodiment;

FIG. 66A is a perspective view showing main part of the fourth modification of the 19th embodiment;

FIG. 66B is a longitudinal sectional view of main part of the fourth modification;

FIG. 66C is a perspective view showing main part of the fifth modification of the 19th embodiment;

FIG. 66D is a longitudinal sectional view showing main part of the fifth modification;

FIG. 69 is a perspective view showing the arrangement of main part of a drum in an endoscope apparatus according to the 21st embodiment of the present invention;

FIG. 70A is a perspective view showing a carrying case in the endoscope apparatus according to the 21st embodiment;

FIG. 70B is a perspective view showing a state wherein a monitor is pulled out from the carrying case;

FIG. 81C is a cross-sectional view of a pneumatic actuator;

FIG. 82A is a cross-sectional view of the first pneumatic actuator in a modification of the 23rd embodiment;

FIG. 82B is a cross-sectional view showing the second pneumatic actuator;

FIG. 82C is a cross-sectional view showing the third pneumatic actuator;

FIG. 83A is a perspective view showing the distal end portion of the insertion portion of an endoscope according to the 24th embodiment of the present invention;

FIG. 83B is a perspective view of a protective member for a pneumatic actuator;

FIG. 84 is a view for explaining the function of a solenoid valve in the controller of the endoscope according to the 22nd embodiment;

FIG. 85 is a schematic view showing the arrangement of the overall system of an endoscope system according to the 25th embodiment of the present invention;

FIG. 86 is a schematic view showing the arrangement of the controller of the endoscope according to the 25th embodiment;

FIG. 87A is a view for explaining the operation of a solenoid valve when the tilt amount of a joystick increases in the endoscope according to the 25th embodiment;

FIG. 87B is a view for explaining the operation of the solenoid valve when the tilt amount of the joystick decreases in the endoscope according to the 25th embodiment;

FIG. 88 is a block diagram showing the controller of the endoscope according to the 25th embodiment;

Figures 89A, 89B:
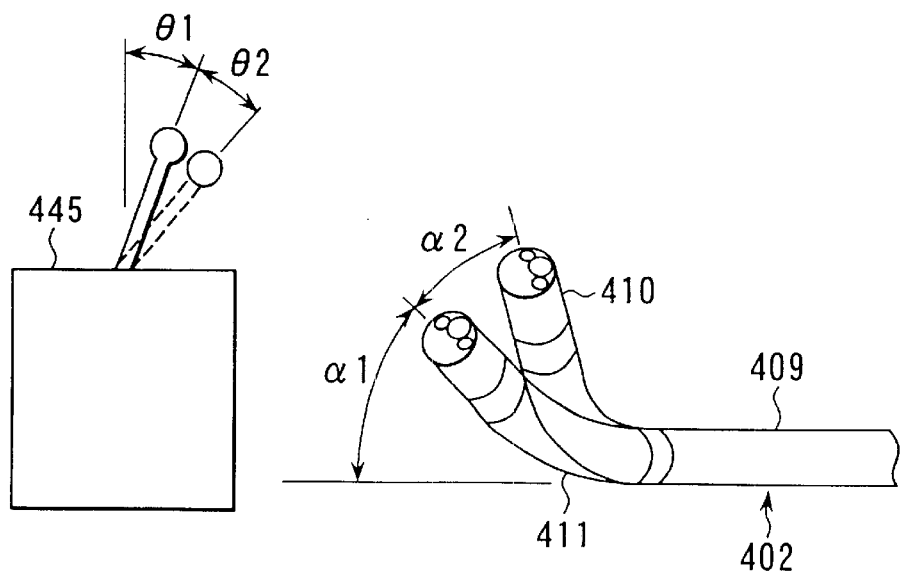
Figure 90A:
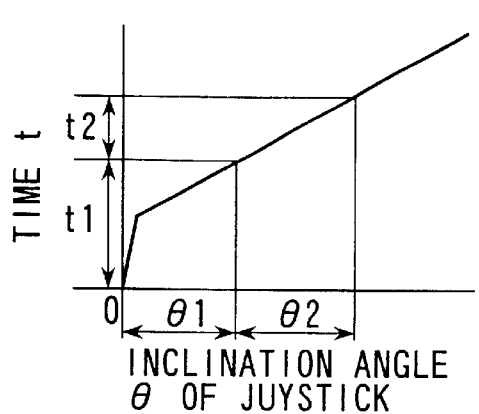
Figure 90B:
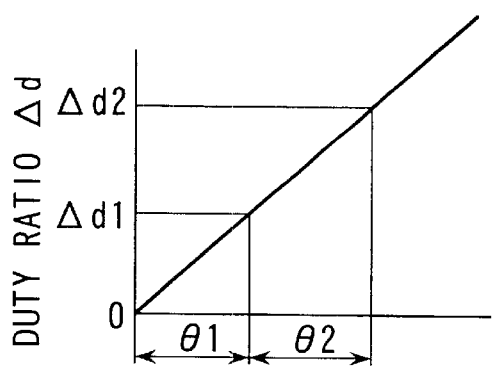
Figures 91A, 91B:
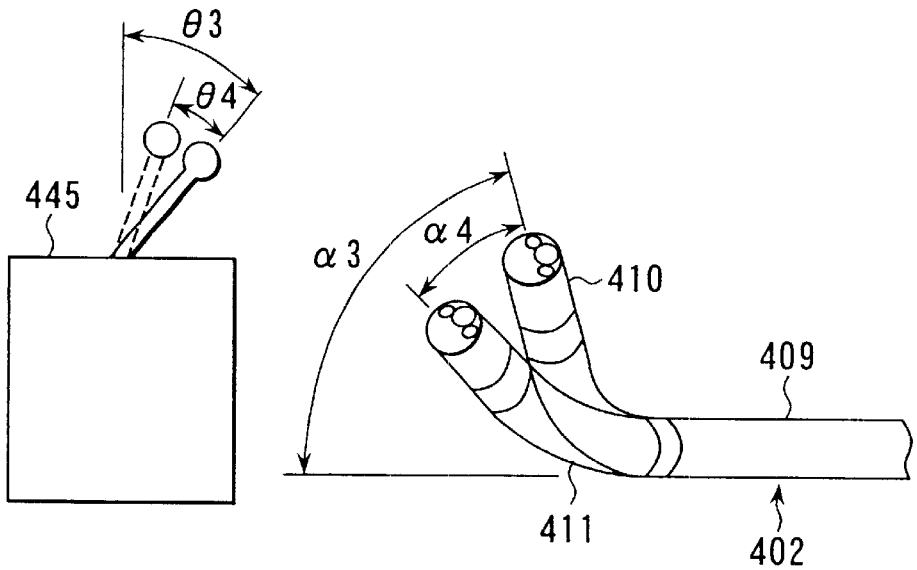
Figure 92:
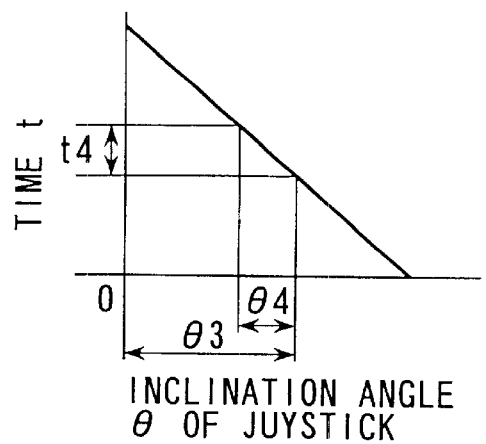
Figure 93:
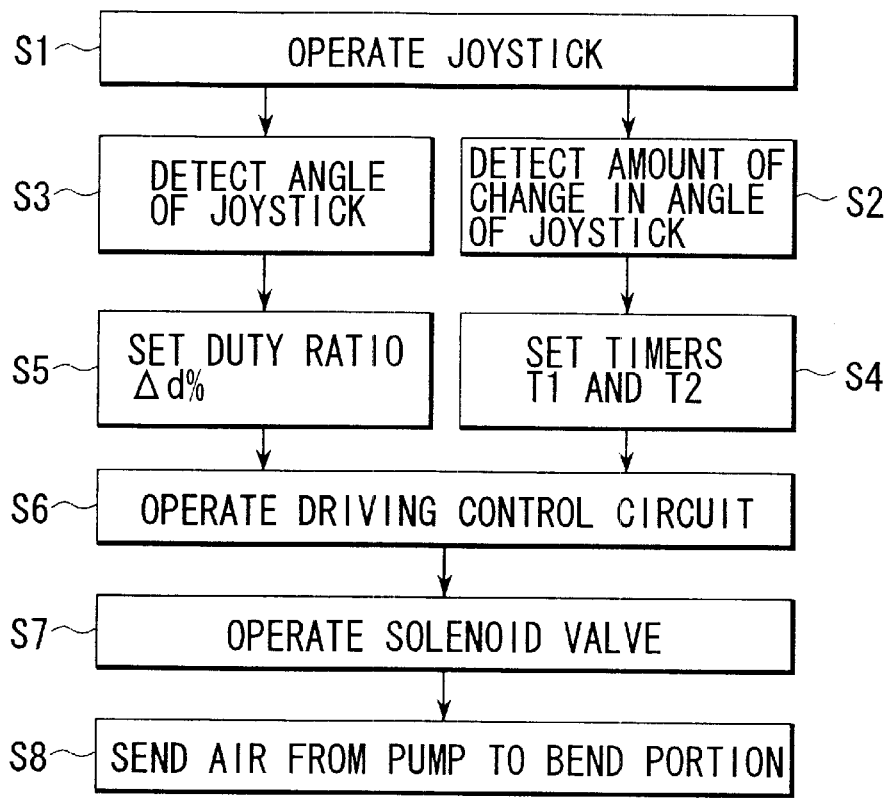
Figure 94:
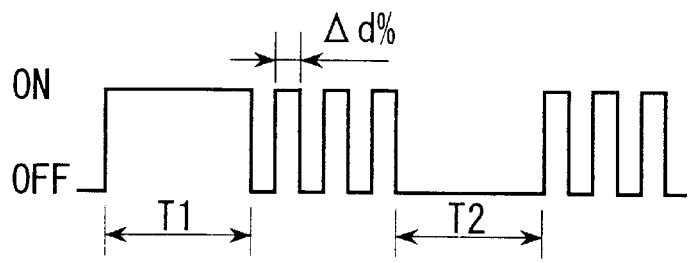
Figure 95:
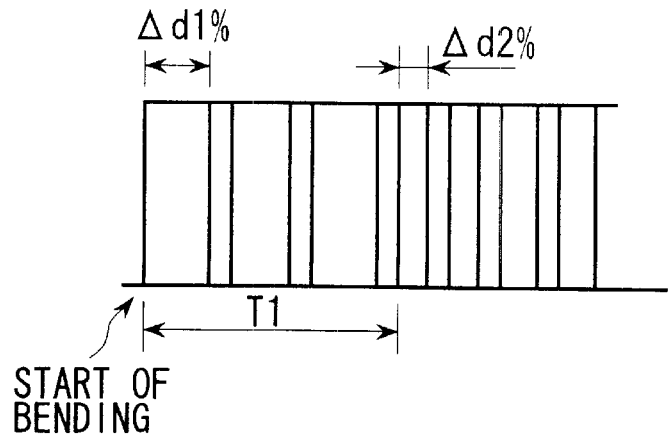
Figure 96:
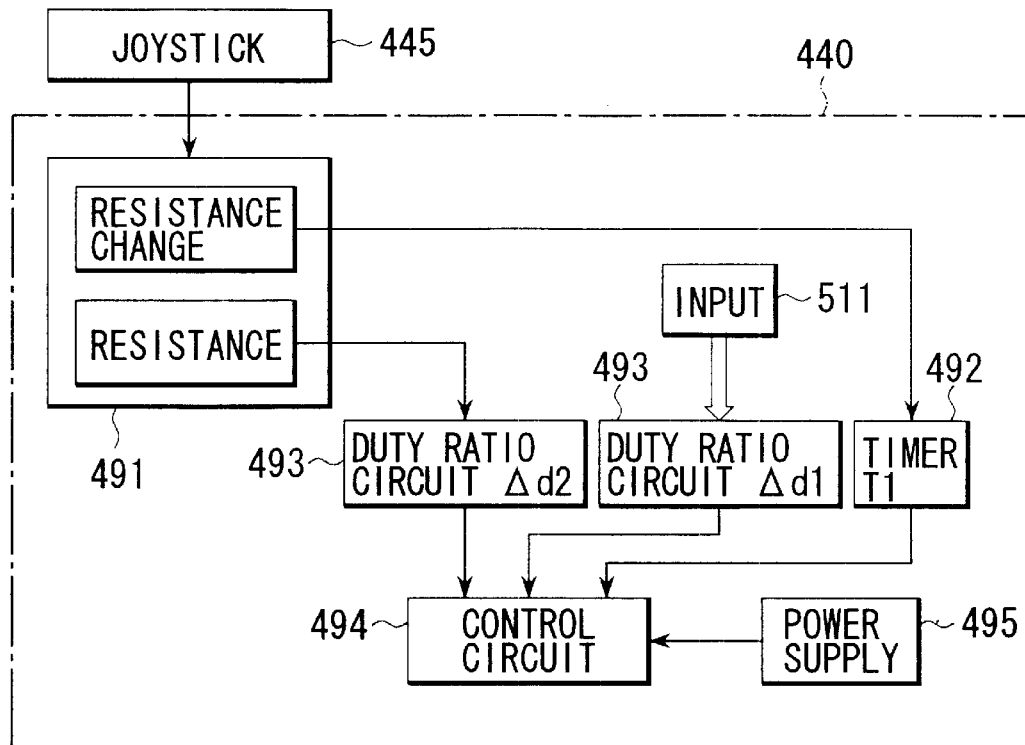
Figure 97:
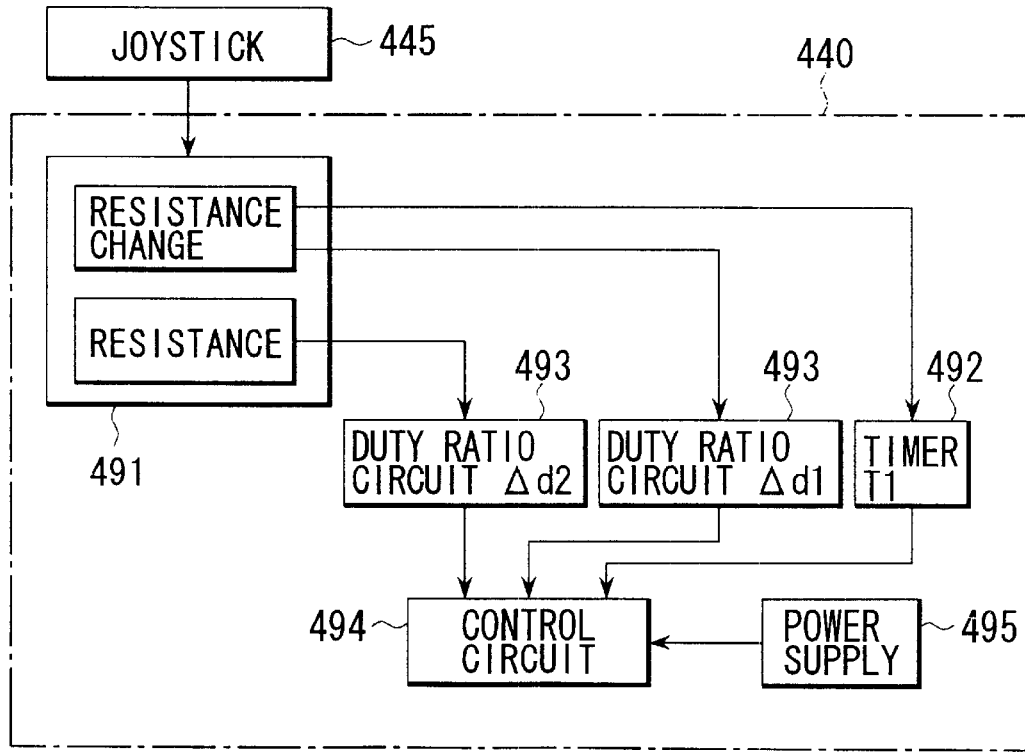
Figure 98:
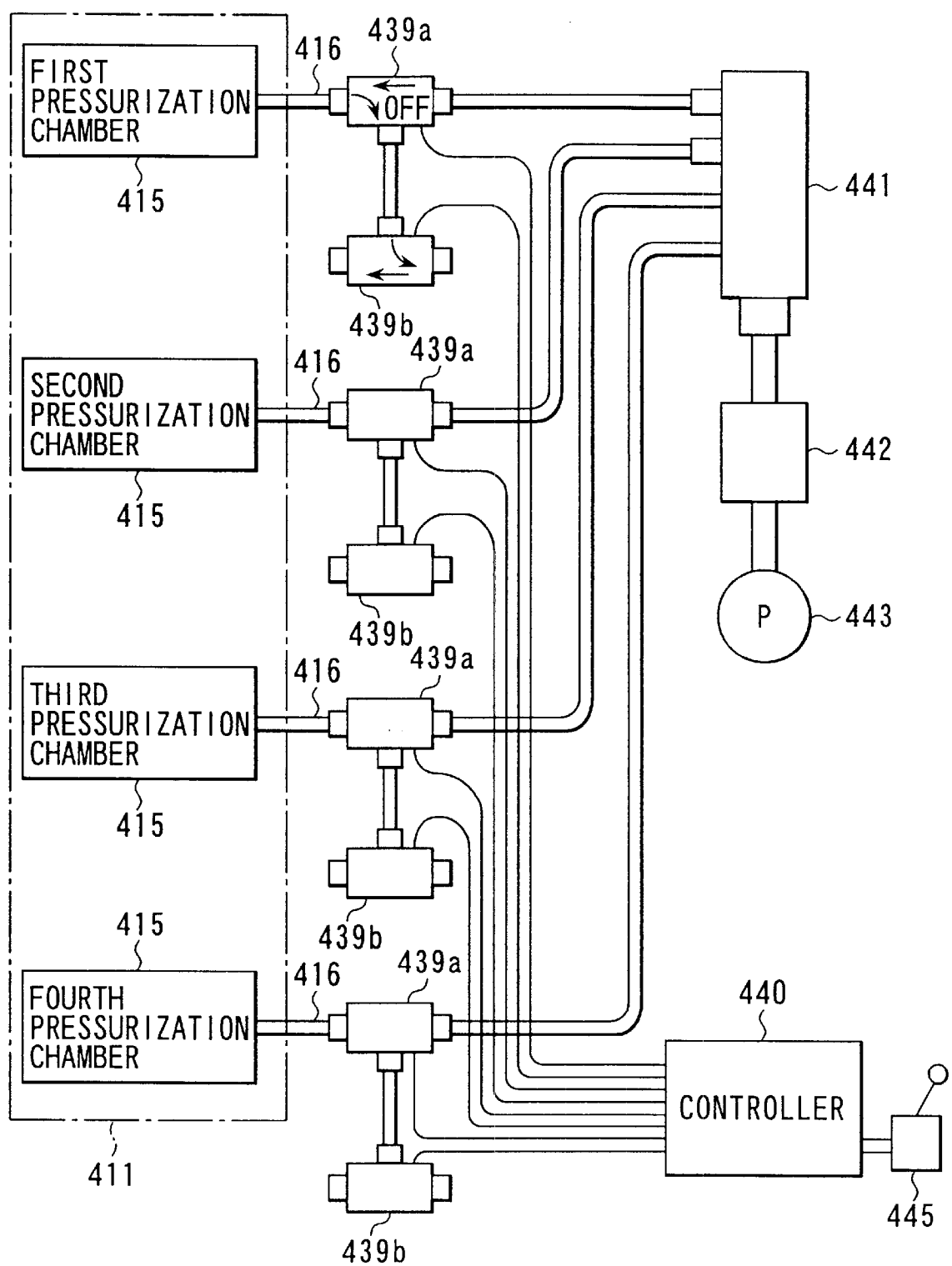
Figure 99:
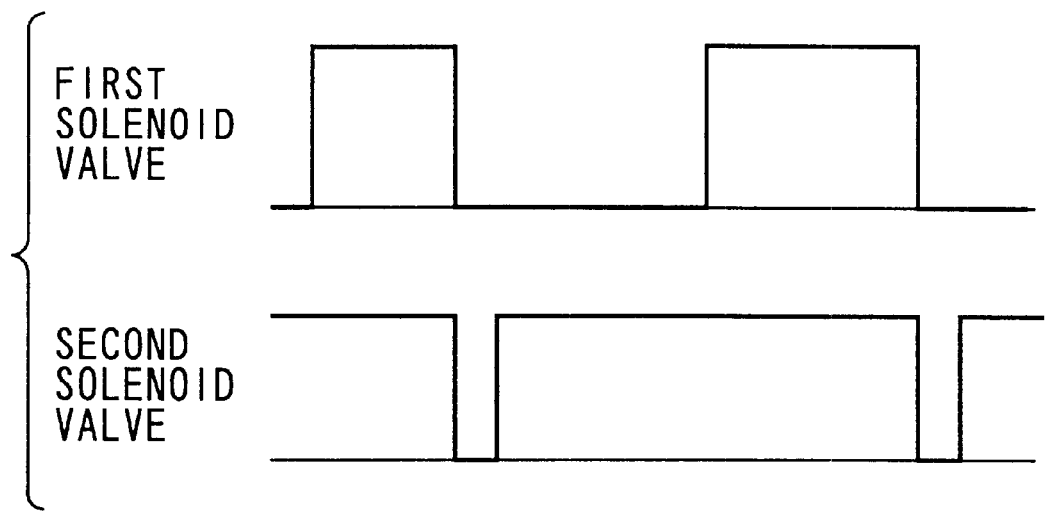
Figure 100:
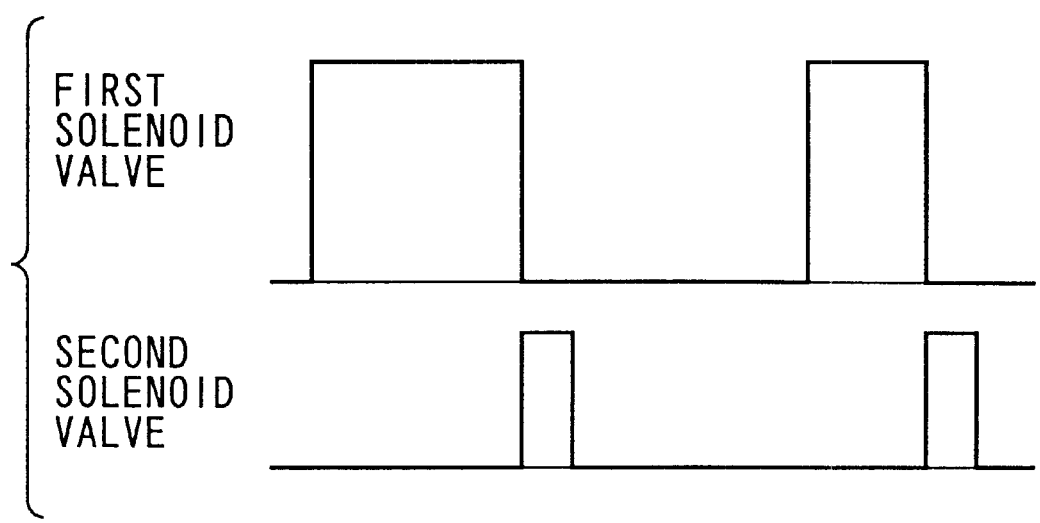
Figure 101A:
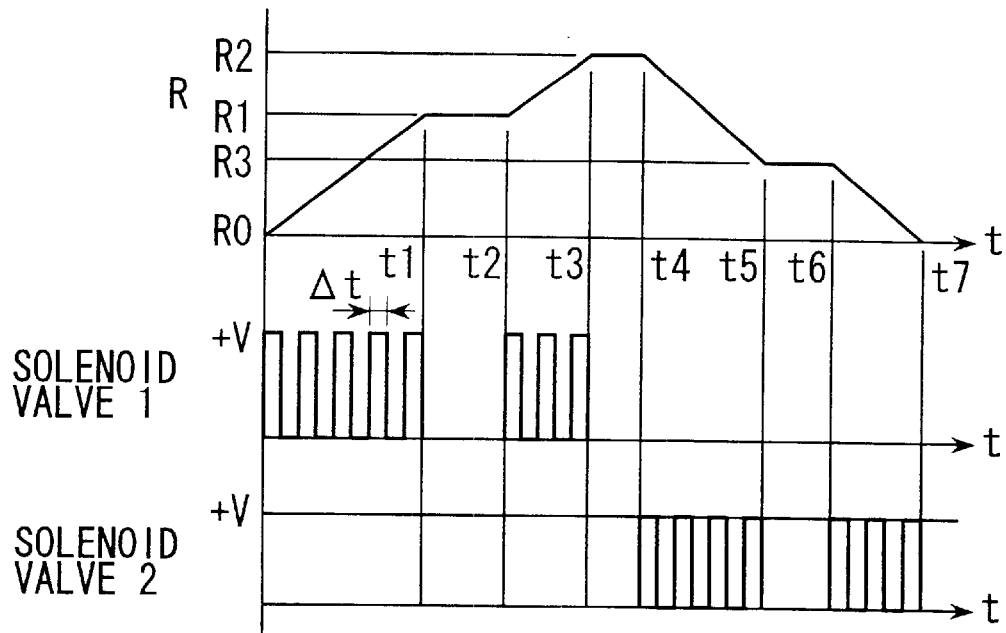
Figure 101B:
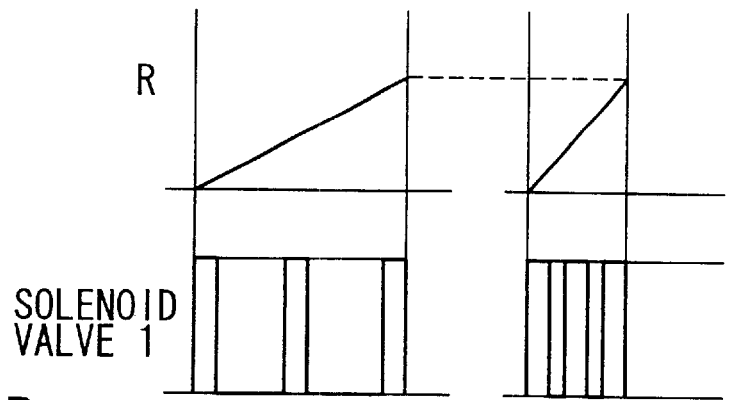
Figure 101C:
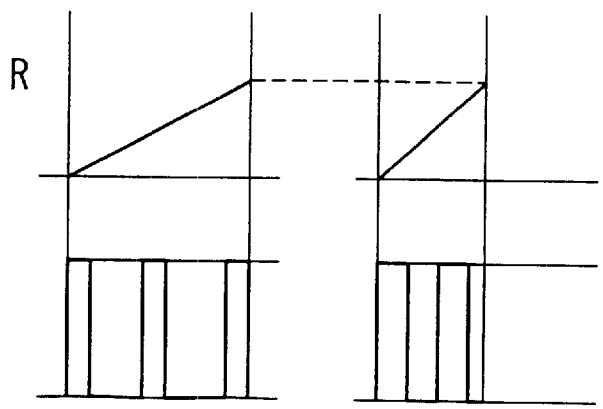
Figure 102:
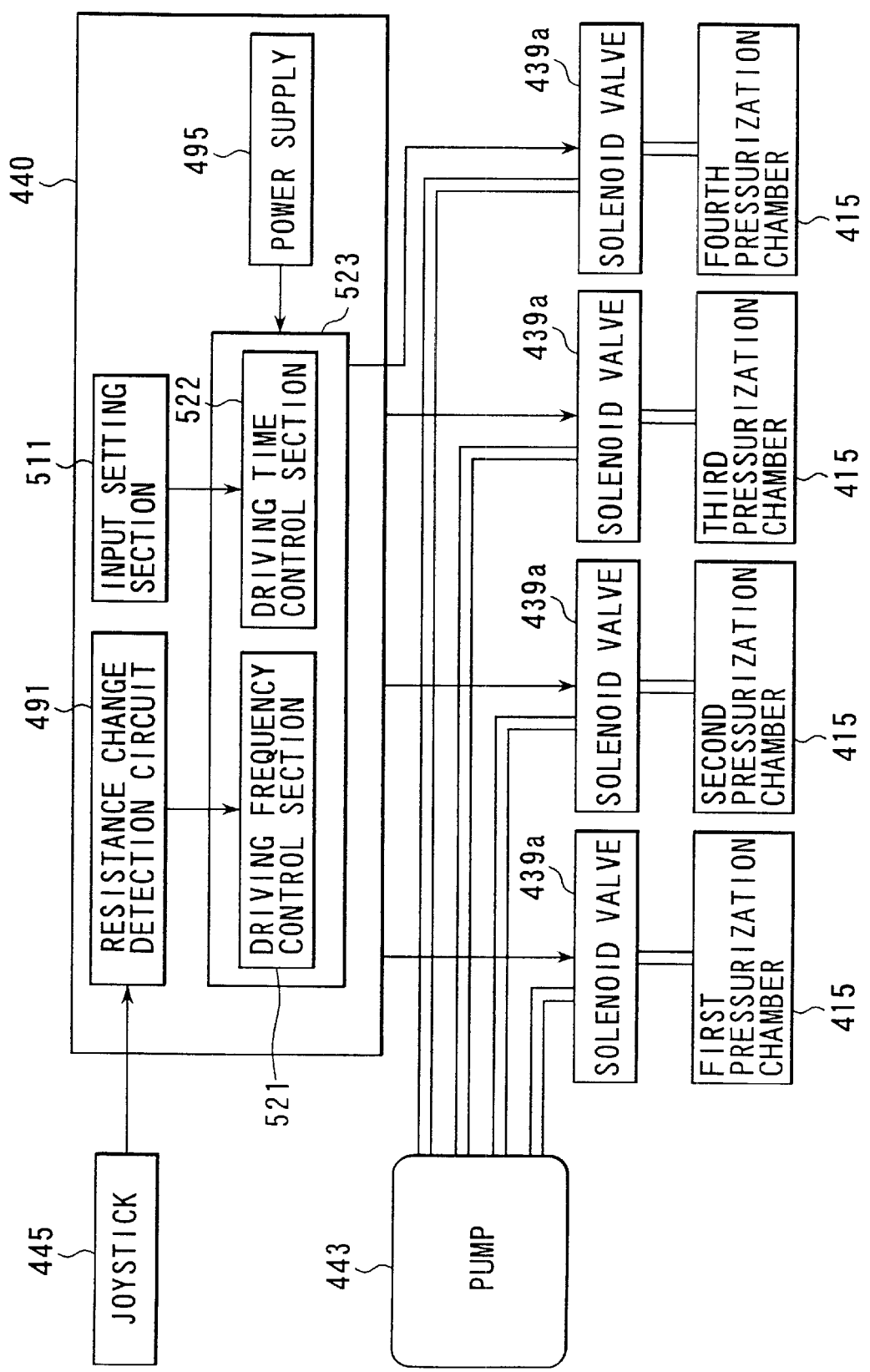
Figure 103:
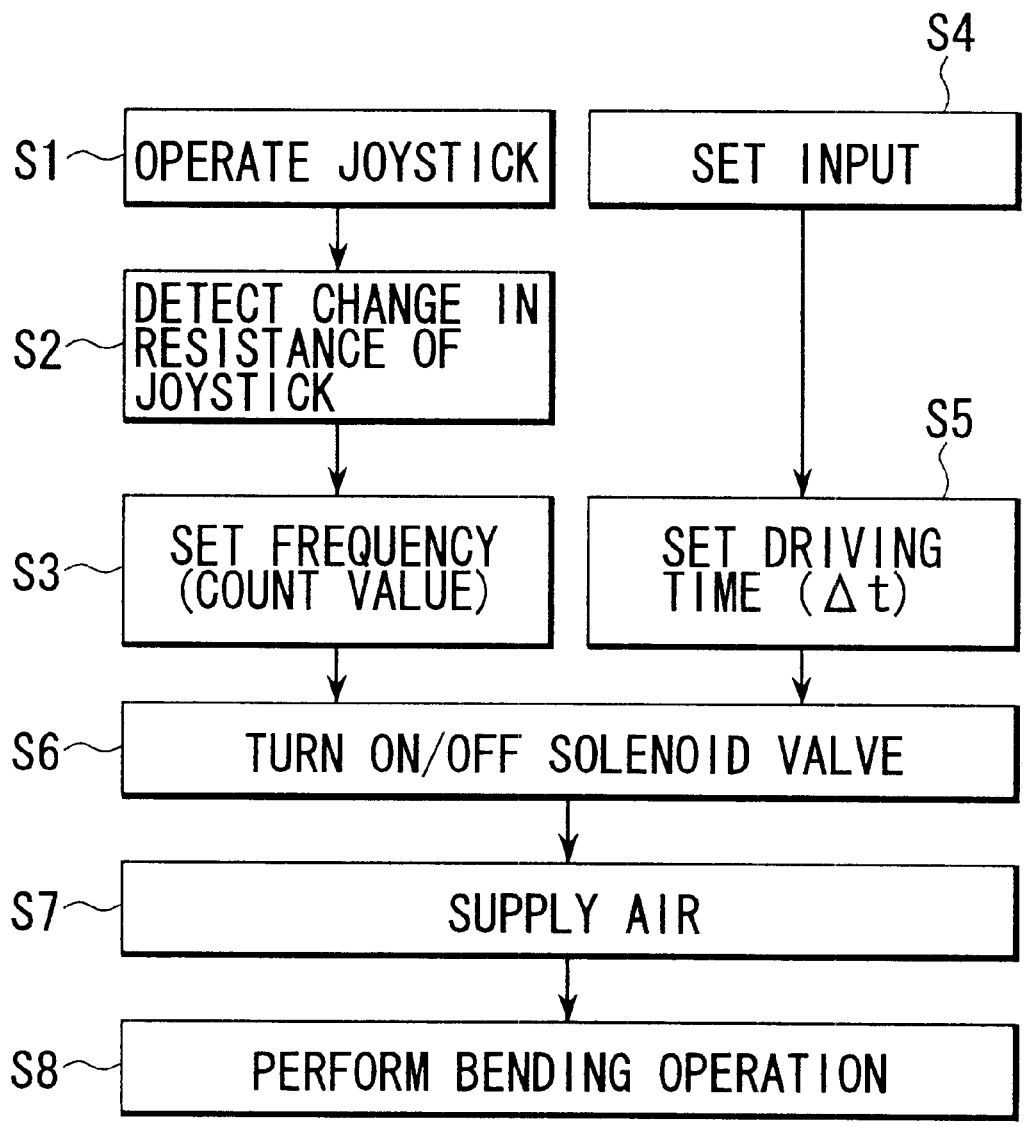
Figure 104:
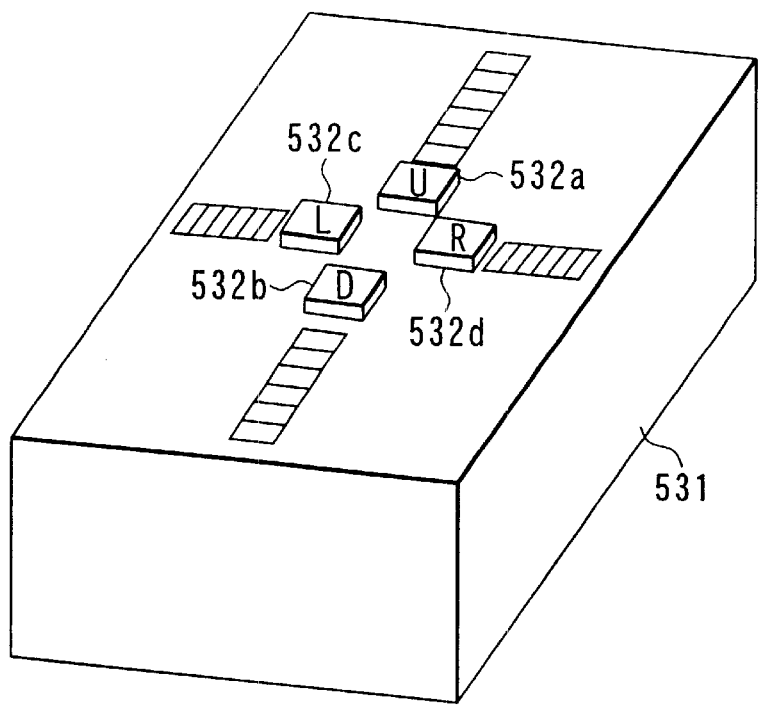
Figure 105:
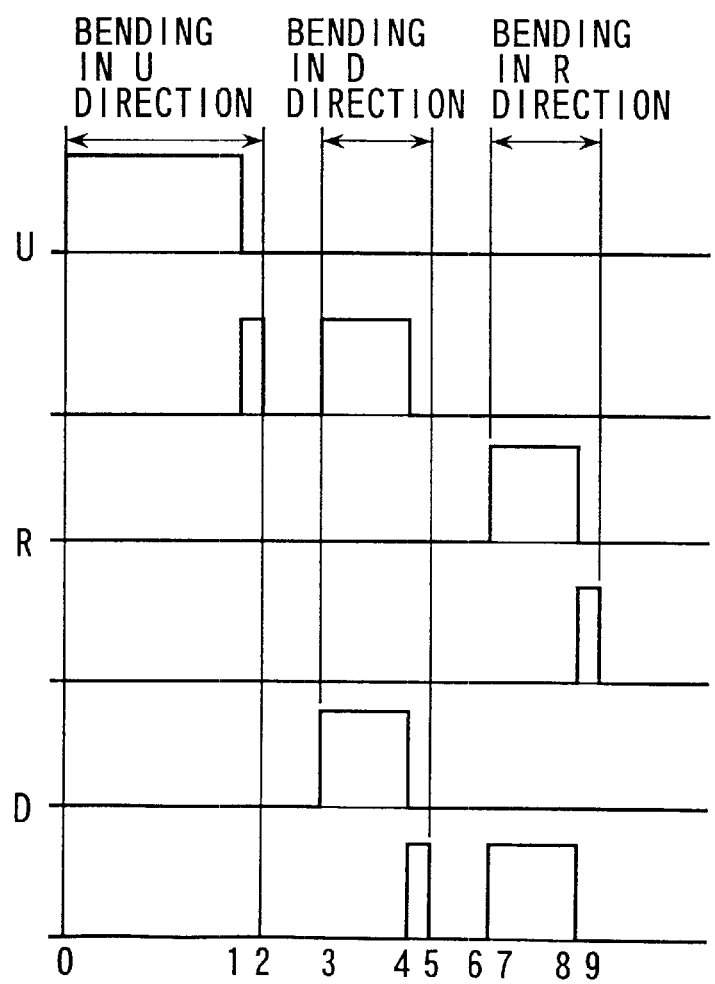
Figure 106:
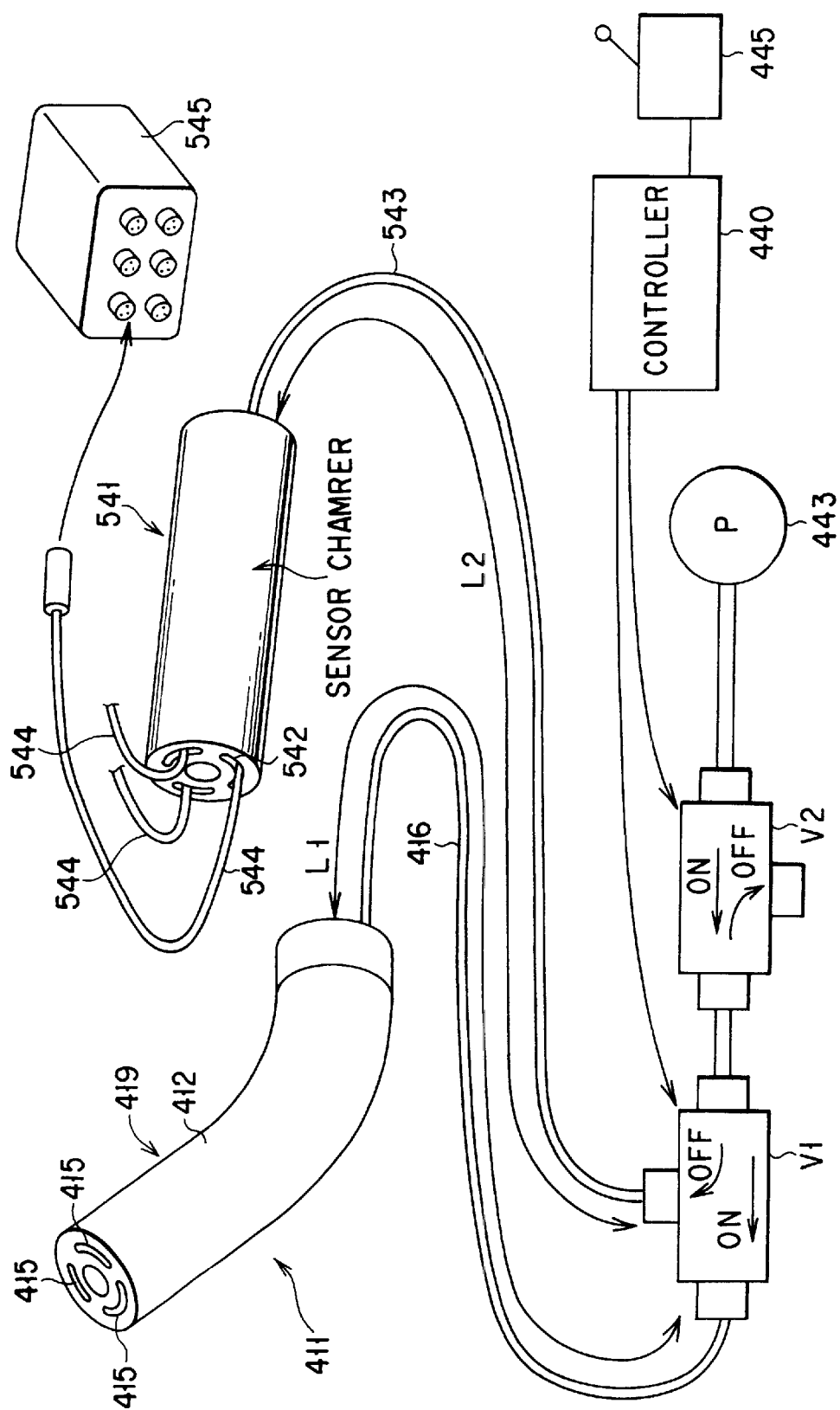
Figure 107A:
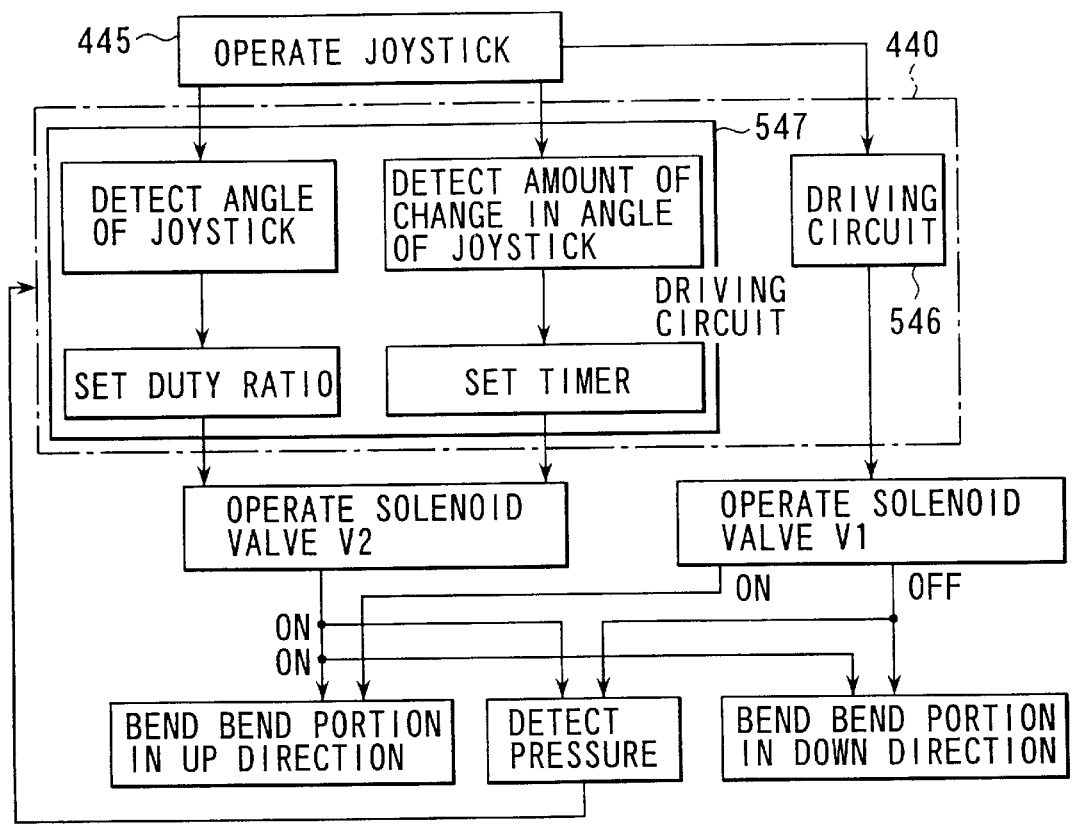
Figure 107B:
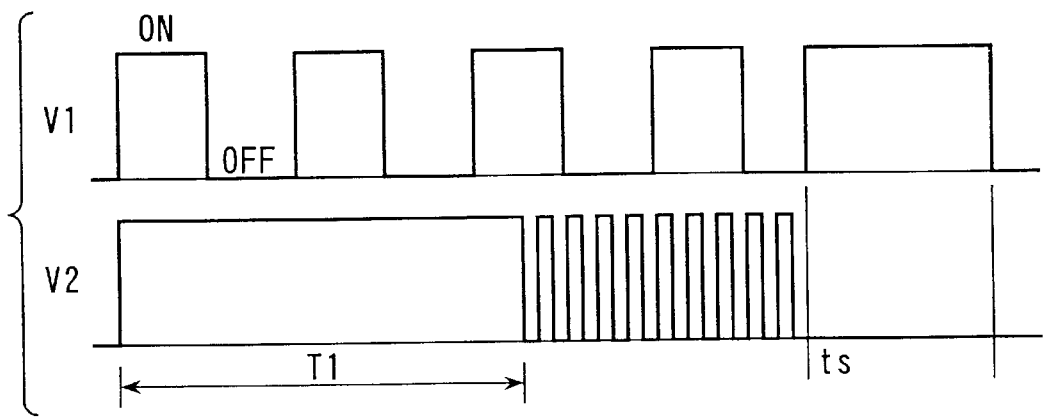

FIG. 89A is a view for explaining the operation of the joystick when the bend amount of the bending portion increases in the endoscope according to the 25th embodiment;

FIG. 89B is a view for explaining the bending operation of the bending portion when the bend amount increases;

FIG. 90A is a graph showing the operation state of the joystick when the bend amount increases in the endoscope according to the 25th embodiment;

FIG. 90B is a graph for explaining a change in physical property value in accordance with the operation of the joystick in FIG. 90A;

FIG. 91A is a view for explaining the operation of the joystick when the bend amount of the bending portion decreases in the endoscope according to the 25th embodiment;

FIG. 91B is a view for explaining the bending operation of the bending portion when the bend amount decreases;

FIG. 92 is a graph for explaining a change in physical property value in accordance with the operation of the joystick when the bend amount decreases in the endoscope according to the 25th embodiment;

FIG. 93 is a flow chart for explaining the operation of the bending portion which is based on the operation of the joystick in the endoscope according to the 25th embodiment;

FIG. 94 is a flow chart for explaining the ON/OFF operation of a solenoid valve in the flow chart of FIG. 93;

FIG. 95 is a graph showing a state wherein a portion T1 in FIG. 87 is replaced with pulses;

FIG. 96 is a block diagram showing the first modification of the controller of the endoscope according to the 25th embodiment;

FIG. 97 is a block diagram showing the second modification of the controller of the endoscope according to the 25th embodiment;

FIG. 98 is a schematic view showing how air tube paths are connected in an endoscope according to the 26th embodiment of the present invention;

FIG. 99 is a view for explaining the operations of solenoid valves in the endoscope according to the 26th embodiment;

FIG. 100 is a view for explaining the operations of solenoid valves in the endoscope according to the 22nd embodiment;

FIG. 101A is a graph for explaining the operations of solenoid valves in accordance with the operation of a joystick in the endoscope according to the 26th embodiment;

FIG. 101B is a graph for explaining the operation of changing the frequency for opening/closing a solenoid valve in accordance with the speed of the joystick;

FIG. 101C is a graph for explaining the operation of changing the duty ratio for opening/closing a solenoid valve in accordance with the speed of the joystick;

FIG. 102 is a block diagram showing a controller in the endoscope according to the 26th embodiment;

FIG. 103 is a flow chart for explaining the operation of the controller in the endoscope according to the 26th embodiment;

FIG. 104 is a perspective view showing an input unit in an endoscope according to the 27th embodiment of the present invention;

FIG. 105 is a view for explaining the operations of solenoid valves with respect to the input unit in the 27th embodiment;

FIG. 106 is a schematic view showing the arrangement of the overall endoscope system having a pressure sensor in an endoscope according to the 28th embodiment of the present invention;

FIG. 107A is a block diagram showing a controller in the endoscope according to the 28th embodiment; and FIG. 107B is a view for explaining the operation of each solenoid valve in the endoscope according to the 28th embodiment.

DETAILED DESCRIPTION OF THE INVENTION

Figure 1:
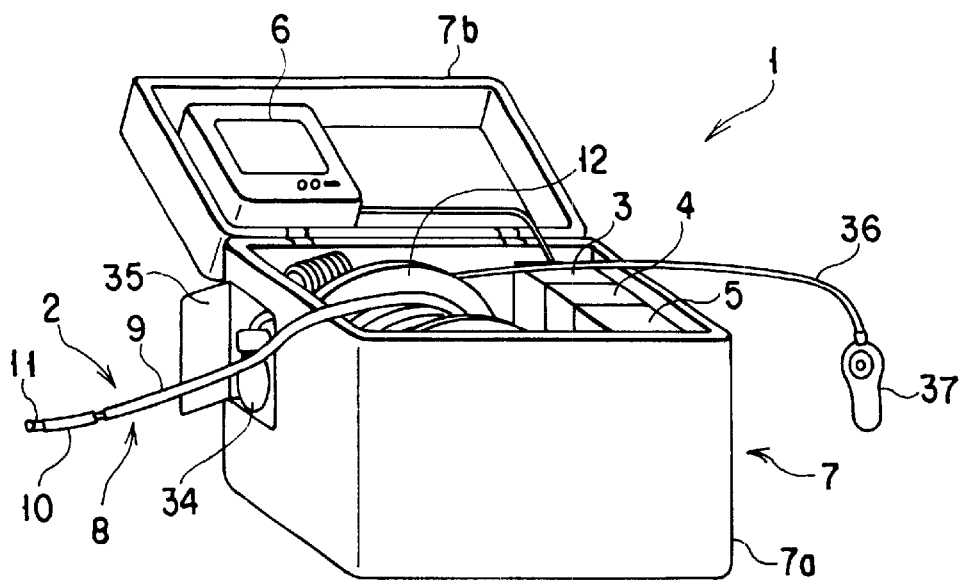
FIG. 1 is a perspective view showing the overall system of an endoscope apparatus according to the first embodiment of the present invention.

The first embodiment of the present invention will be described below with reference to FIGS. 1 to 12. FIG. 1 shows the schematic arrangement of an overall endoscope apparatus 1 as an endoscope system according to this embodiment. The endoscope apparatus 1 includes a plurality of constituent elements such as an endoscope body 2, CCU (Camera Control Unit) 3, light source unit 4, power supply 5, and monitor 6. These constituent elements of the endoscope apparatus 1 are housed in one carrying case (housing case) 7. The carrying case 7 includes a case body 7a having an opening in its upper surface, and a cover 7b that retractably covers the upper surface opening portion of the case body 7a.

Figure 2:
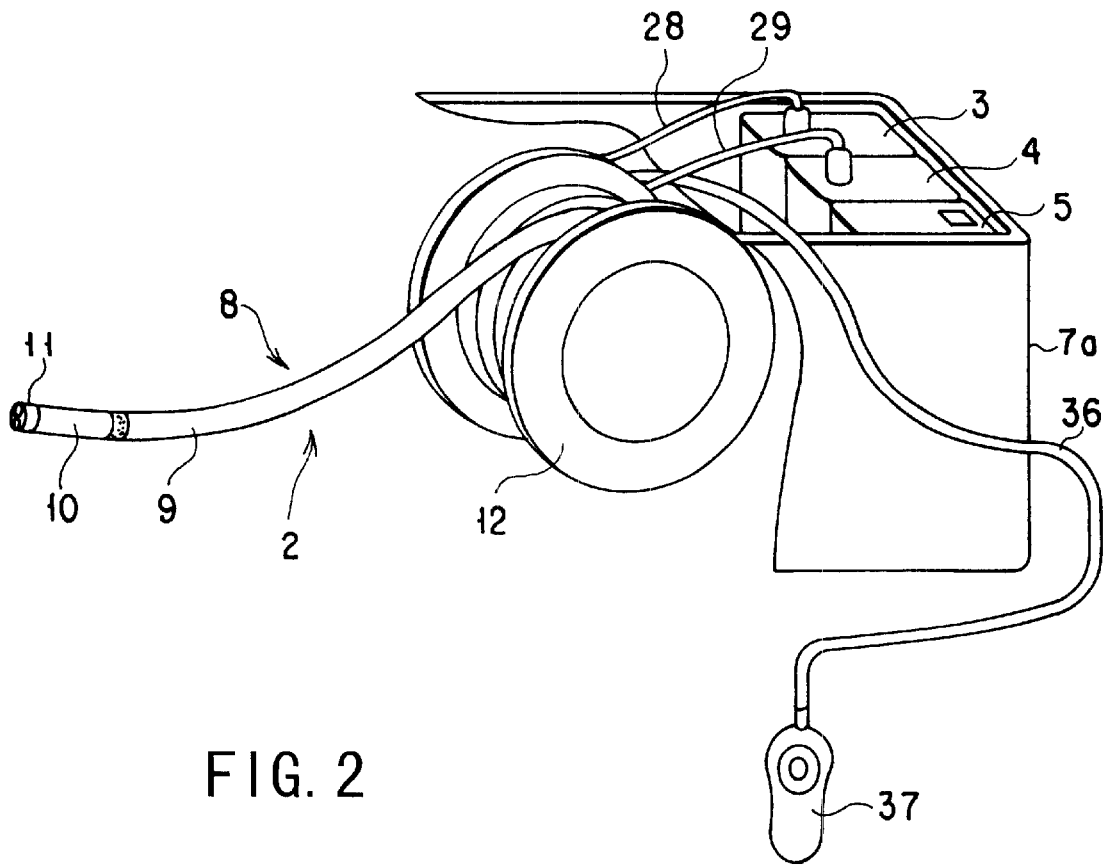
FIG. 2 is a perspective view showing the schematic arrangement of main part of the system of the endoscope apparatus according to the first embodiment.
Figure 3:
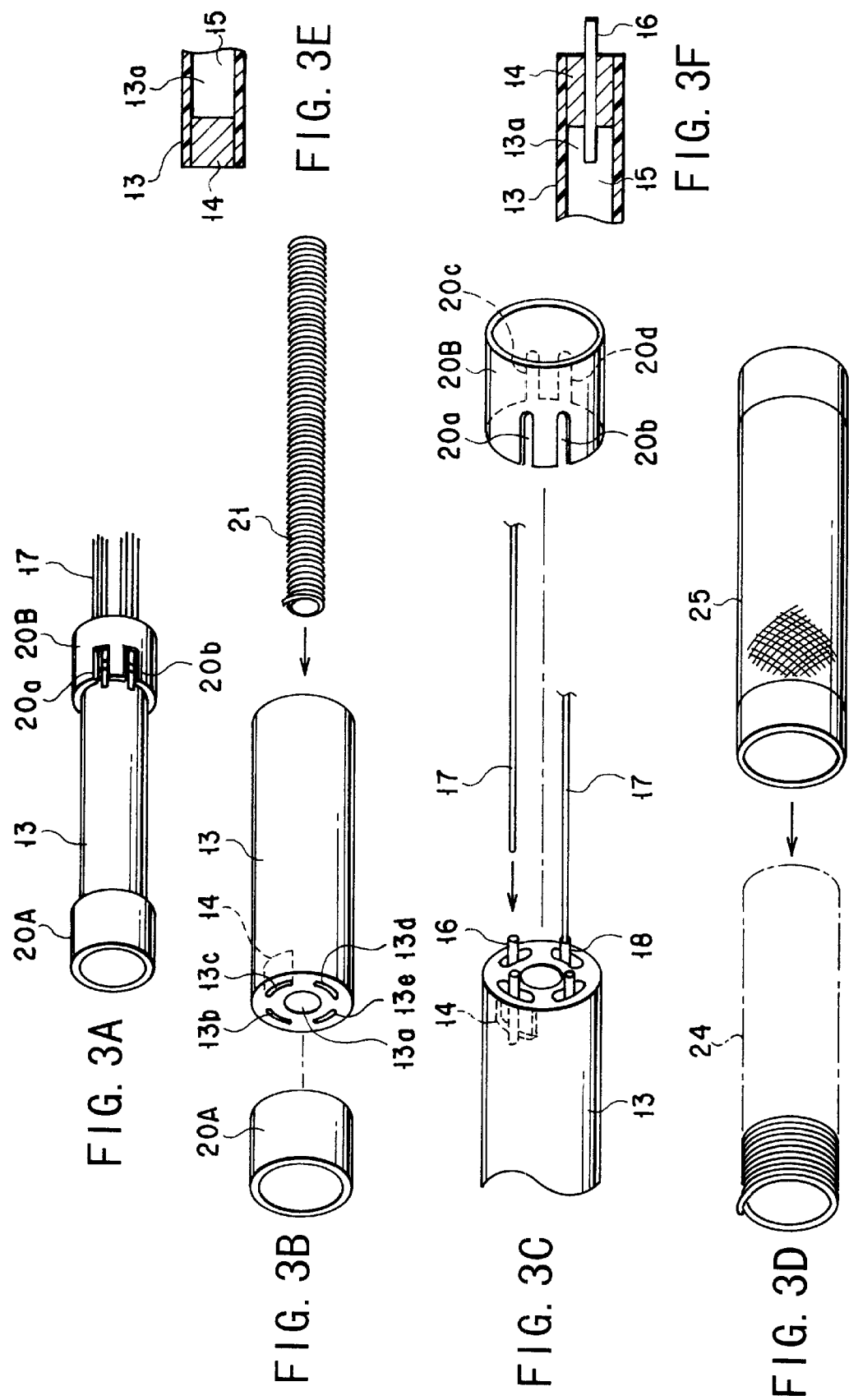
FIG. 3A is a perspective view showing a state wherein front and rear bases are connected to the multi-lumen tube of the bending portion of the endoscope apparatus according to the first embodiment.
FIG. 3B is an exploded perspective view showing the multi-lumen tube, inner contact coil, and front base.
FIG. 3C is a perspective view showing the multi-lumen tube, fluid supply tubes, and rear base.
FIG. 3D is an exploded perspective view showing an outer contact coil and protective member.
FIG. 3E is a longitudinal sectional view showing the main part of a filler sealing portion on the front end side of an arcuated lumen.
FIG. 3F is a longitudinal sectional view showing the main part of the filler sealing portion on the rear end side of the arcuated lumen.

As shown in FIG. 2, the endoscope body 2 has a long insertion portion 8 to be inserted into a tubular cavity. This insertion portion 8 has a long flexible tube portion 9 having flexibility, a bending portion 10 coupled to the distal end portion of the flexible tube portion 9, a distal end constituent portion 11 placed at the very end of the bending portion 10. A cylindrical drum 12 around which the insertion portion 8 of the endoscope body 2 can be wound is housed in the carrying case 7. In this case, the insertion portion 8 of the endoscope body 2 is housed in the carrying case 7 while being wound around the drum 12. The insertion portion 8 of the endoscope body 2 is pulled out from the drum 12 and carrying case 7 to be used, as needed.

The bending portion 10 of the endoscope body 2 in this embodiment has the following arrangement. As shown in FIG. 3B, the main body of the bending portion 10 is formed from a multi-lumen tube 13 made of, e.g., flexible silicone and having a circular cross-section. The multi-lumen tube 13 has a central lumen 13a that is formed in the center of a circular cross-section and extends along the tube axis. A built-in member such as a cable (to be described later) is inserted into the central lumen 13a.

A plurality of (four in this embodiment) lumens 13b, 13c, 13d, and 13e, each having an arcuated cross-section, are formed in the tube wall around the central lumen 13a at equal intervals in the circumferential direction. The two end portions, i.e., the front and rear end portions, of each of the four lumens 13b, 13c, 13d, and 13e, each having an arcuated cross-section, are sealed with a filler 14, e.g., silicone, as shown in FIGS. 3E and 3F. Sealed pressurization chambers 15 are respectively formed in the four lumens 13b, 13c, 13d, and 13e each having an arcuated cross-section.

A connection tube 16 made of silicone extends through the filler 14 in each of the four lumens 13b, 13c, 13d, and 13e on the operator side, as shown in FIG. 3F. The inside end portions of the connection tubes 16 respectively communicate with the pressurization chambers 15 in the four arcuated lumens 13b, 13c, 13d, and 13e.

The distal end portions of fluid supply tubes 17 that are made of Teflon and used to supply/exhaust air into/from the respective pressurization chambers 15 are respectively coupled to the outside end portions of the connection tubes 16. In this case, each fluid supply tube 17 is connected by the following method. As shown in FIG. 3C, the distal end portion of the fluid supply tube 17 is inserted into the connection tube 16. The distal end portion is then tied to the connection tube 16 with a string 18 that is externally wound.

This method is used for the following reason. The multi-lumen tube 13 is made of silicone. The fluid supply tube 17 is made of Teflon. These two materials exhibit poor bond properties. Even if they can be bonded to each other, the bond strength is low. If both the multi-lumen tube 13 and the connection tube 16 are made of silicone, high bond strength can be ensured by using a silicone adhesive. The silicon connection tube 16 and Teflon fluid supply tube 17 can be easily bound together with the string 18, which is wound externally, to prevent air from leaking.

With this arrangement, a hydropneumatic actuator 19 is obtained, which is designed to bend the bending portion 10 by selectively supplying air to the pressurization chambers 15 of the four arcuated lumens 13b, 13c, 13d, and 13e of the multi-lumen tube 13. In this embodiment, the pressurization chambers 15 in the four arcuated lumens 13b, 13c, 13d, and 13e are set to correspond to four bending directions, i.e., the left and right directions and the upward and downward directions.

Front and rear mouth pieces 20A and 20B are respectively connected to the distal and proximal end portions of the multi-lumen tube 13 with an adhesive or the like. In this case, four slits 20a to 20d are formed in the distal end portion of the rear mouth piece 20B at positions respectively corresponding to the connection tubes 16 of the four arcuated lumens 13b, 13c, 13d, and 13e.

Note that the connection tubes 16 of the four arcuated lumens 13b, 13c, 13d, and 13e respectively have engaging projections to engage with the slits 20a to 20d of the rear mouth piece 20B. The engaging projections of the connection tubes 16 respectively engage with the slits 20a to 20d of the rear mouth piece 20B.

An inner contact coil 21 made of stainless steel is inserted in the central lumen 13a of the multi-lumen tube 13. When air is supplied into the pressurization chambers 15 of the four arcuated lumens 13b, 13c, 13d, and 13e, the inner contact coil 21 prevents the multi-lumen tube 13 from expanding inwardly.

Without the inner contact coil 21, the multi-lumen tube 13 expands inwardly when air is supplied into the pressurization chambers 15 of the four arcuated lumens 13b, 13c, 13d, and 13e. In this state, the inwardly expanded portion of the multi-lumen tube 13 comes into contact with the built-in member in the central lumen 13a of the multi-lumen tube 13, and deforms in accordance with the shape of the built-in member. As a consequence, the pressurization chambers 15 of the four arcuated lumens 13b, 13c, 13d, and 13e expand unevenly, possibly resulting in a decrease in durability.

The strand of the inner contact coil 21 may have a circular, elliptic, or rectangular cross-section. The cross-sectional shape of the strand of the inner contact coil 21 exhibits great influence when the actuator of the bending portion 10 is thin. For example, if the actuator of the bending portion 10 is thin, a good effect can be produced when the strand has a rectangular cross-section. The inner contact coil 21 having a strand with a rectangular cross-section is sturdier than a coil having the same thickness (the difference between the outer and inner diameters of the coil) and a different cross-sectional shape. The rectangular cross-section makes it difficult for the coil to deform as the multi-lumen tube 13 expands. In an assembly process, therefore, the contact coil 21 can be easily inserted into the central lumen 13a in the multi-lumen tube 13 because of the sturdiness of the contact coil 21 having a strand with a rectangular cross-section.

Figure 4:
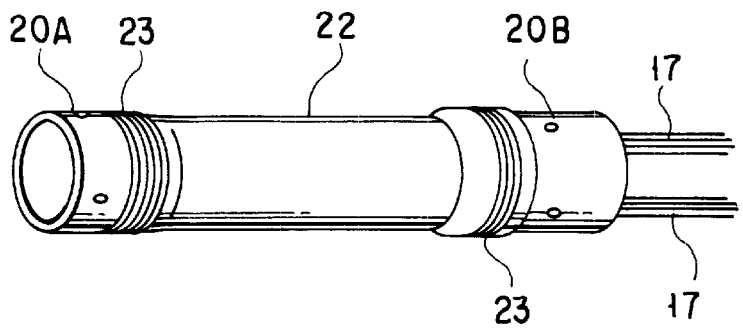
FIG. 4 is a perspective view showing how the front and rear bases are fixed to the multi-lumen tube of the bending portion of the endoscope apparatus according to the first embodiment.

As shown in FIG. 4, an outer tube 22 is fitted on the outer surface of the multi-lumen tube 13. The outer tube 22 is made of a material having high resistance to oil such as gasoline or light oil. For example, fluororubber, nitrile rubber, or polyvinyl is used as such a material. The two end portions of the outer tube 22 are bound to the multi-lumen tube 13 with strings 23 at the positions of the front and rear mouth pieces 20A and 20B of the multi-lumen tube 13, and the strings 23 are fixed with an adhesive externally.

The reason why the outer tube 22 is made of a material having high resistance to oil is that the scope of application of the endoscope system of this embodiment can then be extended to the industrial field as well as the medical field. In industrial applications, this system can be used in the inspections of various pipes. Assume that the multi-lumen tube 13 is made of silicone. In this case, when the multi-lumen tube 13 comes into contact with gasoline or light oil, the bending performance of the tube may be affected. Covering the outer tube 22 with an oil-resistant material can solve this problem.

If the multi-lumen tube 13 is made of nitrile rubber, fluororubber, acrylic rubber, or the like which has high oil resistance, the outer tube 22 can be omitted.

An outer contact coil 24 is fitted on the outer tube 22, as shown in FIG. 3D. The two ends of the outer contact coil 24 are supported and fixed with an adhesive or the like. The strand of the outer contact coil 24 may have, for example, a circular, elliptic, or rectangular cross-section, like the inner contact coil 21. The outer contact coil 24 is covered with a protective member 25 that is woven into a cylindrical shape with stainless wire or the like.

Figure 5:
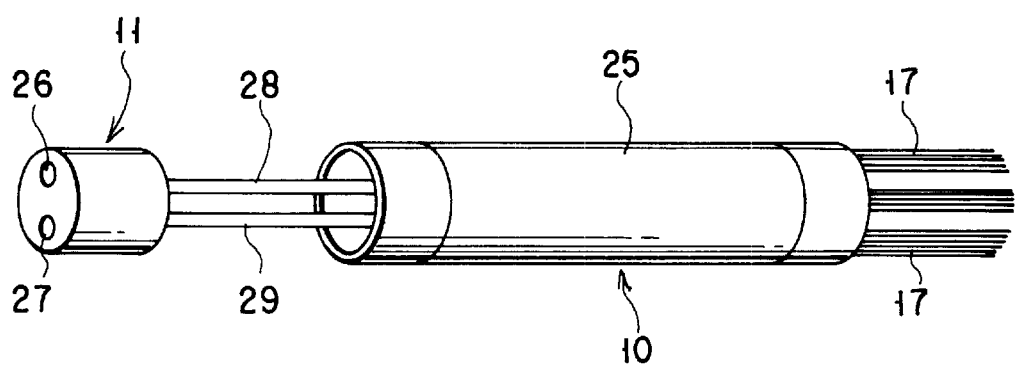
FIG. 5 is a perspective view showing the bending portion and distal end constituent portion of the endoscope body according to the first embodiment before they are assembled.
Figure 6:
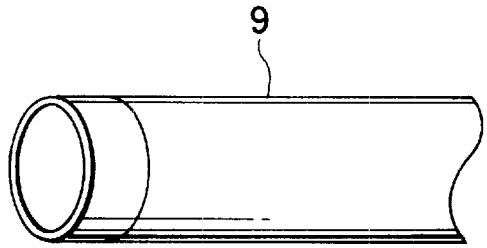
FIG. 6 is a perspective view showing the distal end portion of the flexible tube portion of the endoscope body according to the first embodiment.

As shown in FIG. 5, the distal end constituent portion 11 at the distal end of the bending portion 10 has an observation optical system 26 with a visual function formed by a CCD (image sensing means) and an illumination optical system 27 with an illumination function. In this case, the illumination function of the illumination optical system 27 is formed by a light guide cable 29. A signal line 28 of the CCD of the observation optical system 26 and the light guide cable 29 of the illumination optical system 27 are inserted into the flexible tube portion 9, together with the fluid supply tube 17, through the central lumen 13a of the multi-lumen tube 13 of the bending portion 10.

Figure 7:
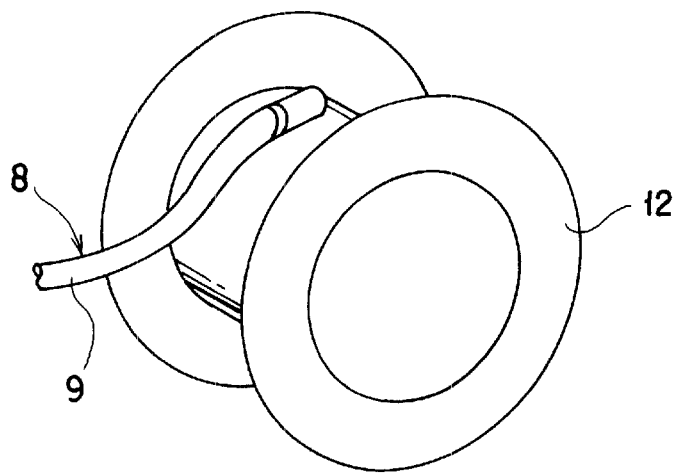
FIG. 7 is a perspective view showing the drum of the endoscope apparatus according to the first embodiment.
Figure 8:
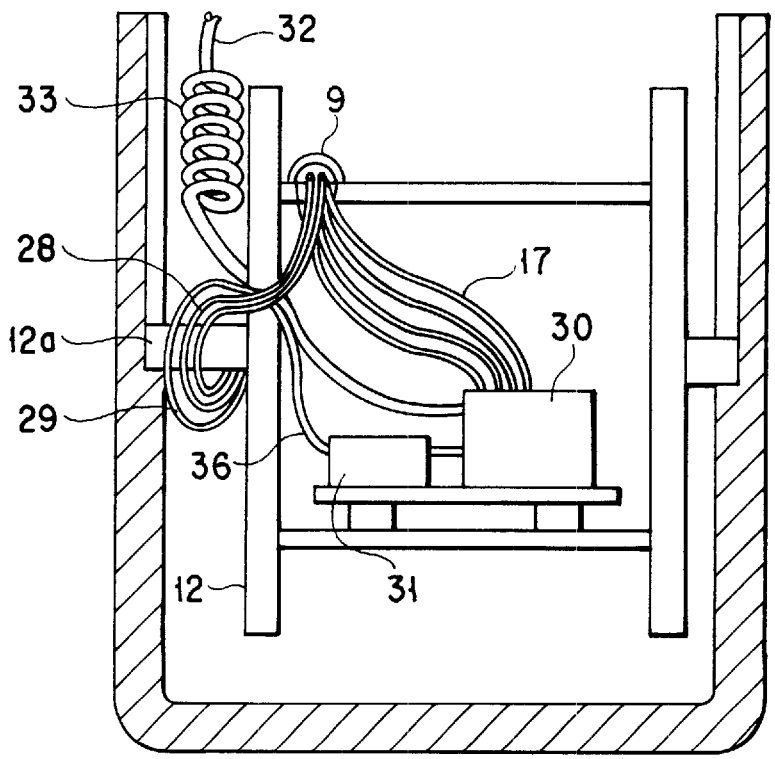
FIG. 8 is a longitudinal sectional view showing the internal arrangement of the carrying case of the endoscope apparatus according to the first embodiment.

As shown in FIG. 7, the operator-side end portion of the flexible tube portion 9 is connected to the drum 12. The signal line 28 of the CCD, light guide cable 29, and four fluid supply tubes 17 inserted into the flexible tube portion 9 are housed in the drum 12, as shown in FIG. 8. In this case, the signal line 28 of the CCD and the light guide cable 29 extend from a side of the drum 12 to the outside of the drum 12 and are held while being wound around a rotating shaft 12a of the drum 12 a plurality of number of times. With this arrangement, the endoscope body 2 can be pulled out and housed without any tension on the signal line 28 and light guide cable 29. The CCU 3 is connected to the proximal end portion of the signal line 28. The proximal end portion of the light guide cable 29 is connected to the light source unit 4.

As shown in FIG. 8, a solenoid valve unit (fluid supply amount control unit) 30 and a solenoid valve controller 93 for controlling the solenoid valve unit 30 are arranged in the drum 12. In this case, the proximal end portions of the four fluid supply tubes 17 are coupled to the solenoid valve unit 30.

One end portion of a fluid tube 32 on the pneumatic pressure source side, through which a fluid is supplied, is coupled to the solenoid valve unit 30. The fluid tube 32 extends from the side of the drum 12 to the outside of the drum 12. A winding portion 33 in a helical form is formed on the extended portion of the fluid tube 32.

A housing chamber 35 for a cylinder 34 as a pneumatic pressure source is formed in one side portion of the carrying case 7, as shown in FIG. 1. The other end portion of the fluid tube 32 is coupled to the small cylinder 34 in the housing chamber 35. Note that as a gas filling the cylinder 34, a nonflammable gas, e.g., carbon dioxide, fluorocarbon, nitrogen, helium, argon, or air is used. The cylinder 34 preferably has a high filling pressure and a large filling gas amount. For example, the filling gas amount of carbon dioxide is larger, but the filling pressure of nitrogen is higher.

One end portion of a signal line 36 is connected to the solenoid valve controller 93 in the drum 12. The signal line 36 extends from a side of the drum 12 to the outside of the drum 12 and is held while being wound around the rotating shaft 12a of the drum 12 a plurality of number of times, like the signal line 28 and light guide cable 29. With this arrangement, the endoscope body 2 can be pulled out and housed without any tension on the signal line 36. The other end portion of the signal line 36 is connected to the power supply 5 and a joystick (operating portion) 37 for bending the bending portion 10 of the endoscope body 2.

Figure 9B:
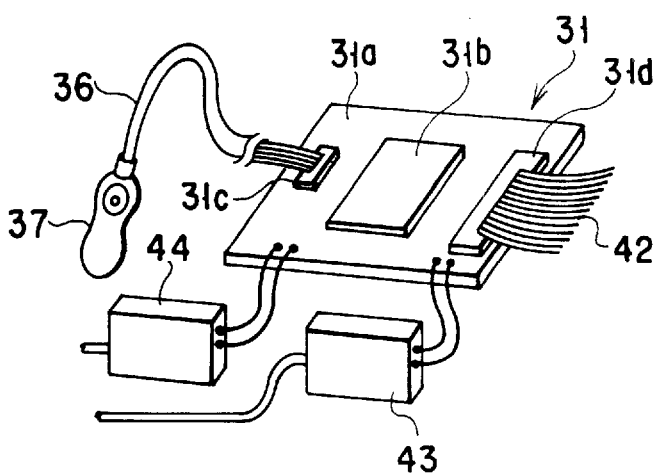
FIG. 9B is a schematic view showing how a solenoid valve controller is connected.
Figure 9C:
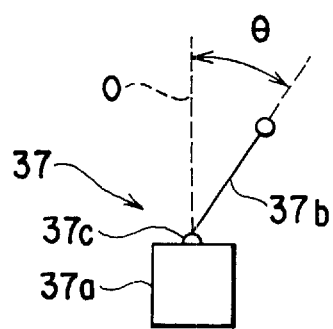
FIG. 9C is a schematic view showing a joystick.

As shown in FIG. 9C, the joystick 37 has a base member 37a and operation lever 37b. The operation lever 37b is supported on a pivot shaft 37c on the base member 37a to be tilted in an arbitrary direction from a 0-point position (neutral position). The joystick 37 also has a biaxial potentiometer (not shown). The resistance value from the potentiometer changes in accordance with an inclination angle θ of the operation lever 37b with respect to the 0-point position.

Figure 9A:
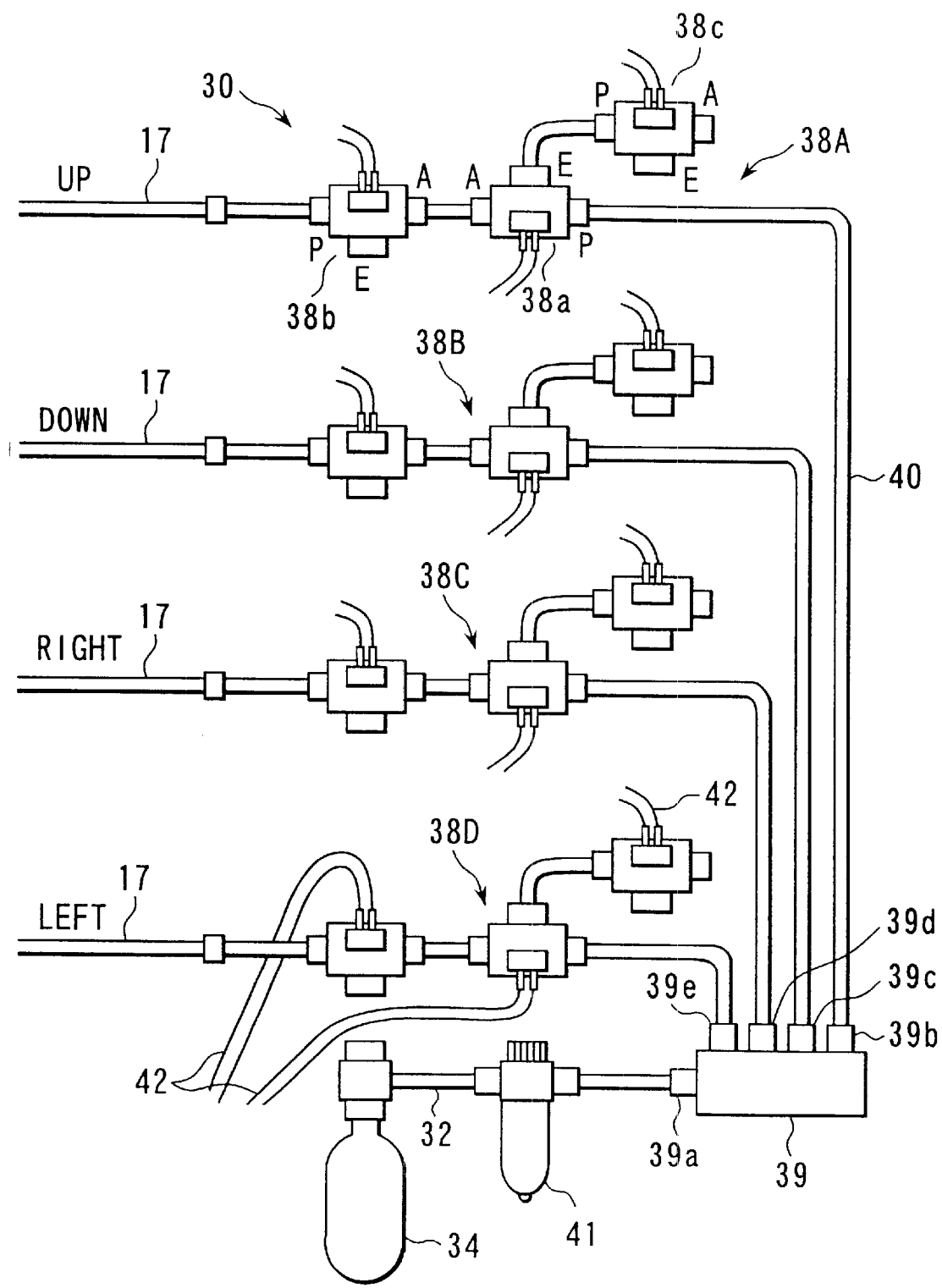
FIG. 9A is a schematic view showing the arrangement of the solenoid valve unit of the endoscope apparatus according to the first embodiment.

As shown in FIG. 9A, the solenoid valve unit 30 includes four flow path switching mechanism portions 38A to 38D for switching the flow paths of the four fluid supply tubes 17 corresponding to four bending directions UP, DOWN, RIGHT, and LEFT, and a tube coupling 39. Each of the flow path switching mechanism portions 38A to 38D has three solenoid valves (3-port valves) 38a, 38b, and 38c. The solenoid valve unit 30 therefore has a total of 12 solenoid valves 38. The flow path switching mechanism portion 38A switches to the flow path in the UP direction; the flow path switching mechanism portion 38B, to the flow path in the DOWN direction; the flow path switching mechanism portion 38C, to the flow path in the RIGHT direction; and the flow path switching mechanism portion 38D, to the flow path in the LEFT direction.

Each solenoid valve 38 is a 3-port valve having three air vents (ports) A, E, and P. When a voltage is applied to each solenoid valve 38, the air vents P and A communicate with each other (open). While no voltage is applied to each solenoid valve 38, the air vents A and E communicate with each other (open). The three solenoid valves 38a, 38b, and 38c are connected to each of the fluid supply tubes 17 in the four bending directions, as shown in FIG. 9A.

In one bending direction, e.g., the UP direction, the two solenoid valves 38a and 38b are connected in series with the flow path switching mechanism portion 38A of the fluid supply tube 17. In this case, the air vent P of the solenoid valve 38b is connected to the outlet end portion of the fluid supply tube 17. The air vent A of the solenoid valve 38a is connected to the air vent A of the solenoid valve 38b. The air vent P of the solenoid valve 38c is connected to the air vent E of the solenoid valve 38a. One end portion of a coupling tube 40 is coupled to the air vent P of the solenoid valve 38a.

In each of the flow path switching mechanism portions 38B, 38C, and 38D of the fluid supply tubes 17 in the three remaining bending directions, i.e., the DOWN, RIGHT, and LEFT directions, the three solenoid valves 38a, 38b, and 38c are connected in the same manner as described above.

The tube coupling 39 has one inlet port 39a and four outlet ports 39b to 39e. The fluid tube 32 on the cylinder 34 side is coupled to the inlet port 39a of the tube coupling 39, and the other end portion of the coupling tube 40 coupled to each of the fluid supply tubes 17 in the four bending directions is coupled to a corresponding one of the four outlet ports 39b to 39e. A regulator 41 is inserted at some point in the fluid tube 32. The tube coupling 39 is connected to the cylinder 34 through the regulator 41. With this arrangement, air from the cylinder 34 is supplied to the solenoid valve unit 30 after the air is adjusted to an appropriate pressure by the regulator 41.

As shown in FIG. 9B, the solenoid valve controller 93 includes an electric circuit board 31a, a CPU 31b mounted on the board 31a, an input terminal 31c, an output terminal 31d, and the like. The signal line 36 of the joystick 37 is connected to the input terminal 31c. A signal line 42 of each solenoid valve 38 of the solenoid valve unit 30 is connected to the output terminal 31d.

When the joystick 37 is operated, an output signal from the joystick 37 is input to the solenoid valve controller 93. The operation of each solenoid valve 38 of the solenoid valve unit 30 is then controlled by the CPU 31b of the solenoid valve controller 93 on the basis of this input signal. With this operation, air from the cylinder 34 of the carrying case 7 is supplied to the hydropneumatic actuator 19 of the bending portion 10 to be selectively sent to the four arcuated lumens 13b, 13c, 13d, and 13e of the multi-lumen tube 13, thereby bending the bending portion 10 in the operating direction of the joystick 37.

Figure 10:
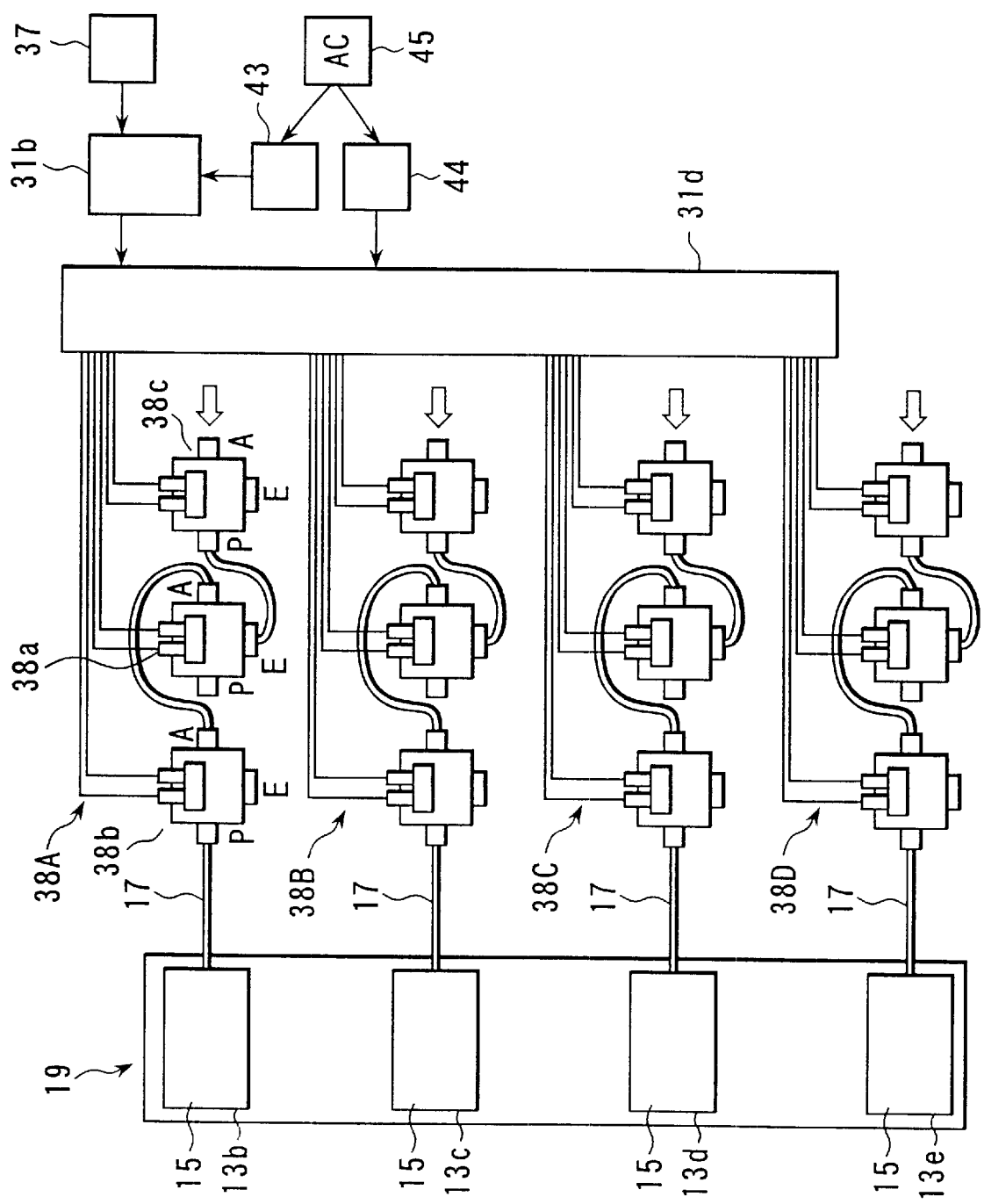
FIG. 10 is a view for explaining the operation of the solenoid valve unit in bending operation of the endoscope according to the first embodiment.

Two power supplies 43 and 44 are connected to the solenoid valve controller 93. The two power supplies 43 and 44 are required because a voltage for driving the CPU 31b serving as the heart of the solenoid valve controller 93 differs from a voltage for driving each solenoid valve 38 of the solenoid valve unit 30. As shown in FIG. 10, the CPU 31b of the solenoid valve controller 93 is driven by DC driving power obtained from an AC power supply 45 through the power supply 43. Each solenoid valve 38 of the solenoid valve unit 30 is driven by DC driving power obtained from the AC power supply 45 through the power supply 44. Note that the number of power supplies required may be decreased to one by using a common operating voltage for the CPU 31b and each solenoid valve 38 of the solenoid valve unit 30.

The function of the above arrangement will be described next. When the endoscope apparatus 1 of this embodiment is to be used to inspect a pipe or the like, the endoscope body 2 is pulled out from the drum 12 in the carrying case 7. The operator then operates the joystick 37, as needed, while inserting the insertion portion 8 of the endoscope body 2 into a tubular cavity as an object under examination such as a pipe. When the joystick 37 is operated, an output signal from the joystick 37 is input to the solenoid valve controller 93. The operation of each guide pins 83 of the solenoid valve unit 30 is then controlled by the CPU 31b of the solenoid valve controller 93 on the basis of the input signal. With this operation, air from the cylinder 34 of the carrying case 7 is supplied to the hydropneumatic actuator 19 of the bending portion 10 to be selectively sent to the pressurization chambers 15 of the four arcuated lumens 13b, 13c, 13d, and 13e.

The pressure in the pressurization chamber 15 to which the air is sent increases. At this time, the circumferential wall portion of the pressurization chamber 15 is bound to expand in the radial direction, but the expansion in the radial direction is restricted by the inner and outer contact coils 21 and 24 of the multi-lumen tube 13. For this reason, the pressurized pressurization chamber 15 extends along the longitudinal direction (the direction of the center line of the insertion portion 8). As a consequence, the bending portion 10 bends in a direction opposite to the extending pressurization chamber 15. In this manner, the bending portion 10 bends in the operating direction of the joystick 37.

The following operation is performed during the operation of the joystick 37. When the operator tilts the joystick 37, the inclination angle of the joystick 37 changes. In accordance with this change in the inclination angle of the joystick 37, the resistance value of the biaxial potentiometer of the joystick 37 changes. The CPU 31b of the solenoid valve controller 93 detects the amount of change in resistance value and a change in speed. In accordance with the detected amount of change in resistance value and change in speed, the CPU 31b sends an operation signal to a switch circuit (not shown) to turn on/off each solenoid valve 38 of the solenoid valve unit 30.

In other words, when the operator tilts the joystick 37, the number of times each solenoid valve 38 is turned on is determined in accordance with the inclination angle of the joystick 37. In addition, the ON time of each solenoid valve 38 is determined in accordance with the speed at which the joystick 37 tilts. A threshold may be set for the speed at which the joystick 37 tilts. In this manner, the time during which the solenoid valve 38 is open is determined in accordance with the speed at which the operator tilts the joystick 37.

The basic operation of the joystick 37 will be described with reference to FIGS. 11A to 11D. Referring to FIGS. 11A to 11D, "J1" to "J4" indicate the operation state of the joystick 37; "a1" to "a4", the operation state of the solenoid valve 38a; "b1" to "b4", the operation state of the solenoid valve 38b; and "c1" to "c4", the operation state of the solenoid valve 38c.

Operation to be performed to increase the inclination of the joystick 37 will be described first. "J1" in FIG. 11A indicates the operation state wherein the operator tilts the joystick 37 from the 0-point position (neutral position) to a position A1 in the UP direction at a speed lower than a predetermined threshold Vsu of the operation speed of the joystick 37. At this time, the solenoid valves 38a, 38b, and 38c corresponding to the UP direction in FIG. 9A are turned on/off, as indicated by "a1", "b1", and "c1" in FIG. 11A, respectively. In accordance with the inclination angle of the joystick 37, the solenoid valves 38a and 38b operate in the same manner, with a predetermined pulse width Δt11, until time t1 at which the joystick 37 stops.

Figure 11A:
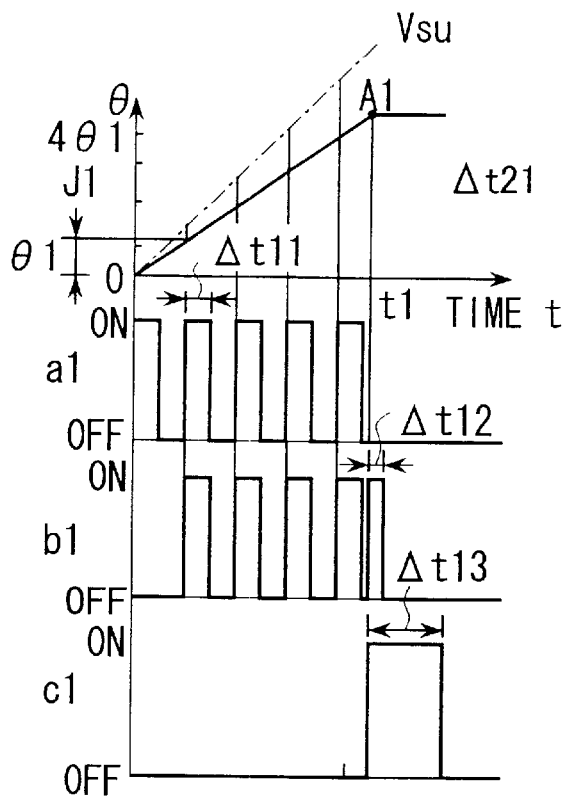
FIG. 11A is a graph for explaining how each solenoid valve operates when the operation speed of the joystick is low in bending the bending portion of the endoscope according to the first embodiment.

While the operator tilts the joystick 37, 1-pulse operation signals for the solenoid valves 38a and 38b are output in accordance with a predetermined amount of change in the inclination angle of the joystick 37. In this case, as shown in FIG. 11A, every time the inclination angle of the joystick 37 changes by θ 1, 1-pulse operation signals are output. In the case shown in FIG. 11A, since the joystick 37 tilts by an angle larger than 4 θ 1, 4-pulse operation signals are output to the solenoid valves 38a and 38b.

After this operation, the solenoid valve 38a is turned off, and the solenoid valve 38b is turned on for only a period of time t1 corresponding to one pulse with a pulse width Δt12 after the operator stops tilting the joystick 37. The solenoid valve 38c is kept off until time t1 at which the operator stops tilting the joystick 37. Thereafter, an operation signal with a pulse width Δt13 is output.

Figure 11B:
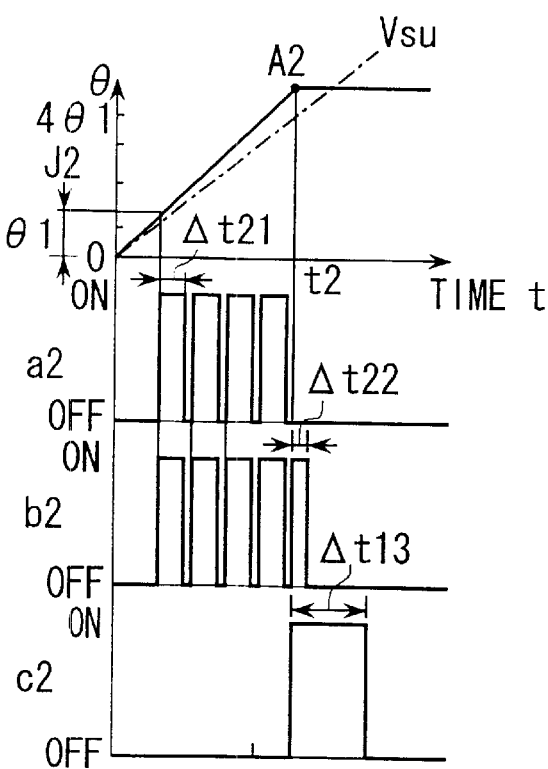
FIG. 11B is a graph for explaining how each solenoid valve operates when the operation speed of the joystick is high in bending the bending portion.

"J2" in FIG. 11B indicates the operation state wherein the operator tilts the joystick 37 from the 0-point position (neutral position) to a position A2 in the UP direction at a speed higher than the predetermined threshold Vsu of the operation speed of the joystick 37. At this time, the solenoid valves 38a, 38b, and 38c corresponding to the UP direction in FIG. 9A are turned on/off, as indicated by "a2", "b2", and "c2" in FIG. 11B, respectively.

In this case, the solenoid valves 38a and 38b operate in the same manner, with a pulse width Δt21 larger than the pulse width Δt11 in the case wherein the operator tilts the joystick 37 at a low speed as shown in FIG. 11A, until time t2 at which the operator stops tilting the joystick 37.

After this operation, the solenoid valve 38a is turned off. When the operator stops tilting the joystick 37, the solenoid valve 38b is turned on for a period of time corresponding to one pulse with a pulse width Δt22 equal to or larger than the pulse width Δt12 in FIG. 11A. Note that the operation of the solenoid valve 38c is the same as that shown in FIG. 11A.

Operation to be performed when the joystick 37 is restored from a tilted state to the initial state will be described next. "J3" in FIG. 11C indicates the state wherein the operator tilts the joystick 37 from a bending position A3 to a position A3' in the UP direction to decrease the bend amount at a speed lower than a predetermined threshold Vsd of the operation speed of the joystick 37. At this time, the solenoid valves 38a, 38b, and 38c corresponding to the UP direction in FIG. 9A are turned on/off as indicated by "a3", "b3", and "c3" in FIG. 11C, respectively.

Figure 11C:
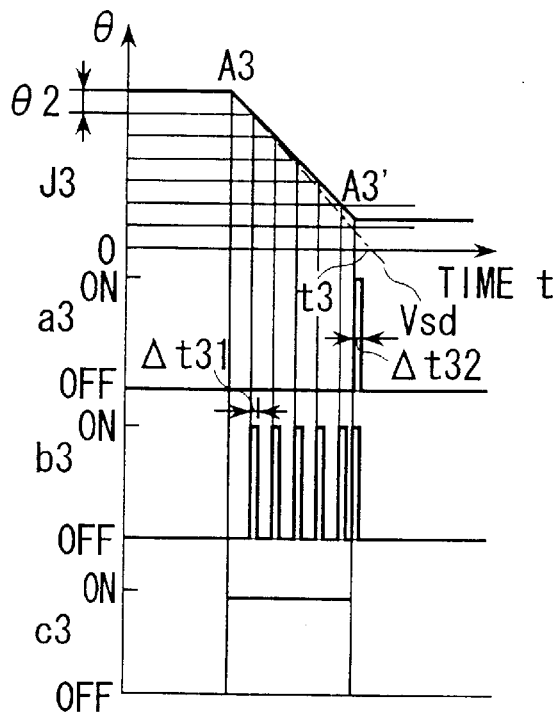
FIG. 11C is a graph for explaining how each solenoid valve operates when the operation speed of the joystick is low in restoring the bending portion to its original state.

A 1-pulse operation signal for the solenoid valve 38b is output in accordance with a predetermined amount of change in the inclination angle of the joystick 37. In this case, as shown in FIG. 11C, every time the inclination angle of the joystick 37 changes by θ2, 1-pulse operation signal is output. The solenoid valve 38b operates in the same manner with a predetermined pulse width Δt31 until time t3 at which the operator stops tilting the joystick 37. The solenoid valve 38a is kept off until time t3 at which the operator stops tilting the joystick 37. At time t3 when the joystick 37 stops, the solenoid valves 38a and 38b are kept on only for a period of time corresponding to one pulse with a pulse width Δt32. Note that the solenoid valve 38c is kept on in the time interval between the instant at which the joystick 37 moves and the instant at which the joystick 37 stops. Thereafter, the solenoid valve 38c is turned off.

Figure 11D:
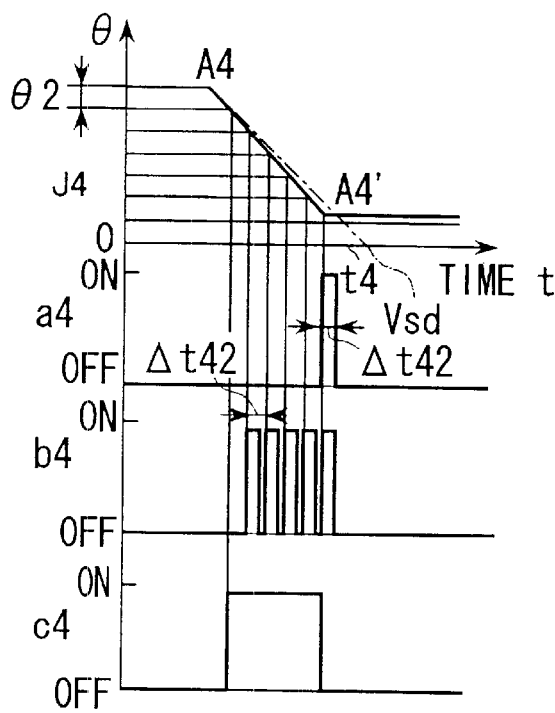
FIG. 11D is a graph for explaining how each solenoid valve operates when the operation speed of the joystick is high in restoring the bending portion to its original state.

"J4" in FIG. 11D indicates the state wherein the operator tilts the joystick 37 from a bending position A4 to a position A4' in the UP direction to decrease the bend amount at a speed higher than the predetermined threshold Vsd of the operation speed of the joystick 37. At this time, the solenoid valves 38a, 38b, and 38c corresponding to the UP direction in FIG. 9A are turned on/off as indicated by "a4", "b4", and "c4" in FIG. 11D, respectively.

The solenoid valve 38b operates in the same manner with a pulse width Δt41 larger than the pulse width Δt31 in FIG. 11C until time t4 at which the operator stops tilting the joystick 37. The solenoid valve 38a is kept off until time t4 when the operator stops operating the joystick 37. At time t4 when the joystick 37 stops, the solenoid valves 38a and 38b are kept on only for a period of time corresponding to one pulse with a pulse width Δt42 equal to or larger than the pulse width Δt32 in FIG. 11C. Note that the solenoid valve 38c is kept on in the time interval between the instant at which the joystick 37 moves and the instant at which the joystick 37 stops.

Thereafter, the solenoid valve 38c is turned off.

Referring to FIGS. 11A to 11D, the pulse widths with which the solenoid valves 38a and 38b operate when the inclination of the joystick 37 increases and decreases can be expressed as follows: Δt11>Δt31, Δt21>Δt41.

As shown in FIG. 9A, in increasing the bend amount of the bending portion 10, compressed air from the cylinder 34 is sent to the pressurization chamber 15 in the arcuated lumen 38b in the UP direction through the air vents P and A of the solenoid valve 38a and the air vents A and P of the solenoid valve 38b when the solenoid valves 38a and 38b are on.

When the solenoid valves 38a and 38b are turned off, air from the cylinder 34 is stopped at the solenoid valve 38a, and the air sent to the pressurization chamber 15 of the arcuated lumen 13b is sealed in the pressurization chamber 15 and fluid supply tube 17, thus holding the bent state of the bending portion 10. At this time, although the solenoid valves 38a and 38b synchronously operate in accordance with identical signals, the air in the pressurization chamber 15 of the arcuated lumen 13b and the air in the fluid supply tube 17 slightly leak from the air vent E of the solenoid valve 38a owing to the length of the tube path between the solenoid valves 38a and 38b. This leakage is too small to interfere with the bending operation of the bending portion 10. In order to efficiently use the air in the cylinder 34 for a long period of time, it is important to minimize the leakage of air.

In this embodiment, therefore, the solenoid valve 38c is connected to the air vent E of the solenoid valve 38a in the manner shown in FIG. 9A. In this case, the solenoid valve 38c is normally off. At the moment when the operator stops tilting the joystick 37, the solenoid valve 38c is turned on for a time $\Delta t13$ longer than an ON time $\Delta t12$ of the solenoid valve 38b. This makes it possible to prevent the leakage of air from the pressurization chamber 15 of the arcuated lumen 13b and the fluid supply tube 17 during bending operation.

When the operator stops tilting the joystick 37 to stop the bending operation of the bending portion 10, the solenoid valve is released to the atmospheric pressure for a 1-pulse period. This operation can quickly stop the bending operation of the bending portion 10. Releasing air from the solenoid valve for a 1-pulse period to stop the bending operation of the bending portion 10 in this manner is effective when the insertion portion 8 of the endoscope body 2 is long. If, for example, the length of the insertion portion 8 is 10 m or more, air is sent from the cylinder 34 on the operator side to the pressurization chamber 15 at the distal end of the insertion portion 8 with a time lag. In this case, the bending operation of the bending portion 10 can be accurately stopped by releasing air from the flow path for a moment upon predicting this time lag. More specifically, the time lag between the instant at which air is sent to the distal end of the insertion portion 8 and the instant at which the entire insertion portion is uniformly pressurized cancels out the time lag with which the internal pressure decreases upon removal of air. This makes it possible to quickly and accurately stop the bending operation of the bending portion 10.

The solenoid valve 38 corresponding to each of the fluid supply tubes 17 in directions in which no bending operation is performed is held in the state wherein the pressurization chamber 15 of the multi-lumen tube 13 is released to the atmosphere through the fluid supply tube 17. If, for example, the bending portion 10 is bending in the UP direction, the solenoid valves 38 operate to release the pressurization chambers 15 in the DOWN, RIGHT, and LEFT directions to the atmosphere through the fluid supply tubes 17.

More specifically, the solenoid valve 38b connected to the pressurization chamber 15 side of the fluid supply tube 17 is turned on, the solenoid valve 38a connected to the cylinder 34 side is turned off, and another solenoid valve 38c is turned on. Each of the solenoid valves 38 in the directions in which the joystick 37 instructs no bending operation always operates in the above manner. The above operation is performed for a predetermined period of time after the joystick 37 tilts to the 0-point position (neutral position) in each direction.

In the above operation, the operator knows the bending direction of the bending portion 10 of the endoscope body 2 from the operating direction of the joystick 37. In addition, the maximum inclination angle of the joystick 37 is set to correspond to the maximum bending angle of the bending portion 10 of the endoscope body 2. This setting allows the operator to estimate the bending angle of the bending portion 10 of the endoscope body 2 from the inclination angle of the joystick 37. By checking the inclination angle and operating direction of the joystick 37, the operator can approximately know a specific bending angle at which the bending portion 10 of the endoscope body 2 bends in a specific direction.

Figure 12:
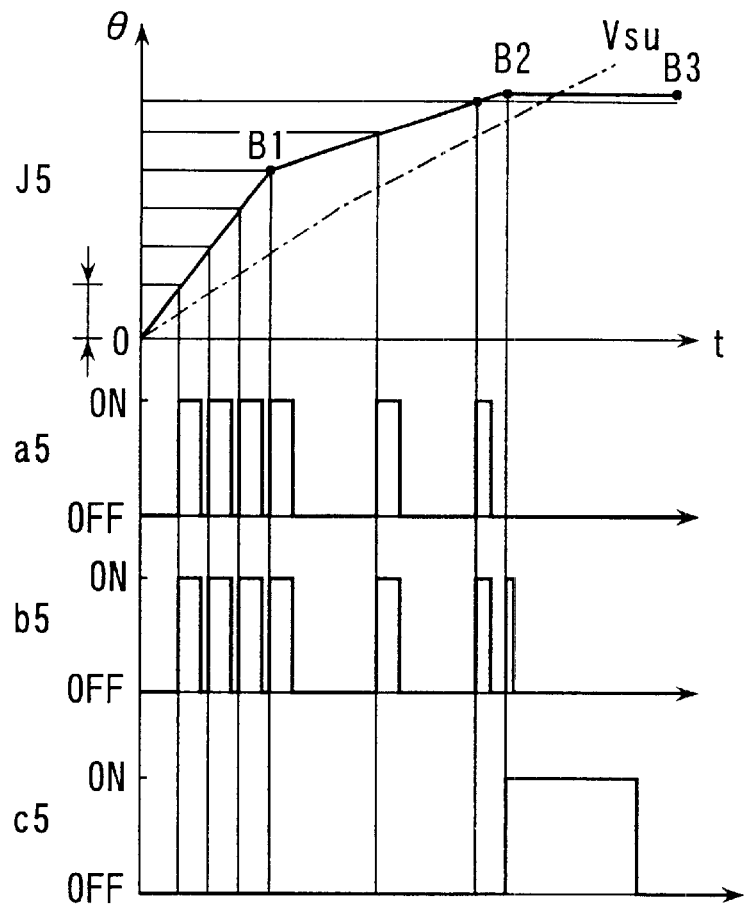
FIG. 12 is a graph for explaining bending operation performed when the operator operates the joystick while changing its operation state in bending the bending portion of the endoscope according to the first embodiment.

The bending operation of the bending portion 10 in a case wherein the operator operates the joystick 37 while changing an operation state such as an operation speed will be described next. "J5" in FIG. 12 indicates the operation state wherein the operator sequentially tilts the joystick 37 from the 0-point position (neutral position) to a position B1, position B2, and position B3 in the order named. In this case, the operation speed between the 0-point position and the position B1 is higher than the threshold Vsu. The operation speed between the position B1 and the position B2 is lower than the threshold Vsu. The operation speed between the position B2 and the position B3 is constant. Referring to FIG. 12, "a5", "b5", and "c5" indicate the ON/OFF operation states of the solenoid valves 38a, 38b, and 38c corresponding to the UP direction in FIG. 9A.

Since the joystick 37 operates at a speed higher than the threshold Vsu between the 0-point position and the position B1, the solenoid valves 38a and 38b are operated in a mode with a large pulse width. Subsequently, the solenoid valves 38a and 38b are operated in a mode with a small pulse width between the position B1 and the position B2.

At the position B2, the joystick 37 stops, a 1-pulse operation signal is output to the solenoid valve 38b, and the solenoid valve 38c is kept on for a predetermined period of time. As a consequence, the bending speed of the bending portion 10 of the endoscope body 2 becomes high between the 0-point position and the position B1, and low between the position B1 and the position B2.

That is, the operator can arbitrarily select one of the bending operation modes of the bending portion 10, e.g., the mode of decreasing the bending speed of the bending portion 10 of the endoscope body 2 by slowly operating the joystick 37, thereby finely adjusting the bend amount of the bending portion 10, and the mode of increasing the bending speed of the bending portion 10 by quickly operating the joystick 37.

The following effects can be obtained with the above arrangement. In this embodiment, since the small cylinder 34 is used as a pneumatic pressure source for supplying a fluid to the hydropneumatic actuator 19 of the bending portion 10 of the endoscope body 2, the cylinder 34 can be housed in the carrying case 7, together with the drum 12, around which the insertion portion 8 of the endoscope body 2 is wound, and the joystick 37 for controlling the bending operation of the bending portion 10. This makes it possible to achieve a reduction in the size of the overall system of the endoscope apparatus 1 as compared with the prior art, thus realizing a compact system with excellent portability as the endoscope apparatus 1.

In addition, since the solenoid valve unit 30 and solenoid valve controller 93 which are used to control the supply of a fluid from the cylinder 34 to the hydropneumatic actuator 19 are housed in the drum 12, the portability of the endoscope apparatus 1 can be further improved.

Since this embodiment includes the bending portion 10 using the hydropneumatic actuator 19, a long endoscope with excellent bending performance can be realized even with the long insertion portion 8 of the endoscope body 2.

In this embodiment, as shown in FIG. 9A, the solenoid valve 38c, which is normally off, is connected to the air vent E of the solenoid valve 38a, and the solenoid valve 38c is turned on for the time $\Delta t13$ longer than the ON time $\Delta t12$ of the solenoid valve 38b at the moment when the joystick 37 stops tilting so that air is prevented from leaking from the pressurization chamber 15 of the arcuated lumen 13*b* during bending operation and the fluid supply tube 17. This makes it possible to implement a control method of efficiently using the air in the small cylinder 34 by controlling the solenoid valve unit 30 through the solenoid valve controller 93. Therefore, the cylinder 34 can be used for a long period of time, and the frequency of replacing the cylinder 34 decreases, resulting in excellent operability and cost effectiveness.

In addition, since control on the bending speed of the bending portion 10 of the endoscope body 2 is linked to the operation speed of the joystick 37, the operator can selectively operate the joystick 37 at high and low speeds. This can improve the operability of the bending operation of the bending portion 10 of the endoscope body 2. Since a nonflammable gas is used as a gas filling the small cylinder 34, safety is assured.

Figure 13:
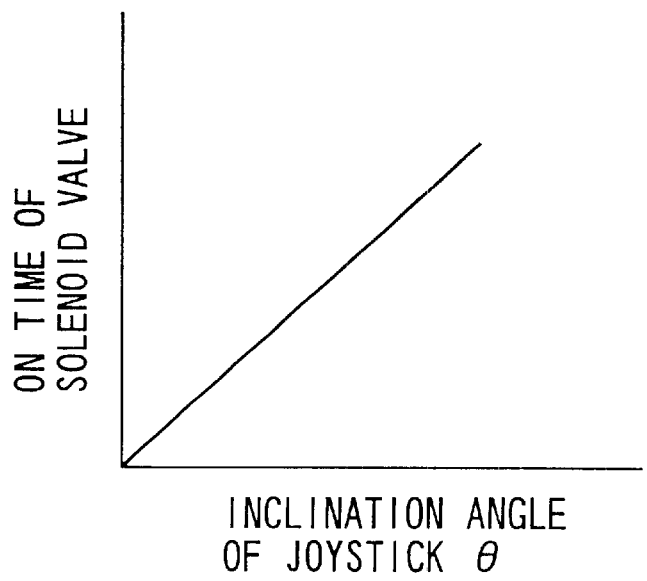
FIG. 13 is a graph showing the relationship between the inclination angle of the lever of a joystick and the ON time of a solenoid valve in an endoscope according to the second embodiment of the present invention.
Figure 14:
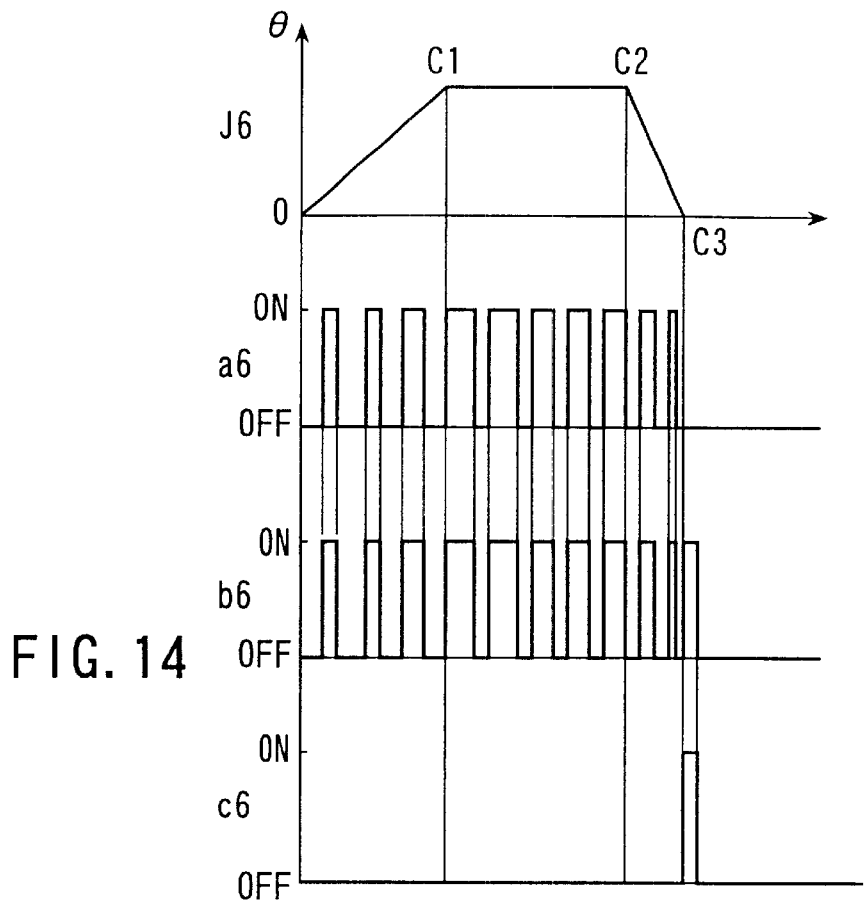
FIG. 14 is a graph for explaining a control method used to control solenoid valves in the endoscope according to the second embodiment.

FIGS. 13 and 14 show the second embodiment of the present invention. In this embodiment, the method of controlling each solenoid valve 38 of the solenoid valve unit 30 in the endoscope apparatus 1 of the first embodiment (see FIGS. 1 to 12) is modified as follows.

In this embodiment, as shown in FIG. 13, an inclination angle θ of an operation lever 37*b* of a joystick 37 is proportional to the time during which a solenoid valve 38 is kept on (open). As the inclination angle θ of the joystick 37 increases, the time during which the solenoid valve 38 is kept on (open) prolongs. While the joystick 37 is tilted, the solenoid valve 38 is kept operated.

Referring to FIG. 14, "J6" indicates the tilting operation state of the joystick 37; "a6", the operation state of a solenoid valve 38*a*; "b6", the operation state of a solenoid valve 38*b*; and "c6", the operation state of a solenoid valve 38*c*. When the operator starts tilting the joystick 37 from the 0-point position (neutral position) to a position C1, the ON time of the solenoid valve 38 gradually prolongs. For example, the solenoid valves 38*a* and 38*b* in the first embodiment are operated while the pulse width is gradually increased, as indicated by "a6" and "b6" in FIG. 14.

When the joystick 37 stops at the position C1 and remains at this position, the pulse width becomes constant to operate the solenoid valves 38*a* and 38*b*. This state continues up to a position C2 at which the joystick 37 is operated.

When the operator returns the joystick 37 from the position C2 to the position C3, the pulse width gradually decreases. When the joystick 37 moves to a position C3, which is the neutral position, the solenoid valve 38*a* stops operating, and the solenoid valves 38*b* and 38*c* are kept on only for a 1-pulse period to exhaust air.

While the joystick 37 tilts, the solenoid valves 38*a* and 38*b* continue to operate. As a consequence, the bending portion 10 continues its bending motion. When the operator wants to stop bending the bending portion 10, he/she returns the joystick 37 to the neutral position.

When the operator wants to quickly bend the bending portion 10, he/she greatly tilts the joystick 37 to send a large amount of air to the pressurization chamber 15. When the operator wants to finely bend the bending portion 10, he/she slightly tilts the joystick 37. In addition, when the operator wants to stop bending the bending portion 10, he/she returns the joystick 37 to the neutral position.

In this embodiment, the bending speed of the bending portion 10 can be changed by arbitrarily adjusting the inclination angle θ of the joystick 37. This allows the operator to quickly or slightly bend the bending portion 10 of the endoscope, thus further improving the operability.

Figure 16:
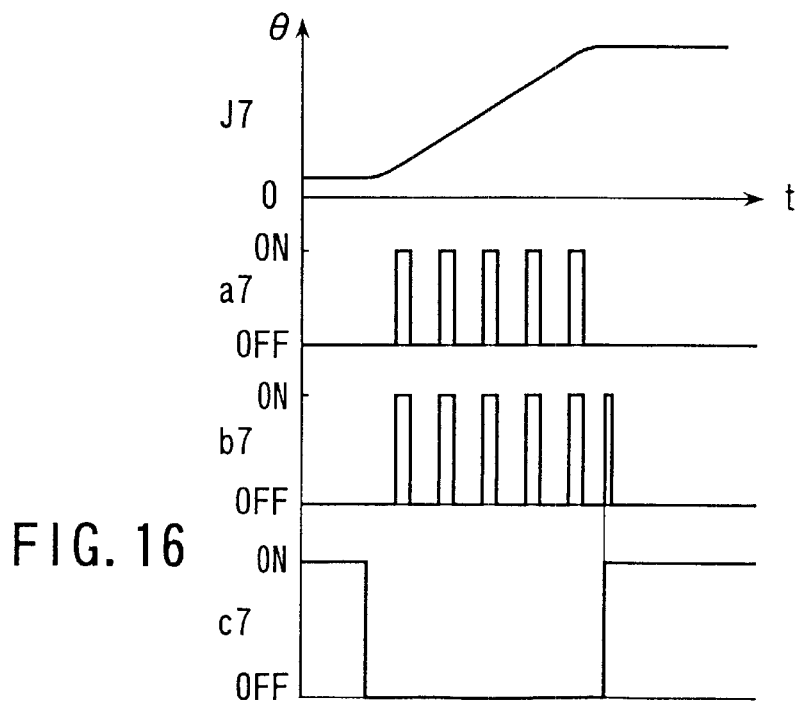
FIG. 16 is a graph showing the relationship between the inclination angle of the lever of a joystick and the ON time of each solenoid valve in the endoscope apparatus according to the third embodiment.
Figure 15:
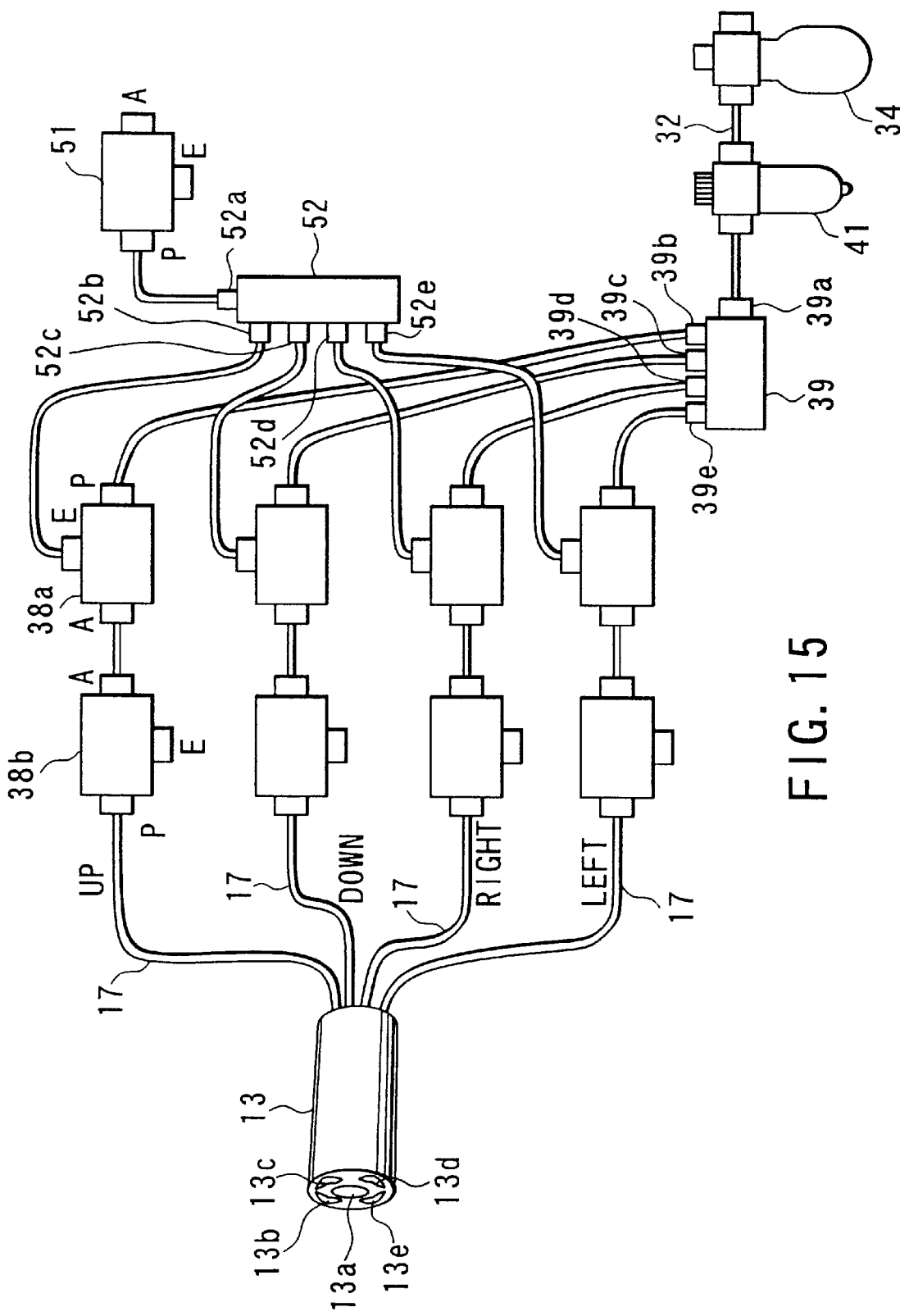
FIG. 15 is a schematic view showing the driving mechanism of a pneumatic actuator in an endoscope apparatus according to the third embodiment of the present invention.

FIGS. 15 and 16 show the third embodiment of the present invention. In this embodiment, the arrangement of the solenoid valve unit 30 in the endoscope apparatus 1 of the first embodiment (see FIGS. 1 to 12) is modified as follows. Since the arrangement of the remaining portion is the same as that in the first embodiment, the same reference numerals as in the first embodiment denote the same parts in FIGS. 15 and 16, and a description thereof will be omitted.

In the first embodiment, each of the flow path switching mechanism portions 38A to 38D of the fluid supply tubes 17 corresponding to the four bending directions, i.e., the UP, DOWN, RIGHT, and LEFT directions, includes the three solenoid valves (3-port valves) 38*a*, 38*b*, and 38*c*. In this embodiment, however, as shown in FIG. 15, only two solenoid valves (3-port valves) 38*a* and 38*b* are connected in series with each of flow path switching mechanism portions 38A to 38D of fluid supply tubes 17 corresponding to the four bending directions, i.e., the UP, DOWN, RIGHT, and LEFT directions, and one solenoid valve 51 commonly used for the respective flow paths in the four bending directions replaces the remaining solenoid valves 38*c*.

A tube coupling 52 is interposed between the solenoid valve 51 and the solenoid valves 38*a* of the respective flow paths in the four bending directions. The tube coupling 52 has one outlet port 52*a* and four inlet ports 52*b* to 52*e*. Air vents E of the solenoid valves 38*a* of the respective flow paths in the four bending directions are respectively coupled to the four inlet ports 52*b* to 52*e* of the tube coupling 52. An air vent P of the solenoid valve 51 is coupled to the outlet port 52*a*. With this arrangement, pipes from the air vents E of the solenoid valves 38*a* of the respective flow paths in the four bending directions are connected as one pipe to the air vent P of the solenoid valve 51 through the tube coupling 52.

The function of the above arrangement will be described next with reference to FIG. 16. Referring to FIG. 16, "J7" indicates the tilting operation state of a joystick 37; "a7", the operation state of the solenoid valve 38*a*; "b7", the operation state of the solenoid valve 38*b*; and "c7", the operation state of the solenoid valve 51. When the joystick 37 is operated in the manner indicated by "J7" in FIG. 16, the solenoid valves 38*a* and 38*b* are ON/OFF-operated as in the first embodiment. While the joystick 37 stops, the solenoid valve 51 is always on. The solenoid valve 51 is off only while the joystick 37 is being operated.

When the operator bends a bending portion 10, the solenoid valve 51 prevents the leakage of air while the solenoid valves 38*a* and 38*b* operate synchronously. While the solenoid valves 38*a* and 38*b* do not operate, the air in the pressurization chambers 15 in the directions in which no bending operation is performed is released to the atmosphere. That is, the solenoid valves 38*a* and 38*b* in the directions in which no bending operation is performed are off, and the air in the pressurization chambers 15 is released from the solenoid valve 51 through the fluid supply tubes 17 and the solenoid valves 38*a* and 38*b*. Other operations are basically the same as those in the first embodiment.

The following effects can be obtained with the above arrangement. In this embodiment, the same effects as those of the first embodiment can be obtained. In addition, according to this embodiment, the number of solenoid valves making up the solenoid valve unit 30 can be decreased, thus offering an advantage in size reduction.

The fourth embodiment of the present invention will be described with reference to FIGS. 17 to 20B. The arrangement of the solenoid valve unit 30 in the endoscope apparatus 1 of the first embodiment (see FIGS. 1 to 12) is modified as follows.

Figure 17:
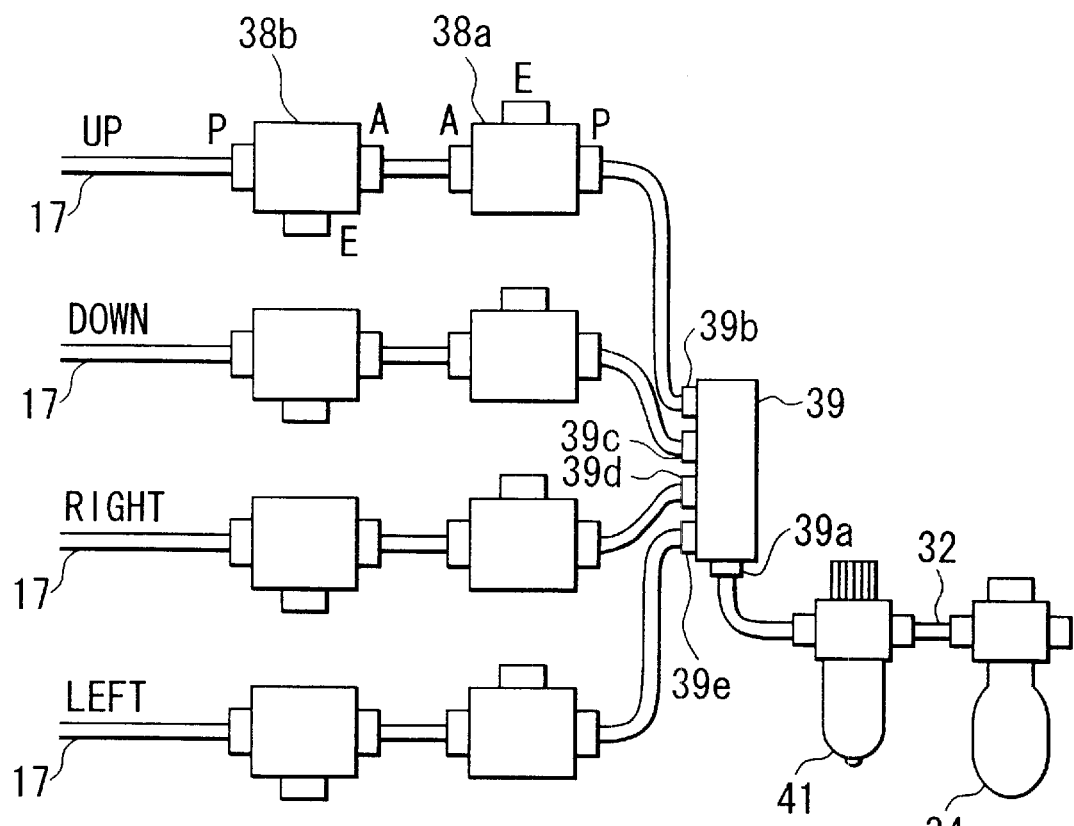
FIG. 17 is a schematic view showing the driving mechanism of a pneumatic actuator in an endoscope apparatus according to the fourth embodiment of the present invention.

As shown in FIG. 17, in this embodiment, only two solenoid valves (3-port valves) 38a and 38b are connected in series with each of flow path switching mechanism portions 38A to 38D of fluid supply tubes 17 corresponding to the four bending directions, i.e., the UP, DOWN, RIGHT, and LEFT directions, and remaining solenoid valves 38c are omitted.

Figure 19:
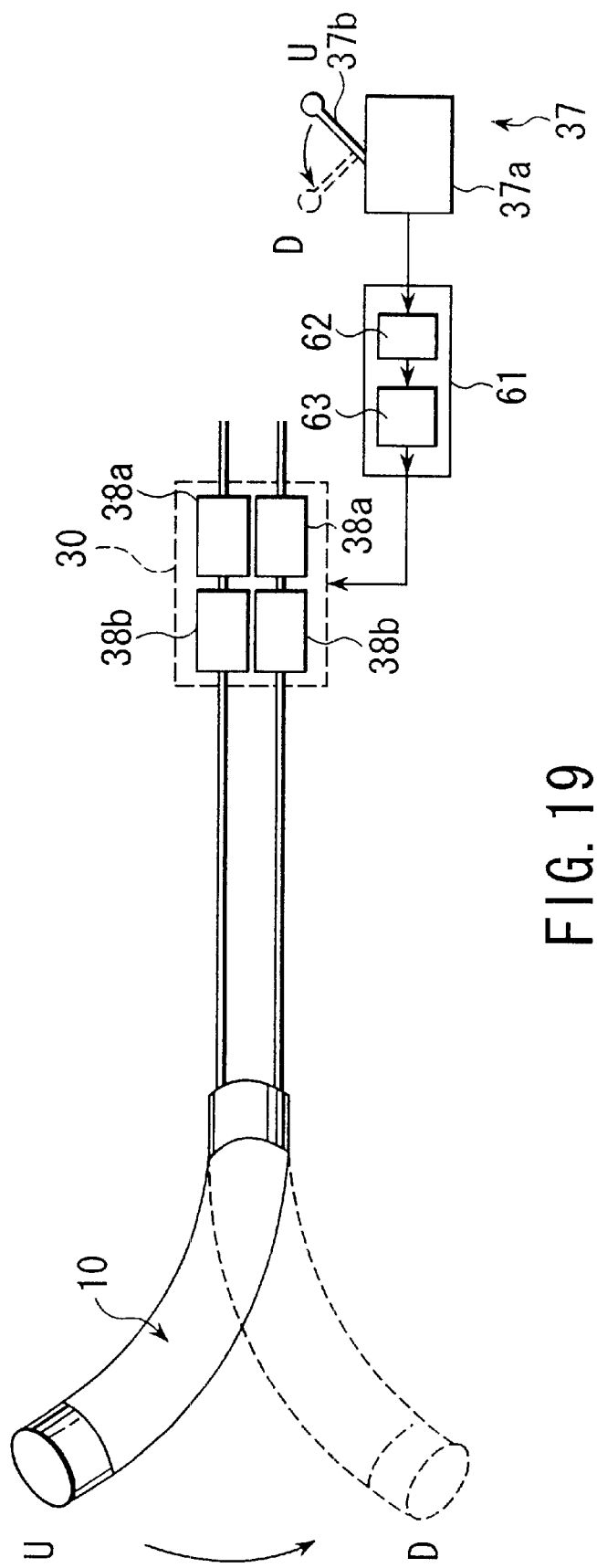
FIG. 19 is a view for explaining operation performed when the operator operates the joystick from the U direction to the D direction in the endoscope apparatus according to the fourth embodiment.

As shown in FIG. 19, a control circuit 61 of a solenoid valve unit 30 includes an arithmetic circuit 62 and signal generating circuit 63. An output signal from a joystick 37 is input to the arithmetic circuit 62. The arithmetic circuit 62 detects the tilting speed of the joystick 37. The signal generating circuit 63 outputs a driving signal to the solenoid valve unit 30 in accordance with the inclination angle of the joystick 37. The arrangements of other portions are the same as those in the first embodiment.

Figure 18A:
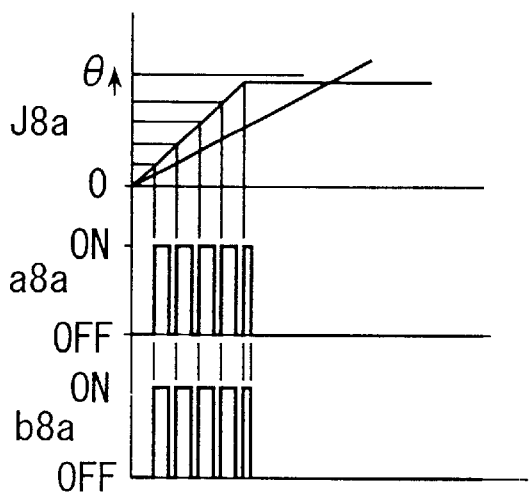
FIG. 18A is a graph showing the relationship between the inclination angle of the lever of a joystick and the ON time of each solenoid valve in the endoscope apparatus according to the fourth embodiment.
Figure 18B:
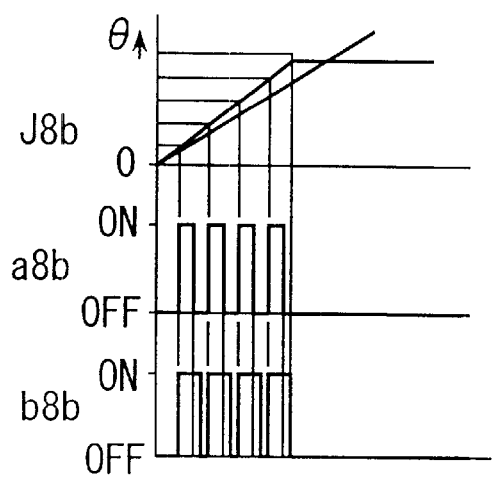
FIG. 18B is a graph showing an example of a control state different from that shown in FIG. 18A.

The function of the above arrangement will be described next with reference to FIGS. 18A and 18B. Referring to FIGS. 18A and 18B, "J8a" and "J8b" indicate the tilting operation state of the joystick 37; "a8a" and "a8b", the operation state of the solenoid valve 38a; and "b8a" and "b8b", the operation state of the solenoid valve 38b. When the joystick 37 is operated in the manner indicated by "J8a" in FIG. 18A, the solenoid valves 38a and 38b in the bending direction corresponding to the operating direction of the joystick 37 are turned on/off as in the first embodiment. As a consequence, air from a cylinder 34 is sent to a pressurization chamber 15 of a multi-lumen tube 13 to bend a bending portion 10 in the bending direction corresponding to the operating direction of the joystick 37.

When the operator stops tilting the joystick 37, identical 1-pulse operation signals are output to the solenoid valves 38a and 38b to slightly exhaust air from the pressurization chamber 15 in the bending direction corresponding to the operating direction of the joystick 37, and the bending operation of the bending portion 10 quickly stops. At this time, even if the two solenoid valves 38a and 38b operate in perfect synchronisity, air slightly leaks from an air vent E of the solenoid valve 38a. However, this amount of air is very small. For this reason, the time during which air in the cylinder 34 can be used becomes slightly shorter than that in the first embodiment.

As indicated by "J8b" in FIG. 18B, when the joystick 37 is to be operated to synchronously operate the solenoid valves 38a and 38b, control may be performed to set the ON time of the solenoid valve 38b to be slightly longer than that of the solenoid valve 38a.

According to this method, when the operator stops tilting the joystick 37, air from the cylinder 34 is blocked by the solenoid valve 38a first. At this time, the solenoid valve 38b is held while the air vent P is communicating with the air vent A to allow compressed air from the cylinder 34 to be sent to the pressurization chamber 15 on the downstream side. For this reason, air in the flow path through which compressed air from the cylinder 34 is sent to the pressurization chamber 15 on the downstream side is released to the operator side with a time lag. In this case, even if the ON time of the solenoid valve 38b is prolonged to some extent, air is not released much or can be released slightly. This makes it possible to stop bending the bending portion 10.

Assume that only a small amount of air can be released to result in difficulty in stopping bending the bending portion 10. In this case, as indicated by "J8b" in FIG. 18B, air may be released by an amount corresponding to one pulse when the operator stops tilting the joystick 37.

Operation to be performed when the operator tilts the joystick 37 from the UP direction to the DOWN direction will be described next with reference to FIGS. 19 to 20B. FIG. 19 shows an operation state wherein when the operator tilts the joystick 37 from the UP position indicated by the solid line to the DOWN position indicated by the dotted line, the bending portion 10 changes from the state of being bent in the UP direction to the state of being bent in the DOWN direction in synchronism with the operation of the joystick 37.

An operation signal is generated in accordance with the inclination angle of the joystick 37. In the control circuit 61, the arithmetic circuit 62 detects the tilting speed of the joystick 37, and the signal generating circuit 63 sends driving signals to the solenoid valves 38a and 38b of the solenoid valve unit 30 in accordance with the inclination angle of the joystick 37.

Figure 20A:
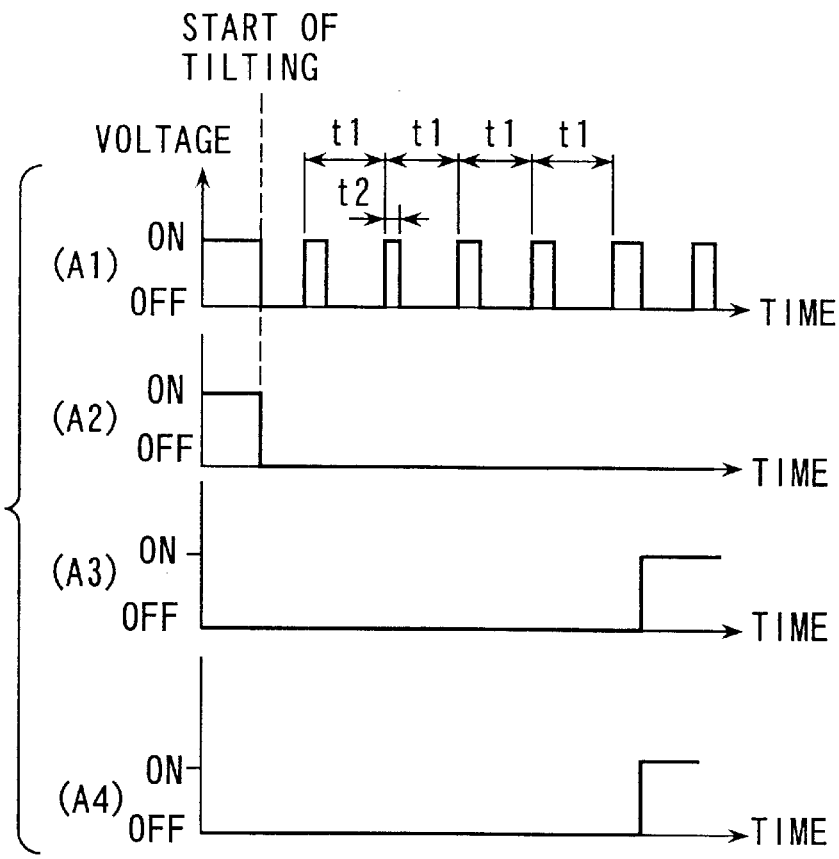
FIG. 20A is a graph for explaining operation performed when the operator slowly tilts the joystick from the U direction to the D direction in the endoscope apparatus according to the fourth embodiment.
Figure 20B:
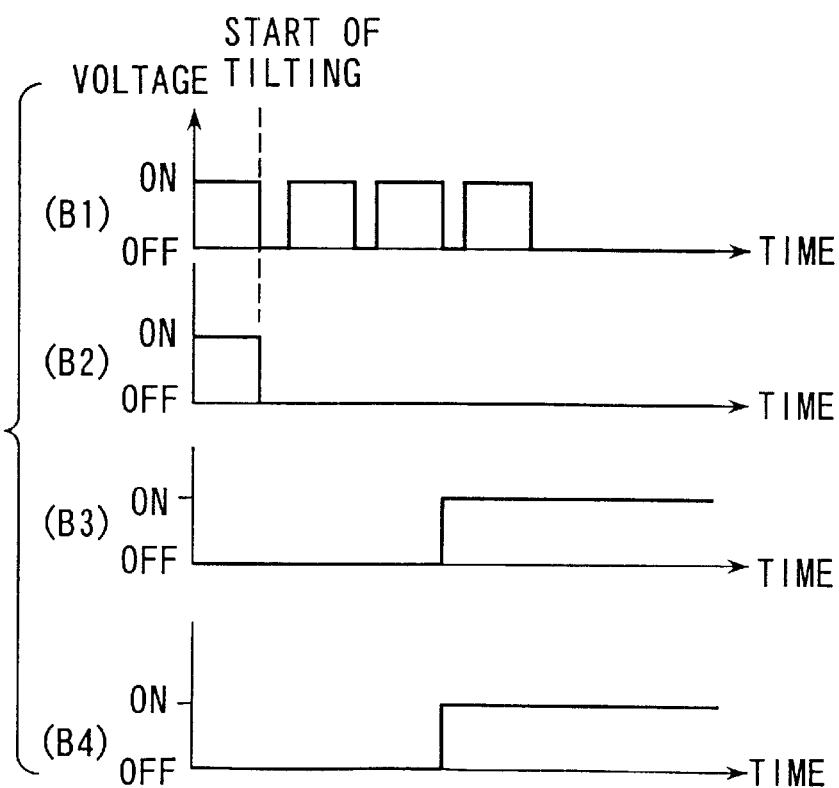
FIG. 20B is a graph for explaining operation performed when the operator quickly tilts the joystick from the UP direction to the DOWN direction.

FIGS. 20A and 20B respectively show the operations of the solenoid valves 38 in the UP and DOWN directions. FIG. 20A shows a case wherein the operator gradually tilts the joystick 37 from the U direction to the D direction. FIG. 20B shows a case wherein the operator quickly tilts the joystick 37. Note that "(A1)" and "(B1)" indicate the operation of the solenoid valve 38b in the U direction; "(A2)" and "(B2)", the operation of the solenoid valve 38a in the U direction; "(A3)" and "(B3)", the operation of the solenoid valve 38b in the D direction; and "(A4)" and "(B4)", the operation of the solenoid valve 38a in the D direction.

When the operator gradually tilts the joystick 37, the operation shown in FIG. 20A is performed. In this case, shown in FIG. 20A each solenoid valve 38b in the U direction is on, and the bending portion 10 is bent in the U direction.

When the operator starts tilting the joystick 37 from the U direction to the D direction, the arithmetic circuit 62 detects the tilting speed of the joystick 37. If the speed is slow, the solenoid valve 38b in the U direction is pulse-driven with a small duty ratio. Note that the duty ratio indicates t2/t1. During this period, the solenoid valve 38a in the U direction is kept off. That is, the fluid in the pressurization chamber 15 is exhausted into the atmosphere only when the solenoid valve 38b is on. Therefore, the exhaust velocity of the fluid from the pressurization chamber 15 in the U direction is low.

After a lapse of a sufficient period of time since the start of tilting the joystick 37, each solenoid valve 38a in the D direction is turned on, and the fluid is supplied from the cylinder 34 into the pressurization chambers 15 in the D direction. As a consequence, the bending portion 10 bends in the D direction.

When the operator quickly tilts the joystick 37, the operation shown in FIG. 20B is performed. When the arithmetic circuit 62 detects that the joystick 37 tilts at a high speed, the solenoid valve 38b in the U direction is driven with a large duty ratio.

At this time, the solenoid valve 38a in the U direction is off. In this state, since the ON time of the solenoid valve 38b is prolonged, the exhaust velocity of the fluid from the pressurization chamber 15 becomes high, and the bending speed of the bending portion 10 becomes also high.

After a lapse of a relatively short period of time since the start of tilting the joystick 37, the two solenoid valves 38a and 38b in the D direction are turned on. Therefore, the bending portion 10 bends in the D direction.

As described above, in this embodiment, in accordance with the tilting speed of the joystick 37, the drive duty ratio of the solenoid valve 38b on the side where the fluid is exhausted and bending operation is performed is changed, and the time during which a solenoid valve on the side where the fluid is taken and bending operation is performed is kept on from the start of tilting is changed. With this operation, when the operator slowly tilts the joystick 37, the fluid can be slowly exhausted, and the timing of starting bending operation in the opposite direction can be delayed. When the operator quickly tilts the joystick 37, the fluid can be quickly exhausted, and the timing of starting bending operation in the opposite direction can be quickened. This improves the operability of the bending portion 10.

According to the above arrangement, since the number of solenoid valves 38 incorporated in the solenoid valve unit 30 can be decreased, the arrangement is simplified, and a reduction in size can be effectively attained. In addition, since the release time of a solenoid valve on the exhaust side is changed in accordance with the tilting speed of the joystick 37, the responsiveness of bending of the bending portion 10 improves, leading to an improvement in operability.

Figure 21:
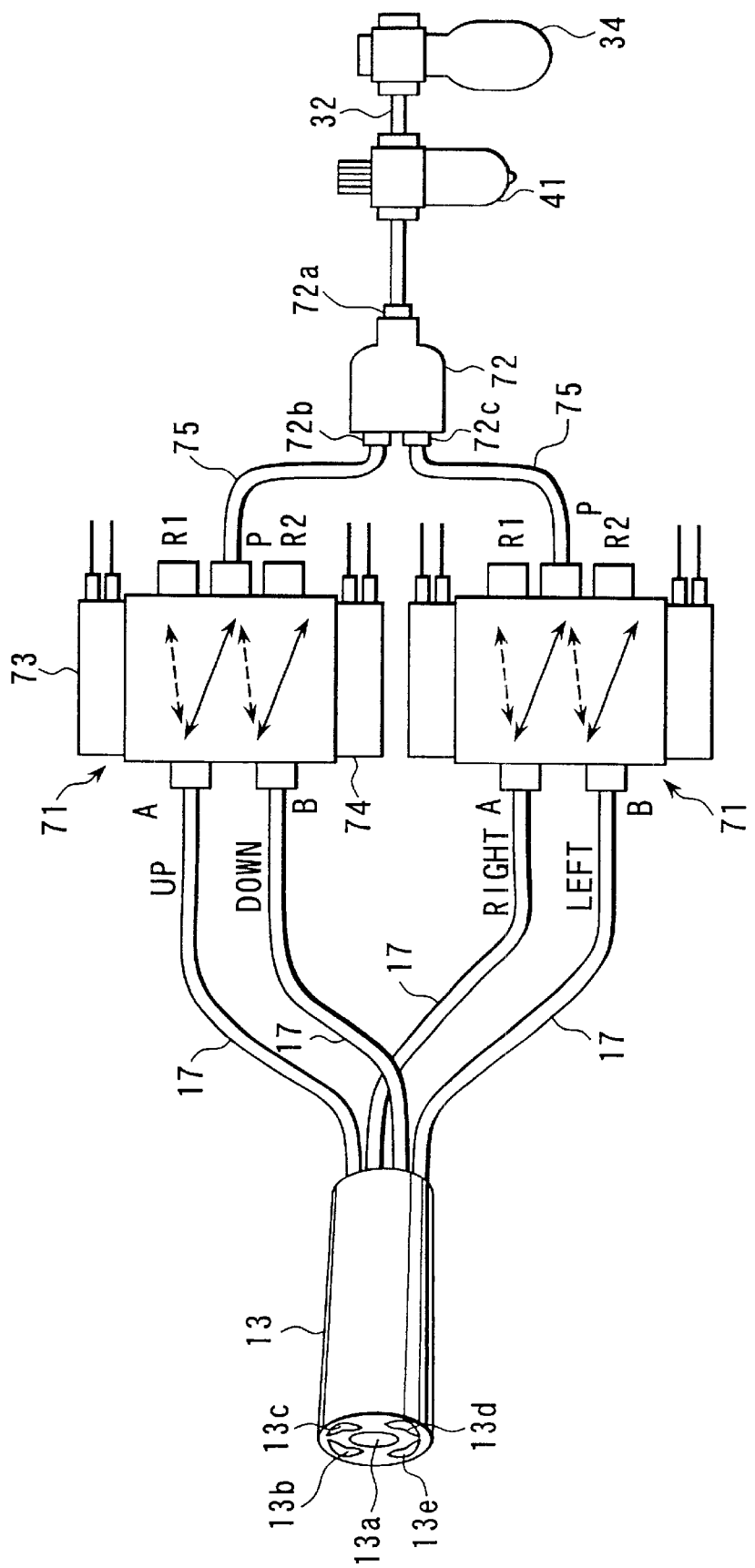
FIG. 21 is a schematic view showing the driving mechanism of a pneumatic actuator in an endoscope apparatus according to the fifth embodiment of the present invention.
Figure 22A:
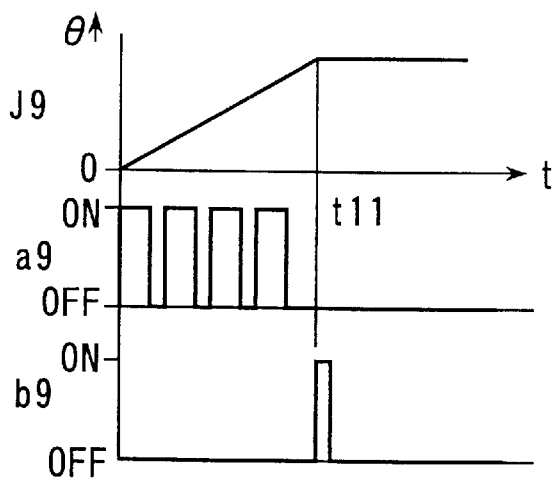
FIG. 22A is a graph showing the relationship between the inclination angle of the lever of a joystick and the ON time of each solenoid valve in the endoscope apparatus according to the fifth embodiment.
Figure 22B:
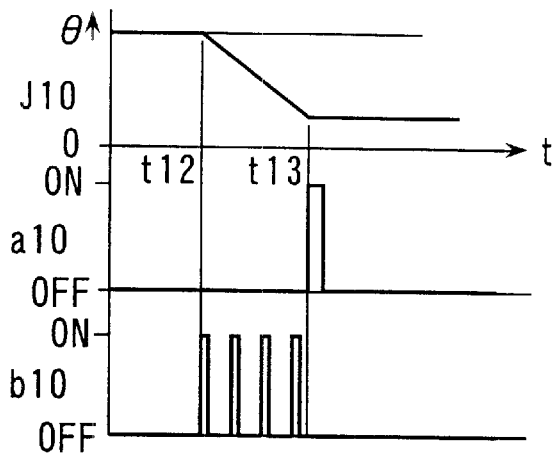
FIG. 22B is a graph showing an example of a control state different from that shown in FIG. 22A.

FIGS. 21 to 22B show the fifth embodiment of the present invention. In this embodiment, the arrangement of the solenoid valve unit 30 in the endoscope apparatus 1 of the first embodiment (see FIGS. 1 to 12) is modified as follows.

A solenoid valve unit 30 in this embodiment has two solenoid valves 71, each formed from a 3-position, 5-port valve, and a tube coupling 72. Each solenoid valve 71 has five air vents (ports) P, A, B, R1, and R2 and two solenoids 73 and 74 for switching the flow paths. The proximal end portions of fluid supply tubes 17 coupled to pressurization chambers 15 in the UP and DOWN directions (or the RIGHT and LEFT directions), which are bending directions, in a hydropneumatic actuator 19 of a bending portion 10 are respectively coupled to the air vents A and B of one solenoid valve 71. The proximal end portions of fluid supply tubes 17 coupled to pressurization chambers 15 in the RIGHT and LEFT directions (or the UP and DOWN directions), which are bending directions, in the hydropneumatic actuator 19 of the bending portion 10 are respectively coupled to the air vents A and B of the other solenoid valve 71.

The tube coupling 72 has one inlet port 72a and two outlet ports 72b and 72c. A fluid tube 32 on the cylinder 34 side is coupled to the inlet port 72a of the tube coupling 72, and the other end portion of each of coupling tubes 75 coupled to the air vents P of the two solenoid valves 71 is coupled to a corresponding one of the two outlet ports 72b and 72c. Air from the tube coupling 72 side is supplied to the air vent P of each solenoid valve 71.

When the two solenoids 73 and 74 of the two solenoid valves 71 are off, all the air vents P, A, B, R1, and R2 are held in the closed state. When one solenoid 73 is turned on, the internal flow paths in the solenoid valve 71 are switched such that the air vents P and R2 respectively communicate with the air vents A and B as indicated by the solid arrows in FIG. 21. When the other solenoid 74 is turned on, the internal flow paths in the solenoid valve 71 switched such that the air vents P and R1 respectively communicate with the air vents B and A as indicated by the dotted arrows in FIG. 21. The arrangements of other portions are the same as those in the first embodiment.

The function of the above arrangement will be described next. In this embodiment, when a joystick 37 is tilted in the UP direction, the solenoid 73 of one solenoid valve 71 of the solenoid valve unit 30 is turned on. In this state, air flows from the air vent P to the air vent A of the solenoid valve 71 on the side where the solenoid 73 is turned on, and is sent to the pressurization chamber 15 in the UP direction. At this time, the air vent B communicates with the air vent R2, and air in the DOWN direction is exhausted outside. As a consequence, the bending portion 10 bends in the UP direction.

When the operator stops operating the joystick 37 while the bending portion 10 is bent in the UP direction, the solenoid 73 is turned off. In this state, therefore, the air vent P of the solenoid valve 71 is closed to prevent air from being sent from the air vent P. In addition, the air vents A and B are closed to seal the air in the fluid supply tube 17 and pressurization chamber 15 in the UP direction. The bending portion 10 is therefore kept bent in the UP direction.

When the bending operation of the bending portion 10 in the UP direction is to be performed in the same manner as in the first embodiment, control operation shown in FIGS. 22A and 22B is performed. Referring to FIGS. 22A and 22B, "J9" and "J10" indicate the operation state of the joystick 37; "a9" and "a10", the operation state of the solenoid 73; and "b9" and "b10", the operation state of the solenoid 74.

When the operator tilts the joystick 37 in the UP direction from the 0-point position as indicated by "J9" in FIG. 22A, the solenoid 73 is turned on/off, as indicated by "a9" in FIG. 22A. When the operator stops tilting the joystick 37 at time t11, the solenoid 73 is turned off. At the same time, a 1-pulse operation signal is output to the solenoid 74, as indicated by "b9" in FIG. 22A. When the solenoid 74 is kept on for a 1-pulse period, air in the pressurization chamber 15 in the UP direction is exhausted, and a small amount of air is supplied into the pressurization chamber 15 in the DOWN direction, thereby quickly stopping the bending operation of the bending portion 10.

When the operator operates the joystick 37 in a direction to return the bent state of the bending portion 10 from the state of being bent in the UP direction at time t12 as indicated by "J10" in FIG. 22B, the solenoid 74 is turned on/off, as indicated by "a11" in FIG. 22B. In this case, therefore, air is released from the pressurization chamber 15 in the UP direction and air is supplied into the pressurization chamber 15 in the DOWN direction, thereby restoring the bent state of the bending portion 10.

When the operator stops tilting the joystick 37 at time t13, the solenoid 74 is turned off. At the same time, a 1-pulse operation signal is output to the solenoid 73, as indicated by "a10" in FIG. 22B. When the solenoid 73 is kept on for a 1-pulse period, air in the pressurization chamber 15 in the DOWN direction is exhausted, and a small amount of air is supplied into the pressurization chamber 15 in the UP direction, thereby quickly stopping the bending operation of the bending portion 10.

In this method, air is supplied into both the pressurization chambers 15 in the UP and DOWN directions (or the RIGHT and LEFT directions), and bending of the bending portion 10 is controlled by this balance between the amounts of air supplied. A pressure is produced in each fluid supply tube 17 (at a level where the bending of the bending portion 10 is not greatly affected), and hence the bending portion 10 quickly starts bending when air for bending operation is sent to the bending portion 10. As described above, with the use of the solenoid valves 71 each formed from a 3-position, 5-port valve, the bending operation of the bending portion 10 can be controlled in the same manner as in the first embodiment.

The following effects can be obtained by the above arrangement. In this embodiment, since the solenoid valve unit 30 uses the two solenoid valves 71 each formed from a 3-position, 5-port valve, the number of solenoid valves incorporated in the solenoid valve unit 30 can be decreased as compared with the first embodiment, and a simple arrangement can be realized.

In addition, since the bending operation of the bending portion 10 can be controlled in the same manner as in the first embodiment, the operator can bend the bending portion 10 quickly and accurately as in the first embodiment.

Figure 23:
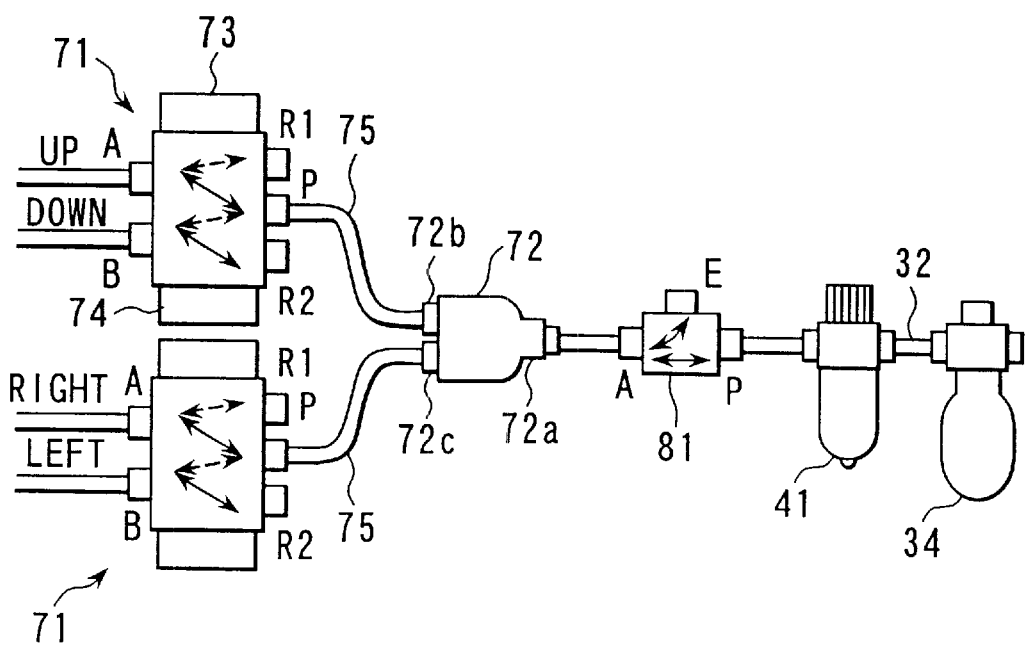
FIG. 23 is a schematic view showing the arrangement of the driving mechanism of a pneumatic actuator in an endoscope apparatus according to the sixth embodiment of the present invention.

FIG. 23 shows the sixth embodiment of the present invention. In this embodiment, the arrangement of the solenoid valve unit 30 in the endoscope apparatus 1 of the first embodiment (see FIGS. 1 to 12) is modified as follows.

In this embodiment, a solenoid valve 81 that is a 3-port valve having three air vents (ports) A, E, and P is interposed between a flowmeter 41 and a tube coupling 72 in a solenoid valve unit 30 including two solenoid valves 71 each formed from a 3-position, 5-port valve as in the fifth embodiment (see FIGS. 21 to 22B). A cylinder 34 is connected to the air vent P of the solenoid valve 81 through the regulator 41. An inlet port 72a of the tube coupling 72 is coupled to the air vent A of the solenoid valve 81. The arrangements of other portions are the same as those in the fifth embodiment.

The function of the above arrangement will be described next. The basic operation of this embodiment is the same as that of the fifth embodiment except that air can be released from pressurization chambers 15 of a hydropneumatic actuator 109 by switching the solenoid valve 81, as needed.

If, for example, the solenoid valve 81 is turned off, and a solenoid 73 of the solenoid valve 71 for vertical bending operation is turned on for a predetermined period of time, air in the DOWN direction is released. In this state, if a solenoid 74 is turned on, air in the UP direction can be released.

If the solenoid valve 71 for horizontal bending operation is operated in the same manner, air in all the pressurization chambers 15 of the hydropneumatic actuator 109 can be released. For example, the bent state of a bending portion 10 can be neutralized by performing this operation when a joystick 37 is moved to the neutral position.

With the above arrangement, the following effect can be obtained. In this embodiment, when the joystick 37 is moved to the neutral position, the bending of the bending portion 10 can be reset to neutralize the bent state of the bending portion 10, as needed.

Figure 24A:
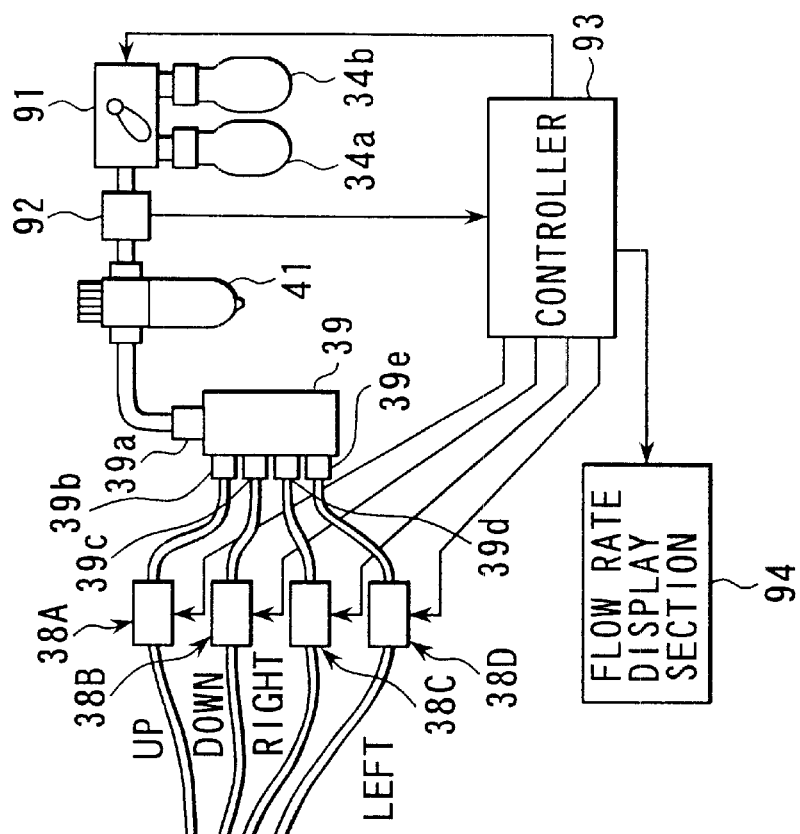
FIG. 24A is a schematic view showing the arrangement of the driving mechanism of a pneumatic actuator in an endoscope apparatus according to the seventh embodiment of the present invention.
Figure 24B:
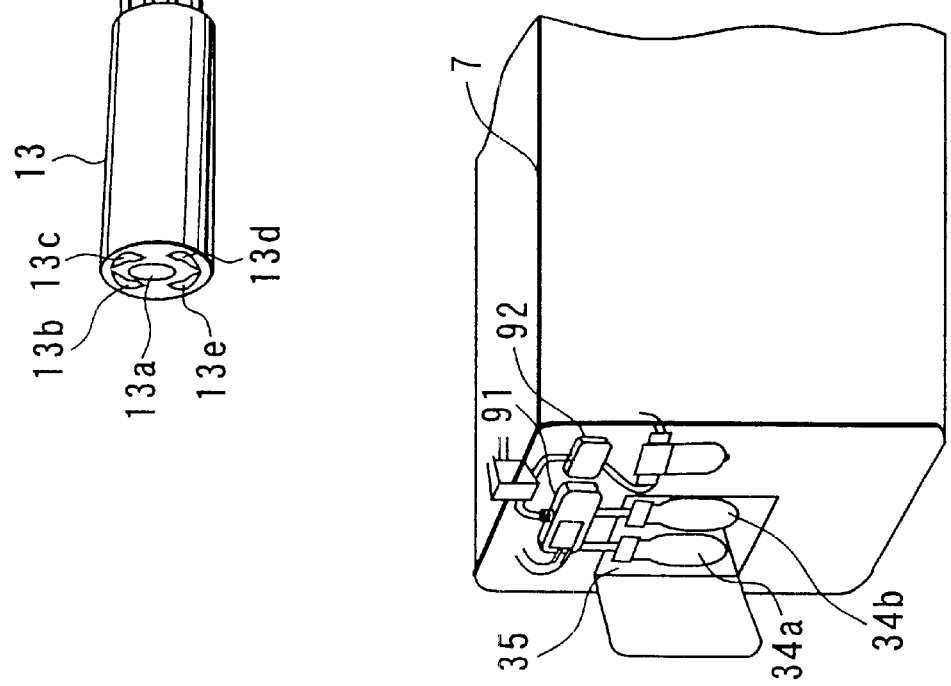
FIG. 24B is a perspective view showing the main part of the endoscope apparatus having two cylinders in a carrying case.

FIGS. 24A and 24B show the seventh embodiment of the present invention. In this embodiment, the arrangement of the solenoid valve unit 30 in the endoscope apparatus 1 of the first embodiment (see FIGS. 1 to 12) is further modified as follows.

In this embodiment, as shown in FIG. 24B, a cylinder 34a and spare cylinder 34b are placed side by side in a housing chamber 35 of a cylinder 34 in a carrying case 7.

FIG. 24A shows a piping method for the two cylinders 34a and 34b. The two cylinders 34a and 34b are coupled to a switching valve 91. A flowmeter 92 is interposed between the switching valve 91 and a regulator 41. A controller 93 is connected to the flowmeter 92.

The switching valve 91, four flow path switching mechanism portions 38A to 38D, and a flow rate display section 94 on a monitor are connected to the controller 93. In bending a bending portion 10, the flowmeter 92 detects the flow rate of air from one of the cylinders 34a and 34b, and the resultant information is stored in the controller 93. The flow rate is then displayed on the flow rate display section 94 on the monitor. The arrangements of other portions are the same as those in the first embodiment.

The function of the above arrangement will be described next. In this embodiment, when the operator bends the bending portion 10, air is sent while the flowmeter 92 detects the flow rate of air flowing from one of the cylinders 34a and 34b. The measurement data about the amount of air is sent from the flowmeter 92 to the controller 93 to display the flow rate (or the remaining amount of air in the cylinder) on the flow rate display section 94. This allows the operator to know the amount of air used (or remaining amount of air) in the cylinder 34a or 34b.

If air in the cylinder 34a (or 34b) in use runs out, the switching valve 91 is used to switch the spare cylinder 34b (or 34a) to the flow path. This makes it possible to continue bending operation by using the spare cylinder 34b (or 34a) even if air in the cylinder 34a (or 34b) in use runs out.

With the above arrangement, the following effect can be obtained. In this embodiment, the operator can know the amount of air used in the cylinder 34a or 34b at a glance by visually checking the flow rate (or the remaining amount of air in the cylinder) displayed on the flow rate display section 94. This makes it possible to know when the cylinder 34a (or 34b) in use needs to be replaced, and facilitates operation for an inspection, e.g., preparing a cylinder.

Note that the switching valve 91 may be formed by a solenoid valve to automatically switch the two cylinders 34a and 34b.

Figures 25A, 25B:
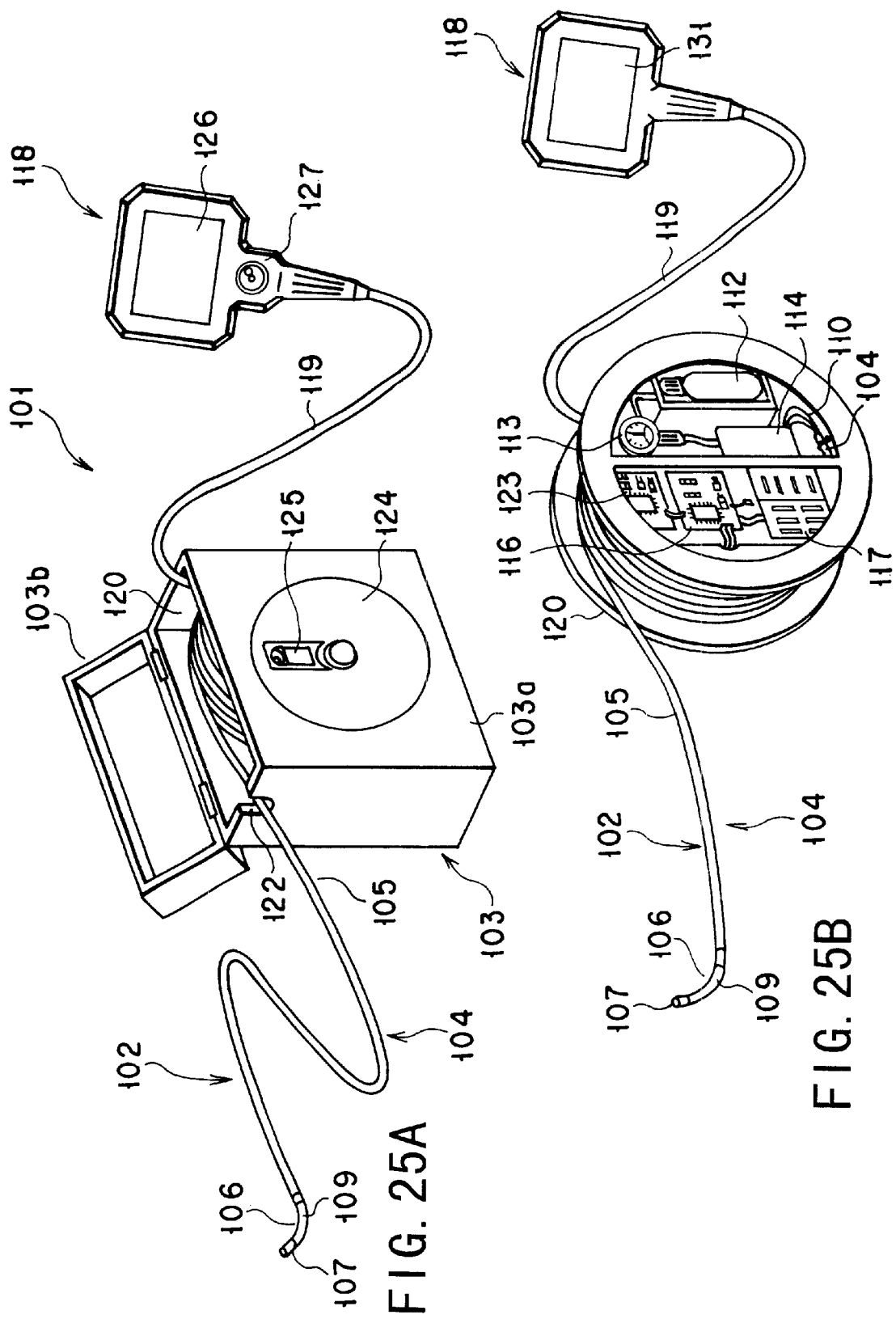
FIG. 25A is a perspective view showing the overall system of an endoscope apparatus according to the eighth embodiment of the present invention.
FIG. 25B is a perspective view showing a state wherein a fluid source is housed in a drum around which the scope insertion portion of the endoscope body is wound.

FIGS. 25A to 27 show the eighth embodiment of the present invention. FIG. 25A shows the schematic arrangement of the overall system of an endoscope apparatus 101 of this embodiment. The endoscope apparatus 101 has an endoscope body 102 and a carrying case 103 for housing the overall system of the endoscope body 102.

In addition, as shown in FIG. 25B, the endoscope body 102 has a long insertion portion 104 to be inserted into a tubular cavity object. The insertion portion 104 has a long flexible portion 105, a bending portion 106 coupled to the distal end portion of the flexible portion 105, and a distal end constituent portion 107 placed at the at the very end of the bending portion 106. The distal end constituent portion 107 has an image sensing function portion 108 for sensing an endoscopic image, as shown in FIG. 26B. The image sensing function portion 108 is a combination of a CCD and an illumination LED.

The bending portion 106 of the endoscope body 102 is formed from a hydropneumatic actuator 109 for performing bending operation by supplying hydropneumatic pressures to pressurization chambers 15 as in the first embodiment (see FIGS. 1 to 12). The hydropneumatic actuator 109 has a multi-lumen tube 13 in which a plurality of (four in this embodiment) lumens 13b, 13c, 13d, and 13e, each having an arcuated cross-section, are formed in the tube wall around a cylindrical central lumen 13a at equal intervals in the circumferential direction as shown in FIGS. 3B and 3C. The two end portions, i.e., the front and rear end portions, of each of the four lumens 13b, 13c, 13d, and 13e of the multi-lumen tube 13, each of which has an arcuated cross-section, are sealed with a filler 14 made of silicone, thereby forming four pressurization chambers 15 respectively corresponding to four bending directions, i.e., UP, DOWN, RIGHT, and LEFT directions. By selectively supplying a fluid into the fourth pressurization chambers 15, the arcuated lumen of the pressurization chamber 15 extends in the longitudinal direction to bend the bending portion 106.

As shown in FIG. 26B, the distal end portions of fluid supply tubes 110 are coupled to the fourth pressurization chambers 15 of the hydropneumatic actuator 109. The proximal end portions of the fluid supply tubes 110 are connected to a fluid source 111 in the carrying case 103. A driving fluid is supplied from the fluid source 111 to the pressurization chambers 15 of the hydropneumatic actuator 109 through the fluid supply tubes 110.

Figure 27:
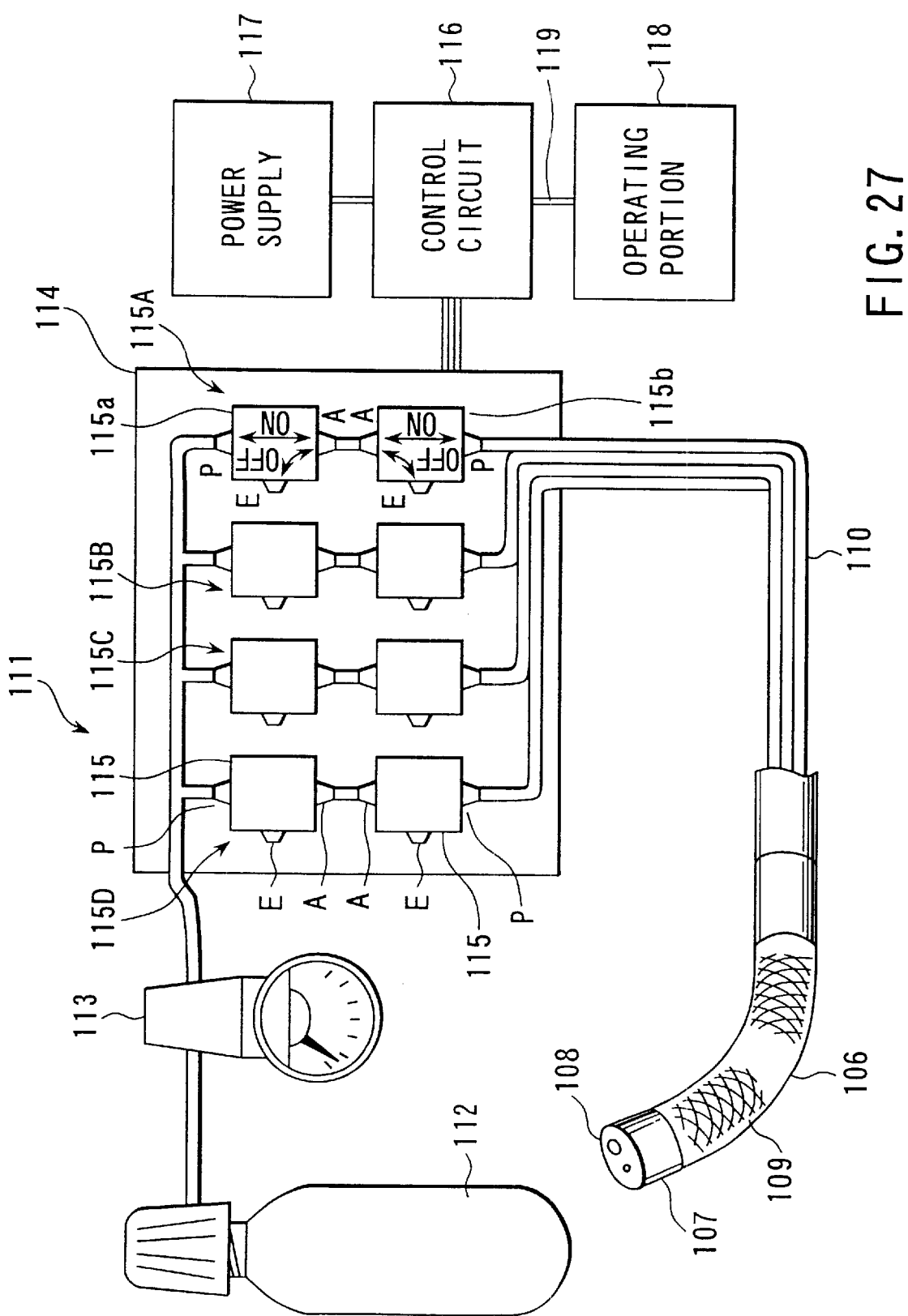
FIG. 27 is a schematic view showing the driving mechanism of a pneumatic actuator in the endoscope apparatus according to the eighth embodiment.

As shown in FIG. 27, the fluid source 111 includes a cylinder 112 serving as a pneumatic pressure source, a regulator 113 for adjusting the pressure of the gas supplied from the cylinder 112, and a valve unit 114 connected to the regulator 113. The gas sent from the cylinder 112 through the regulator 113 is supplied to the valve unit 114. The valve unit 114 controls supply/exhaustion of the gas supplied to each pressurization chamber 15 of the hydropneumatic actuator 109.

A plurality of solenoid valves 115 are incorporated in the valve unit 114. In this embodiment, the valve unit 114 incorporates a total of eight solenoid valves 115, two for each of the fluid supply tubes 110 communicating with the four pressurization chambers 15 corresponding to the respective bending directions, i.e., the UP, DOWN, RIGHT, and LEFT directions, of the hydropneumatic actuator 109.

Note that two solenoid valves 115a and 115b inserted in a flow path in one bending direction are connected in series with each other. The two solenoid valves 115a and 115b in each of the flow paths corresponding to the four bending directions make up a corresponding one of flow path switching mechanism portions 115A to 115D for switching the open and close states of the respective flow paths.

The flow path of the gas supplied from the regulator 113 branches into four branch tube paths corresponding to the four bending directions in the valve unit 114 so as to communicate with the flow path switching mechanism portions 115A to 115D, respectively. The flow path switching mechanism portions 115A to 115D respectively switch the flow paths in the UP, DOWN, RIGHT, and LEFT directions.

Each solenoid valve 115 in the valve unit 114 is a 3-port solenoid valve having air vents P and A and an exhaust vent E. When each valve 115 is turned on, the air vent P communicates with the air vent A. When each valve 115 is turned off, the exhaust vent E communicates with the air vent A, and the air vent P closes.

The two valves 115 in each of the four bending directions, i.e., the solenoid valve 115a placed on the cylinder 112 side and the solenoid valve 115b placed on the hydropneumatic actuator 109 side, are connected to each other through the air vents A in opposite positions.

In the four flow path switching mechanism portions 115A to 115D corresponding to the four bending directions, when the two solenoid valves 115a and 115b in one of the bending directions are on, the gas from the cylinder 112 is sent to the corresponding pressurization chamber 15 in the hydropneumatic actuator 109 through the solenoid valves 115a and 115b, thereby bending the hydropneumatic actuator 109 in that bending direction.

When the solenoid valve 115b is turned off afterward, the gas sent to the pressurization chamber 15 is held. If the solenoid valve 115a is kept on in this state, the gas from the cylinder 112 is kept exhausted from the exhaust vent E of the solenoid valve 115b. In order to save the gas, therefore, the solenoid valve 115a must be turned off to stop the flow of gas from the cylinder 112.

When the gas stored in the hydropneumatic actuator 109 is to be exhausted, the solenoid valve 115b is turned on, and the solenoid valve 115a is turned off. With this operation, the gas is exhausted from the exhaust vent E of the solenoid valve 115a.

A control circuit 116 for controlling the operations of the solenoid valves 115 in the valve unit 114 is connected to the fluid source 111. A power supply 117 is connected to the control circuit 116, and an operating portion 118 for bending the bending portion 106 of the endoscope body 102 is connected to the control circuit 116 through a cable 119.

The carrying case 103 includes a case body 103a having an upper surface opening portion and a cover 103b for retractably covering the upper surface opening portion of the case body 103a. A cylindrical drum 120 around which the insertion portion 104 of the endoscope body 102 can be wound is placed in the carrying case 103. The insertion portion 104 of the endoscope body 102 can be housed in the carrying case 103, together with the drum 120 around which the insertion portion 104 is wound.

As shown in FIG. 26A, a plurality of rollers 121 for rotatably supporting the drum 120 are attached to the bottom portion of the carrying case 103. Each of these rollers 121 is supported to be rotatable around the center axis. The drum 120 is rotatably supported on the rollers 121 on the bottom portion of the carrying case 103.

A scope extraction port 122 is formed in an upper edge portion of one side portion of the case body 103a of the carrying case 103. The insertion portion 104 of the endoscope body 102 which is wound around the drum 120 can be extracted outside through the scope extraction port 122 of the carrying case 103.

As shown in FIG. 25B, a plurality of built-in members are mounted in the drum 120. In this embodiment, the drum 120 houses the cylinder 112 of the fluid source 111 serving as a drive source for driving the bending portion 106 of the endoscope body 102, the regulator 113, the valve unit 114, the control circuit 116, the power supply 117, and an image circuit 123 (to be described later).

A circular drum cover 124 is detachably mounted on the side surface opening portion of the drum 120. Note that the case body 103a of the carrying case 103 has a circular hole which has the same diameter as that of the drum cover 124 and in which the drum cover 124 is fitted. The drum cover 124 has a foldable handle 125 for rotating the drum. The handle 125 is used to take up the insertion portion 104 of the endoscope body 102. The handle 125 can be folded and housed in the drum cover 124 while it is not used.

The operating portion 118 located outside the drum 120 is also housed in the carrying case 103. As shown in FIG. 25A, the operating portion 118 includes a liquid crystal display 126 for displaying the image information obtained by the image sensing function portion 108 of the endoscope body 102, and a joystick 127 for performing bending operation.

As shown in FIG. 26B, the liquid crystal display 126 of the operating portion 118 displays the picture generated by the image circuit 123 in the drum 120 on the basis of a signal sent from the image sensing function portion 108 of the endoscope body 102 to the image circuit 123 through a cable (not shown) placed in the insertion portion 104.

The controlled variable of the control circuit 116 is adjusted by operating the joystick 127 of the operating portion 118. More specifically, in accordance with the inclination angle of the joystick 127 of the operating portion 118, the control circuit 116 controls the fluid source 111 to adjust the amount of fluid supplied from the fluid source 111 to the fluid supply tube 110.

With the above arrangement, the following effects can be obtained. In this embodiment, the insertion portion 104 of the endoscope body 102 is housed in the carrying case 103 while being wound around the drum 120, and the cylinder 112 of the fluid source 111 serving as a drive source for driving the bending portion 106 of the endoscope body 102, the regulator 113, the valve unit 114, the control circuit 116, the power supply 117, and image circuit 123 (to be described later) are also housed in the carrying case 103. This makes it possible to reduce the size of the overall system of the endoscope apparatus 101, thus facilitating carrying and handling the endoscope apparatus.

In addition, the use of the valve unit 114 having the small cylinder 112 and the plurality of solenoid valves 115 incorporated in the fluid source 111 can shorten the time required to pressurize each pressurization chamber 15 of the hydropneumatic actuator 109. Therefore, the bending responsiveness and controllability of the bending portion 106 of the endoscope body 102 can be improved.

Note that the liquid crystal display 126 is not limited to a liquid crystal display as long as it is a display. For example, a small CRT display or plasma display may be used. The image sensing function portion 108 may be a combination of a CMOS image sensor and an illumination LED. The joystick 127 of the operating portion 118 may be a joypad instead of a joystick.

In this embodiment, the drum 120 is rotated with the rotation handle 125. However, a motor may be mounted on the rollers 121 to automatically rotate the drum 120.

In this embodiment, the operating portion 118 of the endoscope body 102 has the liquid crystal display 126 and the joystick 127 for performing bending operation. A touch panel type liquid crystal panel operating portion 131 may replace the joystick 127 of the operating portion 118, as shown in FIG. 25B.

Figure 28:
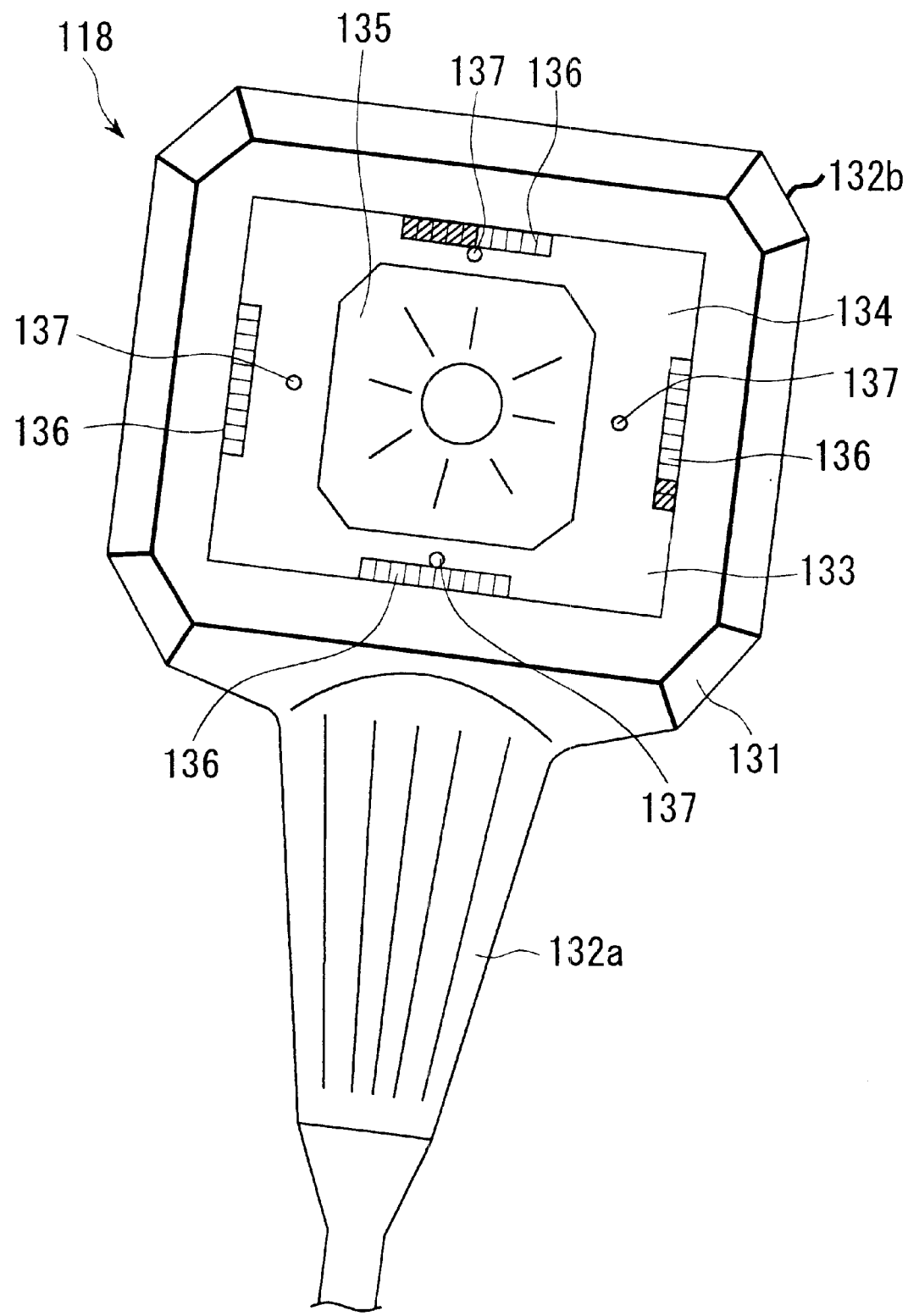
FIG. 28 is a plan view showing the first modification of the operating portion of the endoscope apparatus according to the eighth embodiment.

In this modification, the operating portion 118 has a grip 132*a* and operating portion body 132*b*, as shown in FIG. 28. The liquid crystal panel operating portion 131 is prepared on the operating portion body 132*b*. The liquid crystal panel operating portion 131 has a touch panel type liquid crystal display 133. A touch panel 134 for detecting pressure is placed on the entire surface of the liquid crystal display 133, so the position of a point which the operator touches with his/her finger can be detected.

An image display portion 135 for displaying an endoscopic image from the image sensing function portion 108 at the distal end of the endoscope body 102 is placed in the center of the liquid crystal display 133. In addition, four controlled variable display portions 136 for presenting controlled variables processed by the control circuit 116 and four operation instructing portions 137 indicating portions to be subjected to bending operation are arranged around the image display portion 135. The four controlled variable display portions 136 and four operation instructing portion 137 are arranged in correspondence with the four bending directions, i.e., the UP, DOWN, RIGHT, and LEFT directions.

Each controlled variable display portion 136 presents a controlled variable in the form of a bar graph, and displays the amount of fluid sent to the hydropneumatic actuator 109 (e.g., the open time of the valves 115*a* and 115*b* in the valve unit 114) in the lengths of bars of different colors. As shown in FIG. 28, the controlled variable display portions 136 respectively display controlled variables in the respective bending directions, i.e., the UP, DOWN, RIGHT, and LEFT directions, in the form of bars.

Referring to FIG. 28, if the controlled variable (the amount of gas supplied) in the UP direction is 0, a green bar is displayed on the upper controlled variable display portion 136. As the amount of gas supplied in the UP direction increases, the color of the bar on the controlled variable display portion 136 gradually changes to red from the left end. When the controlled variable reaches its maximum value, the color of the entire bar changes to red.

Circular indicators as the operation instructing portions 137 are displayed near the respective controlled variable display portions 136 in correspondence with the respective bending directions, i.e., the UP, DOWN, RIGHT, and LEFT directions. The operator can give an instruction to the control circuit 116 by pressing one of the operation instructing portions 137 with his/her finger while watching an endoscopic image on the image display portion 135 of the liquid crystal panel operating portion 131.

If, for example, the operator presses the operation instructing portion 137 in the UP direction, the corresponding position signal is sent from the touch panel 134 to the control circuit 116. The control circuit 116 determines from the position signal that the pressed point indicates the UP direction, and drives the valve unit 114 to turn on both the solenoid valves 115*a* and 115*b* corresponding to the UP direction. When the operator moves his/her finger off the touch panel 134, the control circuit 116, which receives the corresponding signal, turns off both the solenoid valves 115*a* and 115*b* to hold the pressure.

When the operator presses the operation instructing portion 137 corresponding to the DOWN direction, the solenoid valve 115*b* corresponding to the UP direction is turned on to release the pressure. Similar operation is performed in other bending directions.

In this modification, since the operating portion 118 has the touch panel type liquid crystal display 133, the operator can perform operation linked to an endoscopic image displayed on the image display portion 135. This makes it possible to improve the operability of the operating portion 118.

In the first modification described above, the control circuit 116 may have a control means for changing the controlled variable in accordance with the bar position of each controlled variable display portion 136 serving as an operation instruction portion when the operator touches the controlled variable display portion 136. If, for example, the operator presses the left side of the bar of each of the upper and lower controlled variable display portions 136, the ON time of the solenoid valves 115*a* and 115*b* shortens. As the pressing position on the bar of the controlled variable display portion 136 shifts to the right, the ON time of the two valves 115*a* and 115*b* is prolonged. Likewise, when the operator presses the lower side of the bar of each of the left and right controlled variable display portions 136, the ON time of the valves shortens. As the pressing position on the bar shifts to the upper side, the ON time is prolonged. In this modification, the operability of the operating portion 118 can be improved.

Figure 29:
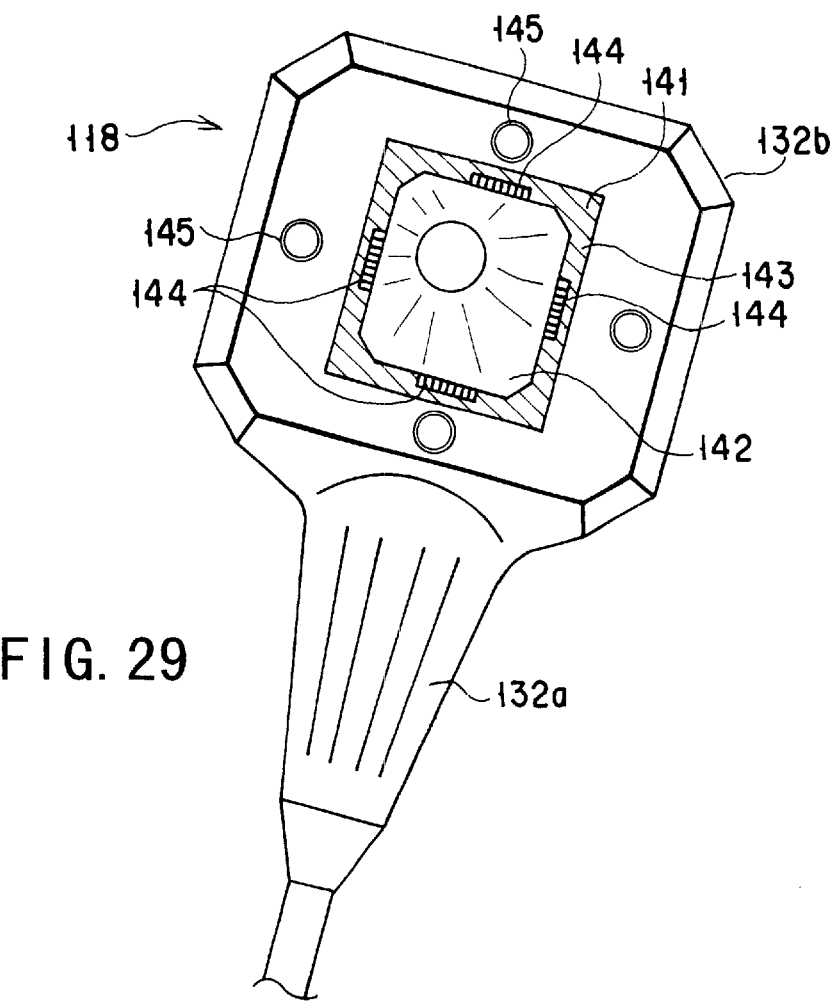
FIG. 29 is a plan view showing the second modification of the operating portion of the endoscope apparatus according to the eighth embodiment.

FIG. 29 shows the second modification of the operating portion 118 according to the eighth embodiment. In this modification, a liquid crystal display 141 is placed in the center of the operating portion body 132*b* of the operating portion 118. An image display portion 142 and a touch panel portion 143 in the form of a substantially rectangular frame, which is placed around the image display portion 142, are arranged on the liquid crystal display 141. The touch panel portion 143 has four controlled variable display portions 144 which also serve as operation instructing portions for bending operation and are arranged around the image display portion 142.

The operator touches the controlled variable display portion 144 located in the direction in which he/she wants to bend the endoscope body 102, i.e., he/she wants to move the image displayed on the image display portion 142, while watching the image display portion 142. The control circuit 116 then controls the valve unit 114 to bend the bending portion 106 in that direction.

In this modification, the four controlled variable display portions 144 that also serve as operation instructing portions are arranged on the touch panel portion 143 on the liquid crystal display 141. Since the touch panel portion 143 has a plurality of functions, the liquid crystal panel and touch panel can be reduced in size.

In the first and second modifications, if a sensor (pressure or flow rate sensor) (not shown) is placed between the valve unit 114 and each fluid supply tube 110 to reflect a signal from the sensor in the controlled variable display portions 136 and 144, high-precision information closer to the actual bending angle of the bending portion 106 can be displayed on the controlled variable display portions 136 and 144. This makes it possible to implement display operation with higher reliability.

As shown in FIG. 29, four bending stop buttons 145 may be arranged around the liquid crystal display 141 in the second modification in correspondence with the respective bending directions. In this case, when the operator presses one of the bending stop buttons 145, the control circuit 116 controls the respective valves 115 in the valve unit 114 to prevent a fluid from flowing into the pressurization chamber 15 in the hydropneumatic actuator 109 in the corresponding direction.

More specifically, if, for example, the operator presses the upper bending stop button 145, a corresponding signal is sent to the control circuit 116. The control circuit 116 then controls the two solenoid valves 115a and 115b corresponding to the UP direction. This prevents a gas from flowing from the cylinder 112 to the pressurization chamber 15 in the hydropneumatic actuator 109 which corresponds to the UP direction, and holds this state. This operation can effectively save the gas in the cylinder 112 when the pressurization chamber 15 of the hydropneumatic actuator 109 punctures.

Assume that the image displayed on the image display portion 142 does not move no matter how the operator operates the operating portion 118 in normal bending operation. One of the conceivable causes for this trouble is a puncture in the pressurization chamber 15 of the hydropneumatic actuator 109 which corresponds to the operating direction. If the operator continues bending operation even after the pressurization chamber 15 punctures, a gas may flow into the punctured pressurization chamber 15 of the hydropneumatic actuator 109, resulting in a waste of gas.

In such a case, when the operator presses the bending stop button 145 to stop the supply of a gas to the punctured pressurization chamber 15 of the hydropneumatic actuator 109, a waste of gas can be suppressed, as in this modification. Therefore, a saving in gas can be expected in this modification.

Figure 30:
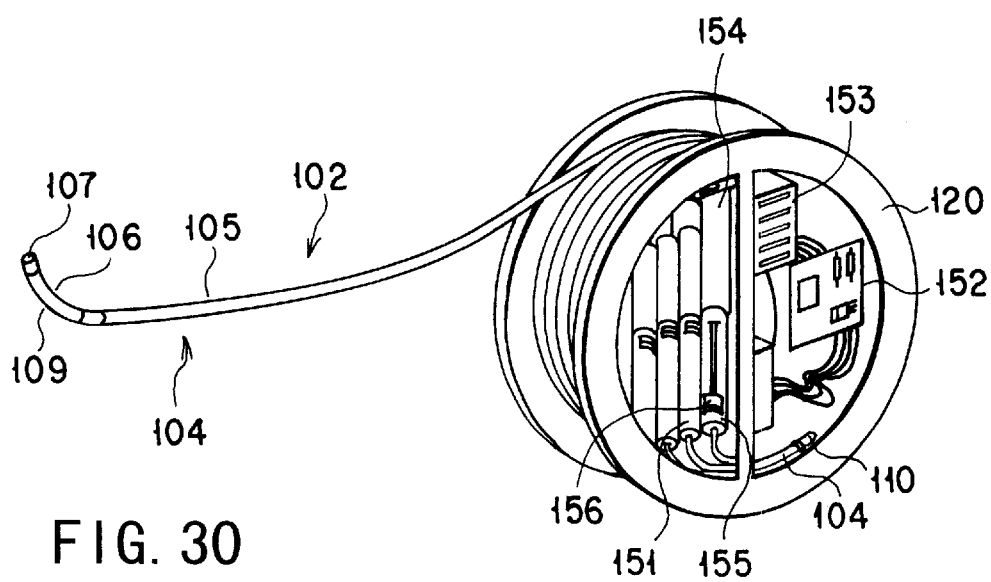
FIG. 30 is a perspective view showing how a fluid source is housed in a drum around which the scope insertion portion of the endoscope body according to the ninth embodiment of the present invention is wound.

FIG. 30 shows the ninth embodiment of the present invention. In this embodiment, the arrangement of the drum 120 in the endoscope apparatus 101 according to the eighth embodiment (see FIGS. 25A to 27) is modified as follows. Since the arrangements of other portions are the same as those in the eighth embodiment, the same reference numerals as in the eighth embodiment denote the same parts in FIG. 30, and a description thereof will be omitted.

In this embodiment, a drum 120 houses four syringe units 151 for sending compressed air to pressurization chambers 15 corresponding to the respective bending directions, i.e., the UP, DOWN, RIGHT, and LEFT directions, a control circuit 152 for controlling each syringe unit 151, and a power supply 153 for driving each syringe unit 151 and the control circuit 152.

Each syringe unit 151 includes a conversion mechanism portion 154 having a linear conversion gear for converting the rotation of a driving motor (not shown) into linear motion, and a syringe 155 for compressing air. A syringe pump is formed such that air is compressed by the linear motion of a piston 156 in the syringe 155.

A fluid supply tube 110 extending from the proximal end of an insertion portion 104 is connected to the distal end of each syringe 155. The proximal end portion of the insertion portion 104 extends into the drum 120 through a hole in the wall of the drum 120 and is fixed to the inner wall of the drum 120.

In bending a bending portion 106, the air compressed by the syringe unit 151 is supplied to a hydropneumatic actuator 109 in the bending portion 106 on the distal end of the endoscope body 102 through the fluid supply tube 110.

The function of the above arrangement will be described next. In this embodiment, when the operator operates a joystick 127 of an operating portion 118 in a desired bending direction, the syringe unit 151 in the bending direction corresponding to the operation of the joystick 127 operates. The air sent from the syringe 155 of the syringe unit 151 is sent to the pressurization chamber 15 of the hydropneumatic actuator 109 of the bending portion 106, thereby bending the bending portion 106.

When the operator stops operating the joystick 127, the bending portion 106 stops bending. In this case, if the insertion portion 104 of the endoscope body 102 is as long as 10 m or more, air from the syringe unit 151 is sent to the pressurization chamber 15 on the distal end with a time lag, and the bending portion 106 may not quickly stop bending. In this case, when the operator stops operating the joystick 127, control is performed to slightly return the piston 156 of the syringe unit 151 for sending air for bending operation in a direction opposite to the pressurizing direction. This makes it possible to stop bending the bending portion 106 more accurately and quickly.

With the above arrangement, the following effects can be obtained. This embodiment has a simple arrangement in which compressed air is supplied to the pressurization chamber 15 of the hydropneumatic actuator 109 by the linear motion of the piston 156 of the syringe unit 151, and the bend amount of the bending portion 106 can be controlled by controlling the position of the syringe 155.

The maximum amount of air compressed is determined by the size of a syringe pump formed by the piston 156 of each syringe unit 151, and excessive pressurization is avoided. Therefore, the bending operation of the bending portion 106 can be accurately controlled.

Figure 31:
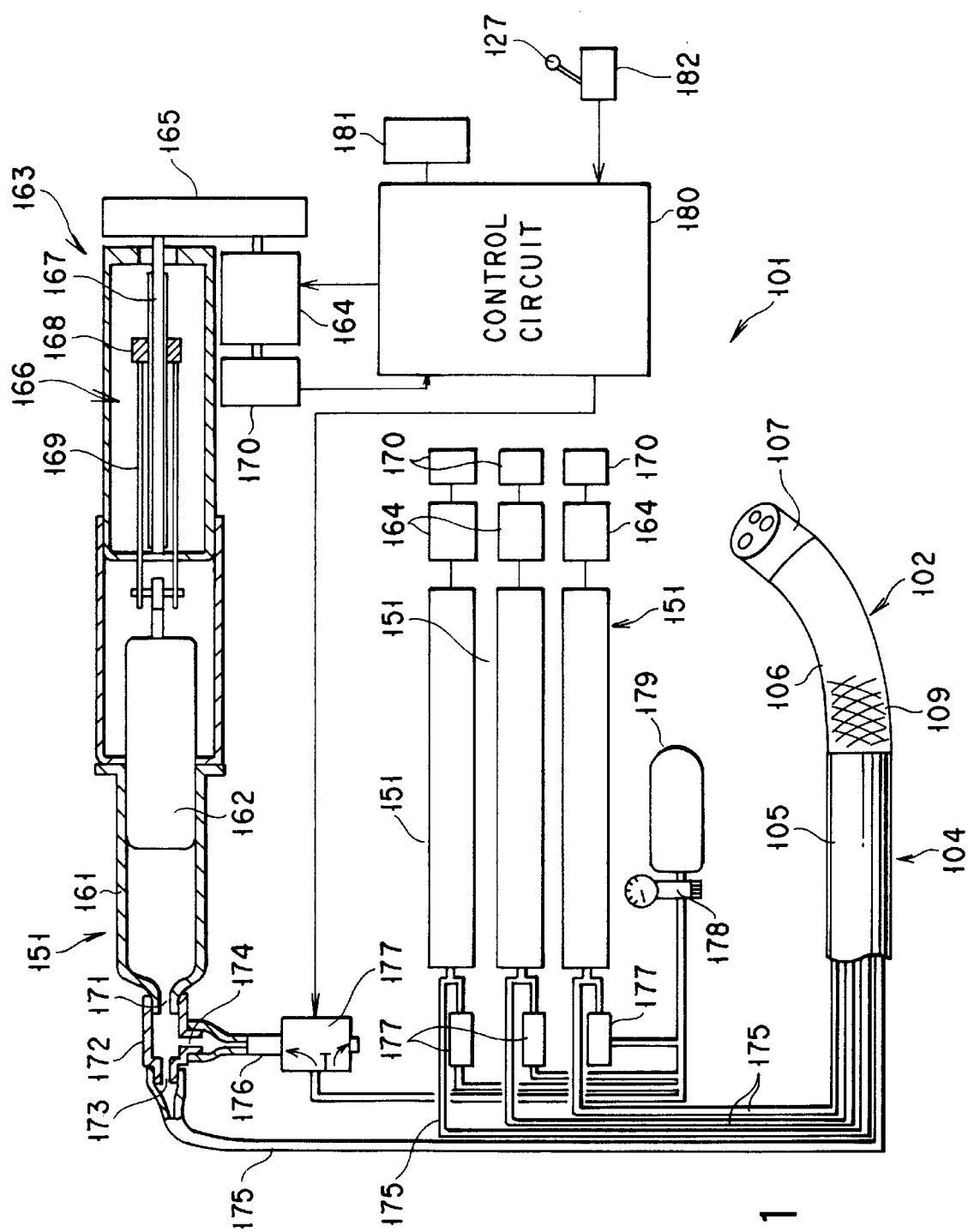
FIG. 31 is a schematic view showing the overall system of an endoscope apparatus according to the 10th embodiment of the present invention.
Figure 32A:
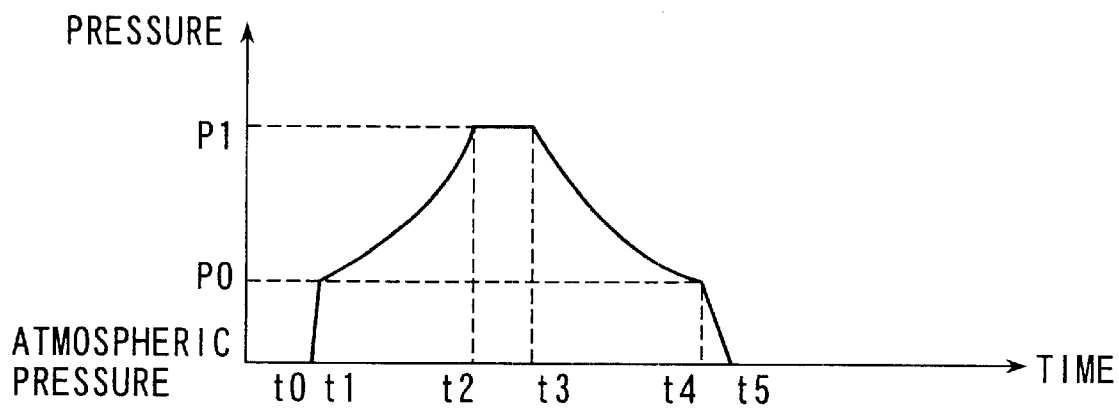
FIG. 32A is a graph showing the relationship between the internal pressure of a syringe housing and time when a bending signal is output in the endoscope apparatus according to the 10th embodiment.
Figure 32B:
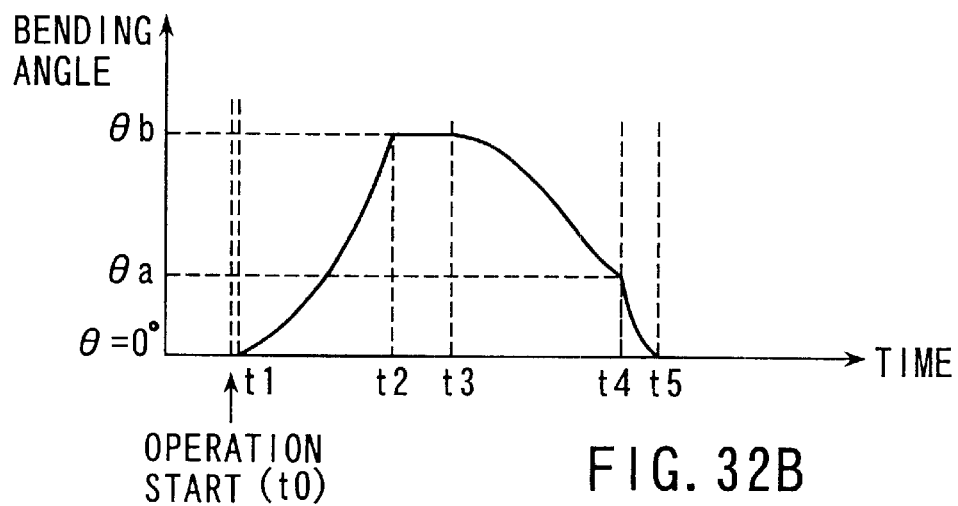
FIG. 32B is a graph showing the relationship between the bending angle of the bending portion and the time in the same case.

FIGS. 31, 32A, and 32B show the 10th embodiment of the present invention. In this embodiment, the arrangement of the syringe unit 151 of the endoscope apparatus 101 according to the ninth embodiment (see FIG. 30) is further modified as follows.

In addition to the arrangement of the syringe units 151 in the four bending directions in the ninth embodiment, this embodiment includes an arrangement for applying a pilot pressure into a syringe pump formed by a piston 156 of each syringe unit 151.

For example, the syringe unit 151 in the UP direction in this embodiment has a syringe housing 161, as shown in FIG. 31. A driving mechanism portion 163 for driving a piston 162 in the syringe housing 161 is coupled to the proximal end portion of the syringe housing 161.

The driving mechanism portion 163 has a motor 164 as a drive source and a linear mechanism 166 for converting the rotation of the motor 164 into linear motion through a reduction gear 165. The linear mechanism 166 is formed by a ball screw mechanism having a rod-like male thread portion 167 and a nut-like female thread portion 168 threadably engaged with the male thread portion 167. A piston shaft 169 of the piston 162 is coupled to the female thread portion 168. When the male thread portion 167 rotates upon transmission of the rotation of the motor 164 through the reduction gear 165, the female thread portion 168 moves back and forth to drive the piston 162. In this manner, the linear mechanism 166 converts the rotation of the motor 164 into reciprocal motion through the reduction gear 165 to drive the piston 162.

An encoder 170 is connected to the motor 164. The encoder 170 functions as a position sensor for the piston 162 in the syringe housing 161.

A discharge port 171 is formed in the distal end portion of the syringe housing 161. A base 172 is attached to the discharge port 171. The discharge port 171 has two tube coupling portions 173 and 174. A fluid supply tube 175 communicating with a pressurization chamber 15 corresponding to the UP direction is connected to the first tube coupling portion 173 as one of the tube coupling portions. One end portion of a fluid tube 176 on the pneumatic pressure source side is coupled to the second tube coupling portion 174 as the other tube coupling portion. The other end of the fluid tube 176 is connected to a cylinder 179 having a pressure adjusting unit 178 through a solenoid valve 177. The solenoid valve 177 can be switched to the following three states: the state wherein the valve causes the cylinder 179 to communicate with (open toward) the syringe housing 161; the state wherein the valve is completely closed; and the state wherein the valve causes the syringe housing 161 to communicate with (open toward) the atmosphere.

The solenoid valve 177 is connected to a control circuit 180. The motor 164 and encoder 170 are connected to the control circuit 180, together with a power supply 181 and a bending operation unit 182 having a liquid crystal display 126 and a joystick 127 for bending operation, like the operating portion 118 in the eighth embodiment (see FIGS. 25A to 27). ON/OFF of the solenoid valve 177 is controlled by a control signal from the control circuit 180.

Each of the syringe units 151 corresponding to the bending directions other than the UP direction, i.e., the DOWN, RIGHT, and LEFT directions, has the same arrangement as that of the syringe unit 151 corresponding to the UP direction. The four syringe pumps are connected in the same manner.

The control circuit 180 and power supply 181 are arranged in a drum 120 having the same arrangement as that in the endoscope apparatus 101 of the ninth embodiment. In bending a bending portion 106 of an endoscope body 102, upon reception of a bending instruction from the joystick 127 of the bending operation unit 182, the control circuit 180 outputs a driving signal to the motor 164 to push the piston 162 in the syringe housing 161 by an appropriate amount. With this operation, the pressurization chamber 15 in the bending direction corresponding to the operating direction of the joystick 127 expands to bend the bending portion 106. At this time, a signal from the encoder 170 is feedback to the control circuit 180 to improve the precision of control on the pushing position of the piston 162 in the syringe housing 161.

The function of the above arrangement will be described next. In this embodiment, before the joystick 127 is operated, i.e., when no operation signal is output from the joystick 127, the piston 162 in the syringe housing 161 is located at the rightmost travel limit position (origin) in FIG. 31.

In bending the bending portion 106 of the endoscope body 102, the operator tilts the joystick 127 in the direction in which he/she wants to bend the bending portion 106, while watching an endoscopic image on the liquid crystal display 126 of the bending operation unit 182. At this time, the control circuit 180 receives a tilting direction/angle signal from the joystick 127, and outputs a driving signal to the corresponding syringe pump.

FIG. 32A shows the relationship between an internal pressure P of the syringe housing 161 and time t when a bending signal corresponding to a given direction is output upon operation of the joystick 127. FIG. 32B shows the relationship between a bending angle $\theta$ of the bending portion 106 and time t in the same instance.

At time t0 at which an operation signal corresponding to a given direction is output upon operation of the joystick 127, the solenoid valve 177 is instantly switched to the state wherein the valve causes the cylinder 179 to communicate with the syringe housing 161. At time t1 at which a short period of time has elapsed since time t0 at which the operation signal was output, a control signal is output to quickly close the solenoid valve 177. At this time, the pressure P in the cylinder 179 has been adjusted to a pressure P0 set immediately before the bending portion 106 started moving upon expansion of the pressurization chamber 15.

At time t1, the motor 164 starts rotating and rotates at a constant speed. While an operation signal is output, the piston 162 in the syringe housing 161 is pushed to the left in FIG. 31 at a constant speed. At time t2 at which an internal pressure P1 is set in the syringe housing 161, the bending angle becomes $\theta$ b.

When, for example, a signal for bending the distal end constituent portion 107 in the opposite direction is input at time t3 after the bending angle $\theta$ b is held for a predetermined period of time, the piston 162 in the syringe housing 161 returns to the origin at a constant speed. At time t4 at which the piston 162 has returned to the origin, the internal pressure in the syringe housing 161 become P0. At this time, since the bending angle of the bending portion 106 exhibits hysteresis with respect to an increase/decrease in pressure due to the characteristics of the bending portion 106, the bending angle of the bending portion 106 does not become 0° at time t4, and the bending portion 106 stops bending at $\theta$ a.

At time t4 at which the piston 162 in the syringe housing 161 returns to the origin, a control signal is output to switch the solenoid valve 177 to the state wherein the valve causes the syringe housing 161 to communicate with the atmosphere. As a consequence, the bending angle of the bending portion 106 becomes 0° at time t5 at which a certain period of time has elapsed since time t4.

With the above arrangement, the following effects can be obtained. In this embodiment, at time t0 at which an operation signal corresponding to a given direction is output upon operation of the joystick 127, a pilot pressure is instantly applied from the cylinder 179 into the syringe housing 161. This makes it possible to bend the bending portion 106 with high responsiveness with respect to the bending operation signal. As a consequence, the operability improves.

Figure 33:
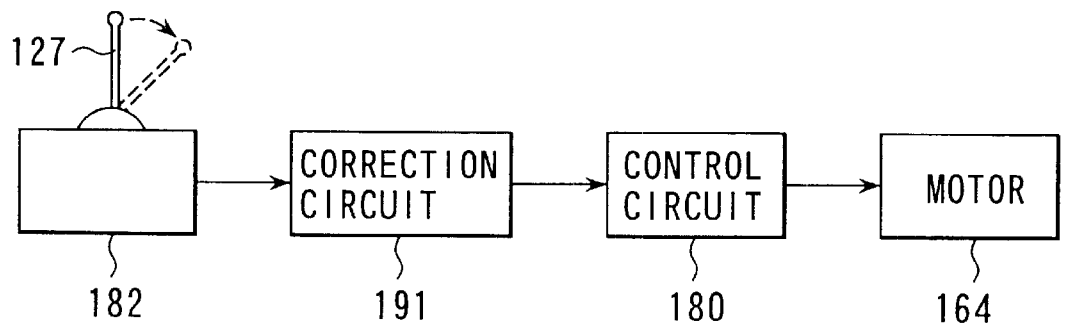
FIG. 33 is a schematic view showing the arrangement of the main part of the first modification of the endoscope apparatus according to the 10th embodiment.
Figure 34A:
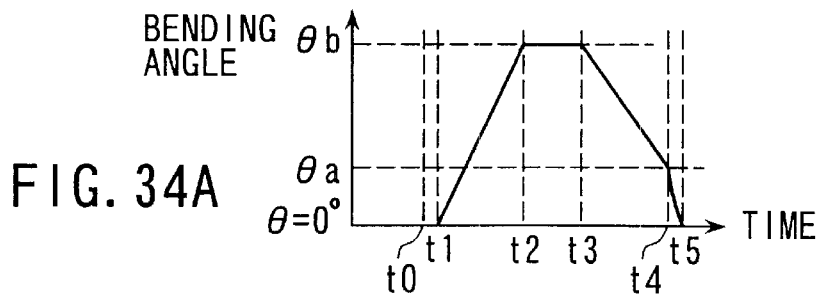
FIG. 34A is a graph showing the relationship between the internal pressure of the syringe housing and the time in a case wherein a bending signal is output in the endoscope apparatus according to the first modification of the 10th embodiment.
Figure 34B:
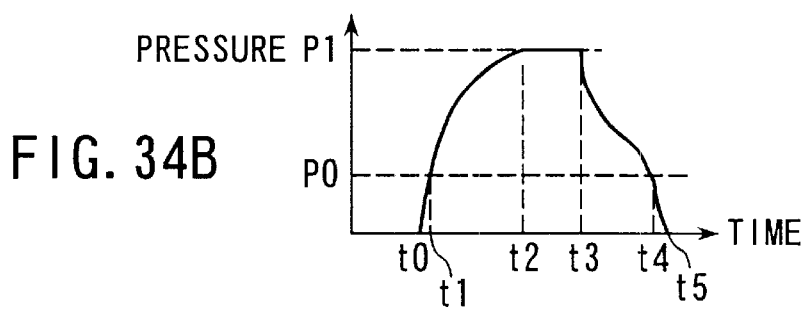
FIG. 34B is a graph showing the relationship between the bending angle of the bending portion and the time in the same case.

FIGS. 33, 34A, and 34B show the first modification of the 10th embodiment (see FIGS. 31, 32A, and 32B). In the endoscope apparatus 101 of the 10th embodiment, according to the relationship between the operation of the piston 162 in the syringe housing 161 and the bending angle $\theta$ of the bending portion 106, the responsiveness in bending operation improves. However, the time during which the bending operation signal is output does not linearly correspond to the bending angle. For this reason, the bending angle θ of the bending portion 106 abruptly increases after a lapse of a certain period of time (see FIG. 32B).

In this modification, therefore, a correction circuit 255 for changing the speed of the motor 164 to establish a linear relationship between the time during which a bending operation signal is output and the bending angle θ is placed between the bending operation unit 182 and the control circuit 180, as shown in FIG. 33.

In this modification, the rotational speed of the motor 164 is controlled to obtain a characteristic curve representing the internal pressure in the syringe housing 161 as shown in FIG. 34A. This makes it possible to linearly change the bending angle θ of the bending portion 106 with respect to time, as shown in FIG. 34B.

Figure 35:
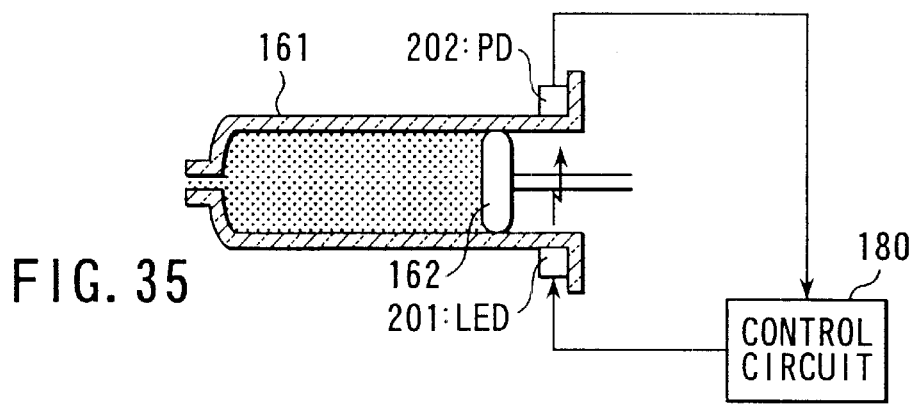
FIG. 35 is a schematic view showing the arrangement of the main part of the second modification of the endoscope apparatus according to the 10th embodiment.

FIG. 35 shows the second modification of the 10th embodiment (see FIGS. 31, 32A, and 32B). In this modification, the encoder 170 in the 10th embodiment is not used, and only the state wherein the piston 162 in the syringe housing 161 returns to the origin is detected.

In this modification, the syringe housing 161 is made of a transparent material. A light-emitting element (LED) 201 and light-receiving element, for example, photodiode device (PD) 202 are mounted on the outer surface of the proximal end portion of the syringe housing 161 so as to be spaced apart from each other by 180° and oppose each other. The light-emitting element 201 and light-receiving element 202 are connected to the control circuit 180. When the piston 162 in the syringe housing 161 passes through between the light-emitting element 201 and the light-receiving element 202, light is blocked, and hence the passage of the piston 162 can be detected. Note that a detection signal from the light-receiving element 202 is input to the control circuit 180.

In this modification, since the origin position of the piston 162 in the syringe housing 161 can be detected in bending the bending portion 106 of the endoscope body 102, the solenoid valve 177 in the 10th embodiment can be controlled. This modification can therefore reduce the size of the overall system as compared with the 10th embodiment using the encoder 170.

Figure 36:
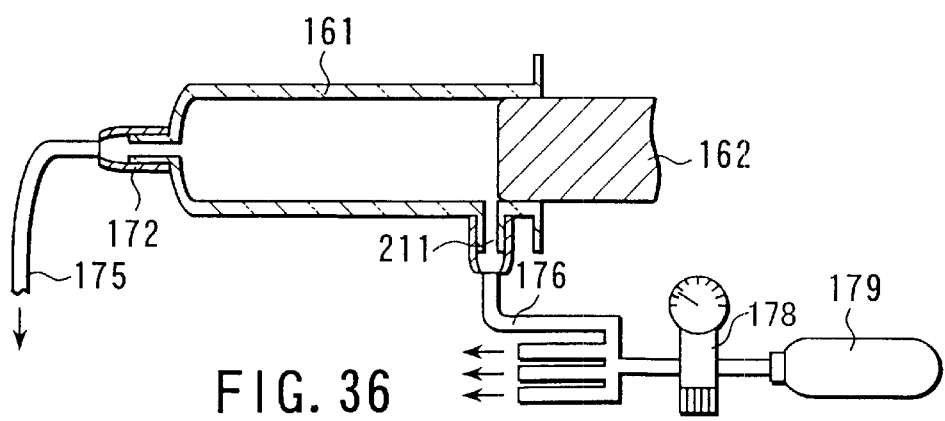
FIG. 36 is a schematic view showing the arrangement of the main part of the third modification of the endoscope apparatus according to the 10th embodiment.

FIG. 36 shows the third modification of the 10th embodiment (see FIGS. 31, 32A, and 32B). In this modification, the solenoid valve 177 used in the 10th embodiment is omitted, and a mechanism for applying a pilot pressure into each syringe pump is used.

In this modification, a tube 175 coupled to the pressurization chamber 15 of a hydropneumatic actuator 109 is directly connected to the discharge port 171 on the distal end of the syringe housing 161.

An origin-side opening portion 211 is formed in the outer surface of the syringe housing 161 on the proximal end side. The fluid tube 176 connected to the cylinder 179 through the pressure adjusting unit 178 is connected to the origin-side opening portion 211.

In this modification, in bending the bending portion 106 of the endoscope body 102, the pressure adjusting unit 178 has been adjusted to the pressure P0 immediately before the start of bending the bending portion 106. In this case, whenever the piston 162 is located at the origin position, the internal pressure in the syringe housing 161 is set to P0.

When the piston 162 in the syringe housing 161 moves forward in bending the bending portion 106, the piston 162 closes the origin-side opening portion 211.

According to the arrangement of this modification, since the solenoid valve 177 used in the 10th embodiment can be omitted, and the mechanism for applying a pilot pressure into each syringe pump can be used, the overall system of the endoscope apparatus can be reduced in size.

Note that the driving mechanism portion 163 of the syringe unit 151 in the 10th embodiment is not limited to the combination of the motor 164 and the linear mechanism 166 having a linear conversion gear. A linear motor may be used.

FIGS. 37 to 42 show the 11th embodiment of the present invention. In this embodiment, the arrangement of the drum 120 in the endoscope apparatus 101 according to the eighth embodiment (see FIGS. 25A to 27) is modified as follows. Since the arrangements of other portions are the same as those in the eighth embodiment, the same reference numerals as in the eighth embodiment denote the same parts in FIGS. 37 to 42, and a description thereof will be omitted.

Figure 37:
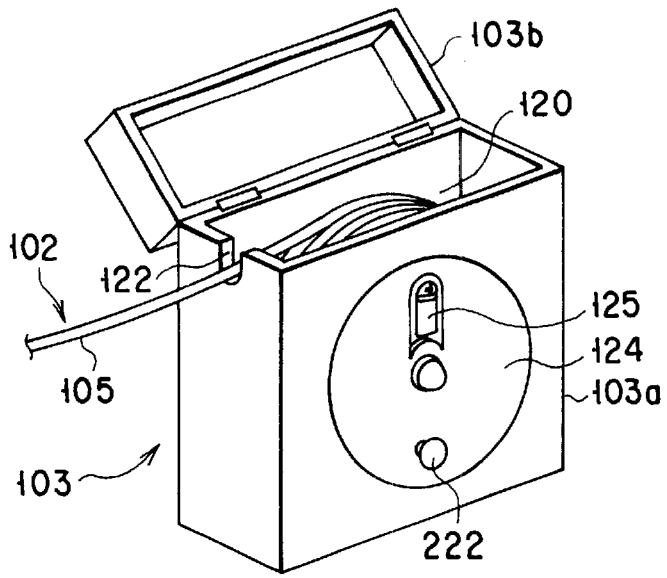
FIG. 37 is a schematic view showing the arrangement of the overall system of an endoscope apparatus according to 11th embodiment of the present invention.

Referring to FIG. 37, the operating portion 118 in FIG. 25A is omitted.

Figure 38:
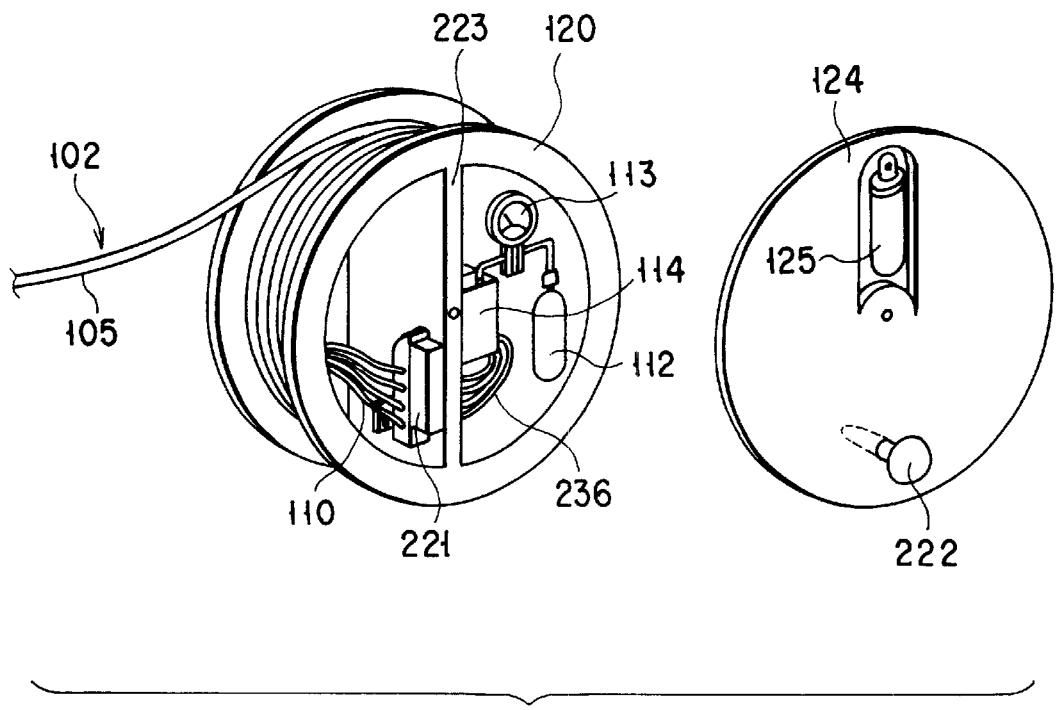
FIG. 38 is a perspective view showing the arrangement of a drum portion in the endoscope apparatus according to the 11th embodiment.

In this embodiment, as shown in FIG. 38, the drum 120 in the endoscope apparatus 101 according to the eighth embodiment incorporates a batch release valve 221 for forcibly releasing the pressures in fluid supply tubes 110 respectively coupled to four pressurization chambers 15 of a hydropneumatic actuator 109 to the atmosphere. A drum cover 124 has a batch release button 222 for operating the batch release valve 221.

FIG. 38 shows the internal structure of the drum 120 and the arrangement of the drum cover 124. The batch release valve 221 is attached to an intermediate wall 223 that partitions the internal space of the drum 120 into left and right spaces. The batch release valve 221 is placed at some point in the fluid supply tubes 110 coupled to a valve unit 114. The batch release button 222 is located at a position corresponding to the position of the batch release valve 221 when the drum cover 124 is mounted on the drum 120. As shown in FIGS. 39A and 39B, the batch release valve 221 has a fixed portion 224 fixed to the intermediate wall 223 and a movable portion 225 retractably coupled to the fixed portion 224. In this case, one end portion (the upper end portion in FIGS. 39A and 39B) of the movable portion 225 is coupled to the fixed portion 224 to be pivotal on a pivot shaft 226. A button bearing portion 225a extends from the lower end portion of the movable portion 225 to a position below the lower end portion of the fixed portion 224.

A through hole 228 is formed in the drum cover 124 to allow a shaft portion 227 of the batch release button 222 to move in the axial direction. The position of the through hole 228 corresponds to the button bearing portion 225a of the movable portion 225 in the batch release valve 221.

The batch release valve 221 has a spring 229 for always biasing the movable portion 225 against the fixed portion 224, and a spring press plate 230 fixed to the intermediate wall 223 as shown in FIG. 40A. The spring 229 is spaced apart from the through hole 228 of the drum cover 124 and opposes the through hole 228 through the button bearing portion 225a of the movable portion 225 of the batch release valve 221.

The movable portion 225 of the batch release valve 221 is always biased against the fixed portion 224 (this state corresponds to the closed position of the batch release valve 221) by the biasing force of the spring 229. In this case, the batch release button 222 is held while protruding outward from the drum cover 124, as shown in FIG. 39A.

When the operator presses the batch release button 222, the shaft portion 227 of the batch release button 222, which extends through the through hole 228 of the drum cover 124, moves in the axial direction, as shown in FIG. 39B. As a consequence, the movable portion 225 of the batch release valve 221 rotates about the pivot shaft 226 while the spring 229 is compressed by the pressing force from the shaft portion 227 of the batch release button 222. Thus, the movable portion 225 of the batch release valve 221 is set in an open state wherein it separates from the fixed portion 224 (i.e., moves to the open position of the batch release valve 221).

Four intermediate flow paths 231 coupled to the fluid supply tubes 110 in the four bending directions of a bending portion 106 are formed in the fixed portion 224 and movable portion 225 of the batch release valve 221.

FIG. 40A shows how the intermediate flow path 231 in the batch release valve 221 is coupled to the fluid supply tube 110 in one bending direction. The intermediate flow path 231 has a fixed-portion-side flow path 231a integrally formed in the fixed portion 224 and intermediate wall 223, and a movable-portion-side flow path 231b formed in the movable portion 225.

A first tube coupling portion 232 coupled to one end portion of the movable-portion-side flow path 231b extends from the movable portion 225. The fluid supply tube 110 is coupled to the first tube coupling portion 232. A coupling orifice portion 233 coupled to the other end portion of the movable-portion-side flow path 231b is formed on that surface of the movable portion 225 which comes into contact with the fixed portion 224.

A flow path coupling portion 234 coupled to one end portion of the fixed-portion-side flow path 231a is formed on that surface of the fixed portion 224 which comes into contact with the movable portion 225. As shown in FIG. 39A, while the fixed portion 224 is in contact with the movable portion 225, the coupling orifice portion 233 of the movable portion 225 is detachably coupled to the flow path coupling portion 234 of the fixed portion 224.

As shown in FIG. 40A, a second tube coupling portion 235 coupled to the other end portion of the fixed-portion-side flow path 231a is formed on the intermediate wall 223. One end portion of a valve-unit-side tube 236 of the fluid supply tube 110 is coupled to the second tube coupling portion 235. The valve unit 114 is connected to the other end portion of the valve-unit-side tube 236.

The function of the above arrangement will be described next. In this embodiment, in normal operation, the batch release valve 221 held in the closed state, as shown in FIG. 39A. In this state, as shown in FIG. 40A, since the coupling orifice portion 233 of the movable portion 225 is coupled to the flow path coupling portion 234 of the fixed portion 224, the fixed-portion-side flow path 231a in the fixed portion 224 and intermediate wall 223 is kept coupled to the movable-portion-side flow path 231b in the movable portion 225. Since the flow path 231 extends through the intermediate wall 223, fixed portion 224, and movable portion 225, a gas from the valve unit 114 can be supplied to the hydropneumatic actuator 109.

When the operator presses the batch release button 222, the movable portion 225 of the batch release valve 221 moves to the open position spaced away from the fixed portion 224 while the spring 229 is compressed by the biasing force from the shaft portion 227 of the batch release button 222, as shown in FIG. 39B. As a consequence, the coupling orifice portion 233 of the movable portion 225 is separated from the flow path coupling portion 234 of the fixed portion 224. Therefore, the fixed-portion-side flow path 231a in the fixed portion 224 and intermediate wall 223 is disconnected from the movable-portion-side flow path 231b in the movable portion 225.

With the above arrangement, the following effect can be obtained. In this embodiment, if an excessive amount of gas is supplied to the hydropneumatic actuator 109 because of a failure in a control circuit 116 or the valve unit 114, the pressures in the fluid supply tubes 110 can be forcibly released to the atmospheric pressure by operating the batch release valve 221 upon pressing the batch release button 222. This makes it possible to prevent the hydropneumatic actuator 109 and other portions from being damaged when, for example, an excessive amount of gas is kept supplied to the hydropneumatic actuator 109 because of a failure in the control circuit 116 or valve unit 114. This can minimize various kinds of damage to the hydropneumatic actuator 109 which are caused when an excessive amount of gas is supplied. Therefore, adverse effects on the endoscope body 102 in the event of a failure can be minimized.

FIG. 40B shows the arrangement of a fluid source 111 in the endoscope apparatus 101 according to the 11th embodiment. Referring to FIG. 40B, the batch release valve 221 described above is omitted. In the 11th embodiment, pressure sensors 237 for detecting pressures in the fluid supply tubes 110 are respectively interposed between the flow path switching mechanism portions 115A to 115D and the fluid supply tubes 110. The pressure sensors 237 are electrically connected to the control circuit 116. Signals from the respective pressure sensors 237 are transferred to the control circuit 116.

Figure 41A:
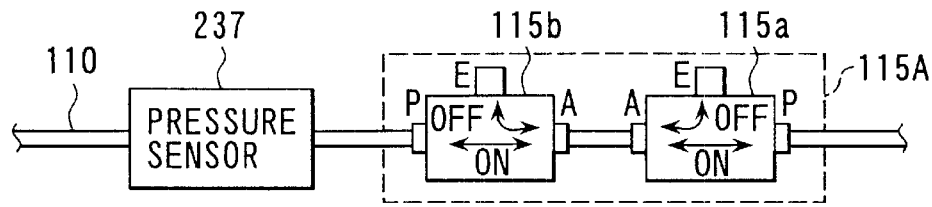
FIG. 41A is a schematic view of main part of the endoscope apparatus according to the 11th embodiment, showing the connected state of a pressure sensor coupled to a flow supply tube in one bending direction.

FIG. 41A shows the details of a portion including the pressure sensor 237 coupled to the fluid supply tube 110 in one bending direction (UP direction) and the flow path switching mechanism portion 115A. In this case, two solenoid valves 115a and 115b of the flow path switching mechanism portion 115A are 3-port solenoid valves, as described in the eighth embodiment.

When the solenoid valves 115a and 115b are turned on, the bending portion 106 is bent by the hydropneumatic actuator 109. While the solenoid valves 115a and 115b are off, the bent state of the bending portion 106 is held by the hydropneumatic actuator 109. When one solenoid valve 115a is off, and the other solenoid valve 115b is on, the corresponding pressurization chamber 15 in the hydropneumatic actuator 109 is released, and the bending portion 106 is restored to the initial form (not bent) by the hydropneumatic actuator 109.

Figure 42:
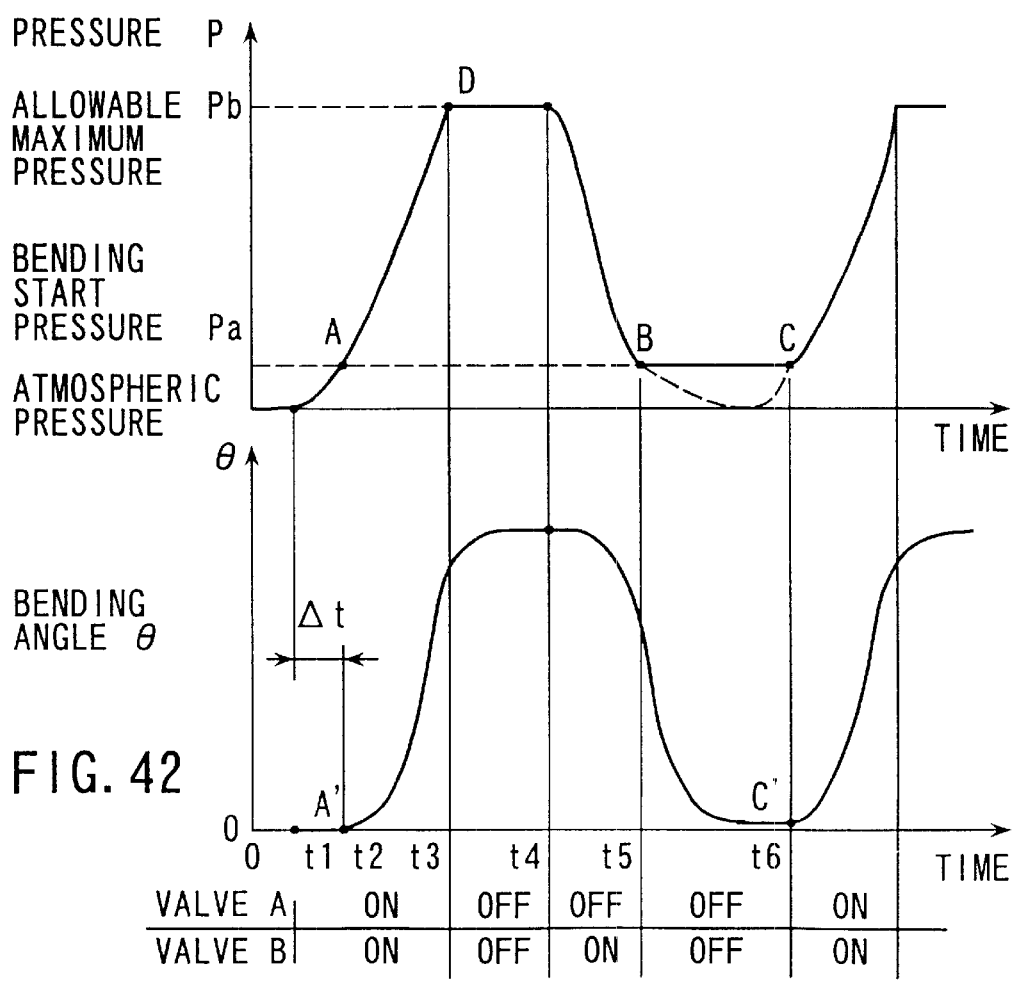
FIG. 42 is a graph showing the relationship among the operation of each valve of a flow path switching mechanism portion in one bending direction, pressure, and bent state in the endoscope apparatus according to the 11th embodiment.

FIG. 42 is a graph indicating the relationship between a pressure P detected by the pressure sensor 237, the operation states of the two solenoid valves 115a and 115b (valves A and B) of the flow path switching mechanism portion 115A in one bending direction (UP direction), and a bending angle θ of the bending portion 106.

When the bending portion 106 is to be bent in one bending direction (UP direction), the following operation is performed. As shown in FIG. 42, first of all, at time t1 at which the bending angle is 0, both the solenoid valves 115a and 115b are turned on to send a gas from the cylinder 112, and the pressure P in the pressurization chamber 15 in the hydropneumatic actuator 109 starts increasing.

The bending portion 106 does not start bending for a certain period of time after the start of a rise in pressure. At time t2 after a lapse of a time Δt, the pressure exceeds a bending start pressure Pa (a point A in FIG. 42), and the bending portion 106 starts bending.

If the gas is kept sent, the bending portion 106 further bends as the pressure P in the pressurization chamber 15 in the hydropneumatic actuator 109 increases. At time t3 at which the pressure P detected by the pressure sensor 237 exceeds a predetermined allowable maximum pressure Pb (a point D in FIG. 42), the control circuit 116 automatically turns off both the solenoid valves 115a and 115b. As a consequence, the increase in pressure stops, and the bent state of the bending portion 106 is held.

After a lapse of a certain period of time, only the solenoid valve 115b is turned on at time t4 to start releasing the pressure in the pressurization chamber 15 in the hydropneumatic actuator 109. The bending angle also starts decreasing with a slight time lag.

At time t5 (a point B in FIG. 42) at which the pressure in the pressurization chamber 15 in the hydropneumatic actuator 109 decreases, and the pressure detected by the pressure sensor 237 becomes lower than the bending start pressure Pa, both the valves 115a and 115b are turned off again. As a consequence, the supply of the gas is stopped, and the gas pressure in the hydropneumatic actuator 109 and fluid supply tube 110 is held. Since this pressure is lower than the bending start pressure Pa, the bending angle of the bending portion 106 returns to the initial angle, 0°, with a slight time lag.

After a lapse of a certain period of time, the two valves 115a and 115b are turned on at time t6 (points C and C' in FIG. 42) to bend the bending portion 106 again. At this time, since the gas has been held in the hydropneumatic actuator 109, the internal pressure quickly exceeds the bending start pressure Pa, and the bending portion 106 quickly starts bending.

When the bent state of the bending portion 106 is to be restored to the initial state, the gas pressure in the hydropneumatic actuator 109 and fluid supply tube 110 is held near the bending start pressure Pa. This makes it possible to quickly start bending the bending portion 106 unlike in normal operation in which it takes the time Δt to start bending the bending portion 106.

In addition, setting of the allowable maximum pressure Pb for the pressure P in the pressurization chamber 15 in the hydropneumatic actuator 109 can prevent the hydropneumatic actuator 109 or its peripheral portion from being damaged by an excessive pressure acting on the hydropneumatic actuator 109.

With the above arrangement, the following effect can be obtained. In this embodiment, the pressure sensor 237 is used to detect the pressure in each fluid supply tube 110, and the bending start pressure Pa, at which the bending portion 106 starts bending, and allowable maximum pressure Pb are set. This makes it possible to quickly start bending the bending portion 106 and prevent the application of an excessive pressure.

The arrangement of this embodiment having the batch release valve 221 can be applied to not only the scheme using the cylinder 112 for the hydropneumatic pressure source 109 but also the scheme using the syringe unit 151 as in the eighth embodiment (see FIGS. 25A to 27). In this case, as in this embodiment, the pressure in each flow path can be released to the atmospheric pressure in the event of runaway due to a failure in the control circuit 116 or syringe unit 151.

In this embodiment, the batch release valve 221 is open only while the batch release button 222 is pressed. However, a click action mechanism for locking the batch release button 222 in a pressed state may be used to lock the batch release button 222 in a pressed state once the batch release button 222 is pressed, thereby keeping the batch release valve 221 open.

Figure 41B:
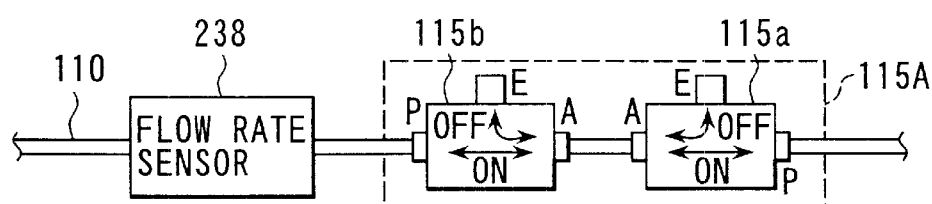
FIG. 41B is a schematic view showing the arrangement of main part of a modification of the 11th embodiment.

As shown in FIG. 41B, a flow rate sensor 238 may be interposed between each fluid supply tube 110 and each of the flow path switching mechanism portions 115A to 115D in the valve unit 114 in the respective bending directions in place of the pressure sensor 237 for detecting the pressure in each fluid supply tube 110. The function of this arrangement is almost the same as that of the arrangement having the pressure sensors 237. In this modification, however, the amount of fluid supplied (the amount obtained by subtracting the amount of fluid exhausted from the amount of fluid supplied) is detected instead of the pressure detected by the pressure sensor 237. In addition, in FIG. 42 the allowable maximum pressure Pb is replaced with an allowable maximum flow rate, the bending start pressure Pa is replaced with a bending start flow rate, and the atmospheric pressure is replaced with a flow rate of 0.

FIGS. 43A to 46 show the 12th embodiment of the present invention. In this embodiment, the arrangement of the endoscope body 102 of the endoscope apparatus 101 according to the eighth embodiment (see FIGS. 25A to 27) is modified as follows.

Figure 43A:
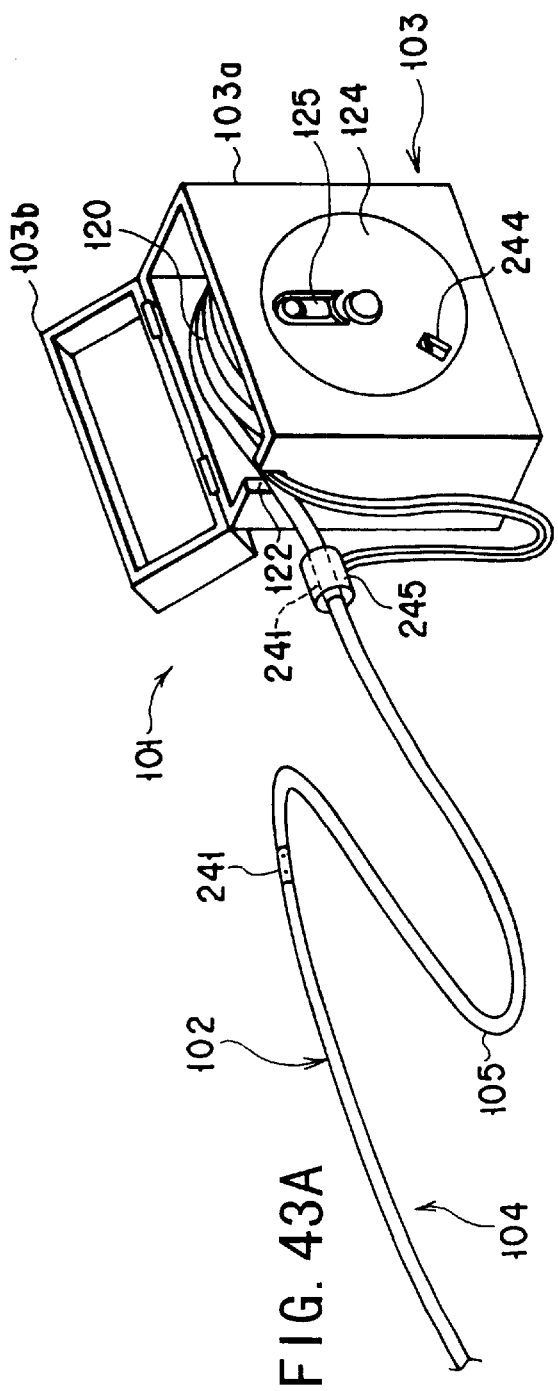
FIG. 43A is a perspective view showing the overall system of an endoscope apparatus according to the 12th embodiment of the present invention.
Figure 43B:
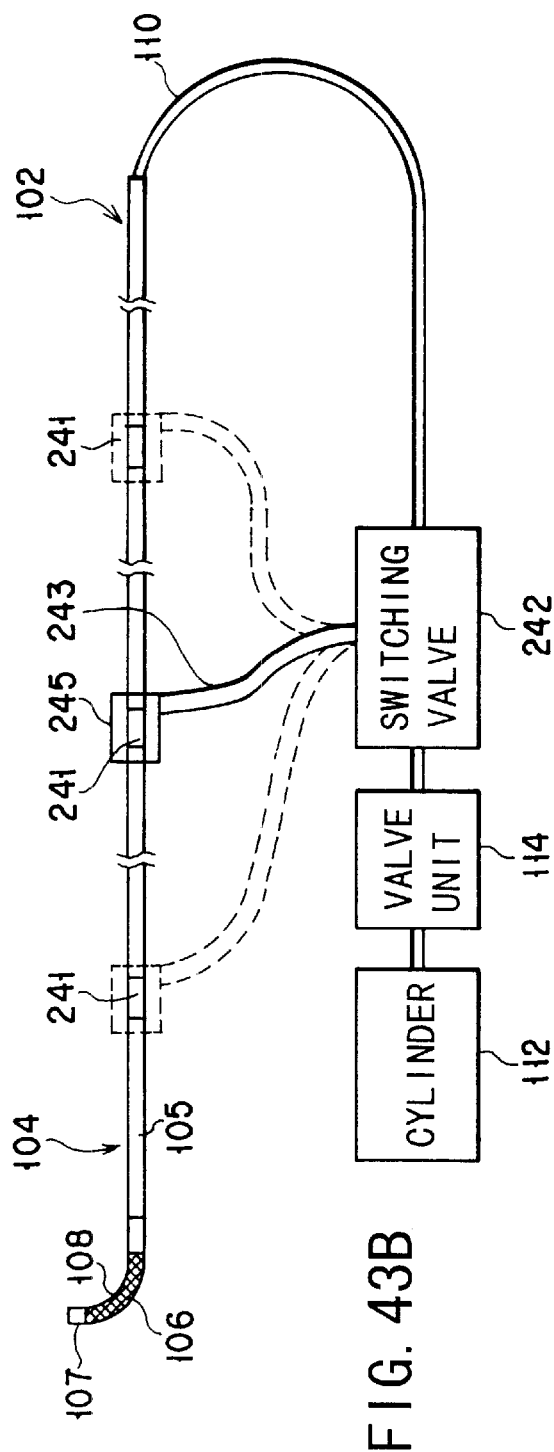
FIG. 43B is a schematic view showing how a fluid supply connector is used.

As shown in FIGS. 43A and 43B, an endoscope body 102 of this embodiment has a plurality of fluid supply orifice members 241 formed at intermediate points in a flexible portion 105 of an insertion portion 104. These fluid supply orifice members 241 are connected to fluid supply tubes 110 in the flexible portion 105.

The fluid supply orifice members 241 are arranged in the flexible portion 105 at, e.g., intervals of 5 m (every 5 m). Note that only one fluid supply orifice member 241 may be formed in the flexible portion 105.

In this embodiment, a switching valve 242 is also interposed between the valve unit 114 and the fluid supply tube 110, as shown in FIG. 43B. The switching valve 242 is housed in the drum 120.

One end portion of an auxiliary tube 243 is coupled to the switching valve 242. The switching valve 242 is operated to switch between the state wherein the valve unit 114 communicates with the fluid supply tube 110 and the state wherein the valve unit 114 communicates with the auxiliary tube 243.

A drum cover 124 has a selection switch 244 of the switching valve 242. The switching valve 242 is connected to the selection switch 244. The selection switch 244 is operated to switch the switching valve 242 to select either the state wherein the valve unit 114 communicates with the fluid supply tube 110 or the state wherein the valve unit 114 communicates with the auxiliary tube 243.

A fluid supply connector 245 is coupled to the other end portion of the auxiliary tube 243. The fluid supply connector 245 is selectively and detachably coupled to the fluid supply orifice members 241 of the flexible portion 105.

Figure 44A:
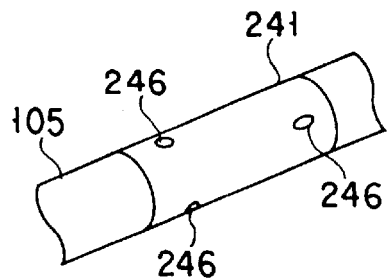
FIG. 44A is a perspective view showing a fluid supply orifice member of the insertion portion of the endoscope apparatus according to the 12th embodiment.

As shown in FIG. 44A, the fluid supply orifice members 241 has a substantially cylindrical shape. The outer diameter of the fluid supply orifice members 241 is set to be almost the same as that of the flexible portion 105 of the insertion portion 104.

Four supply holes 246, which are equal in number to the fluid supply tubes 110 arranged in the flexible portion 105, are formed in the fluid supply orifice members 241. The respective supply holes 246 communicate with the fluid supply tubes 110 in the fluid supply orifice members 241.

Check valves 247 are attached to the coupling portions between the supply holes 246 of the fluid supply orifice members 241 and the fluid supply tubes 110. The coupling portions between the fluid supply orifice members 241 and the fluid supply tubes 110 are normally closed by the check valves 247 to close the paths between the fluid supply tubes 110 and supply holes 246.

Figure 44B:
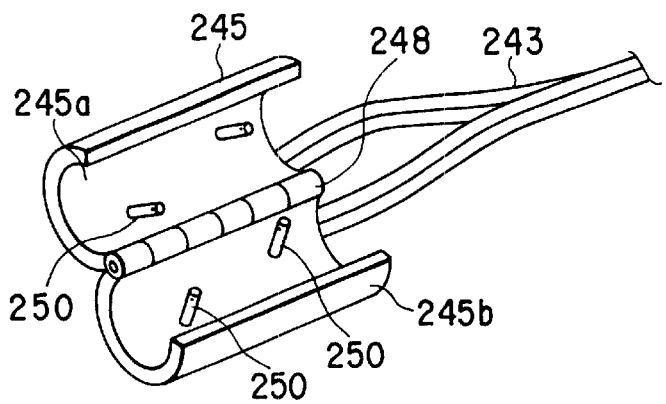
FIG. 44B is a perspective view showing the outer appearance of a fluid supply connector.

As shown in FIG. 44B, the fluid supply connector 245 is a cylindrical member divided into two connector constituent members 245a and 245b, each having a semicircular cross-sectional shape. One end portion of the connector constituent member 245a is pivotally coupled to one end of the connector constituent member 245b through a hinge 248.

Figure 45A:
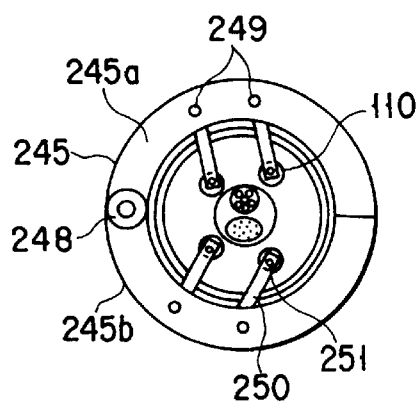
FIG. 45A is a cross-sectional view showing how a fluid supply connector is connected to the fluid supply orifice member in the endoscope apparatus according to the 12th embodiment.

A magnet (not shown) is mounted on the edge portion of the other end portion of each of the two connector constituent members 245a and 245b. As shown in FIG. 45A, while the two connector constituent members 245a and 245b are joined to each other, the joint surface of the other end portion of the connector constituent member 245a is attracted/fixed to the joint surface of the other end portion of the connector constituent member 245b with the magnetic force of the magnets (not shown).

Figure 45B:
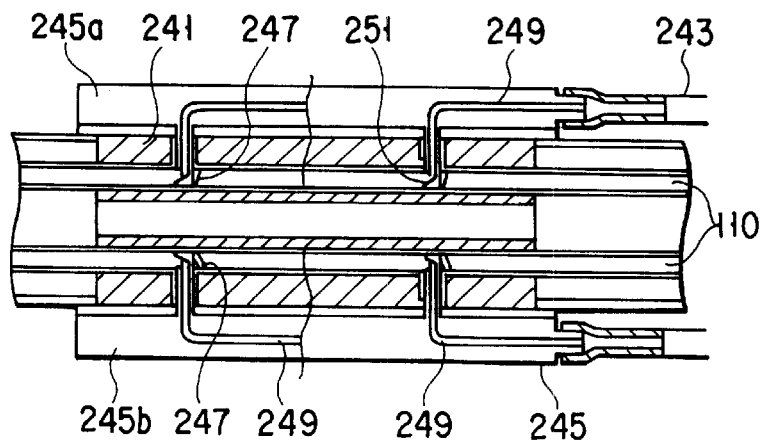
FIG. 45B is a longitudinal sectional view of the endoscope apparatus.

As shown in FIG. 45B, four flow paths 249, equal in number to the auxiliary tubes 243, are formed in the tube wall of the fluid supply connector 245. The auxiliary tubes 243 are coupled to the proximal end portions of the flow paths 249.

Four capillary-like supply pins 250 protrude inwardly from the inner surface of the fluid supply connector 245. The distal end portions of the flow paths 249 of the fluid supply connector 245 are respectively coupled to the proximal end portions of the supply pins 250.

The outer diameter of each supply pin 250 is almost equal to the diameter of each supply hole 246 of the fluid supply orifice member 241. A pin hole 251 for the supply of a gas is formed in the distal end portion of each supply pin 250.

Figure 46:
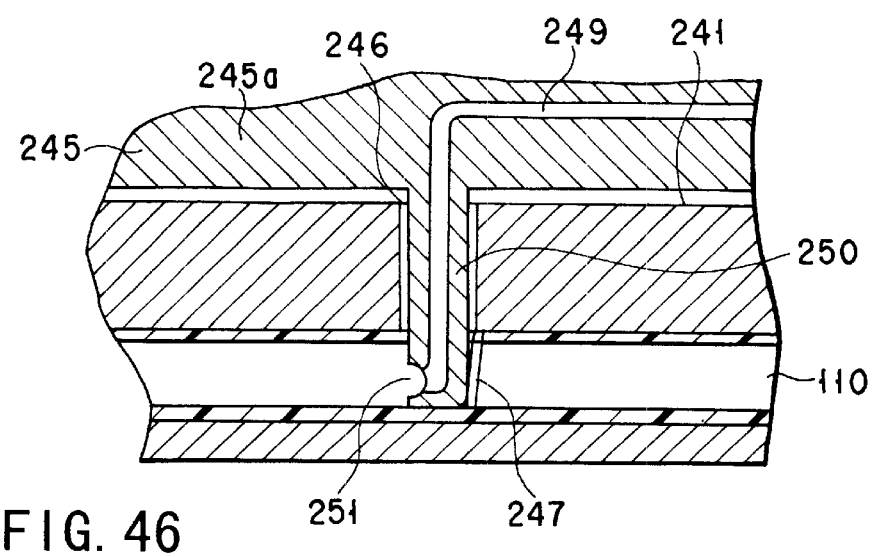
FIG. 46 is a longitudinal sectional view of main part of the endoscope apparatus according to the 12th embodiment, showing how a supply pin is fitted in a supply hole.

When the fluid supply connector 245 is coupled to one of the fluid supply orifice members 241, the fluid supply connector 245 is joined to the fluid supply orifice member 241, as shown in FIGS. 45A and 45B. At this time, the supply pins 250 of the fluid supply connector 245 are detachably inserted and fitted in the supply holes 246 of the fluid supply orifice member 241, as shown in FIG. 45B. In this case, the distal end portion of the supply pin 250 comes into contact with the check valve 247 through the corresponding supply hole 246, and is inserted into the fluid supply tube 110 while the check valve 247 is pushed/tilted to the inside of the fluid supply tube 110, as shown in FIG. 46.

When the supply pin 250 is inserted into the fluid supply tube 110, the fluid supply tube 110 is closed/sealed with the supply pin 250. When the supply pin 250 is inserted into the fluid supply tube 110, the pin hole 251 of the supply pin 250 faces a bending portion 106. Therefore, a gas supplied through the pin hole 251 is supplied to a flow path in the fluid supply tube 110 which is located on the bending portion 106 side. At this time, the gas supplied through the pin hole 251 does not flow into the flow path in the fluid supply tube 110 which is located on the operator side.

When the fluid supply connector 245 is coupled to one of the fluid supply orifice members 241 of the flexible portion 105, flow paths in the fluid supply orifice members 241, the fluid supply connectors 245, the auxiliary tubes 243, and the switching valve 242 are independently formed in correspondence with the fluid supply tubes 110 in the four bending directions.

The function of the above arrangement will be described next. In using the endoscope apparatus 101 of this embodiment, the selection switch 244 of the drum cover 124 is operated to switch the switching valve 242 to select the state wherein the valve unit 114 communicates with the fluid supply tube 110 or the state wherein the valve unit 114 communicates with the auxiliary tube 243. Assume that the state wherein the valve unit 114 communicates with the fluid supply tube 110 is selected. In this case, when the operator bends the bending portion 106 of the endoscope body 102, the gas supplied through the valve unit 114 is sent from the rear end of the insertion portion 104 to the hydropneumatic actuator 109 on the distal end side through the fluid supply tube 110.

If, for example, the total length of the insertion portion 104 is as long as about 10m, the fluid supply tube 110 is also long. Since the distance by which a gas is sent becomes long, a delay may occur in transmitting a pressure. If the delay in transmitting the pressure becomes large as in this case, it takes much time to actually bend the bending portion 106 at the distal end of the insertion portion 104 after the operator operates a joystick 127 of an operating portion 118 on the operator side. Owing to this time lag, responsiveness/controllability may deteriorate.

As the total length of the insertion portion 104 and the pressure transfer distance decrease, better responsiveness and controllability can be obtained. Since a gas is supplied from the proximal end of the insertion portion 104, even if, for example, the insertion portion 104 that is extracted from a drum 120 and actually used is as short as above several m, and the remaining portion is kept wound around the drum 120, the gas sent to the hydropneumatic actuator 109 flows through the total length of the insertion portion 104.

In this embodiment, therefore, a gas can be supplied to the hydropneumatic actuator 109 through the auxiliary tube 243 shorter than the insertion portion 104 by operating the switching valve 242 to select the state wherein the valve unit 114 communicates with the auxiliary tube 243 through the selection switch 244.

FIG. 43 B is a schematic view for explaining how the fluid supply connector 245 is used in this embodiment. In this embodiment, the plurality of fluid supply orifice members 241 are arranged at intermediate points in the insertion portion 104, and one of the fluid supply orifice members 241 is selected in accordance with the length of a flow path to be used. The fluid supply connector 245 is then connected to the selected fluid supply orifice member 241. This makes it possible to supply a gas to the hydropneumatic actuator 109 through the auxiliary tube 243 shorter than the insertion portion 104. For this reason, the gas supply distance can be decreased to about the length of the insertion portion 104 that is actually used. If the insertion portion 104 to be actually used is short as in this case, the gas supply distance can be short. This can greatly improve the responsiveness and controllability in bending the bending portion 106.

With the above arrangement, the following effect can be obtained. In this embodiment, the operator operates the selection switch 244 to switch the switching valve 242 to select the state wherein the valve unit 114 communicates with the auxiliary tube 243. In this state, one of the fluid supply orifice members 241 is selected in accordance with the length of the insertion portion 104 to be used, and the fluid supply connector 245 of the auxiliary tube 243 is connected to the selected fluid supply orifice member 241, thereby supplying a gas to the hydropneumatic actuator 109 through the auxiliary tube 243 shorter than the insertion portion 104. Since the fluid supply path can be shortened in accordance with the length of the insertion portion 104 that is extracted from the drum 120 and actually used, the responsiveness and controllability in bending the bending portion 106 can be improved.

Figure 47:
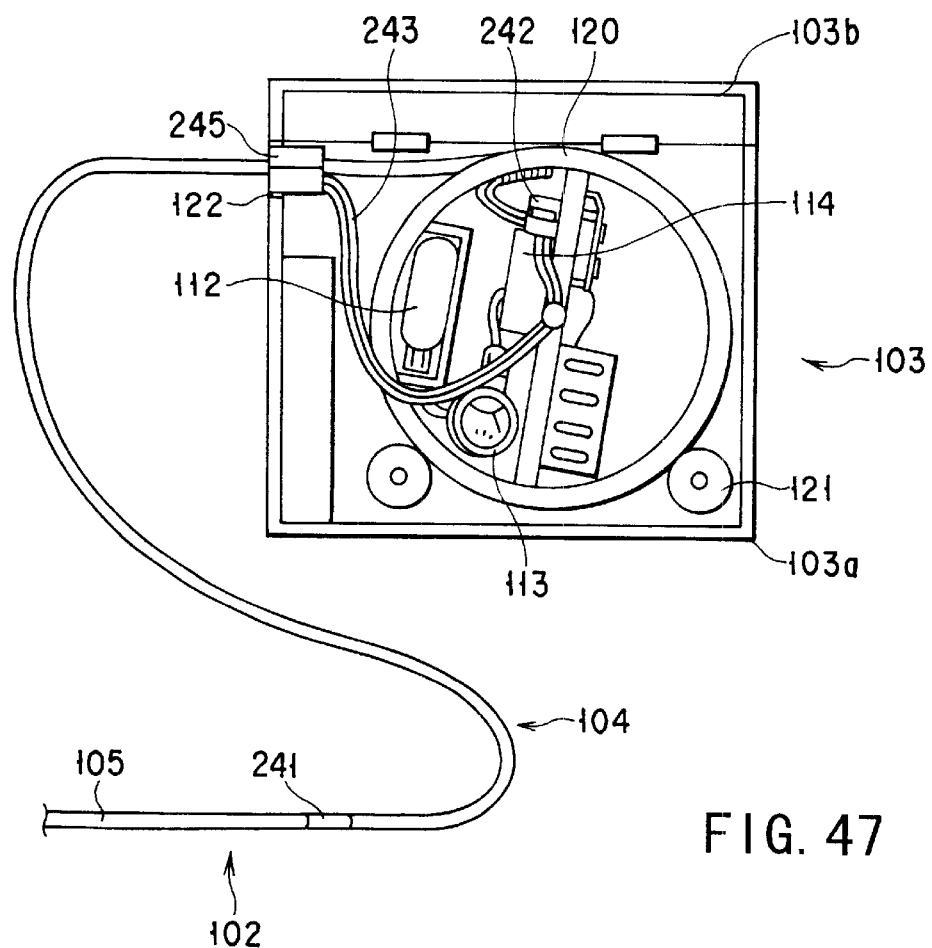
FIG. 47 is a schematic view showing the arrangement of main part of a modification of the 12th embodiment.

FIG. 47 shows a modification of the 12th embodiment (see FIGS. 43A to 46). In the 12th embodiment, the fluid supply connector 245 is only connected to the auxiliary tube 243 and can be extracted from a carrying case 103 to some extent. In this modification, however, the fluid supply connector 245 is fixed to a scope extraction port 122 of the carrying case 103.

With the above arrangement, the following effect can be obtained. In this embodiment, the fluid supply connector 245 is integrally formed with the carrying case 103 to facilitate handling the apparatus.

In this embodiment, the syringe unit 151 may be used as a fluid source as in the ninth embodiment (see FIG. 30) instead of the cylinder 112 and valve unit 114.

FIGS. 48 to 50A show the 13th embodiment of the present invention. The arrangement of the bending portion 106 of the endoscope body 102 of the endoscope apparatus 101 according to the eighth embodiment (see FIGS. 25A to 27) is modified as follows.

Figure 50A:
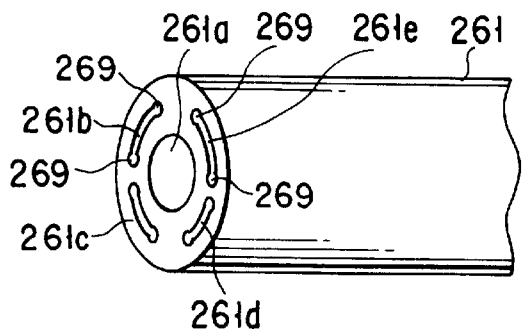
FIG. 50A is a perspective view showing the shape of a cross-section of the multi-lumen tube of the bending portion of the endoscope according to the 13th embodiment.

As shown in FIG. 50A, a bending portion 106 in this embodiment has a multi-lumen tube 261 made of silicone resin. A plurality of (four in this embodiment) rumens 261b, 261c, 261d, and 261e are arranged in the tube wall around a cylindrical central lumen 261a at equal intervals in the circumferential direction.

Figure 49:
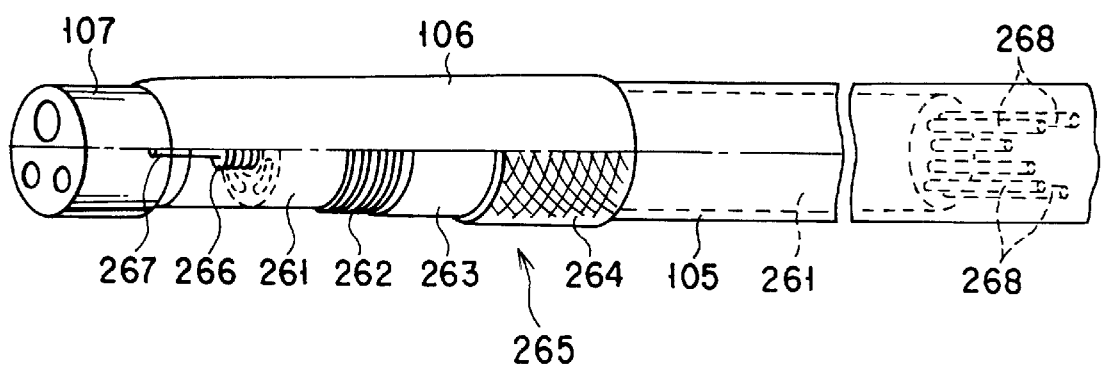
FIG. 49 is a partly cutaway perspective view showing the structure of the bending portion of the endoscope apparatus according to the 13th embodiment.

As shown in FIG. 49, an inside close coil 266 is placed in the central lumen 261a, and built-in members 267 such as a CCD signal line and light guide fiber extend through the inside close coil 266.

In this embodiment, as shown in FIG. 50A, each of the four lumens 261b to 261e has a cross-section in the form of a flat slit. Round portions 269 for reducing stress are formed at the two end portions of the slit of each of the lumens 261b to 261e.

The front and rear end portions of each of the four slit-like lumens 261b, 261c, 261d, and 261e of the multi-lumen tube 261 are sealed with a filler consisting of silicone to form four pressurization chambers 15 corresponding to the four bending directions, i.e., UP, DOWN, RIGHT, and LEFT directions. The rear end sides of the respective pressurization chambers 15 are sealed with fluid supply tubes 268 connected thereto.

As shown in FIG. 49, a multilayer structure 265 formed by sequentially stacking an outside close coil 262, rubber tube 263, and mesh tube 264 is fitted on the multi-lumen tube 261 of the bending portion 106. Note that the multilayer structure 265 outside the multi-lumen tube 261 may be formed by stacking the rubber tube 263, outside close coil 262, and mesh tube 264 in the order named.

Figure 48:
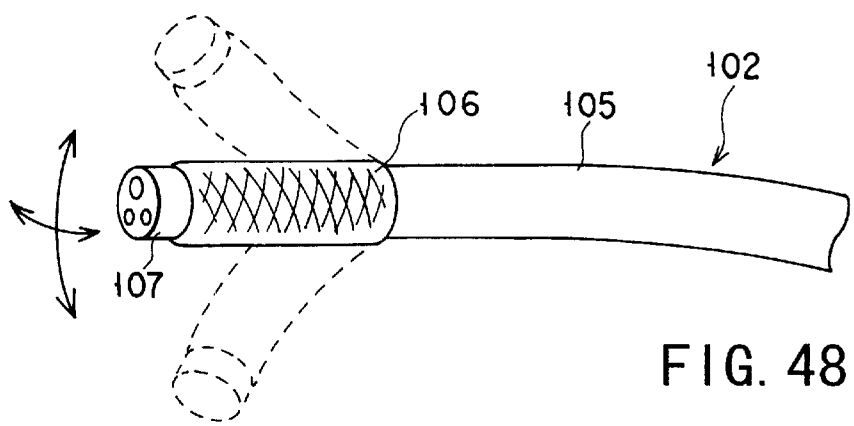
FIG. 48 is a perspective view showing the distal end portion of the insertion portion of the endoscope according to the 13th embodiment of the present invention.

When a fluid is supplied to an arbitrary pressurization chamber 15, the pressurization chamber 15 expands. The expansion of the pressurization chamber 15 in the radial direction is suppressed by the effect of the outside close coil 262 and mesh tube 264. As a consequence, the pressurization chamber 15 extends in the axial direction. With this operation, the bending portion 106 bends in a direction opposite to the expanding direction of the pressurization chamber 15. The bend amount of the bending portion 106 can be controlled by adjusting the pressure of the fluid supplied to the pressurization chamber 15. In addition, the bending portion 106 can be bent in any direction, as shown in FIG. 48, by adjusting the balance between the pressures in the pressurization chambers 15.

The total length of an insertion portion 104 of the endoscope body 102 in this embodiment is 10 m or more. In using the endoscope body 102 of this embodiment, the insertion portion 104 is pulled out from the carrying case 103 by a necessary length in accordance with the object under examination.

While the insertion portion 104 of the endoscope body 102 is inserted into a tubular cavity object as an object under examination, an endoscopic inspection image in the tubular cavity as the object under examination can be obtained by an image sensing function portion 108 of a distal end constituent portion 107 of the endoscope body 102. The operator therefore outputs a bending instruction corresponding to a desired direction by using the joystick while watching the endoscopic inspection image on the monitor of the bending operation unit. The function of the bending portion 106 of the endoscope body 102 is the same as that in the eighth embodiment, and hence the operator can bend the bending portion 106 in an arbitrary direction.

With the above arrangement, the following effect can be obtained. According to the multi-lumen tube 261 in this embodiment, each of the four lumens 261b to 261e forming the four pressurization chambers 15 corresponding to the four bending directions has a cross-section in the form of a flat slit, and the round portions 269 for reducing a stress are formed at the two end portions of each of the lumens 261b to 261e, as shown in FIG. 50A. With this structure, the outer diameter of the multi-lumen tube 261 can be reduced to a target size while the thickness of the multi-lumen tube 261 can be ensured to obtain practically sufficient durability.

In general, in an industrial endoscope system, an endoscope insertion portion 105 is required to have a small outer diameter. More specifically, when the outer diameter of the endoscope insertion portion 105 is set to be about 6 mm, the system can be applied to many objects. For this purpose, the multi-lumen tube 261 used for the bending portion 106 must be realized with an outer diameter of about 4 to 5 mm as a set value. In this embodiment, as described above, the outer diameter of the multi-lumen tube 261 can be reduced to a target size while the thickness of the multi-lumen tube 261 can be ensured to obtain practically sufficient durability.

Figure 50B:
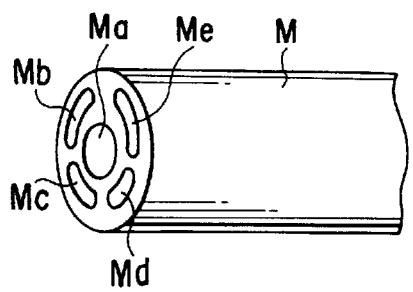
FIG. 50B is a perspective view showing the shape of a cross-section of a conventional multi-lumen tube.

According to a conventional multi-lumen tube M shown in FIG. 50B, each of four lumens Mb, Mc, Md, and Me in the tube wall around a central lumen Ma is formed by a through hole having a substantially elliptic cross-section. If the outer diameter of the conventional multi-lumen tube M having pressurization chambers formed by the lumens Mb, Mc, Md, and Me each having a substantially elliptic cross-section is realized with the above set value, the multi-lumen tube M must be formed thin. As a consequence, the conventional multi-lumen tube M cannot ensure practically sufficient durability for the multi-lumen tube that repeatedly expands and shrinks.

For this reason, according to the multi-lumen tube 261 of this embodiment, each of the four lumens 261b to 261e forming the pressurization chambers 15 in the four bending directions is formed into a flat, slit-like shape, and the round portions 269 for reducing stress are formed at the two end portions of each of the lumens 261b to 261e. This structure can reduce the size of the multi-lumen tube 261 and is effective in realizing a low-profile endoscope.

Figure 51:
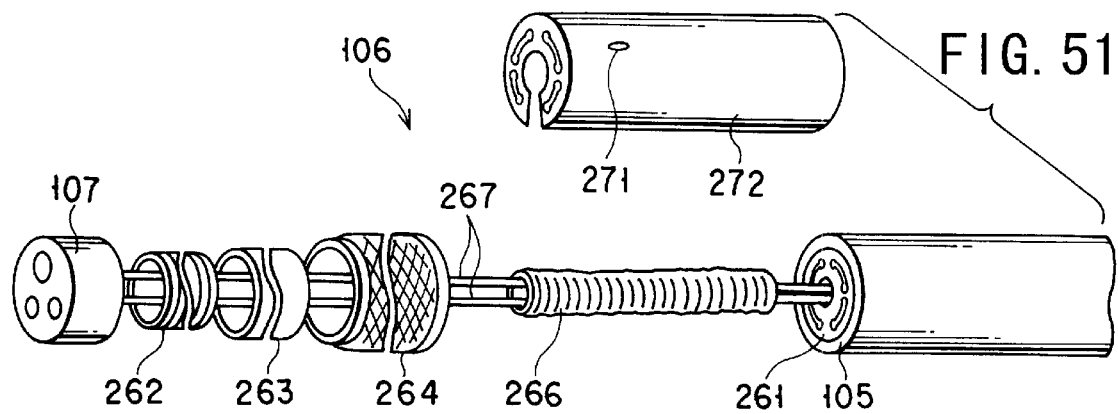
FIG. 51 is an exploded perspective view for explaining a procedure for replacing the multi-lumen tube of the bending portion of an endoscope apparatus according to the 14th embodiment of the present invention.
Figure 52:
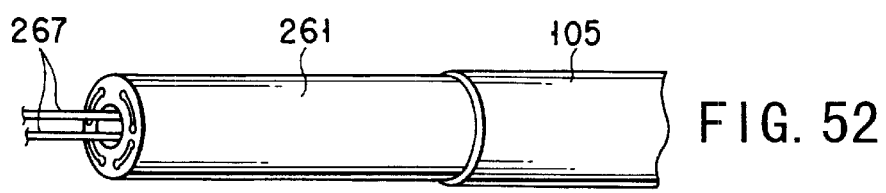
FIG. 52 is a perspective view showing a multi-lumen tube after the maintenance of the bending portion of the endoscope apparatus according to the 14th embodiment.

FIGS. 51 and 52 show the 14th embodiment of the present invention. In this embodiment, the arrangement of the bending portion 106 of the endoscope body 102 of the endoscope apparatus 101 according to the 13th embodiment (see FIGS. 48 to 50A) is modified as follows.

The total length of a multi-lumen tube 261 in this embodiment is set to be several times longer than the length of a bending portion 106. Only the distal end portion of the multi-lumen tube 261 is placed in the bending portion 106, and the remaining portion is inserted into a flexible portion 105. In this case, the insertion tube of the flexible portion 105 has an extensible structure.

Fluid supply tubes 268 are respectively connected to pressurization chambers 15 of a hydropneumatic actuator 109 on the proximal end side of the multi-lumen tube 261. The multi-lumen tube 261 is sealed to prevent a fluid from leaking from each pressurization chamber 15.

In bending the bending portion 106, a pressurized fluid is supplied from the fluid supply tube 268 to the pressurization chamber 15 of the hydropneumatic actuator 109 which corresponds to the bending direction. In this case, the pressurization chamber 15 is bound to expand throughout the total length, but the portion placed in the flexible portion 105 is suppressed by the insertion tube of the flexible portion 105 having the extensible structure and does not expand. Of the total length of the pressurization chamber 15 in the multi-lumen tube 261, therefore, only that portion of the bending portion 106 which is located on the distal end side of the multi-lumen tube 261 actually expands.

According to the structure of the bending portion 106 in this embodiment, since the bending portion 106 bends upon expansion of the multi-lumen tube 261, even if a sufficient thickness is ensured for the multi-lumen tube 261, each pressurization chamber 15 eventually punctures due to a deterioration in tube material over years or an unexpected factor. According to the arrangement of the bending portion 106 in this embodiment, even if the pressurization chamber 15 punctures, the multi-lumen tube 261 of the bending portion 106 can be replaced without any complicated disassembly process.

A procedure for replacing the multi-lumen tube 261 of the 106 with a new one will be described next with reference to FIGS. 51 and 52. In replacing the multi-lumen tube 261 of the bending portion 106, steps (1) to (7) are sequentially performed.

(1) As shown in FIG. 51, a distal end constituent portion 107 of the endoscope body 102 is disconnected from the bending portion 106 and separated from the bending portion 106, together with built-in members 267 such as a CCD signal line and light guide fiber, by axially shifting the distal end constituent portion 107.

(2) A multilayer structure 265 of the bending portion 106, which is formed by sequentially stacking an outside close coil 262, rubber tube 263, and mesh tube 264, is separated from the multi-lumen tube 261 by axially shifting the multilayer structure 265. In addition, an inside close coil 266 is also separated from the multi-lumen tube 261 by axially shifting the inside close coil 266 in the same manner.

(3) A distal end portion 272 including a punctured portion 271 of the exposed multi-lumen tube 261 is cut off. At this time, the distal end portion 272 is cut off without damaging the built-in members 267 such as a CCD signal line and light guide fiber. Thereafter, as shown in FIG. 51, the cut distal end portion 272 including the punctured portion 271 of the multi-lumen tube 261 is partially cut open, and is removed from the built-in members 267 such as a CCD signal line and light guide fiber.

(4) As shown in FIG. 52, the remaining portion of the multi-lumen tube 261 is pulled forward from the insertion tube of the flexible portion 105 in accordance with the length of the bending portion 106.

(5) The distal end portions of the pressurization chambers 15 of the multi-lumen tube 261 pulled forward are sealed.

(6) The multilayer structure 265 formed by sequentially stacking the multi-lumen tube 261, rubber tube 263, and mesh tube 264 is fitted on the multi-lumen tube 261.

(7) The distal end constituent portion 107 of the endoscope body 102 is connected to the bending portion 106.

According to the arrangement of the bending portion 106 in this embodiment, the multi-lumen tube 261 of the bending portion 106 can be replaced by the above procedure for replacement. Since there is no need to disconnect the built-in members 267 such as a CCD signal line and light guide fiber, the ease of maintenance of the bending portion 106 of the endoscope body 102 can be improved.

Figure 53A:
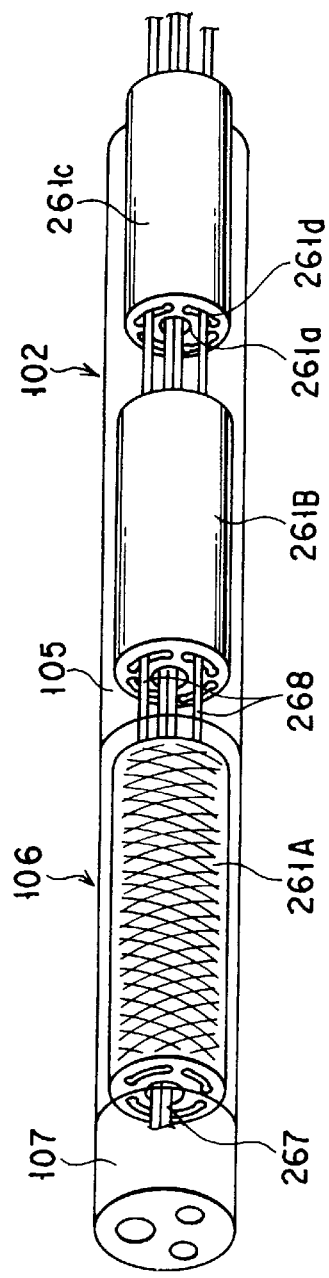
FIG. 53A is a perspective view showing the schematic arrangement of a portion near the bending portion of an endoscope apparatus according to the 15th embodiment of the present invention.
Figure 53B:
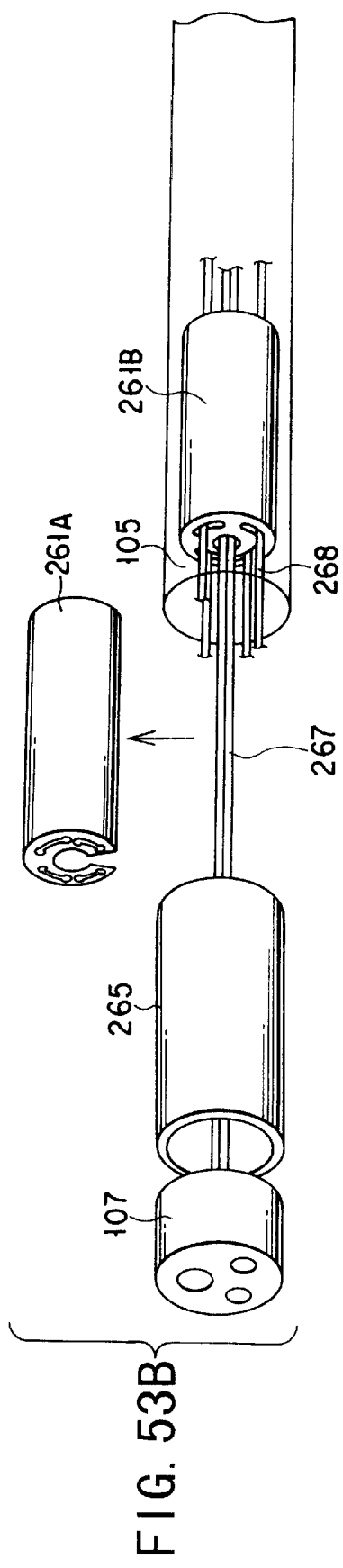
FIG. 53B is a perspective view showing a state wherein the multi-lumen tube is detached from the bending portion.
Figure 53C:
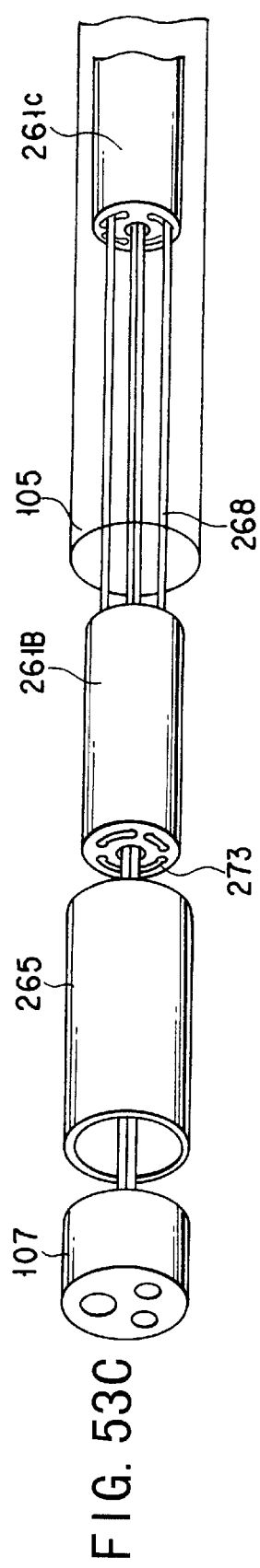
FIG. 53C is a perspective view of main part of the apparatus and shows a state wherein the next multi-lumen tube is pulled out from an insertion tube.

FIGS. 53A to 53C show the 15th embodiment of the present invention. In this embodiment, the arrangement of the bending portion 106 of the endoscope body 102 of the endoscope apparatus 101 according to the 13th embodiment (see FIGS. 48 to 50A) is modified as follows.

In this embodiment, as shown in FIG. 53A, a plurality of multi-lumen tubes 261 (three multi-lumen tubes 261A, 261B, and 261C in the embodiment) each having a length almost equal to the total length of the bending portion 106 are prepared. One multi-lumen tube 261A is placed in the bending portion 106, whereas the remaining multi-lumen tubes 261B and 261C are arranged as spare tubes in line in an insertion tube forming a flexible portion 105.

In the multi-lumen tube 261A placed in the bending portion 106, fluid supply tubes 268 are connected to the rear end portions of pressurization chambers 15 corresponding to the four bending directions. The front and rear portions of the pressurization chambers 15 are sealed.

A multilayer structure 265 formed by sequentially stacking an outside close coil 262, rubber tube 263, and mesh tube 264 and fitted on the multi-lumen tube 261A of the bending portion 106 is the same as that in the 13th embodiment. In addition, built-in members 267 such as a CCD signal line and light guide fiber extend through central lumens 261a of the spare multi-lumen tubes 261B and 261C, and fluid supply tubes 268 extend through four lumens 261b, 261c, 261d, and 261e around each central lumen 261a.

A procedure for replacing the multi-lumen tube 261 in the structure of the bending portion 106 of this embodiment will be described next with reference to FIGS. 53B and 53C. In replacing the multi-lumen tube 261 of the bending portion 106 with a new one, steps (1) to (7) are sequentially performed as follows.

(1) As shown in FIG. 53B, a distal end constituent portion 107 of the endoscope body 102 is disconnected from the bending portion 106 and separated from the bending portion 106, together with built-in members 267 such as a CCD signal line and light guide fiber, by axially shifting the distal end constituent portion 107.

(2) The multilayer structure 265 of the bending portion 106, which is formed by sequentially stacking the outside close coil 262, rubber tube 263, and mesh tube 264, is separated from the multi-lumen tube 261A by axially shifting the multilayer structure 265. In addition, an inside close coil 266 is also separated from the multi-lumen tube 261A by axially shifting the inside close coil 266 in the same manner.

(3) The exposed multi-lumen tube 261A is partially cut open, and the built-in members 267 such as a CCD signal line and light guide fiber are removed. In addition, the fluid supply tube 268 coupled to the rear end portion of each pressurization chamber 15 of the multi-lumen tube 261A is cut off.

(4) As shown in FIG. 53C, the multi-lumen tube 261B is pulled forward from the insertion tube of the flexible portion 105.

(5) The distal end portions of the pressurization chambers 15 of the multi-lumen tube 261B are sealed. The tubes 268 are connected to the proximal end portions of the pressurization chambers 15 of the multi-lumen tube 261B and sealed.

(6) The multilayer structure 265 formed by sequentially stacking the outside close coil 262, rubber tube 263, and mesh tube 264 is fitted on the multi-lumen tube 261B, and the inside close coil 266 is fitted in the multilayer structure 265.

(7) The distal end constituent portion 107 of the endoscope body 102 is connected to the bending portion 106.

According to the arrangement of the bending portion 106, the multi-lumen tube 261A of the bending portion 106 can be replaced by the above procedure for replacement. Since there is no need to disconnect the built-in members 267 such as a CCD signal line and light guide fiber, the ease of maintenance of the bending portion 106 of the endoscope body 102 can be improved.

Figure 54:
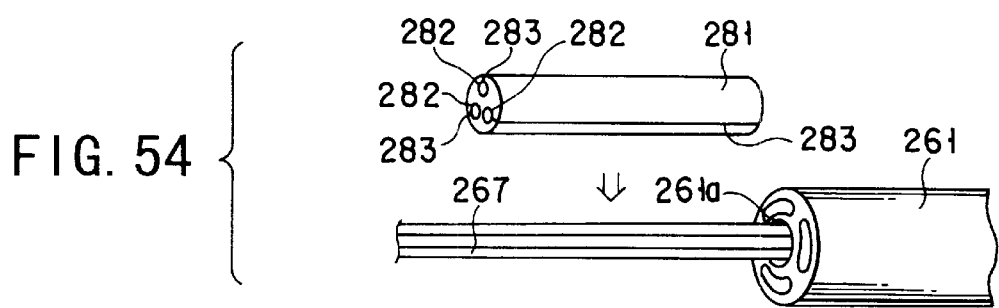
FIG. 54 is a perspective view showing main part of an endoscope apparatus according to the 16th embodiment of the present invention and shows a state before a buffer member is placed in the bending portion.
Figure 55:
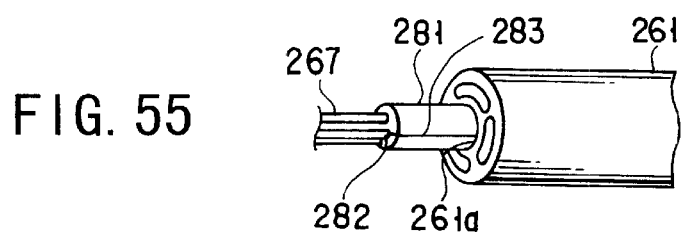
FIG. 55 is a perspective view of main part of the endoscope apparatus according to the 16th embodiment and shows a state wherein the buffer member is placed in the bending portion.

FIGS. 54 and 55 show the 16th embodiment of the present invention. In this embodiment, the arrangement of the bending portion 106 of the endoscope body 102 of the endoscope apparatus 101 according to the 13th embodiment (see FIGS. 48 to 50A) is modified as follows.

This embodiment includes a buffer member 281 for protecting built-in members 267 such as a CCD signal line and light guide fiber extending through a central lumen 261a of a multi-lumen tube 261. As shown in FIG. 54, the buffer member 281 is made of a material with high impact absorbency, e.g., an urethane or silicone material, in a multi-lumen form. A cut 283 is formed in each lumen 282 of the buffer member 281.

The built-in members 267 such as a CCD signal line and light guide fiber can be fitted in each lumen 282 through the cut 283 of the buffer member 281. Thereafter, the buffer member 281 is housed in the central lumen 261a of the multi-lumen tube 261.

In this embodiment, since the buffer member 281 can be used in place of an inside close coil 266, even if the bending portion 106 crushes due to an unexpectedly large external force, the built-in members 267 such as a CCD signal line and light guide fiber housed in the central lumen 261a of the multi-lumen tube 261 can be protected.

In addition, since the buffer member 281 does not influence the procedure for replacing the multi-lumen tube 261 in each of the 14th and 15th embodiments, the multi-lumen tube 261 of the bending portion 106 can be easily replaced.

Figure 56:
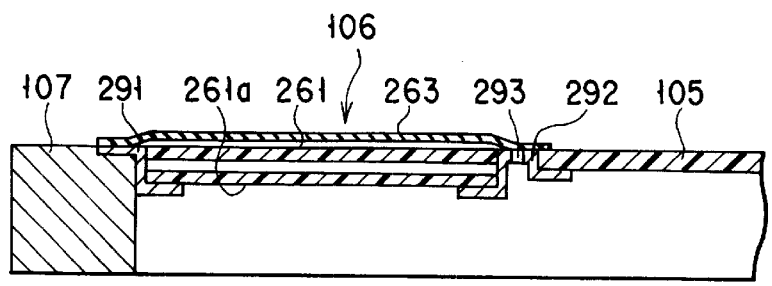
FIG. 56 is a longitudinal sectional view of main part of the first modification of the 16th embodiment.

FIG. 56 shows a modification of the structure of the bending portion 106 of the 16th embodiment (FIGS. 54 and 55). In this modification, the distal end constituent portion 107 of the endoscope body 102 is connected to the front end portion of the bending portion 106 through a front base 291. In addition, the rear end portion of the bending portion 106 is connected to the front end portion of the insertion tube of the flexible portion 105 through a rear base 292.

Furthermore, a rubber tube 263 of a multilayer structure 265 of the bending portion 106 is fixed on the distal end constituent portion 107 and flexible portion 105 to completely cover the two bases 291 and 292, thereby keeping the endoscope body 102 watertight. Referring to FIG. 56, the outside close coil 262 and mesh tube 264 of the multilayer structure 265 are omitted. The rear base 292 has a hole 293 that opens toward the inside of the rubber tube 263.

In this modification, when air is sent from the operator side into the endoscope body 102 while the bending portion 106 is immersed in water, the air enters the rubber tube 263 through the hole 293 of the rear base 292. If, therefore, a pin hole exists in the rubber tube 263, air bubbles form from the surface of the bending portion 106. By checking the formation of air bubbles from the surface of the bending portion 106, therefore, the operator can check whether a pin hole is formed in the rubber tube 263.

Figure 57:
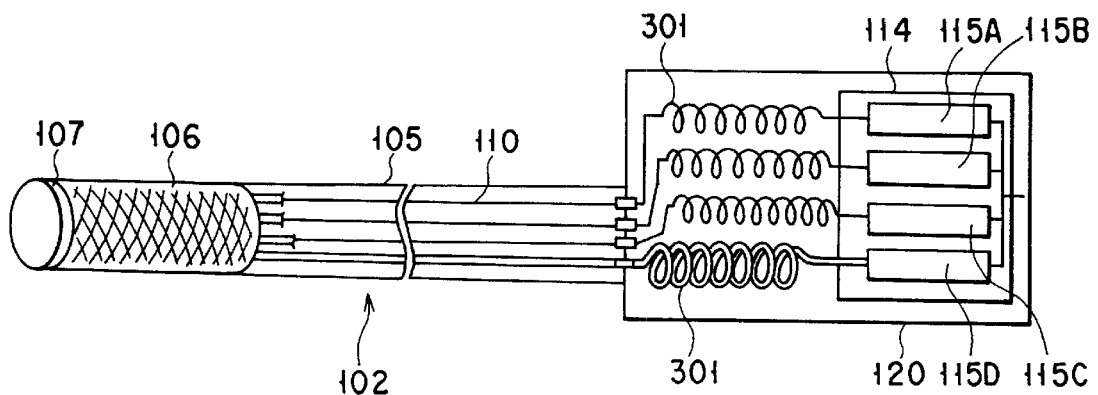
FIG. 57 is a longitudinal sectional view of main part of the second modification of the 16th embodiment.

FIG. 57 shows a modification of the internal arrangement of the drum 120 of the endoscope apparatus 101 according to the eighth embodiment (see FIGS. 25A to 27).

In this modification, a length adjustment tube 301 is interposed between the hydropneumatic pressure unit (the cylinder 112 and valve unit 114 in the eight embodiment; the syringe pump of the syringe unit 151 in the ninth embodiment (see FIG. 30)) placed in the drum 120 and the fluid supply tubes 110 coupled to the pressurization chambers 15 of the multi-lumen tube. This length adjustment tube 301 can be replaced with tubes having various lengths in accordance with application purposes.

In general, in an industrial endoscope, the total length of the insertion portion 104 of the endoscope body 102 is 10 m or more. For example, there are several types of endoscopes with insertion portions having lengths 10 m, 15 m, and 20 m. Assume that a gas is used as a bending/driving fluid used to transfer a pressure to each pressurization chamber 15 of the hydropneumatic actuator 109 of the bending portion 106. In this case, when the fluid supply tube 110 changes in length, the transfer time delay changes. In setting the correction circuit described with reference to FIG. 20, for example, different values must be set as the length of the fluid supply tube 110 changes.

According to the arrangement of this modification, the correction circuit is set in accordance with an endoscope of a type in which the insertion portion 104 of the endoscope body 102 has the greatest total length. In this case, when an endoscope of a type using a short insertion portion is to be connected and used, the length adjustment tube 301 is replaced with another one corresponding to the difference between the length of the short insertion portion and that of the insertion portion of the endoscope of the type having the longest insertion portion. This makes it possible to always obtain the same operability as that of the endoscope of the type having the longest insertion portion without changing the setting in the correction circuit.

In addition, the length adjustment tube 301 in this modification is formed into a coil-like shape, and hence can be housed in the drum 120 in a compact form.

Figure 58:
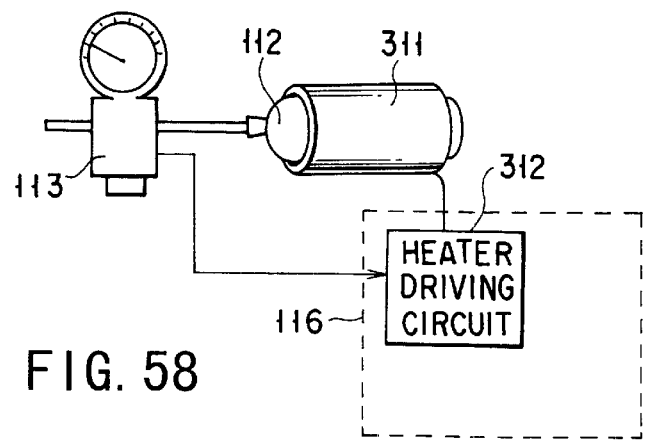
FIG. 58 is a longitudinal sectional view of main part of the third modification of the 16th embodiment.

FIG. 58 shows a modification of the internal arrangement of the drum 120 of the endoscope apparatus 101 according to the eighth embodiment (see FIGS. 25A to 27). This modification uses a nitrogen gas cylinder 112 using nitrogen gas as a gas filling the cylinder 112 incorporated in the drum 120. In addition, a heater 311 is wound around the nitrogen gas cylinder 112. The heater 311 is connected to a heater driving circuit 312 in the control circuit 116. The temperature of the heater 311 is controlled by the heater driving circuit 312 in the control circuit 116.

As the regulator 113 serving as a pressure adjusting device, a regulator incorporating a pressure sensor is used. A pressure value is always feedback to the heater driving circuit 312. The temperature of the heater 311 is controlled by the heater driving circuit 312 in the control circuit 116 to prevent the pressure from lowering below the set pressure in the regulator 113.

In the nitrogen gas cylinder 112 using nitrogen gas as a gas filling the cylinder 112 incorporated in the drum 120, nitrogen gas normally exists in the form of liquid nitrogen. When this nitrogen gas cylinder 112 is used, evaporation heat is lost upon evaporation of the liquid nitrogen at the discharge port of the cylinder 112. As a consequence, the temperature of the cylinder 112 drops. As the temperature of the cylinder 112 drops in this manner, the evaporation amount of nitrogen decreases, and the pressure of nitrogen gas decreases. For this reason, a pressure required for bending operation may be not obtained.

In this modification, therefore, the temperature of the heater 311 is controlled by the heater driving circuit 312 in the control circuit 116 to prevent the pressure from decreasing below the set pressure in the regulator 113. This makes it possible to prevent a decrease in the pressure of the cylinder 112 during operation and deterioration in bending performance. In addition, the service life of the cylinder 112 can be prolonged.

A certain effect can be obtained by covering the cylinder 112 with a heat insulator instead of using the heater 311.

FIGS. 59A and 59B show the 17th embodiment of the present invention. In this embodiment, the arrangement of a syringe unit 151 serving as a pneumatic pressure source in the endoscope apparatus 101 according to the 10th embodiment (see FIGS. 31, 32A, and 32B) is modified as follows.

As shown in FIG. 59A, as a pneumatic pressure source in an endoscope apparatus 101, two syringe units 321 are arranged. As shown in FIG. 59B, each syringe unit 321 includes two cylinders 322a and 322b coupled to the left and right sides of a unit case 328, and a piston unit 323. In the piston unit 323, rubber members 326a and 326b are attached to two ends of a male thread portion 325 having a helical thread groove. The rubber members 326a and 326b at the ends of the male thread portion 325 move in the cylinders 322a and 322b to send out the air in the cylinders 322a and 322b, thus forming a piston.

A nut-like rotating member 327 is rotatably supported in the unit case 328 through a bearing 329. A thread hole portion to threadably engage with the male thread portion 325 of the piston unit 323 is formed in the inner surface of the rotating member 327. The male thread portion 325 is linearly driven back and force in the axial direction upon rotation of the rotating member 327, thus forming a ball screw mechanism 330. A gear 331 is integrally fixed on one end portion of the rotating member 327.

A driving motor 332 is fixed to the unit case 328. A driving gear 334 is coupled to the rotating shaft of the driving motor 332 through a reduction gear 333. The gear 331 of the rotating member 327 meshes with the driving gear 334. The rotation of the driving motor 332 is transferred to the driving gear 334 through the reduction gear 333, and the gear 331 of the rotating member 327 is rotated by the driving gear 334. At this time, the rotating member 327 is rotated, together with the gear 331, and the male thread portion 325 is linearly driven back and force in the axial direction upon rotation of the rotating member 327. With this operation, the rubber members 326a and 326b at the ends of the male thread portion 325 move in the cylinders 322a and 322b, thereby sending out the air in the cylinders 322a and 322b.

Release holes 335 are formed in the cylinders 322a and 322b to release the insides of the cylinders 322a and 322b to the atmosphere. In a neutral state wherein the male thread portion 325 of the piston unit 323 moves to the middle position between the two cylinders 322a and 322b, the insides of the cylinders 322a and 322b are released to the atmosphere through the release holes 335.

The two syringe units 321 in this embodiment are connected, as shown in FIG. 59A. A fluid supply tube 337b corresponding to the DOWN direction is connected to a discharge port 336a of one cylinder 322a of one syringe unit 321, and a fluid supply tube 337a corresponding to the UP direction is connected to a discharge portion 336b of the other cylinder 322b. Fluid supply tubes 337c and 337d respectively corresponding to the RIGHT and LEFT directions are connected to the other syringe unit 321 in the same manner.

The function of the above arrangement will be described next. In this embodiment, when the driving motor 332 is driven to move the male thread portion 325 of the piston unit 323 in the cylinders 322a and 322b of the syringe unit 321 to the right in FIG. 59B, the air in the right cylinder 322b is sent to the fluid supply tube 337a. At this time, as the inside of the left cylinder 322a corresponding to the DOWN direction is released to the atmosphere through the release hole 335, the bending portion 106 is bent in the UP direction.

In the above arrangement, the two syringe units 321 shown in FIG. 59A are arranged as a pneumatic pressure source in the endoscope apparatus 101. The fluid supply tubes 337b and 337a respectively corresponding to the DOWN and UP directions are connected to one syringe unit 321, and the fluid supply tubes 337c and 337d respectively corresponding to the RIGHT and LEFT directions are connected to the other syringe unit 321 in the same manner. This makes it possible to realize a pneumatic pressure source with a compact, simple arrangement.

Note that solenoid valves may be connected to the release holes 335 in the cylinders 322a and 322b of each syringe unit 321 in the 17th embodiment, and the cylinders may be connected to these solenoid valves.

In this modification, before the motor 332 is driven, the solenoid valve is operated to send air from the air cylinder to the cylinder 322a or 322b corresponding to the bending direction to apply a pilot pressure. The piston unit 323 is then driven to bend the bending portion 106. In this modification, therefore, the responsiveness in bending the bending portion 106 can be improved.

Figure 60:
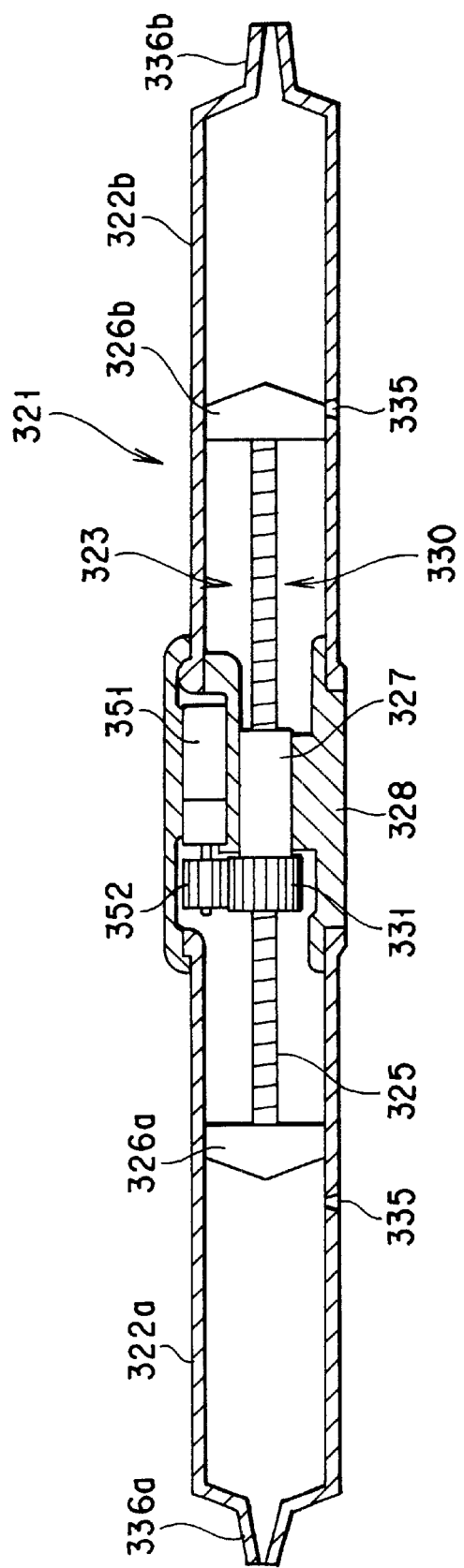
FIG. 60 is a schematic view showing the arrangement of main part of the driving mechanism of a pneumatic actuator in the endoscope apparatus according to the 18th embodiment of the present invention.

FIG. 60 shows the 18th embodiment of the present invention. In this embodiment, the arrangement of the syringe unit 321 in the 17th embodiment (see FIGS. 59A and 59B) is further modified as follows.

In the syringe unit 321 in this embodiment, a small motor 351 with a planetary gear replaces the driving motor 332 in the 18th embodiment. A driving gear 352 on the motor 351 side meshes with a gear 331 of a rotating member 327. Other portions are the same as those in the 18th embodiment.

This embodiment has the effect of further reducing the apparatus size as compared with the 18th embodiment.

Figure 61:
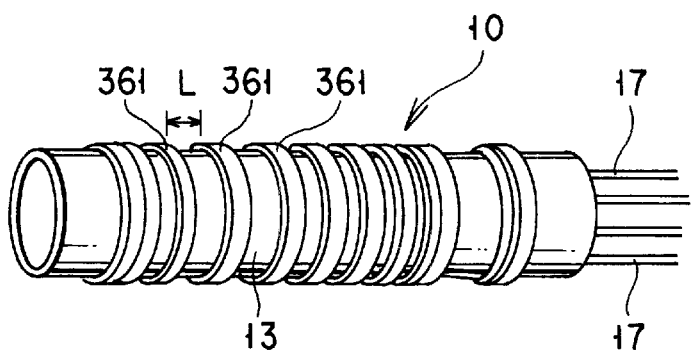
FIG. 61 is a perspective view showing the arrangement of main part of the bending portion of an endoscope apparatus according to the 19th embodiment of the present invention.
Figure 62:
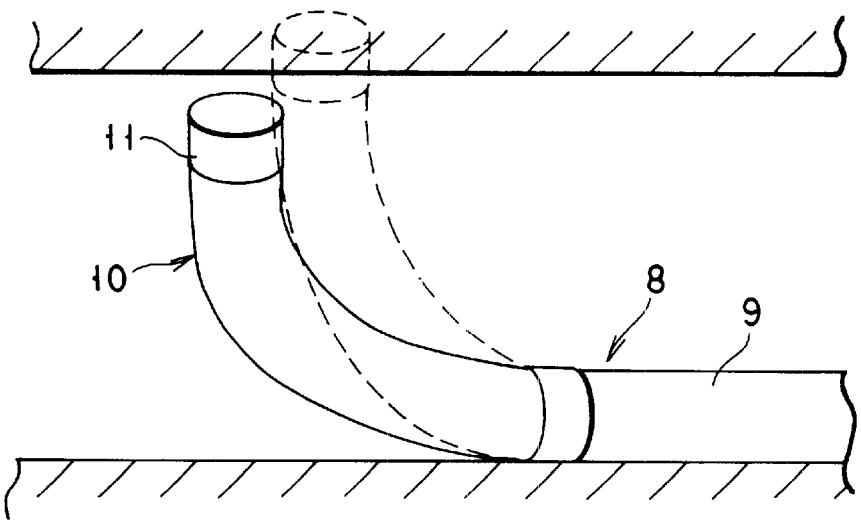
FIG. 62 is a view for explaining how the bending portion of the endoscope according to the 19th embodiment bends.

FIGS. 61 and 62 show the 19th embodiment. In this embodiment, the arrangement of the bending portion 10 of the endoscope apparatus 1 according to the first embodiment (see FIGS. 1 to 12) is further modified as follows.

As shown in FIG. 61, a plurality of ring members 361 are arranged outside a multi-lumen tube 13 in place of the outer contact coil 24 of the bending portion 10 in the first embodiment. In this case, for example, spaces L between the ring members 361 increase toward the distal end of the bending portion 10.

In this embodiment, when the operator bends the bending portion 10, the distal end side of the bending portion 10 bends greatly while the proximal end side bends a little, as indicated by the solid lines in FIG. 62. That is, the embodiment has the effect of increasing the bend in the distal end side of the bending portion 10. For this reason, as shown in FIG. 62, when an insertion portion 8 of an endoscope body 2 is inserted into a thin tube, the distal end side of the bending portion 10 in this embodiment can be bent greatly as compared with the bent shape of the bending portion 10 with a general arrangement indicated by the dotted lines in FIG. 62, provide that the two bending portions 10 have the same length. When, therefore, the bending portion 10 of the endoscope body 2 in this embodiment is bent, a distal end constituent portion 11 can be made to squarely face (oppose) the inner surface of the thin tube, as shown in FIG. 62. This makes it possible to inspect the tube wall with high precision as compared with a case wherein the inner surface of the thin tube is observed obliquely.

The bending portion 10 having the general arrangement indicated by the dotted lines in FIG. 62 must be shortened to squarely inspect the tube wall of the thin tube. If the bending portion 10 is short, it is difficult to greatly bend the bending portion 10, resulting in difficulty in controlling the bending portion 10. In contrast to this, according to this embodiment, the inner surface of a thin tube can be inspected with high precision.

Figure 63:
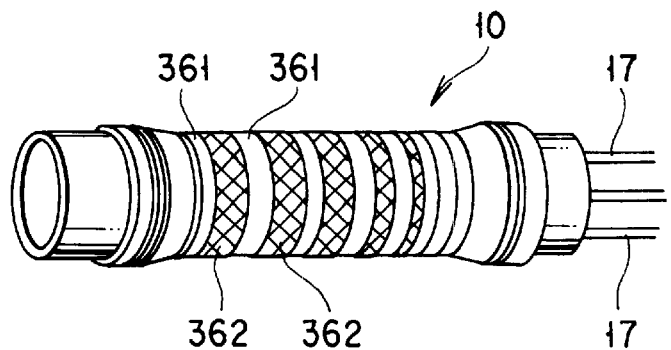
FIG. 63 is a perspective view showing the first modification of the bending portion of the endoscope apparatus according to the 19th embodiment.

As in the modification of this embodiment, which is shown in FIG. 63, ring members 362 made of a flexible rubber material or the like may be placed between the respective ring members 361 to inhibit the movement of the ring members 361.

If the ring members 362 are not used, the ring members 361 may be fixed to the outer surface of the multi-lumen tube 13 with an adhesive or the like.

Furthermore, as in the modification shown in FIG. 64, the bending portion 10 may be designed such that a plurality of ring members 371 are fitted on the bending portion 10, and the positions of the ring members 371 are arbitrarily changed. The same effect as that in the case shown in FIG. 61 can be obtained by increasing spaces L between the ring members 371 toward the distal end of the bending portion 10.

As shown in FIG. 65, a flat coil 372 may be placed around the bending portion 10 in place of the ring members 371 in FIG. 64, and the spaces between the coil rings may be increased toward the distal end of the bending portion 10.

Furthermore, the bending portion 10 may be designed to use an outer tube 381 as the modification shown in FIGS. 66A and 66B in place of the outer tube 22 in the first embodiment. This outer tube 381 has a thin portion 381*a* placed at the distal end side of the bending portion 10, and a thick portion 381*b* placed at the rear end side of the bending portion 10.

In still another modification shown in FIGS. 66C and 66D, one outer tube 384 is formed by combining a first tube 382 and a second tube 383 which is longer than the first tube 382. In this case, the first and second tubes 382 and 383 are stacked on the rear end portion of the bending portion 10 to form a stacked portion, whereas only the distal end portion of the second tube 383 extends from the distal end of the bending portion 10 to form a single-tube portion.

The same effect as that of the 19th embodiment (see FIGS. 61 and 62) can be obtained with the outer tube 381 in FIGS. 66A and 66B or the outer tube 384 in FIGS. 66C and 66D.

Figure 67:
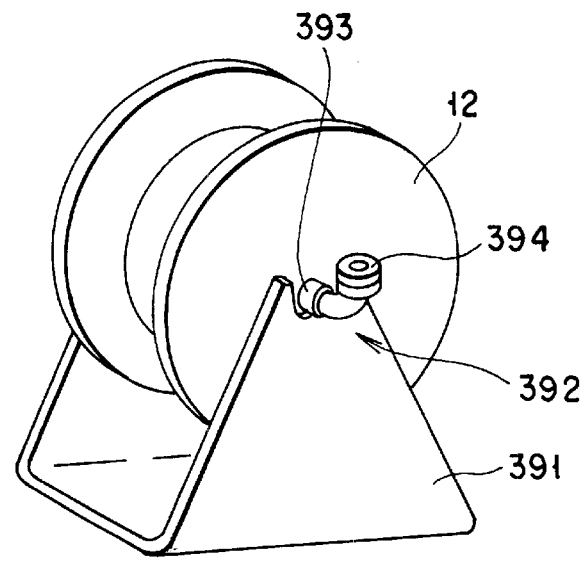
FIG. 67 is a perspective view showing the arrangement of main part of a drum in an endoscope apparatus according to the 20th embodiment of the present invention.
Figure 68:
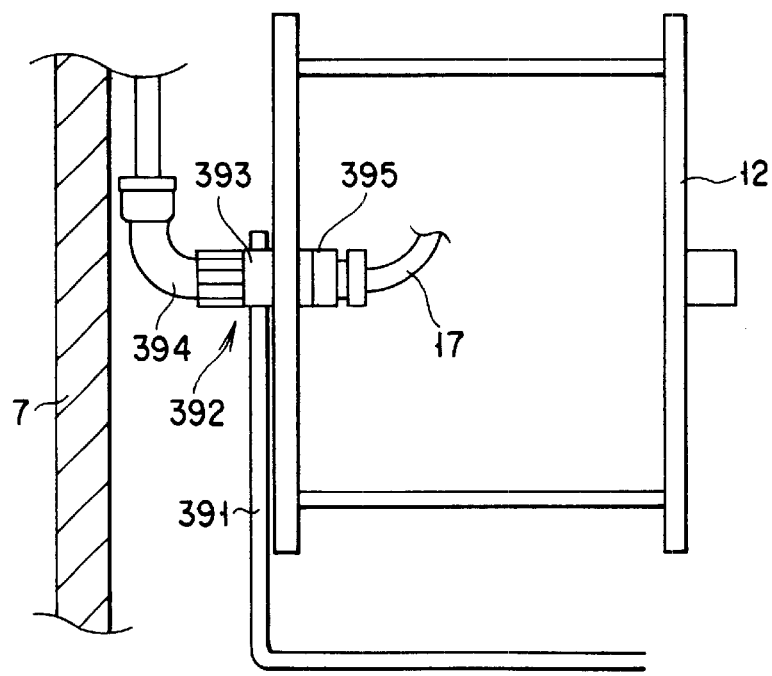
FIG. 68 is a longitudinal sectional view showing the arrangement of main part of the drum in the endoscope apparatus according to the 20th embodiment.

FIGS. 67 and 68 show the 20th embodiment of the present invention. In this embodiment, the arrangement of the drum 12 of the endoscope apparatus 1 according to the first embodiment (FIGS. 1 to 12) is modified as follows.

In this embodiment, a rotary joint portion 394 is placed at the central portion of a drum 12 rotatably supported by a support leg portion 391 of the drum 12. In this arrangement, when the drum 12 rotates, the rotary joint portion 394 rotates to prevent a fluid supply tube 17 from being entangled.

The rotating shaft of the drum 12 has a pipe-like fixed shaft 393. The elbow-like rotary joint portion 394 is rotatably connected to one end portion of the fixed shaft 393.

A coupling 395 is connected to the other end portion of the fixed shaft 393. The fluid supply tube 17 is coupled to the coupling 395. The coupling 395 is also connected to a solenoid valve unit 30, and a cylinder 34 as a pneumatic pressure source is connected to the rotary joint portion 394 through a regulator 41.

In addition, electrical signal lines may be connected through slip rings, and a white LED as illumination at the distal end may be connected through a slip ring.

In this embodiment, when an insertion portion 8 of an endoscope body 2 is pulled out from the drum 12, the rotary joint portion 394 rotates, together with the drum 12, to prevent the fluid supply tube 17 from being entangled. If other signal lines are connected through slip rings, the entanglement of all cables can be prevented.

With the above arrangement, the following effect can be obtained. In this embodiment, when the insertion portion 8 of the endoscope body 2 is pulled out, the fluid supply tube 17 for sending air need not be wound around the drum 12 or set in a helical form. This makes it possible to realize a simple arrangement with a small space. As a consequence, the size of the apparatus can be reduced.

Figure 71:
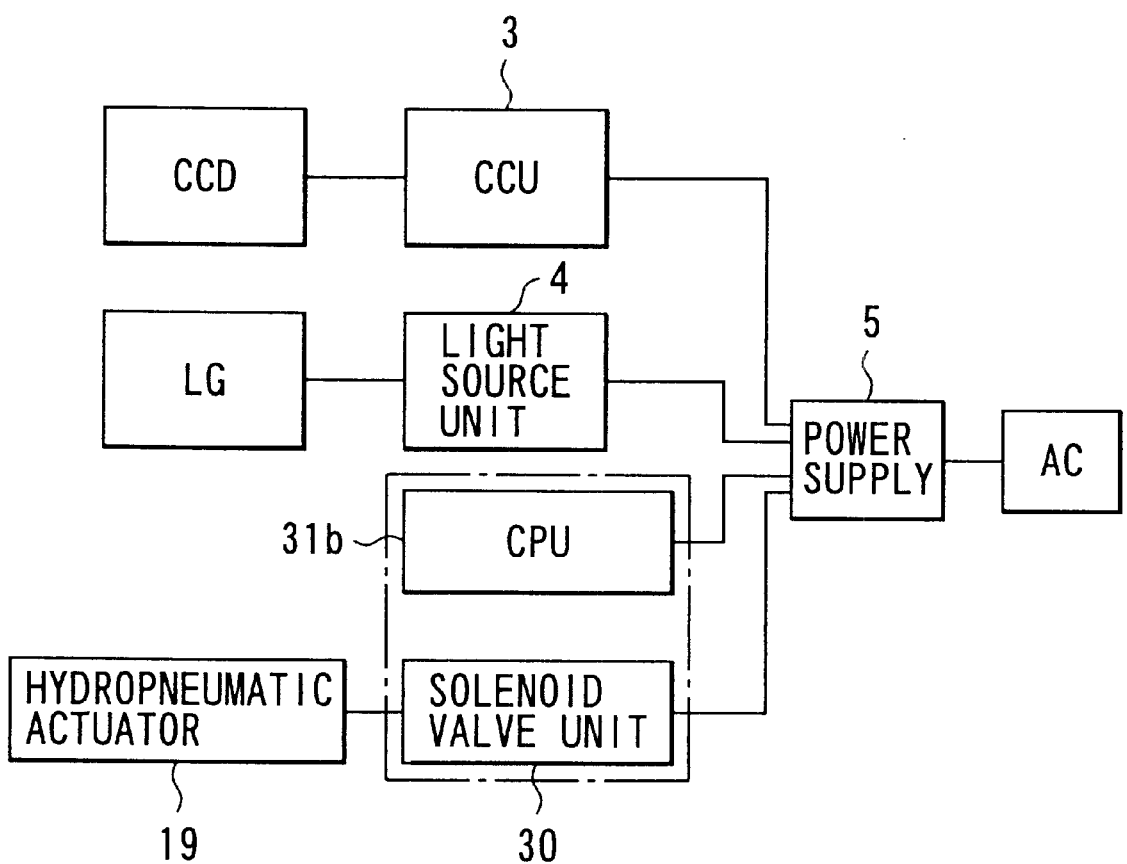
FIG. 71 is a schematic view showing the arrangement of the endoscope apparatus according to the 21st embodiment.

FIGS. 69 to 71 show the 21st embodiment of the present invention. In this embodiment, the arrangement of the endoscope apparatus 1 according to the first embodiment (see FIGS. 1 to 12) is modified as follows.

In this embodiment, as shown in FIG. 69, a CCU 3, a light source unit 4, a controller 31 for bending operation, and a solenoid valve unit 30 are housed in a drum 12.

As shown in FIG. 70A, only a monitor 6 and joystick 37 are directly housed in a carrying case 7. In this case, the joystick 37 is pulled out and the monitor 6 is set upright as shown in FIG. 70B when they are used.

As shown in FIG. 71, the CCU 3, the light source unit 4, a CPU 31*b* of the controller 31, and the solenoid valve unit 30 are connected to one power supply 5 serving as a common power supply for the operations of the respective units.

With the above arrangement, the following effects can be obtained. In this embodiment, since the CCU 3, the light source unit 4, the controller 31 for bending operation, the solenoid valve unit 30, and the like are housed in the drum 12, wiring outside the drum 12 can be reduced. This makes it possible to simplify the wiring outside the drum 12. In addition, there is no chance that signal lines entangle with the drum 12 when the insertion portion 8 of the endoscope body 2 is pulled out.

The present invention is not limited to the embodiments described above. For example, in the first embodiment, proportionally controlled valves (pressure control valves) may replace the solenoid valves. In this case, a total of four proportionally controlled valves are respectively used for the pressurization chambers of the hydropneumatic actuator 19 which are used for bending operations in the four directions.

In this modification, the pressure of a fluid from the cylinder 34 is controlled by controlling the proportionally controlled valves. When, for example, the operator tilts the joystick 37, a pressure instruction corresponding to the tilt is input, and the fluid is controlled in accordance with the pressure by the proportionally controlled valve. When the pressure of the fluid reaches the instructed pressure, the supply of the fluid is stopped to keep the pressure in the pressurization chamber 15 to hold the bend in the bending portion 10.

When the operator returns the joystick 37 to its initial position, the pressure is decreased to restore the bend in the bending portion 10. When the operator stops the joystick 37, the bending portion 10 stops bending at that position.

According to this embodiment having the above arrangement, since the pressure of the fluid from the cylinder 34 can be controlled by controlling the proportionally controlled valves, the bending direction and bend amount of the bending portion 10 can be controlled with high precision in accordance with a bending instruction.

Figure 72:
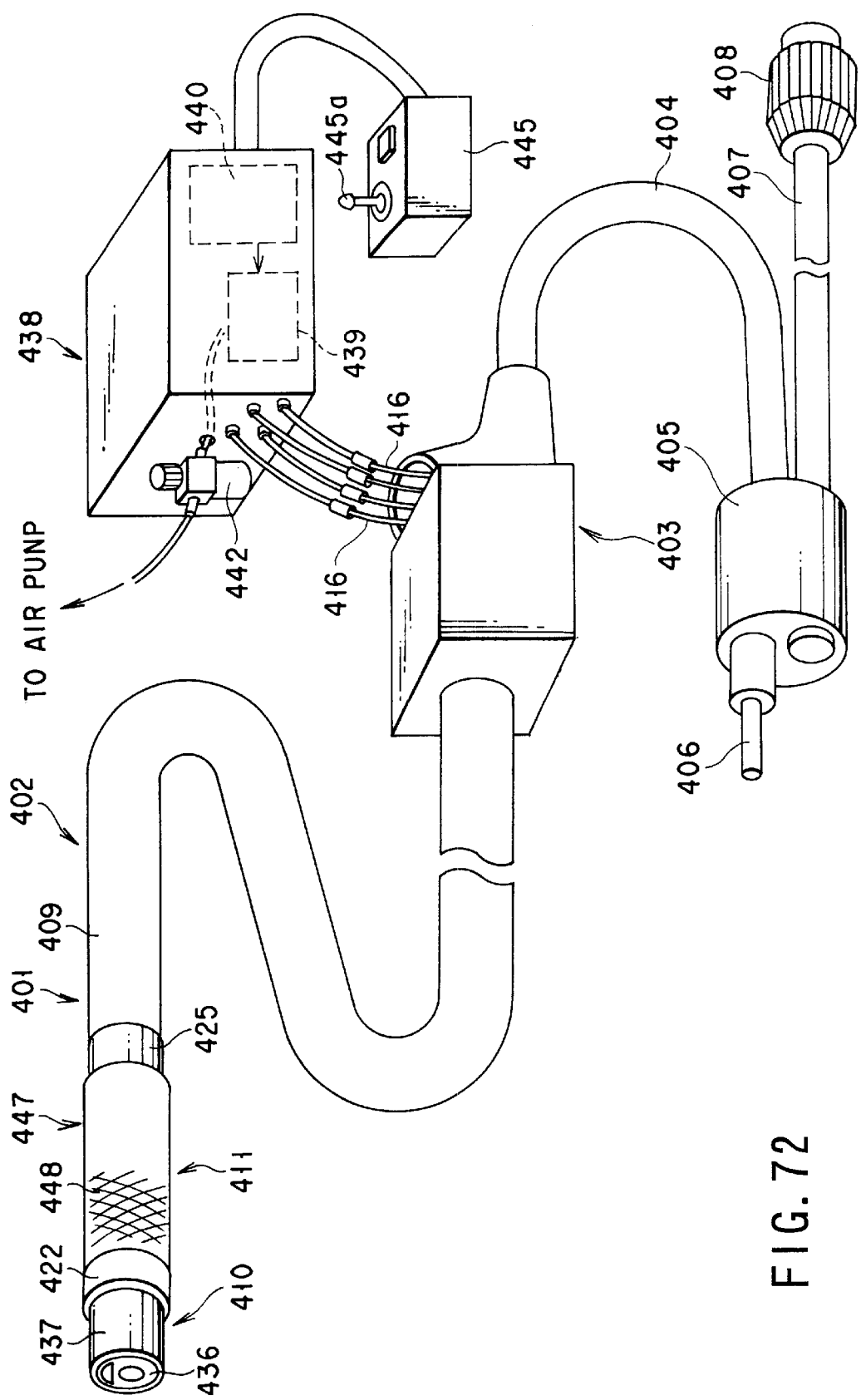
FIG. 72 is a schematic view showing the arrangement of the overall system of an endoscope apparatus according to the 22nd embodiment of the present invention.

The 22nd embodiment of the present invention will be described next with reference to FIGS. 72 to 79. FIG. 72 shows the schematic arrangement of the overall system of an industrial endoscope 401 of this embodiment. This endoscope 401 has a long, narrow insertion portion 402 to be inserted into a tubular cavity. A branch portion 403 is placed at the proximal end portion of the insertion portion 402.

One end portion of a connection cable 404 is coupled to the branch portion 403. The other end portion of the connection cable 404 is coupled to a connector 405. A connection portion 406 of a light guide to be connected to a light source unit (not shown) extends vertically from the connector 405, and one end portion of an electric code 407 is connected to the connector 405. The other end portion of the electric code 407 is coupled to a second connector 408. This second connector 408 is connected to a camera control unit (CCU) (not shown).

The insertion portion 402 of the endoscope 401 has a long, narrow hose 409 having flexibility. A distal end constituent portion 410 is placed at the very end of the insertion portion 402. A bending portion 411 is interposed between the proximal end portion of the distal end constituent portion 410 and the distal end portion of the hose 409.

Figure 74A:
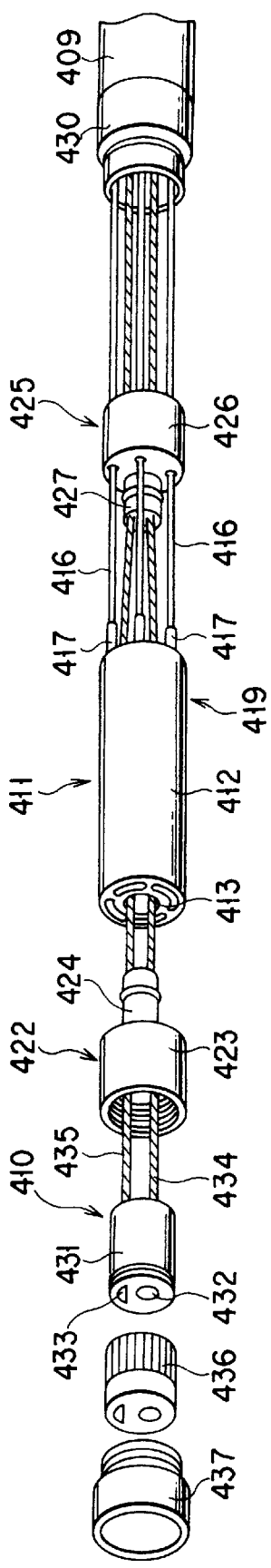
FIG. 74A is an exploded perspective view of the distal end portion of the insertion portion of the endoscope apparatus according to the 22nd embodiment.

A multi-lumen tube (elastic tubular member) 412 made of, e.g., silicone resin is placed in the bending portion 411. As shown in FIG. 74C, the multi-lumen tube 412 has an axial portion lumen 413 at an axial portion, which extends along the axial direction. A plurality of (four in this embodiment) circumferential portion lumens 414a to 414d are arranged in the tube wall around the axial portion lumen 413 at almost equal intervals in the circumferential direction.

The two end portions of each of the four circumferential portion lumens 414a to 414d are sealed. The circumferential portion lumens 414a to 414d are hermetically sealed to form pressurization chambers (air chambers) 415.

Figure 75A:
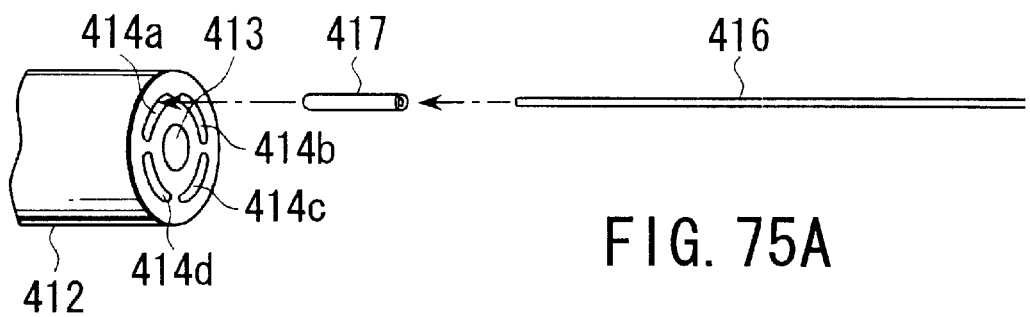
FIG. 75A is an exploded perspective view showing a connection portion for an air tube of a pneumatic actuator in the endoscope according to the 22nd embodiment.
Figure 75B:
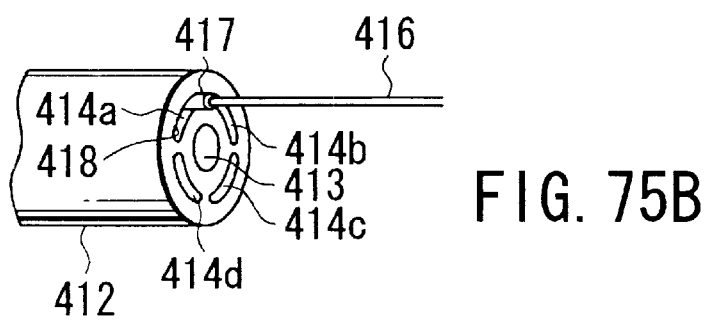
FIG. 75B is a perspective view showing how the air tube of the pneumatic actuator is connected.

As shown in FIG. 75B, one end portion of an air tube 416 made of Teflon (tradename in Dupont) is coupled to the sealed portion of each of the circumferential portion lumens 414a to 414d on the rear end side while extending through the pressurization chamber 415. As shown in FIG. 75A, one end portion of the air tube 416 is fixed in advance while being inserted into a silicone tube 417.

The inner diameter of the silicone tube 417 is almost equal to or slightly smaller than the outer diameter of the air tube 416, so the air tube 416 is forcibly inserted into the silicone tube 417. To prevent the air tube 416 from slipping off the silicone tube 417, the air tube 416 may be tied to the silicone tube 417 with a string, metal wire, or the like, which is externally wound around the silicone tube 417. Alternatively, the outer surface of the air tube 416 may be roughened by a file-like member to make it difficult for the air tube 416 to slip off.

Figure 77:
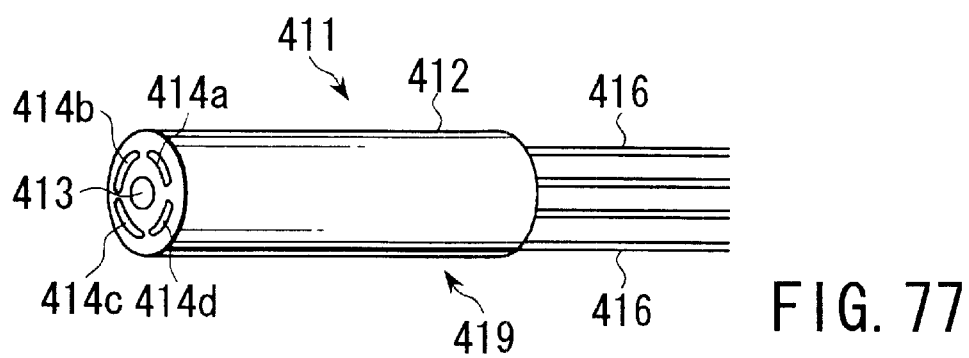
FIG. 77 is a perspective view showing main part of the endoscope according to the 22nd embodiment and shows how the pneumatic actuator is assembled.
Figure 78:
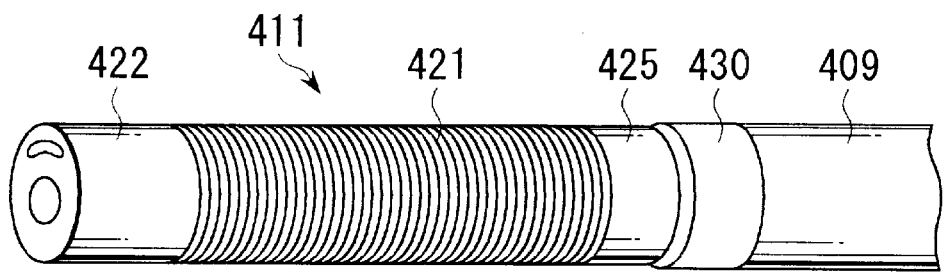
FIG. 78 is a perspective view showing the distal end portion of the insertion portion of the endoscope according to the 22nd embodiment.

This silicone tube 417 is inserted into an opening portion in each of the circumferential portion lumens 414a to 414d on the rear end side. A silicone sealing agent 418 is then injected into the space between the rear-end opening portion of each of the circumferential portion lumens 414a to 414d and the silicone tube 417 to seal the rear-end opening portion of each of the circumferential portion lumens 414a to 414d. As a consequence, as shown in FIG. 77, a pneumatic actuator unit 419 of the bending portion 411 is formed, in which the four pressurization chambers 415 of the multi-lumen tube 412 are coupled to the four air tubes 416.

Figure 74B:
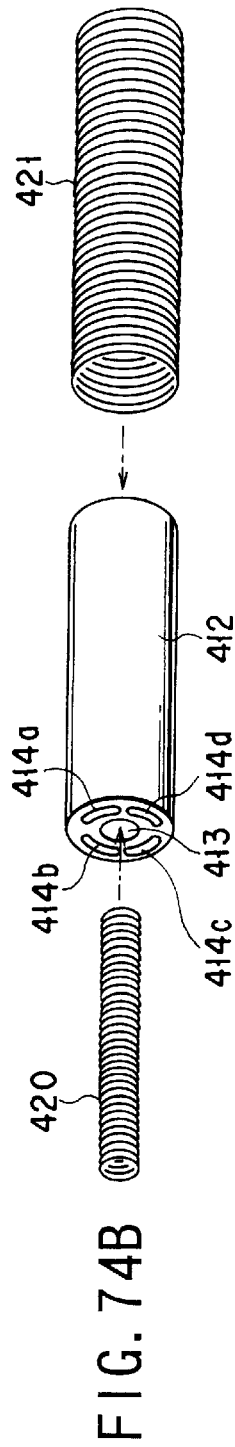
FIG. 74B is an exploded perspective view of the bending portion.
Figure 74C:
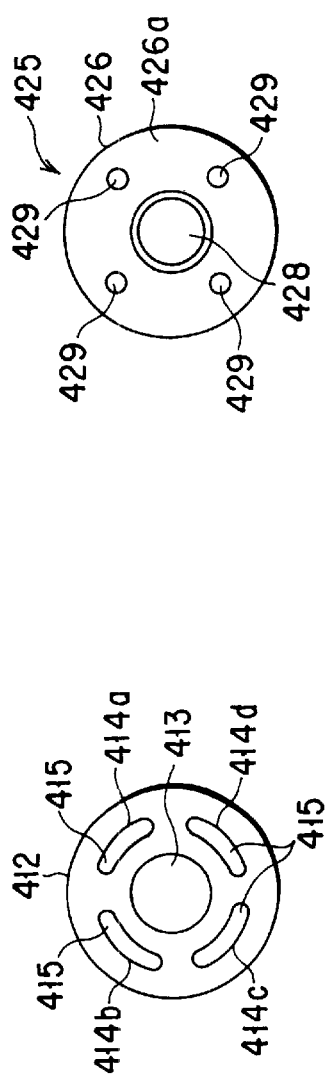
FIG. 74C is a cross-sectional view of a pneumatic actuator.

As shown in FIG. 74B, an internal deformation restricting member 420 made of a close coil having a diameter slightly smaller than the inner diameter of the axial portion lumen 413 is inserted into the axial portion lumen 413 of the multi-lumen tube 412. In addition, an external deformation restricting member 421 made of a close coil having a diameter slightly larger than the outer diameter of the multi-lumen tube 412 is fitted on the multi-lumen tube 412.

Even if the size of the internal deformation restricting member 420 is almost equal or slightly larger than that of the axial portion lumen 413, bending operation can be performed as long as the internal deformation restricting member 420 can be inserted into the axial portion lumen 413 of the multi-lumen tube 412. Likewise, the size of the external deformation restricting member 421 may be almost equal or slightly smaller than the outer diameter of the multi-lumen tube 412. In consideration of ease of assembly and bending performance, however, the arrangement described first is preferable.

Figure 76:
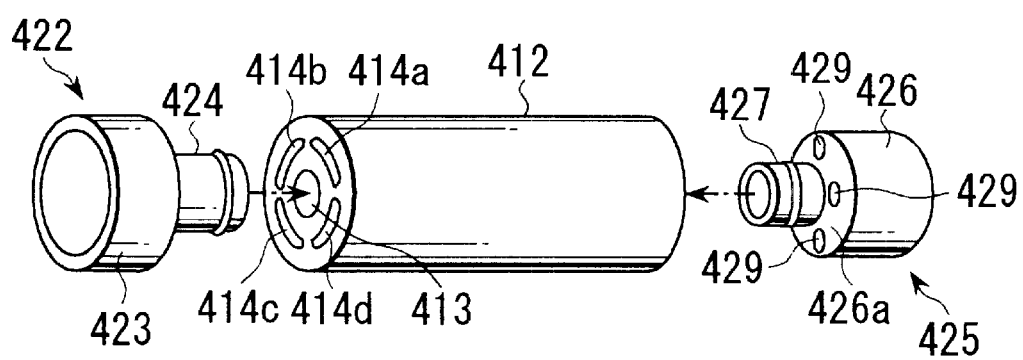
FIG. 76 is an exploded perspective view showing the pneumatic actuator and base members in the endoscope according to the 22nd embodiment before they are connected to each other.

As shown in FIG. 76, a front mouth piece 422 made of, e.g., stainless steel is placed at the front end portion of the multi-lumen tube 412. The front mouth piece 422 has a cylindrical portion 423 having a diameter equal to the outer diameter of the multi-lumen tube 412, and a small-diameter coupling portion 424 vertically extending backward from the axial portion of the rear end face of the cylindrical portion 423. The front mouth piece 422 is fixed/coupled to the multi-lumen tube 412 with an adhesive while the coupling portion 424 is inserted into the axial portion lumen 413 of the multi-lumen tube 412.

A rear mouth piece 425 made of, e.g., stainless steel is placed at the rear end portion of the multi-lumen tube 412. The rear mouth piece 425 has a cylindrical portion 426 having a diameter equal to the outer diameter of the multi-lumen tube 412, and a small-diameter coupling portion 427 vertically extending forward from the axial portion of a front end face 426a of the cylindrical portion 426. The rear mouth piece 425 is fixed/coupled to the multi-lumen tube 412 with an adhesive while the coupling portion 427 is inserted into the axial portion lumen 413 of the multi-lumen tube 412.

Figure 74D:
FIG. 74D is a cross-sectional view showing the front end face of a base member.

As shown in FIG. 74D, an axial hole 428 is formed in the axial portion of the front end face 426a of the cylindrical portion 426 of the rear mouth piece 425. Four tube through holes 429 are formed around the axial hole 428 at equal intervals in the circumferential direction. The four air tubes 416 of the pneumatic actuator unit 419 of the bending portion 411 are respectively inserted into the four tube through holes 429. The four air tubes 416 of the pneumatic actuator unit 419 extend toward the branch portion 403 through the rear mouth piece 425 and hose 409. Note that a hose-side mouth piece 430 fixed to the distal end portion of the hose 409 is coupled/fixed to the cylindrical portion 426 of the rear mouth piece 425.

As shown in FIG. 74A, a CCD unit 431 is housed in the cylindrical portion 423 of the front mouth piece 422. The CCD unit 431 incorporates a CCD (solid-state image sensing element) 432 serving as an image sensing means in an observation optical system and an illumination optical system 433.

In addition, a CCD signal line 434, a light guide 435 serving as an optical transmission means for an illumination optical system, and the like extend from the rear end portion of the CCD unit 431. The CCD signal line 434, the light guide 435, and the like extend toward the branch portion 403 through the front mouth piece 422, the axial portion lumen 413 of the multi-lumen tube 412, the rear mouth piece 425, and the hose 409. The CCD signal line 434 is connected to a camera control unit (not shown) through the branch portion 403, connection cable 404, connector 405, electric code 407, and second connector 408. The light guide 435 is connected to a light source unit (not shown) through the branch portion 403, connection cable 404, and connector 405.

An optical adapter 436 is placed on the front surface of the CCD unit 431. As the optical adapter 436, a plurality of types of replacement adapters having different optical characteristics are prepared. One of the optical adapters 436 which has desired optical characteristics can be selectively used, as needed.

A protective distal end cover 437 is mounted on the outer surface of the optical adapter 436. The distal end cover 437 is detachably mounted on the cylindrical portion 423 of the front mouth piece 422.

Figure 73:
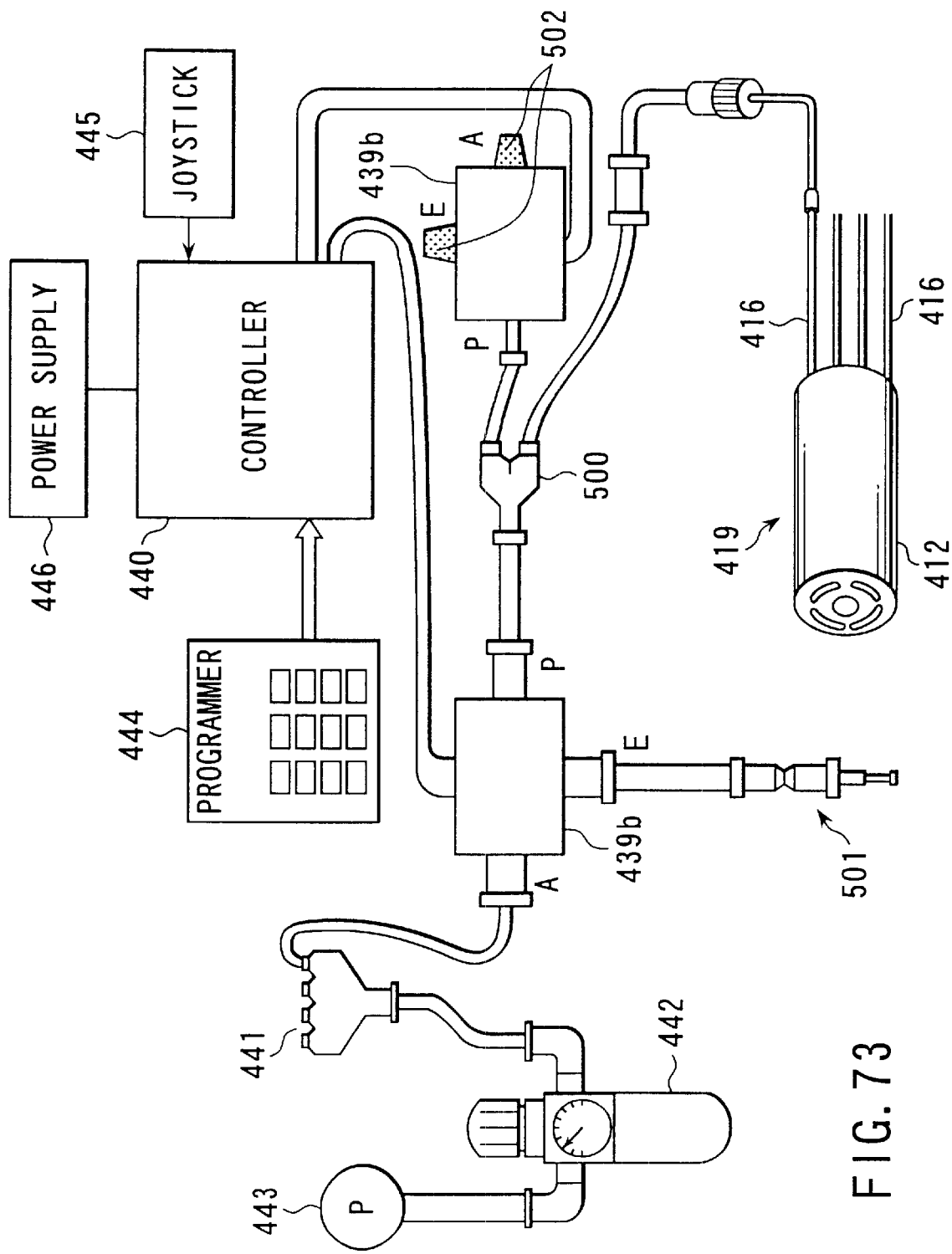
FIG. 73 is a schematic view showing the arrangement of the controller of the endoscope apparatus according to the 22nd embodiment.

The system of the industrial endoscope 401 according to this embodiment has a bending control unit 438 for controlling the bending operation of the bending portion 411 of the endoscope 401. As shown in FIG. 73, the bending control unit 438 incorporates eight solenoid valves 439 for independently controlling the supply/exhaustion of air to/from the four air tubes 416 connected to the pneumatic actuator unit 419 of the bending portion 411, and a controller 440 for controlling these solenoid valves 439.

Two (first and second) solenoid valves 439a and 439b are connected to each of the air tubes 416 connected to the pneumatic actuator unit 419.

An air vent A of the first solenoid valve 439a is coupled to an air pump 443 serving as a pneumatic pressure source through a distributor 441 and a filter regulator 442. The second solenoid valve 439b and one air tube 416 are connected to an air vent P through a distributor 500. A plug 501 is fitted in the air vent E so as not to allow air flow. As described above, the air vent P of the second solenoid valve 439b is connected to the air vent P of the first solenoid valve 349a. A silencer 502 is connected to the other air vents A and E, which are released to the atmosphere.

Figure 84:
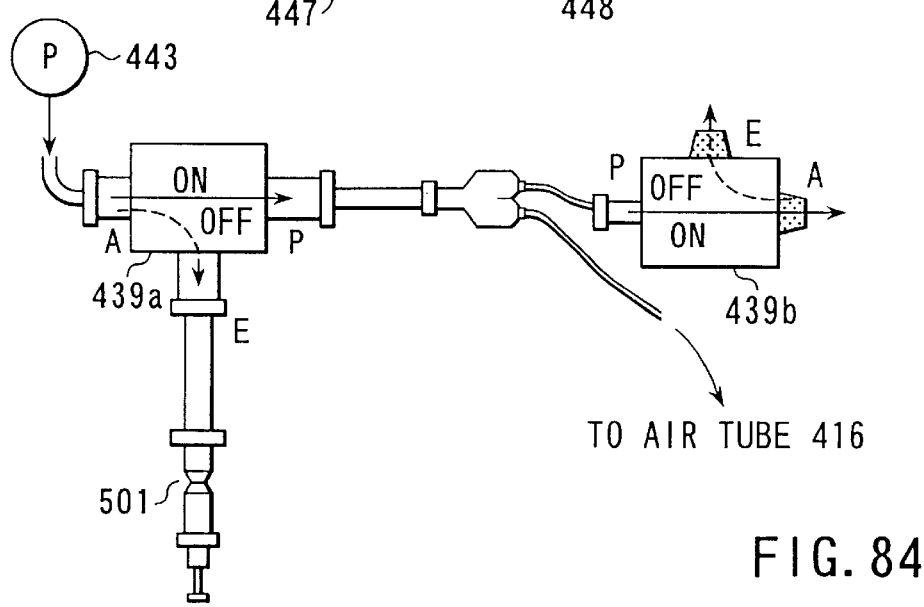

While the first and second solenoid valves 439a and 439b are off, air flows from the air vent A to the air vent E in each solenoid valve, as indicated by the dotted line in FIG. 84. When a voltage is applied to each solenoid valve to turn it on, air flows from the air vent A to the air vent P, as indicated by the solid line in FIG. 84. The first and second solenoid valves 439a and 439b are normally off, and compressed air from the air pump 443 stays in the first solenoid valve 439a. When a voltage is applied to the first solenoid valve 349a to turn it on, the compressed air flows through the air vent P of the first solenoid valve 439a and is set to the pressurization chamber 415 through the air tube 416, thereby bending the bending portion 411. At this time, the second solenoid valve 439b is off. When the operator stops the bending instruction, the first solenoid valve 439a is turned off, and the second solenoid valve 439b is turned on. As a consequence, air from the pressurization chamber 415 is exhausted outside through the air tube 416 and the air vents P and A of the second solenoid valve 439b.

Although FIG. 73 shows only the solenoid valves and air tube paths corresponding to one bending direction, there are three other similar arrangements.

An input unit 444 such as a keyboard for setting operations for the eight solenoid valves 439, a joystick 445 for controlling the bending operation of the bending portion 411, and a power supply 446 are connected to the controller 440.

As the operator operates an operation lever 445a of the joystick 445, the bending control unit 438 independently controls the supply/exhaustion of air to/from the four air tubes 416 to selectively pressurize the four pressurization chambers 415 of the pneumatic actuator unit 419, thereby bending the multi-lumen tube 412 in a predetermined direction, i.e., a direction opposite to the pressurized pressurization chamber 415.

Figure 79:
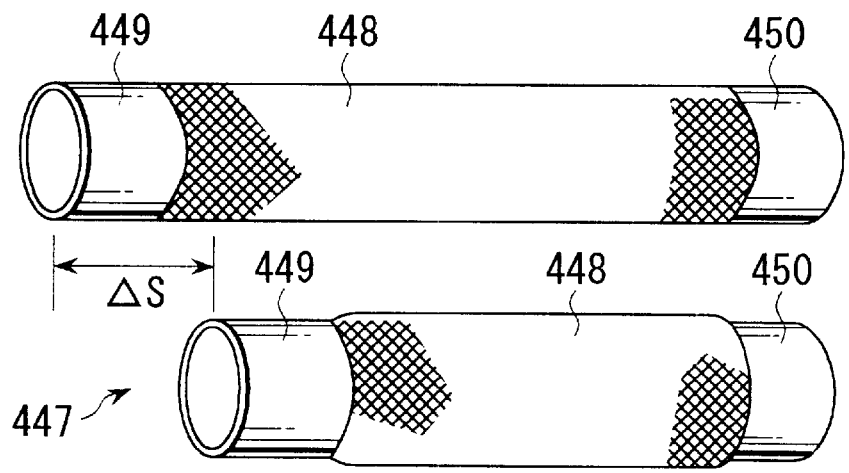
FIG. 79 is a perspective view of main part of the endoscope according to the 22nd embodiment and explains how a protective member is mounted.

A bending portion protecting means 447 is mounted on that outer surface portion of the bending portion 411 of the endoscope 401, which is located between the front and rear ends of the bending portion 411. As shown in FIG. 79, the bending portion protecting means 447 has a substantially cylindrical braid (cylindrical protective member) 448. The braid 448 is formed to be extensible in the axial and radial directions by braiding many fiber elements made of low-elasticity fibers (nonextensible fibers) such as Kevlar (tradename), Teflon, or metal fibers into a cylindrical shape. The braid 448 expands radially when it shrinks axially, and vice versa.

Front and rear mouth pieces 449 and 450 are respectively mounted on the front and rear end portions of the braid 448. Referring to FIG. 79, the braid 448 on the upper side indicates a state wherein the length in the axial direction is held as the natural length, whereas the braid 448 on the lower side indicates a state wherein the length in the axial direction is reduced from the natural length by ΔS. In this embodiment, as indicated at the lower side in FIG. 79, the braid 448 is mounted between the two ends of the bending portion 411 while the length in the axial direction is reduced from the natural length by AS.

Consider the relationship between the inner diameter of the braid 448 and the outer diameter of the external deformation restricting member 421 at this time. In the case shown in FIG. 79, the inner diameter of the braid 448 is almost equal to or slightly larger than the outer diameter of the external deformation restricting member 421. In this case, the front and rear mouth pieces 449 and 450 of the braid 448 are respectively fixed to the front and rear mouth pieces 422 and 425 of the multi-lumen tube 412 with screws while being sealed with an adhesive.

The function of the above arrangement will be described next. In using the endoscope 401 of this embodiment, as the operator tilts the operation lever 445a of the joystick 445, the bending portion 411 bends in a desired direction. At this time, as the operator operates the operation lever 445a of the joystick 445, the bending control unit 438 independently controls the supply/exhaustion of air to/from the four air tubes 416. The air is then supplied to one or two of the four pressurization chambers 415 of the pneumatic actuator unit 419 to selectively pressurize the pressurization chambers.

In bending operation, a bending direction is selected by selectively turning on the four first solenoid valves 439a. In stopping bending operation, the second solenoid valve 439b paired with the ON first solenoid valve 439a is turned on to exhaust air from the pressurization chamber 415 through the air tube 416 and the air vents P and A of the second solenoid valve 439b. In this case, when the operator raises the joystick 445 upright to give an instruction to stop the bending operation, the second solenoid valve 439b is turned on simultaneously or with a slight time lag. In holding the bend in the bending portion, the first and second solenoid valves 439a and 439b are turned off after bending operation so as to close the space in the pressurization chamber 415 and air tube 416. The bending speed can be adjusted by turning on/off each solenoid valve in a pulse-like manner and changing the pulse width, or can be increased by initially pressurizing the four pressurization chambers 415.

The pressurized pressurization chamber 415 expands in both the axial and radial directions. At this time, since the external deformation restricting member 421 and internal deformation restricting member 420 respectively located outside and inside the multi-lumen tube 412 restrict the expansion of the pressurization chamber 415 in the radial direction of the bending portion 411, the pressurization chamber 415 can efficiently expand mainly in the axial direction.

When the bending portion 411 bends, the outside portion of the bend in the multi-lumen tube 412 becomes longer than when the bending portion 411 does not bend. Since the expansion of the pressurization chamber 415 of the multi-lumen tube 412, which is pressurized by compressed air, is restricted in the radial direction, and the pressurization chamber 415 extends in the longitudinal direction, the bending portion 411 bends with the pressurized pressurization chamber 415 being located outside the bend. At this time, the braid 448 of the bending portion protecting means 447 of the bending portion 411 deforms such that the outside portion of the bend returns from a shrunk state to a natural length state, and hence the braid 448 can be easily deformed as the bending portion 411 bends.

With the above arrangement, the following effect can be obtained. In this embodiment, the braid 448 is placed between the two ends of the outer surface of the bending portion 411 with the length in the axial direction being smaller than the natural length by ΔS, and the front and rear mouth pieces 449 and 450 of the braid 448 are respectively fixed to the front and rear mouth pieces 422 and 425 of the multi-lumen tube 412 with screws while being sealed with an adhesive. In this structure, when the bending portion 411 bends, the braid 448 deforms such that the outside portion of the bend returns from a shrunk state to a natural length state. This allows the braid 448 to easily deform as the bending portion 411 bends. Since there is no chance that the deformation of the braid 448 acts as a resistance force against the bending operation of the bending portion 411, the bending angle of the bending portion 411 can be increased as compared with the prior art, thus improving bending performance.

Figure 80:
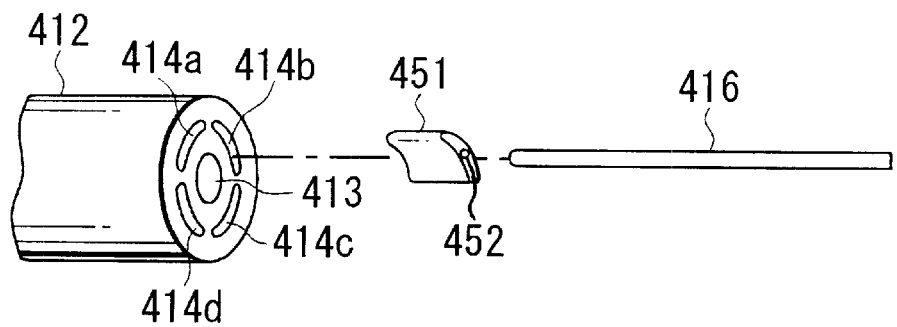
FIG. 80 is an exploded perspective view showing a modification of the connection portion for each air tube of the pneumatic actuator in the endoscope according to the 22nd embodiment.

FIG. 80 shows a modification of the connection portion of each air tube 416 in the pneumatic actuator unit 419 of the endoscope 401 according to the 22nd embodiment of the present invention. This embodiment includes a connection member 451 having substantially the same cross-sectional shape as that of each of the arcuated circumferential portion lumens 414a to 414d of the multi-lumen tube 412. For example, the connection member 451 is made of a metal material such as stainless steel or the same silicone resin as that used for the multi-lumen tube 412. An air tube connection hole 452 is formed in the connection member 451. One end of the air tube 416 is inserted and bonded/fixed in the air tube connection hole 452 of the connection member 451.

In addition, the connection members 451 are fixed to the four arcuated circumferential portion lumens 414a to 414d with a silicone adhesive while being inserted into the edge portions of the circumferential portion lumens 414a to 414d.

In this modification, the multi-lumen tube 412 is connected to the air tubes 416 by using the connection members 451 each having substantially the same cross-sectional shape as that of each of the four circumferential portion lumens 414a to 414d of the multi-lumen tube 412. This makes it possible to easily connect the multi-lumen tube 412 and the air tubes 416 to each other, which are difficult to bond.

Figure 81A:
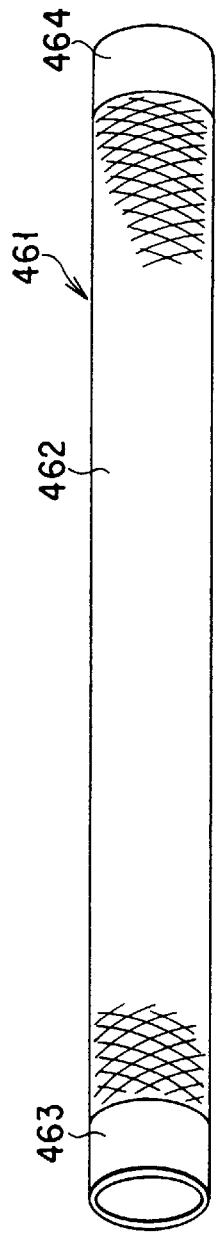
FIG. 81A is a perspective view showing a protective member for the pneumatic actuator of the triple bending portion of an endoscope according to the 23rd embodiment of the present invention.
Figure 81B:
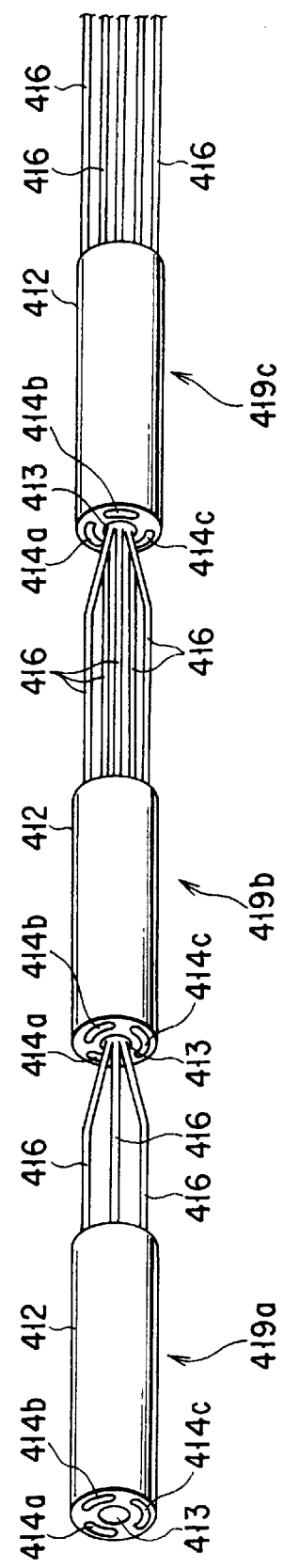
FIG. 81B is an exploded perspective view showing the pneumatic actuator of the triple bending portion in the endoscope.
Figure 81C:
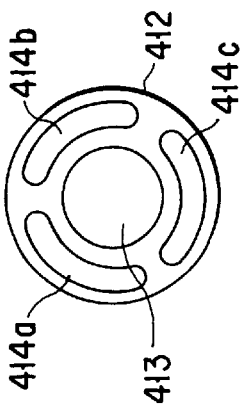

FIGS. 81A to 81C show the 23rd embodiment of the present invention. In this embodiment, the arrangement of the bending portion 411 of the endoscope 401 according to the 22nd embodiment (see FIGS. 72 to 79) is modified as follows.

In this embodiment, a bending portion 411 has three pneumatic actuators 419a, 419b, and 419c connected in line, as shown in FIG. 81B, each of which is identical to the pneumatic actuator unit 419 in the 22nd embodiment.

As shown in FIG. 81C, three arcuated circumferential portion lumens 414a to 414c are arranged, at equal intervals in the circumferential direction, in the tube wall around an axial portion lumen 413 in each multi-lumen tube 412 having the triple pneumatic actuator units 419a, 419b, and 419c. Three air tube 416 in the pneumatic actuator unit 419a at the very end position are inserted into the axial portion lumen 413 of the pneumatic actuator unit 419b at the second stage.

Three air tubes 416 in the second pneumatic actuator unit 419b are inserted into the axial portion lumen 413 of the third pneumatic actuator unit 419c, together with the three air tubes 416 in the pneumatic actuator unit 419A at the very end position. Therefore, a total of six air tubes 416 are inserted into the axial portion lumen 413 of the third pneumatic actuator unit 419c.

Three air tubes 416 in the third pneumatic actuator unit 419c extend toward a branch portion 403 through a coupling portion 427 of a rear mouth piece 425 and a hose 409, together with the three air tubes 416 in each of the first and second pneumatic actuator units 419c.

This embodiment further includes a bending portion protecting means 461 for the triple pneumatic actuator units 419a, 419b, and 419c. The bending portion protecting means 461 has one braid (cylindrical protective member) 462 commonly covering the outer surfaces of the triple pneumatic actuator units 419a, 419b, and 419c.

Front and rear mouth pieces 463 and 464 are respectively mounted on the front and rear end portions of the braid 462. In this embodiment, the braid 462 is placed between the two ends of a row of the triple pneumatic actuator units 419a, 419b, and 419c of the bending portion 411 while the length in the axial direction is made shorter than the natural length. In this case, the front and rear mouth pieces 463 and 464 of the braid 462 are respectively fixed to a front mouth piece 422 of the multi-lumen tube 412 of the pneumatic actuator unit 419a at the very end position and the rear mouth piece 425 of the multi-lumen tube 412 of the third pneumatic actuator unit 419c with screws while being sealed with an adhesive.

In this embodiment, since the bending portion 411 has the triple pneumatic actuator units 419a, 419b, and 419c coupled in line, as shown in FIG. 81B, each of which is identical to the pneumatic actuator unit 419 in the 22nd embodiment, the bending portion 411 can be bent in a more complicated shape than in the 22nd embodiment.

Figure 82A:
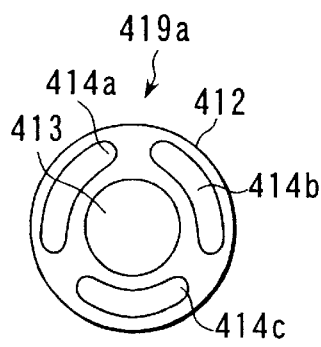
Figure 82B:
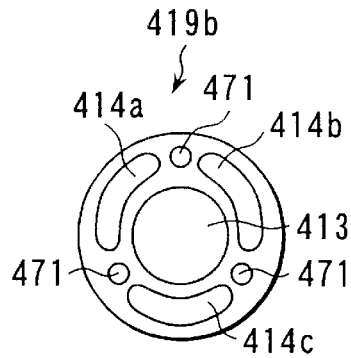
Figure 82C:
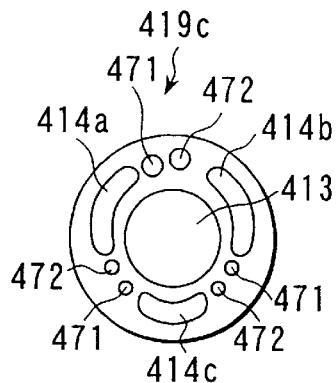

FIGS. 82A to 82C show a modification of the 23rd embodiment (see FIGS. 81A to 81C). In this modification, as shown in FIG. 82B, three tube through holes 471 for allowing the three air tubes 416 in the pneumatic actuator unit 419a at the very end position to extend through are formed in the multi-lumen tube 412 of the second pneumatic actuator unit 419b.

As shown in FIG. 82C, the multi-lumen tube 412 of the third pneumatic actuator unit 419c has three tube through holes 471 for allowing the three air tubes 416 in the pneumatic actuator unit 419a and three tube through holes 472 for allowing the three air tubes 416 in the second pneumatic actuator unit 419b to extend through.

Since the bending portion 411 in this modification has the triple pneumatic actuator units 419a, 419b, and 419c as in the 23rd embodiment, the bending portion 411 can be bent in a more complicated shape than in the 22nd embodiment. In addition, since the air tubes 416 are not inserted into the axial portion lumens 413 of the pneumatic actuator units 419a, 419b, and 419c on the respective stages, larger quantities of built-in members can be housed in the axial portion lumens 413 of the pneumatic actuator units 419a, 419b, and 419c on the respective stages.

Figure 83A:
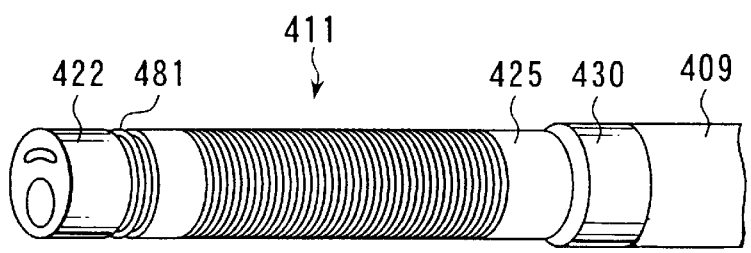
Figure 83B:
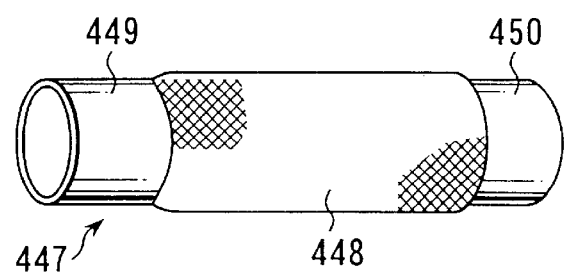

FIGS. 83A and 83B show the 24th embodiment of the present invention. In this embodiment, the method of fixing the braid 448 to the bending portion 411 of the endoscope 401 according to the 22nd embodiment (see FIGS. 72 to 79) is modified as follows.

In this embodiment, an O ring 481 is fitted on a front mouth piece 422 at the front end portion of a multi-lumen tube 412, and a front mouth piece 449 of a braid 448 is fixed with the O ring 481 on the front mouth piece 422 by pressure welding.

In addition, the size of the O ring 481 and the inner diameter of the front mouth piece 449 of the braid 448 may be adjusted to allow the O ring 481 to slide in bending operation. Note that a rear mouth piece 450 of the braid 448 is fixed to a rear mouth piece 425 of the multi-lumen tube 412 with a screw while being sealed with an adhesive as in the 22nd embodiment.

This embodiment can provide the same effect as that of the 22nd embodiment. In addition, according to this embodiment, that position of the braid 448 at which the front mouth piece 449 is mounted can be easily adjusted.

Figure 85:
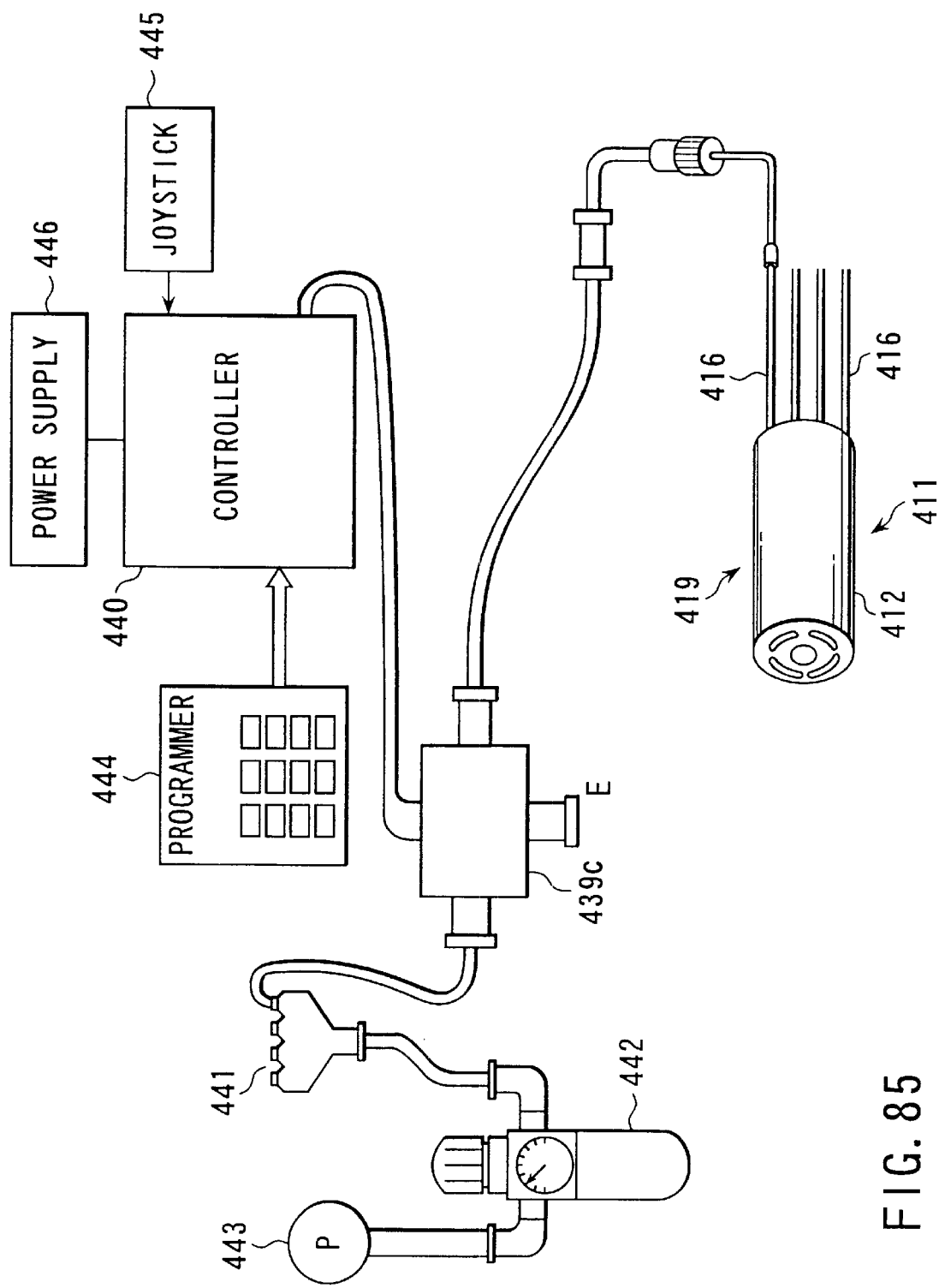
Figure 86:
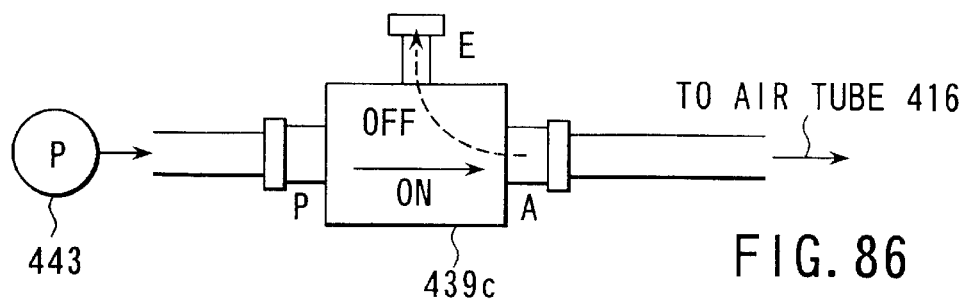

FIGS. 85 to 95 show the 25th embodiment of the present invention. In the system of the endoscope 401 according to the 22nd embodiment (FIGS. 72 to 79), the two solenoid valves 439a and 439b are connected. In contrast to this, according to this embodiment, as shown in FIG. 85, one solenoid valve 439c is used to pressurize a pressurization chamber 415 and exhaust air from the pressurization chamber 415.

In this embodiment, one solenoid valve 439c is connected to each of four air tubes 416 connected to a pneumatic actuator unit 419. An air vent A of each solenoid valve 439c is coupled to an air pump 443 serving as a pneumatic pressure source through a distributor 441 and filter regulator 442. An air vent P is connected to one of the air tubes 416.

In this embodiment, as shown in FIG. 85, when the solenoid valve 439c is turned on, compressed air is sent from the air pump 443 to the air tube 416. When the solenoid valve 439c is turned off, compressed air from the air pump 443 is blocked, and the air in the pressurization chamber 415 is exhausted from the air tube 416 through the solenoid valve 439c. With this arrangement, the solenoid valve 439c supplies/exhausts a compressed fluid from the air pump 443.

This embodiment further includes a bending control means for turning on the solenoid valve 439c to continuously release the air pump 443 and pneumatic actuator unit 419 in increasing the bend in a bending portion 411, and pulse-operating the solenoid valve 439c in holding the bend. This means increases the pulse width as the bend amount increases.

Figure 88:
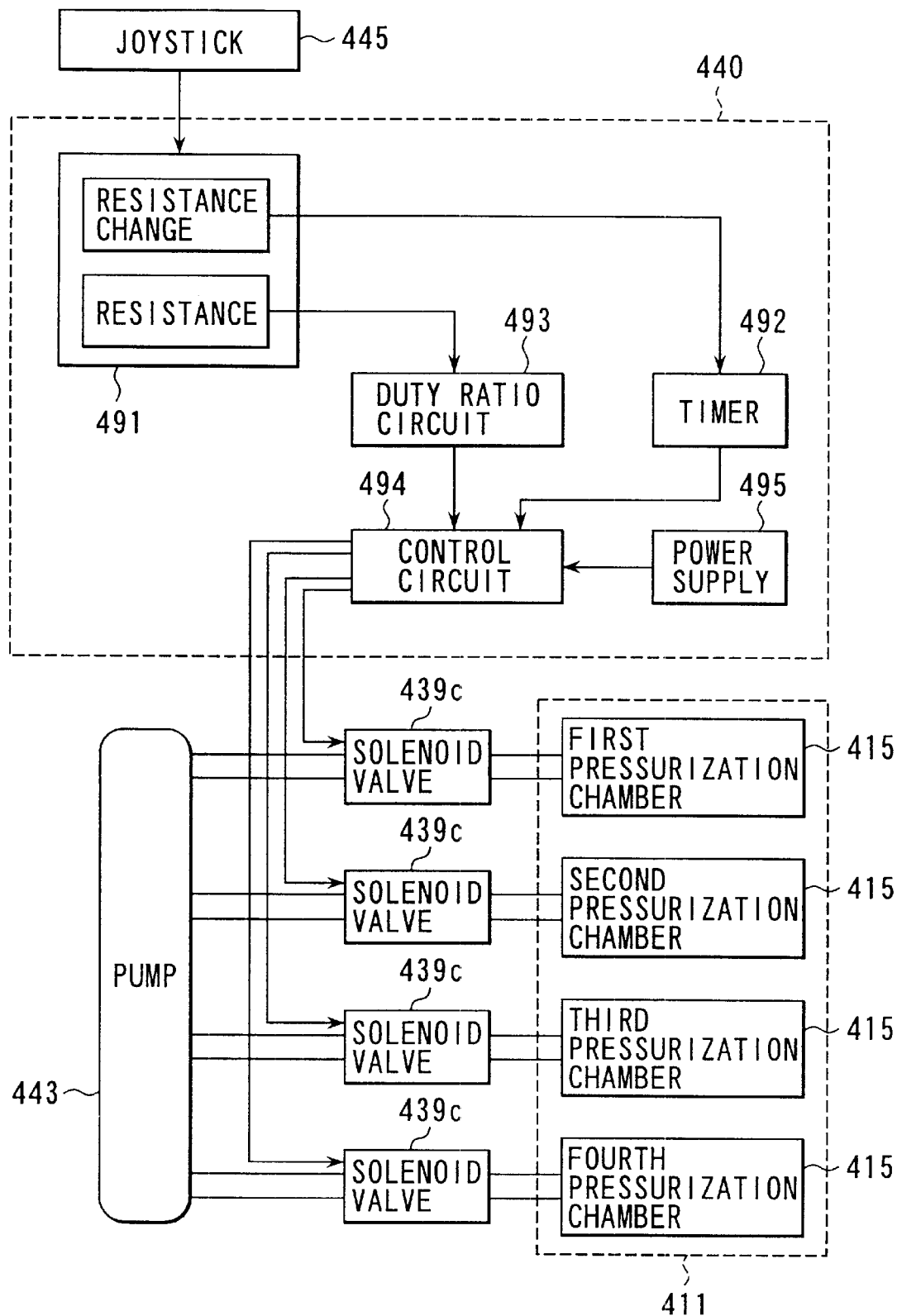

FIG. 88 shows the schematic arrangement of a controller 440 in this embodiment. The controller 440 in this embodiment includes a resistance change detection circuit 491, timer 492, duty ratio circuit 493, control circuit 494, and power supply 495. The solenoid valves 493c inserted in the four air tubes 416 of the pneumatic actuator unit 419 are connected to the control circuit 494.

The function of the above arrangement will be described next. In this embodiment, the operation of the bending portion 411 is controlled in accordance with the flow chart of FIG. 93. First of all, the operator operates a joystick 445 (step S1). The operator then releases the joystick 445 when he/she wants to stop tilting the bending portion. At this time, the solenoid valve 439c is set at an opening/closing frequency having a waveform like the one shown in FIG. 87A.

While the joystick 445 is kept on, the solenoid valve 439c is on. In holding the bend, the solenoid valve 439c is repeatedly turned on/off in a pulse-like manner.

During operation of the joystick 445, the duty ratio is changed in accordance with the ON time of the joystick 445. As t1 is prolonged, T'/T increases. As the duty ratio increases, the bending angle increases.

When the joystick 445 is operated in step S1, the operation speed (the amount of change in the angle of the joystick 445) is detected (step S2), and the position (the angle of the joystick 445) is detected (step S3). As a consequence, timer set times T1 and T2 (step S4) and a duty ratio Δd (step S5) are determined. The control circuit 494 operates in accordance with Ti, T2, and Δd (step S6) to control the operation of the solenoid valve 439c (step S7). With this operation, a compressed fluid from the air pump 443 is supplied to the pressurization chamber 415 of the bending portion 411 (step S8).

Figure 87A:
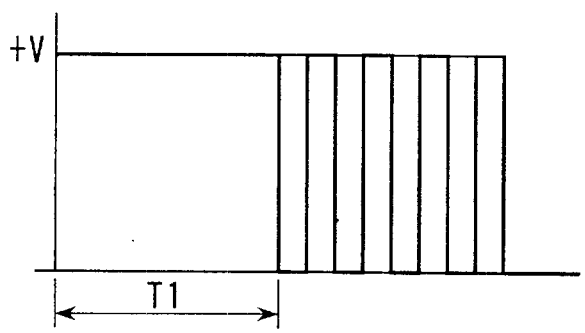

When the operator operates the joystick 445 in a direction to increase the inclination, the timer T1 is set as shown in FIGS. 94 and 87A to supply air from the air pump 443 to the pressurization chamber 415 of the bending portion 411 for a predetermined period of time, thereby increasing the bend in the bending portion 411.

Figure 87B:
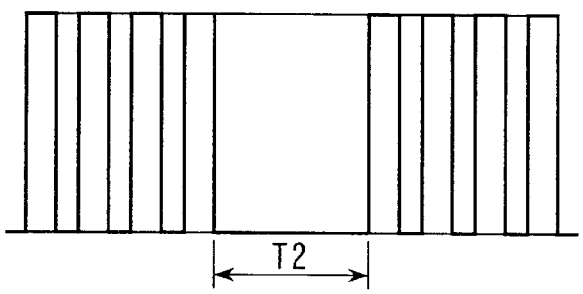

When the operator operates the joystick 445 in a direction to decrease the inclination, the time T2 is set as shown in FIG. 87B to exhaust air from the bending portion 411 for a predetermined period of time, thereby decreasing the bend. In this case, the bend is held at a duty ratio corresponding to the angle of the joystick 445.

FIG. 89A is a view for explaining the operation of the joystick 445 in increasing the bend in the bending portion 411 of the endoscope 401 according to the 25th embodiment. FIG. 89B is a view for explaining the bending operation of the bending portion 411 in increasing the bend. FIG. 90 is a view for explaining a change in physical property value in accordance with the operation of the joystick 445 in decreasing the bend in the endoscope 401 according to the 25th embodiment.

FIG. 91A is a view for explaining the operation of the joystick 445 when the bend amount of the bent portion 411 decreases in the endoscope 401 according to the 25th embodiment, FIG. 89B is a view for explaining the bending operation of the bending portion 411 when the bend amount decreases, and FIG. 92 is a graph for explaining a change in physical property value in accordance with the operation of the joystick 445 when the bend amount decreases in the endoscope 401 according to the 25th embodiment.

With the above arrangement, the following effect can be obtained. This embodiment includes the bending control means for turning on the solenoid valve 439c to continuously release the air pump 443 and pneumatic actuator unit 419 in increasing the bend in the bending portion 411, and pulse-operating the solenoid valve 439c in holding the bend. This means increases the pulse width as the bend amount increases. With this arrangement, the bending speed of the bending portion 411 can be increased, and bending of the bending portion 411 can be accurately stopped. Even if, therefore, the endoscope 401 has a long insertion portion 402, bending operation can be quickly and accurately performed. FIG. 95 shows a state wherein a portion T1 in FIG. 87A is replaced with pulses.

FIG. 96 shows the first modification of the controller 440 in the endoscope according to the 25th embodiment. The controller 440 of this modification has two duty ratio circuits 493. An input setting section 511 is connected to one duty ratio circuit 493.

When the operator tilts the joystick 445, the resistance change detection circuit 491 detects the resistance and its change. A duty ratio $\Delta d2$ and the timer T1 are respectively set in accordance with the resistance and the resistance change. A duty ratio $\Delta d1$ is input/set by the input setting section 511. The control circuit 494 controls the solenoid valve 439c in accordance with these values $\Delta d1$, $\Delta d2$, and T1.

FIG. 97 shows the second modification of the controller in the endoscope according to the 25th embodiment. In this modification, a change in duty ratio $\Delta d1$ is set in accordance with resistance change. FIGS. 98 to 103 show the 26th embodiment of the present invention. In this embodiment, the arrangement of the overall system of the endoscope 401 according to the 22nd embodiment (see FIGS. 72 to 79) is modified as follows.

As shown in FIG. 98, a system of an industrial endoscope 401 of this embodiment incorporates eight solenoid valves 439 for independently controlling the supply/exhaustion of air to/from four air tubes 416 connected to a pneumatic actuator unit 419 of a bending portion 411, and a controller 440 for controlling the solenoid valves 439.

In this case, two (first and second) solenoid valves 439a and 439b are connected to each of the four air tubes 416 connected to the pneumatic actuator unit 419. The connected state of the two (first and second) solenoid valves 439a and 439b in this embodiment differs from that in the 22nd embodiment. FIG. 99 shows how the solenoid valves 439a and 439b in this embodiment operate. FIG. 100 shows how the solenoid valves 439a and 439b in the 22nd embodiment operate. In this embodiment, in bending the bending portion 411, the second solenoid valve 439b is kept on to be released to the atmosphere.

FIG. 102 shows the schematic arrangement of the controller 440 in this embodiment. The controller 440 in this embodiment includes a resistance change detection circuit 491, driving frequency control section 521, driving time control section 522, input setting section 511, and power supply 495. Solenoid valves 439c inserted in the four air tubes 416 of the pneumatic actuator unit 419 are connected to a control circuit 523 including the driving frequency control section 521 and driving time control section 522.

The function of the above arrangement will be described next. In this embodiment, the operation of the bending portion 411 is controlled in accordance with the flow chart of FIG. 103. First of all, the operator operates the joystick 445 (step S1). Upon movement of the joystick 445, a resistance change (R1–R0) at time t1 in FIG. 101(A) is detected (step S2). A frequency (count value) in the interval between t0 and t1 in FIG. 101(A) is determined in accordance with this resistance change (R1–R0) (step S3).

A driving time $\Delta t$ is set in advance in step S4 by the driving time control section 522 in accordance with the input setting section 511 (step S5). A driving pulse frequency for the solenoid valve 439a is determined in this set value (step S6). Likewise, frequencies are respectively determined in the interval between t2 and t3, the interval between t4 and t5, and the interval between t6 and t7 in accordance with resistance changes over time in the respective intervals.

When the operator operates the joystick 445, the resistance change detection circuit 491 in the controller 440 detects the tilting speed (a resistance change over time) of the joystick 445 and inclination angle. A driving frequency is set in accordance with this speed and inclination angle, and the solenoid valve 493a is turned on/off for the driving time $\Delta t$ determined in advance by input setting. With this operation, compressed air from the air pump 443 is supplied to the pressurization chamber 415 to bend the bending portion 411.

Referring to FIG. 101B, the frequency at which the solenoid valve 439a is opened/closed is changed in accordance with the speed of the joystick 445. Referring to FIG. 101C, the duty ratio at which the solenoid valve 349a is opened/closed is changed in accordance with the speed of the joystick 445.

With the above arrangement, the following effect can be obtained. According to this embodiment, in the pneumatic bending operation of bending the bending portion by controlling air from the air pump 443 by turning on/off the solenoid valve 439a, the controller 440 is used to change the ON time per unit time for only a predetermined period of time in accordance with the tilting speed of the joystick 445, thereby changing the number of times the solenoid valve 439a is turned on in accordance with the inclination angle (change in resistance) of the joystick 445. As the tilting speed of the joystick 445 increases, the pulse width increases. Thereafter, the pulse width is restored to a standard value. With this control, the bending speed increases with an increase in the tilting speed of the joystick 445, thus improving controllability. This makes it possible to prevent the response speed from decreasing with a small bending angle as in a case wherein the flow amount is controlled by changing the duty ratio in accordance with the inclination angle of the joystick 445.

FIGS. 104 and 105 show the 27th embodiment of the present invention. This embodiment uses a push-button type operating portion 531 in place of the joystick 445 for controlling the bending operation of the bending portion 411 of the endoscope 401 according to the 22nd embodiment (see FIGS. 72 to 79). The operating portion 531 has four push buttons 532a to 532d for bending the bending portion 411 in the respective bending directions, i.e., the UP, DOWN, LEFT, and RIGHT directions. In addition, a plurality of LEDS are arranged in lines around the respective push buttons 532a to 532d to constitute a display portion for displaying the pushing amounts (time) of the push buttons 532a to 532d.

FIGS. 106, 107A and 107B show the 28th embodiment of the present invention. In this embodiment, the arrangement of the overall system of the endoscope 401 according to the 22nd embodiment (see FIGS. 72 to 79) is modified as follows.

This embodiment includes a sensor unit 541 having almost the same structure as that of the pneumatic actuator unit 419 of the bending portion 411 of the endoscope 401 according to the 22nd embodiment. This sensor unit 541 has second pressurization chambers 542 equal in number to the pressurization chambers 415 of the pneumatic actuator unit 419, each having the same structure as that of each of the pressurization chambers 415, and second air tubes 543 almost identical to the air tubes 416.

In this case, a length L1 of the air tube 416 is almost equal to a length L2 of the second air tube 543. A pressure sensor 544 is inserted into each second pressurization chamber 542 of the sensor unit 541. Note that the proximal end portion of each pressure sensor 544 is connected to an amplifier 545.

The sensor unit 541 is connected in parallel with a first solenoid valve V1, together with the pneumatic actuator unit 419, thus forming a control means for simultaneously performing bending operation and pressure detection by turning on/off the solenoid valve V1. Note that reference symbol V2 denotes a second solenoid valve.

FIG. 107A shows the schematic arrangement of a controller 440 in this embodiment. The controller 440 in this embodiment has driving circuits 548 and 549 for driving the two solenoid valves V1 and V2.

In this embodiment, when the operator operates the joystick 445, a duty ratio and timer are set in accordance with the angle and amount of change in angle of the joystick 445, and the solenoid valve V2 is operated by the corresponding signal. In addition, as the operator operates the joystick 445, the solenoid valve V1 is turned on/off at a duty ratio of 50%. As shown in FIG. 107B, bending operation and pressure detection are performed in accordance with the operations of the solenoid valves V1 and V2. A change in the pressure detected by the pressure detection at the time of stopping the joystick 445 is detected and feedback to the controller 440, thereby adjusting the two solenoid valves V1 and V2.

With the above arrangement, the following effect can be obtained. This embodiment has the sensor unit 541 having almost the same structure as that of the pneumatic actuator unit 419 of the bending portion 411 of the endoscope 401. This sensor unit 541 is connected in parallel with the first solenoid valve V1, together with the pneumatic actuator unit 419, thus forming the control means for simultaneously performing bending operation and pressure detection by turning on/off the solenoid valve V1. Therefore, the internal pressure of the bending portion 411 can be measured by the sensor unit 541, and feedback control can be accurately performed.

In addition, the sensor unit 541 has the second pressurization chambers 542 equal in number to the pressurization chambers 415 of the bending portion 411, each having the same structure as that of each of the pressurization chambers 415, and the second air tubes 543 almost identical to the air tubes 416, thereby forming branch paths from an air pump 443 through the solenoid valve V1. With this arrangement, therefore, the solenoid valve V1 is turned on/off in a pulse-like manner. In this case, when the solenoid valve V1 is on, bending operation can be performed. When the solenoid valve V1 is off, the pressure in the sensor unit 541 can be detected.

Since this embodiment includes the sensor unit 541 having almost the same structure as that of the pneumatic actuator unit 419 of the bending portion 411 of the endoscope 401, there is no need to place any sensor in each pressurization chamber 415 in actually measuring the inside of the pressurization chamber 415 during pneumatic bending operation. For this reason, there is no need to prepare any sensor seal structure in each pressurization chamber 415, and hence the arrangement of the pneumatic actuator unit 419 of the bending portion 411 can be simplified.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system comprising:
   an insertion portion to be inserted into a tubular cavity under examination;
   an image sensor provided at a distal end of the insertion portion;
   a bending portion provided behind said image sensor;
   a hydropneumatic actuator for bending said bending portion by applying hydropneumatic pressure, said hydropneumatic actuator having a multi-lumen tube including at least one pressurization chamber;
   a cylinder filled with a fluid to be supplied to said hydropneumatic actuator;
   a fluid flow rate adjusting portion for adjusting a flow rate of the fluid supplied from said cylinder;
   a control unit for controlling said fluid flow rate adjusting portion by a pulse operation;
   an operating portion for operating a controlled variable of said control unit; and
   a control device for causing said control unit to control said fluid flow rate adjusting portion in accordance with a signal output from said operating portion so as to stop both supply and exhaustion of the fluid to and from said at least one pressurization chamber at an arbitrary pressure.

2. An endoscope system according to claim 1, wherein said multi lumen tube comprises a central hole housing a built-in member, and a plurality of pressurization chambers arranged around the central hole.

3. An endoscope system according to claim 2, wherein said fluid flow rate adjusting portion comprises:
   a first solenoid valve for supplying the fluid from said cylinder to said at least one pressurization chamber and stopping supply of the fluid, and
   a second solenoid valve for controlling sealing and exhaustion of the fluid supplied from said cylinder to said at least one pressurization chamber.

4. An endoscope system according to claim 3, wherein:
   said operating portion comprises a joystick having an operation lever, and
   said control unit comprises a circuit section for changing ON times of said first and second solenoid valves in accordance with at least one of an operation amount and operation speed of the operation lever of said joystick.

5. An endoscope system according to claim 3, wherein:
said first and second solenoid valves are identical 3-port valves each having first, second, and third ports for allowing the fluid to flow,
the first port communicates with the second port and the third port closes when a power supply is turned on,
the second port communicates with the third port and the first port closes when the power supply is turned off,
said cylinder is connected to the first port of said first solenoid valve,
the second port of said first solenoid valve is connected to the second port of said second solenoid valve, and
the first port of said second solenoid valve is connected to said at least one pressurization chamber.

6. An endoscope system according to claim 3, wherein:
said first and second solenoid valves are identical 3-port valves each having first, second, and third ports for allowing the fluid to flow,
the first port communicates with the second port and the third port closes when a power supply is turned on,
the second port communicates with the third port and the first port closes when the power supply is turned off,
said cylinder is connected to the first port of said first solenoid valve,
the second port of said first solenoid valve is connected to said at least one pressurization chamber, and
the third port of said first solenoid valve is connected to the third port of said second solenoid valve.

7. An endoscope system according to claim 1, wherein said cylinder is sheathed with a heater, and said heater includes a temperature control circuit for controlling a heating temperature of said cylinder.

8. An endoscope system according to claim 1, wherein the fluid filled in said cylinder is a compressed fluid.

9. An endoscope system according to claim 8, wherein the compressed fluid comprises one of nitrogen and air.

10. An endoscope system according to claim 1, wherein the fluid filled in said cylinder is a liquefied gas.

11. An endoscope system according to claim 10, wherein the fluid filled in said cylinder is liquefied carbon dioxide.

12. An endoscope system according to claim 1, further comprising a take-up drum which is connected to a proximal end portion of said insertion portion and around which said insertion portion can be wound, and a housing case which integrally houses said operating portion, said control unit, and said cylinder.

13. An endoscope system according to claim 12, wherein said cylinder and said control unit are provided in said drum.

14. An endoscope system according to claim 1, further comprising:
a flow rate detector which is interposed between said fluid flow rate adjusting portion and said hydropneumatic actuator, and which detects a flow rate of the fluid to said hydropneumatic actuator, and
wherein the control device controls said fluid flow rate adjusting portion in exhausting the fluid from said hydropneumatic actuator to stop exhausting the fluid from said hydropneumatic actuator if a flow rate value obtained by subtracting an amount of fluid flow rate exhausted from said hydropneumatic actuator from a detection value of the flow rate detected by said flow rate detector is smaller than a predetermined value of a bending start flow rate.

15. An endoscope system according to claim 1, further comprising:
a pressure detector which is interposed between said fluid flow rate adjusting portion and said hydropneumatic actuator, and which detects a pressure of the fluid supplied to said hydropneumatic actuator, and
wherein the control device controls said fluid flow rate adjusting portion in exhausting the fluid from said hydropneumatic actuator to stop exhausting the fluid from said hydropneumatic actuator if a detection value of the pressure detected by said pressure detector is smaller than a predetermined value of a bending start pressure.

16. An endoscope system according to claim 1, further comprising:
a flow rate detector which is interposed between said fluid flow rate adjusting portion and said hydropneumatic actuator, and which detects a flow rate of the fluid to said hydropneumatic actuator, and
wherein the control device controls said fluid flow rate adjusting portion in supplying the fluid to said hydropneumatic actuator to stop supplying the fluid if the flow rate detected by said flow rate detector is higher than a predetermined allowable maximum flow rate.

17. An endoscope system according to claim 1, further comprising:
a pressure detector which is interposed between said fluid flow rate adjusting portion and said hydropneumatic actuator, and which detects a pressure of the fluid supplied to said hydropneumatic actuator, and
wherein the control device controls said fluid flow rate adjusting portion in supplying the fluid to said hydropneumatic actuator to stop supplying the fluid if the pressure detected by said pressure detector is higher than a predetermined allowable maximum pressure.

18. An endoscope system according to claim 1, wherein said fluid flow rate adjusting portion comprises:
a first solenoid valve for supplying the fluid and stopping supply of the fluid, said first solenoid valve being located on a side of the cylinder,
a second solenoid valve for controlling switching between a state wherein the fluid is supplied from said cylinder to said at least one pressurization chamber through said first solenoid valve and a state wherein the fluid is exhausted, and
a third solenoid valve for controlling exhaustion of the fluid from said at least one pressurization chamber through said first and second solenoid valves.

19. An endoscope system according to claim 18, wherein:
said first, second, and third solenoid valves are identical 3-port valves each having first, second, and third ports for allowing the fluid to flow,
the first port communicates with the second port and the third port closes when a power supply is turned on,
the second port communicates with the third port and the first port closes when the power supply is turned off,
said cylinder is connected to the first port of said first solenoid valve,
the second port of said first solenoid valve is connected to the second port of said second solenoid valve,
the first port of said second solenoid valve is connected to said at least one pressurization chamber, and
the first port of said third solenoid valve is connected to the third port of said second solenoid valve.

20. An endoscope system according to claim 1, wherein said fluid flow rate adjusting portion comprises at least one solenoid valve unit including at least one solenoid valve for supplying the fluid from said cylinder to said at least one pressurization chamber and stopping supply of the fluid, and sealing/exhausting the fluid in/from said at least one pressurization chamber.

21. An endoscope system according to claim 20, wherein said hydropneumatic actuator includes first and second pressurization chambers with which said bending portion bends in opposite directions when said pressurization chambers are pressurized, and piping is performed in said hydropneumatic actuator to supply/exhaust the fluid from said cylinder to/from said first and second pressurization chambers by using said at least one solenoid valve.

22. An endoscope system according to claim wherein:
   said at least one solenoid valve is a 3-position 5-port valve and includes first and second solenoids for switching connection states of the five ports,
   the first and second ports communicates with each other and the third and fifth ports communicate with each other when said first solenoid is turned on,
   the first and third ports communicate with each other and the second and fourth ports communicate with each other when said second solenoid is turned on, and the second and third ports communicate with each other and the first port closes when said second solenoid is turned off,
   all the ports close when both said first and second solenoid are turned off,
   said cylinder is connected to the first port,
   said first and second pressurization chambers are respectively connected to said second and third ports, and
   the fourth and fifth ports are released to the atmosphere.

23. An endoscope system comprising:
   an insertion portion to be inserted into a tubular cavity under examination;
   an image sensor provided at a distal end of the insertion portion;
   a bending portion provided behind said image sensor;
   a hydropneumatic actuator for bending said bending portion by applying hydropneumatic pressure, said hydropneumatic actuator including at least one pressurization chamber;
   a cylinder filled with a fluid to be supplied to said hydropneumatic actuator;
   a fluid flow rate adjusting portion for adjusting a flow rate of the fluid supplied from said cylinder;
   a control unit for controlling said fluid flow rate adjusting portion;
   an operating portion for operating a controlled variable of said control unit;
   a control device for causing said control unit to control said fluid flow rate adjusting portion in accordance with a signal output from said operating portion so as to stop both supply and exhaustion of the fluid to and from said at least one pressurization chamber at an arbitrary pressure; and
   a signal correcting section for correcting a time lag between an operation signal from said operating portion and a bending operation of said bending portion performed by said hydropneumatic actuator.

24. An endoscope system comprising:
   an insertion portion to be inserted into a tubular cavity under examination;
   an image sensor provided at a distal end of the insertion portion;
   a bending portion provided behind said image sensor;
   a hydropneumatic actuator for bending said bending portion by applying hydropneumatic pressure, said hydropneumatic actuator including at least one pressurization chamber;
   a cylinder filled with a fluid to be supplied to said hydropneumatic actuator;
   a fluid flow rate adjusting portion for adjusting a flow rate of the fluid supplied from said cylinder;
   a control unit for controlling said fluid flow rate adjusting portion;
   an operating portion for operating a controlled variable of said control unit;
   a control device for causing said control unit to control said fluid flow rate adjusting portion in accordance with a signal output from said operating portion so as to stop both supply and exhaustion of the fluid to and from said at least one pressurization chamber at an arbitrary pressure; and
   a signal correcting section for correcting a time lag between an operation signal from said operating portion and a bending operation of said bending portion performed by said hydropneumatic actuator;
   wherein said signal correcting section comprises a detecting section for detecting a bending speed instruction from the signal output from said operating portion, and an exhaustion timing adjusting section for adjusting an exhaustion timing of said fluid flow rate adjusting portion in accordance with the bending speed instruction detected by said detecting section.

* * * * *